US009226518B2

(12) United States Patent
Llagostera et al.

(10) Patent No.: US 9,226,518 B2
(45) Date of Patent: Jan. 5, 2016

(54) ***SALMONELLA* BACTERIOPHAGE COMPOSITIONS AND USES THEREOF**

(75) Inventors: Montserrat Llagostera, Cerdanyola del Valles (ES); Jorge Barbé, Cerdanyola del Valles (ES); Carlota Bardina, Cerdanyola del Valles (ES); Maria Pilar Cortés, Cerdanyola del Valles (ES); Denis Augusto Spricigo, Cerdanyola del Valles (ES)

(73) Assignee: UNIVERSITAT AUTONOMA DE BARCELONA, Bellaterra (Cerdanyola del Valles) (ES)

( * ) Notice: Subject to any disclaimer, the term of this patent is extended or adjusted under 35 U.S.C. 154(b) by 46 days.

(21) Appl. No.: 14/235,287

(22) PCT Filed: Jul. 27, 2012

(86) PCT No.: PCT/EP2012/064797
§ 371 (c)(1), (2), (4) Date: Apr. 2, 2014

(87) PCT Pub. No.: WO2013/014273
PCT Pub. Date: Jan. 31, 2013

(65) Prior Publication Data
US 2014/0219968 A1 Aug. 7, 2014

(30) Foreign Application Priority Data
Jul. 27, 2011 (EP) .................................... 11382257

(51) Int. Cl.

| | |
|---|---|
| *A23K 3/00* | (2006.01) |
| *A23K 1/17* | (2006.01) |
| *A23K 1/18* | (2006.01) |
| *A23B 4/22* | (2006.01) |
| *A23B 5/14* | (2006.01) |
| *A23B 7/155* | (2006.01) |
| *A61K 35/76* | (2015.01) |
| *A23K 1/00* | (2006.01) |
| *C12N 7/00* | (2006.01) |

(52) U.S. Cl.
CPC ... *A23K 3/00* (2013.01); *A23B 4/22* (2013.01); *A23B 5/14* (2013.01); *A23B 7/155* (2013.01); *A23K 1/009* (2013.01); *A23K 1/17* (2013.01); *A23K 1/184* (2013.01); *A23K 1/1813* (2013.01); *A23K 1/1826* (2013.01); *A61K 35/76* (2013.01); *C12N 7/00* (2013.01); *C12N 2795/10211* (2013.01); *C12N 2795/10231* (2013.01)

(58) Field of Classification Search
None
See application file for complete search history.

*Primary Examiner* — Nicole Kinsey White
(74) *Attorney, Agent, or Firm* — Michael B Fein; Eckert Seamans Cherin & Mellott, LLC

(57) ABSTRACT

The present invention relates to novel bacteriophages and bacteriophage cocktails containing the novel bacteriophages and or parts and/or products of them, all of them belonging to the Caudovirales order. The novel bacteriophages and the bacteriophage cocktails containing the novel bacteriophages and or parts and/or products of them are *Salmonella* specific bacteriophages and have lytic activity against *Salmonella*.

13 Claims, 13 Drawing Sheets

FIG.7

| Serovar | Strain | Year of isolation | Origin[¥] |
|---|---|---|---|
| Enteritidis | 65 | 1983 | A |
| | 951* | 1989 | A |
| | 6824 | 2000 | A |
| | 7129 | 2000 | A |
| | 7358* | 2000 | A |
| | 7385 | 2000 | A |
| | 7593 | 2000 | A |
| | 7616 | 2000 | A |
| | 8044 | 2001 | A |
| | 8419 | 2001 | A |
| | 9310* | 2003 | A |
| | 9451 | 2003 | A |
| | 9449* | 2003 | A |
| | 9609* | 2003 | A |
| | F20.5CP/94 | 1994 | H |
| | O/20.9 CG/98 | 1998 | H |
| | 2123/F06 | 2006 | H |
| | 1861/F06 | 2006 | H |
| Hadar | 10152 | | A |
| | 8546 | | E |
| | 05S72 | | H |
| Infantis | 1056 | | A |
| | 05S44 | | H |
| Typhimurium | 1 | 1979 | A |
| | 16 | 1981 | A |
| | 124 | 1983 | A |
| | 421 | 1986 | A |
| | 976 | 1989 | A |
| | 887* | 1989 | A |
| | 3360 | 1992 | A |
| | 4516 | 1994 | A |
| | S4426* | 1994 | A |
| | S4354 | 1994 | A |
| | S5832 | 1994 | A |
| | S5833 | 1994 | A |
| | S6254* | 1994 | A |
| | MG86 | 1994 | A |
| | MG98 | 1994 | A |
| | 5419 | 1996 | A |
| | S5827 | 1997 | A |
| | S5857 | 1997 | A |
| | 5833 | 1997 | A |
| | S5801 | 1997 | A |

| Serovar | Strain | Year of isolation | Origin[¥] |
|---|---|---|---|
| | S5812 | 1997 | A |
| | S5974 | 1997 | A |
| | 6231 | 1998 | A |
| | 6269 | 1998 | A |
| | 7627 | 2000 | A |
| | 7320 | 2000 | A |
| | 7653 | 2001 | A |
| Typhimurium | 7987 | 2001 | A |
| | 8429 | 2001 | A |
| | 8647 | 2002 | A |
| | 8695 | 2002 | A |
| | 8862 | 2002 | A |
| | 8880* | 2002 | A |
| | 9208 | 2002 | A |
| | 9222 | 2002 | A |
| | 9434 | 2003 | A |
| | 9849 | 2004 | A |
| | 9813 | 2004 | A |
| | 10182 | 2005 | A |
| | 10082 | 2005 | A |
| | 10175 | 2005 | A |
| | 10127 | 2005 | A |
| | J/10.2 CP/96 | 1996 | H |
| | D/20.5 CP/99 | 1999 | H |
| | J/11.16 CP/01 | 2001 | H |
| | 1992/F06 | 2006 | H |
| | 1557/F06 | 2006 | H |
| | 1711/F06* | 2006 | H |
| | 1624/F06* | 2006 | H |
| Virchow | 9781 | | A |
| | 791/S | | H |

FIG.8

| Bacteria | | Phage | | |
|---|---|---|---|---|
| Serovar | Strain | UAB_Phi20 | UAB_Phi78 | UAB_Phi87 |
| Enteritidis | 65 | + | + | + |
| | 951 | + | + | + |
| | F20.5CP/94 | + | + | + |
| | O/20.9 CG/98 | + | + | + |
| | 6824 | + | + | + |
| | 7129 | + | + | + |
| | 7358 | + | + | + |
| | 7385 | + | + | + |
| | 7593 | + | + | + |
| | 7616 | + | + | + |
| | 8044 | + | + | + |
| | 8419 | + | + | + |
| | 9310 | + | + | + |
| | 9451 | + | + | + |
| | 9449 | + | + | + |
| | 9609 | + | + | + |
| | 2123/F06 | + | + | + |
| | 1861/F06 | + | + | + |
| | LK5 | + | + | + |
| Hadar | 05S72 | + | + | + |
| | 10152 | + | + | + |
| | 8546 | + | + | + |
| Infantis | 05S44 | + | + | + |
| | 1056 | + | - | + |
| Typhimurium | 1 | + | + | + |
| | 16 | - | - | - |
| | 124 | + | + | + |
| | 421 | + | + | + |
| | 976 | - | + | - |
| | 887 | + | + | + |
| | 3360 | + | + | + |
| | 4516 | + | + | + |
| | S4426 | + | + | + |
| | S4354 | + | - | + |
| | S5832 | + | + | + |
| | S5833 | + | + | + |
| | 56254 | + | + | + |
| | MG86 | + | + | - |
| | MG98 | - | - | - |
| | J/10.2 CP/96 | + | + | + |
| | 5419 | + | + | + |
| | S5827 | + | + | + |
| | S5857 | + | + | + |
| | 5833 | + | + | + |
| | S5801 | + | + | + |
| | S5812 | + | + | + |
| | S5974 | + | + | + |
| | 6231 | + | - | + |

| Bacteria | | Phage | | |
|---|---|---|---|---|
| Serovar | Strain | UAB_Phi20 | UAB_Phi78 | UAB_Phi87 |
| Typhimurium | 6269 | + | + | + |
| | D/20.5 CP/99 | + | + | + |
| | 7627 | + | + | + |
| | 7320 | + | + | + |
| | 7653 | + | + | + |
| | 7987 | + | + | + |
| | 8429 | + | + | + |
| | J/11.16 CP/01 | + | + | + |
| | 8647 | + | + | + |
| | 8880 | + | + | + |
| | 9208 | + | + | + |
| | 8695 | + | + | + |
| | 8862 | + | + | + |
| | 9222 | + | + | + |
| | 9434 | + | + | + |
| | 9849 | + | + | + |
| | 9813 | + | + | + |
| | 10182 | + | + | + |
| | 10082 | + | + | - |
| | 10175 | + | + | + |
| | 10127 | + | + | + |
| | 1992/F06 | + | + | + |
| | 1557/F06 | + | + | + |
| | 1711/F06 | + | + | + |
| | 1624/F06 | + | + | + |
| | ATCC 14028 | + | + | + |
| Virchow | 791/S | + | - | + |
| | 9781 | + | - | + |

+ Indicates the capacity to infect.
- Indicates the inability to infect.

FIG.9

| Phage | pH value | Percentage of infectivity (%) | | | |
|---|---|---|---|---|---|
| | | Time of exposure (min) | | | |
| | | 30 | 60 | 90 | 120 |
| UAB_Phi20 | 2.0 | 79.3 | 71.2 | 62.0 | 49.4 |
| | 4.0 | 100.0 | 98.8 | 100.0 | 90.0 |
| | 6.0 | 100.0 | 98.8 | 100.0 | 100.0 |
| | 9.0 | 98.8 | 98.8 | 98.8 | 98.8 |
| UAB_Phi78 | 2.0 | 80.4 | 52.4 | 36.5 | 29.2 |
| | 4.0 | 98.7 | 98.7 | 97.5 | 87.8 |
| | 6.0 | 100.0 | 100.0 | 100.0 | 100.0 |
| | 9.0 | 98.7 | 98.7 | 97.5 | 97.5 |
| UAB_Phi87 | 2.0 | 61.3 | 28.4 | 11.4 | 11.4 |
| | 4.0 | 94.3 | 94.3 | 93.2 | 85.2 |
| | 6.0 | 100.0 | 100.0 | 100.0 | 100.0 |
| | 9.0 | 100.0 | 98.8 | 98.8 | 98.8 |

FIG.10

| Time of conservation (month) | Percentage of infectivity (%) | | |
|---|---|---|---|
| | UAB_Phi20 | UAB_Phi78 | UAB_Phi87 |
| 2 | 100 | 100 | 100 |
| 4 | 99 | 98.8 | 98.8 |
| 6 | 98 | 95.4 | 97.7 |
| 12 | 97.8 | 94.6 | 97.3 |

FIG.11

| Phage | Temperature (°C) | Percentage of infectivity (%) | | | | | | |
|---|---|---|---|---|---|---|---|---|
| | | Time (day) | | | | | | |
| | | 1 | 2 | 3 | 4 | 5 | 6 | 7 |
| UAB_Phi20 | 25 | 100.0 | 100.0 | 100.0 | 100.0 | 100.0 | 100.0 | 100.0 |
| | 37 | 98.3 | 97.5 | 96.6 | 96.4 | 95.8 | 95.5 | 95.3 |
| UAB_Phi78 | 25 | 100.0 | 100.0 | 100.0 | 99.6 | 98.8 | 98.1 | 98.0 |
| | 37 | 98.7 | 97.4 | 96.8 | 95.1 | 95.0 | 94.8 | 94.8 |
| UAB_Phi87 | 25 | 99.3 | 99.1 | 98.4 | 98.1 | 98.0 | 98.0 | 98.0 |
| | 37 | 96.4 | 95.6 | 95.6 | 95.3 | 95.1 | 94.9 | 94.9 |

FIG.12

| Time (h) | *Salmonella* concentration ($Log_{10}$ cfu/cm$^2$ ± SD)* | | | | | |
|---|---|---|---|---|---|---|
| | Typhimurium | | | Enteritidis | | |
| | Control | Phage Treatment | Reduction | Control | Phage Treatment | Reduction |
| 0 | 2.6 ± 0.19 | 2.6 ± 0.19 | - | 2.0 ± 0.11 | 2.0 ± 0.11 | - |
| 3 | 2.9 ± 0.17 | < -0.097 | >2.9 | 2.2 ± 0.08 | < -0.097 | >2.2 |
| 6 | 4.0 ± 0.03 | < -0.097 | >4.0 | 3.2 ± 0.05 | 1.21 ± 0.13 | 2.0 |

*Mean ± SD of six independent experiments.

FIG.13

| Time (min) | *Salmonella* concentration ($Log_{10}$ cfu/g ± SD)* | | | | | |
|---|---|---|---|---|---|---|
| | Typhimurium | | | Enteritidis | | |
| | Control | Phage Treatment | Reduction | Control | Phage Treatment | Reduction |
| 0 | 4.3 ± 0.04 | 4.3 ± 0.04 | - | 4.0 ± 0.08 | 4.0 ± 0.08 | - |
| 30 | 4.3 ± 0.03 | 0.9 ± 0.7 | 3.4 | 4.3 ± 0.1 | 2.4 ± 0.01 | 1.9 |
| 60 | 4.2 ± 0.04 | 0.3 ± 0.6 | 3.9 | 4.5 ± 0.3 | 2.3 ± 0.4 | 2.2 |

*Mean ± SD of five independent experiments.

FIG.14

| Bacteriophage | *Salmonella* concentration ($Log_{10}$ cfu/g ± SD) | |
|---|---|---|
| | Typhimurium | Enteritidis |
| No phage | 5.2 ± 0.05 | 5.4 ± 0.03 |
| UAB_Phi20 | 1.8 ± 0.3 | 3.9 ± 0.02 |
| UAB_Phi78 | 4.8 ± 0.07 | 4.8 ± 0.04 |
| UAB_Phi87 | 2.6 ± 0.09 | 5.1 ± 0.05 |
| Bacteriophage cocktail | 1.7 ± 0.2 | 3.3 ± 0.06 |

*Mean ± SD of five independent experiments.

FIG.15

| Time (day) | *Salmonella* concentration ($Log_{10}$ cfu/g ± SD)* | | | | | |
|---|---|---|---|---|---|---|
| | Typhimurium | | | Enteritidis | | |
| | Control | Phage Treatment | Reduction | Control | Phage Treatment | Reduction |
| 0 | 4.6 ± 0.03 | 4.6 ± 0.03 | - | 4.4 ± 0.06 | 4.4 ± 0.06 | - |
| 1 | 4.4 ± 0.2 | 2.8 ± 0.2 | 1.6 | 4.4 ± 0.1 | 3.7 ± 0.2 | 0.7 |
| 2 | 4.2 ± 0.1 | 2.6 ± 0.2 | 1.6 | 4.4 ± 0.2 | 3.4 ± 0.1 | 1 |
| 5 | 4.0 ± 0.1 | 2.6 ± 0.2 | 1.4 | 4.0 ± 0.1 | 3.0 ± 0.3 | 1 |
| 7 | 4.2 ± 0.1 | 2.0 ± 0.2 | 2.2 | 4.0 ± 0.2 | 3.1 ± 0.3 | 0.9 |

*Mean ± SD of five independent experiments.

*SALMONELLA* BACTERIOPHAGE COMPOSITIONS AND USES THEREOF

CROSS REFERENCE TO RELATED APPLICATIONS

This is a National Stage of International Application No. PCT/EP2012/064797 filed Jul. 27, 2012, claiming priority based on Spanish Patent Application No. 11382257.1 filed Jul. 27, 2011, the contents of all of which are incorporated herein by reference in their entirety.

TECHNICAL FIELD

The present invention relates to novel bacteriophages and bacteriophage cocktails containing the novel bacteriophages and or parts and/or products of them, all of them belonging to the Caudovirales order. The novel bacteriophages and the bacteriophage cocktails containing the novel bacteriophages and or parts and/or products of them are *Salmonella* specific bacteriophages and have lytic activity against *Salmonella*. The novel bacteriophages and the bacteriophage cocktails containing the novel bacteriophages and/or parts and/or products of them, when administered to animals are useful for the control of different *Salmonella* serovars. The invention refers to the use of the novel bacteriophages and the novel and safe phage cocktail compositions as an antimicrobial for the control of populations of *Salmonella* in animal therapy and livestock in general, as well as, a sanitization and sterilization composition to be applied on slaughterhouses, animal transportation, food processing industries and foods.

BACKGROUND OF THE INVENTION

Salmonellosis, due to non-typhoid *Salmonella enterica* serovars, is one of the most frequently reported food-borne diseases worldwide. Since 1993 to 2003, Enteritidis (84%), Typhimurium (7%), Virchow (1%), Infantis (1%) and Blockley (1%), were the serovars of *S. enterica* mainly isolated from human salmonellosis in European Union. More recently, data from 2006 to 2007 corroborate that Enteritidis and Typhimurium continue to be the most prevalent, although an increase of Typhimurium (16.5%) and a decrease of Enteritidis (64.5%) must be noted (EFSA, 2010).

Poultry and swine are known reservoirs of these zoonotic pathogens. *S.* Enteritidis is the most frequent cause of human salmonellosis at European Community level. In general, this serovar is also the most frequently isolated from poultry meat and especially in table eggs, whereas it is less commonly found from pigs and cattle and products thereof. The second most prevalent serovar in humans, *S.* Typhimurium, is the most frequently isolated serovar in pigs, cattle and products thereof and was also among the top three serovars isolated from broilers and table eggs (EFSA, 2010). It is also well documented that in the last decade, the antibiotic resistance is increasing in non-typhoid *S. enterica*, which means that animals are both pathogen and resistance reservoirs.

Due to the great concern about *Salmonella* zoonoses, a new *Salmonella* control program in breeding flocks of *Gallus gallus* was implemented. This control program aim to meet the *Salmonella* reduction targets set by the Regulation (EC) No 1003/2005 and covers the following serovars: *S.* Enteritidis, *S.* Typhimurium, *S.* Infantis, *S.* Virchow and *S.* Hadar. Likewise, a control or monitoring program for *Salmonella* in pig herds or slaughter pigs have been implemented in different countries with the aim to have more robust data about *Salmonella* prevalence in swine production. Different strategies and measures to reduce *Salmonella* have been proposed. In fact, the intensified control of *Salmonella* in animal populations, particularly in poultry, and a better hygiene throughout the food chain should be the cause of the decrease of the notification rate of *Salmonella* cases in the European Union. One of these measures has been the use of life or inactivated vaccines to control *S.* Enteritidis in poultry. However, some authors doubt of its long term effectiveness (Baumler et al., 2000; Rabsch et al., 2000). In this context, it is necessary to open the scope for further research to explore new approaches to existing ones, and new weapons with which to combat these zoonotic pathogens.

Within this aim, the potential use of bacteriophages in human and animal therapy has been extensively reviewed in these lasts years (Barrow and Soothil, 1997; Barrow, 2001; Sulakvelidze et al., 2001; Summers, 2001; Merrill et al., 2003; Matsuzaki et al., 2005; Parisien et al., 2008;). Moreover, its interest as biocontrol agents of zoonotic bacteria in food and animal production and also of others involved in biodeterioration has also arisen and some strategies have been proposed (Barrow and Soothil, 1997; Joerger, 2002; Callaway et al., 2004; Greer, 2005; Hudson et al., 2005). The special characteristics of phages among which are its high specificity and its ability to selfreplicate when infecting, make them especially attractive to prevent food-borne illness, by using them as biocontrol agents in poultry and swine industries and in food production. However, the narrow host-range of bacteriophages is a great restriction to find good candidate phages for bacteriophage therapy against *Salmonella enterica* because these phages must be able to infect a wide range of strains and serovars of this bacterial species.

There is a consensus about lytic bacteriophages are the best suitable to achieve a significant reduction of bacterial populations due its rapid bacterial killing. Furthermore, safety criteria related to the spread of virulence genes or antibiotic resistance that could be in the phage genome must also be taken into account. Therefore, it is necessary to obtain genomic data demonstrating the impossibility of a lysogenic cycle and the absence of both potential virulence factors and/or antimicrobial resistance genes in the genomes of phage for therapy applications. In addition, it must be noted that the effectiveness of phages in food is likely to vary with each phage, each food matrix, and with the conditions of application including environmental factors (EFSA, 2009).

There are some works testing the effect of different bacteriophages for their inhibitory effect against *Salmonella enterica*. Thus, it has been reported a reduction of *S.* Typhimurium in the digestive tract of chickens after oral inoculation of lytic bacteriophages, although high titter of bacteriophages were needed and the inoculation was performed soon after infection to maximized the effect (Berchieri et al., 1991). More recently, much more significant decreases in *S.* Enteritidis in the cecal contents of broilers orally inoculated with bacteriophages, some of them belonging to the Myoviridae and Siphoviridae family, have been obtained at different times (Fiorentin et al., 2005a; Atterbury et al., 2007; Filho et al., 2007; Borie et al., 2008) and also in *S.* Typhimurium in experiments that combine the oral inoculation of bacteriophages with competitive exclusion cultures (Toro et al., 2005). In another field of application which included food safety, treatment with bacteriophages also reduced the concentration of *S.* Enteritidis in poultry products and turkey (Goode et al., 2003; Higgins et al., 2005; Fiorentin et al. 2005b; Bigwood et al., 2008). However, all these works are partial studies because any of them show nor a morphological and genomic characterization of bacteriophages, the phage host range, the efficiency of bacteriophages for reducing *Salmonella* in poultry over long periods and its efficiency in different matrices and neither some criteria related to safety.

The present invention describes the novel lytic bacteriophages UAB_Phi20 and UAB_Phi78, belonging to the Podoviriade family and UAB_Phi87, belonging to the Myoviridae family, all of them of the Caudovirales order. Those bacteriophages are *Salmonella* specific bacteriophages that infect different serovars of *Salmonella* and a high percentage of clonally unrelated strains of the serovars Typhimurium and Enteritidis. Those bacteriophages maintain their infective ability at a wide pH range. The genome of those bacteriophages does not include any known or similar gene to those involved in bacterial virulence.

The present invention also describes bacteriophage cocktail compositions containing at least one of the bacteriophages and/or parts and/or products of the bacteriophages of the invention. Those cocktail compositions can also contain other lytic bacteriophages and/or parts and/or products of them. The novel bacteriophages, when administered to animals, are useful for the bacteriophage therapy over the time of different *Salmonella* serovars. The present invention refers to the use of these novel bacteriophages and the novel bacteriophage cocktail compositions to reduce the concentration of different *Salmonella* serovars, providing doses and schedule of administration in animals and in different matrices. The invention refers to the use of the novel bacteriophages and the novel safe phage cocktail compositions as an antimicrobial for the biocontrol of populations of *Salmonella* in animal therapy and livestock in general as well as a sanitization and sterilization composition to be applied on slaughterhouses, animal transportation, food processing industries and foods.

OBJECTS OF INVENTION

The present invention embrace the novel bacteriophages UAB_Phi20, UAB_Phi78 and UAB_Phi87 belonging to the Caudovirales order. UAB_Phi20 and UAB_Phi78 belong to the Podoviridae family whereas UAB_Phi87 belongs to the Myoviridae family, and all of them are *Salmonella* specific bacteriophages. The novel bacteriophages and/or parts and or products of them, when administered to animals, are useful for the control of different *Salmonella* serovars. The present invention also describes bacteriophage cocktail compositions containing at least one of the novel bacteriophages of the invention and/or parts and products of them. These cocktail compositions are administered to animals and are useful for the control of different *Salmonella* serovars. The present invention refers to the use of the novel bacteriophage cocktail compositions to control different *Salmonella* serovars, providing methods and schedule of administration, doses and different matrices on/in which *Salmonella* titres decrease. The invention refers to the use of the novel safe phage cocktails to reduce populations of *Salmonella* in food, that is, as an antimicrobial for the control of populations of *Salmonella* in animal therapy and livestock in general, as well as, a sanitization and sterilization composition to be applied on slaughterhouses, animal transportation, food processing industries and foods.

Bacteriophage (Phage): Refers to any virus that infects prokaryotic cells.

*Salmonella* and *Salmonella* serovars: As referred by the present invention, *Salmonella* is a bacterial genus belonging to Enterobacteriaceae family. The *Salmonella* genus contains three species: *Salmonella enterica, Salmonella bongori* and *Salmonella subterranea. Salmonella enterica* comprises six subspecies. The subspecies I includes pathogenic strains either to humans or to other warm-blooded animals. The strains of *Salmonella* are serologically classified into serovars (serotypes) using the Kauffmann-White scheme. More than 2,540 serovars have been defined. Among them, *S.* Enteritidis, *S.* Typhimurium, *S.* Infantis, *S.* Virchow and *S.* Hadar are target to be reduced in breeding flocks of *Gallus gallus* in the European Union. In relation to human salmonellosis in European Union, the most prevalent serovars are Enteritidis and Typhimurium although an increase of Typhimurium and a decrease of Enteritidis is now seen.

*Salmonella* specific bacteriophage: Refers to any bacteriophage able to infect specifically *Salmonella* cells.

Cocktail, phage cocktail, cocktail composition, phage cocktail composition: As comprised by the present invention, all of them are equivalent and can be used without distinction. They refer to any formulation containing at least one of the bacteriophages UAB_Phi20, UAB_Phi78, UAB_Phi87 and/or parts and/or products of them, for example bacteriophages enzymes as enzybiotics and tail proteins. In those cocktails, bacteriophages UAB_Phi20, UAB_Phi78, UAB_Phi87 and/or parts and/or products of them can be in similar or different proportion. Those cocktails additionally can also contain other lytic bacteriophages and/or parts and/or products of them. Those lytic bacteriophages are selected between lytic bacteriophages that specifically infect *Salmonella*, wherein those bacteriophages do not include any known or similar gene to those involved in bacterial virulence. Mainly, those bacteriophages could belong to some of the three families of bacteriophages (Myoviridae, Siphoviridae and Podoviridae) included in the Caudovirales order that were specific for *Salmonella.*

These compositions can also contain any of the known carriers of the state of the art, such as carriers adapted for the use according of the present invention, e.g. solvents, including water-based formulations or other technologies such as encapsulation of bacteriophages or parts and products of them.

Pharmaceutically acceptable carrier: Refers to a carrier or diluent that does not cause significant irritation to an organism and does not abrogate the biological activity and properties of the administered compound. For formulation of the composition into a liquid preparation, a pharmaceutically acceptable carrier which is sterile and biocompatible may be used such as saline, sterile water, Ringer's solution, buffered physiological saline, etc.

Animals: As comprised by the present invention, animal refers to any warm-blooded animal, included humans. In a preferred embodiment, animals are selected by the group comprising *Gallus gallus*, turkeys and other avian species, pigs and cattle.

Food: Any plant, animal or any substance or material from plants and animals (vegetables, meat, eggs, etc) that provides nutritional support for the life of humans and animals.

Lytic pathway (cycle): A series of steps after bacteriophage infection that lead to bacteriophage replication and the destruction (lysis) of the bacterial host cell.

Lysogenic pathway (cycle): A series of steps that after bacteriophage infection leads to a genetic state (lysogeny) where the bacteriophage genome is replicate as a prophage along with that of the genome of the bacterial host.

Virulence factors: Molecules synthesized by bacterial pathogen cells that participate in the pathogenic process of those bacteria.

Antimicrobial resistance genes: Genes that codify some molecule that allows the growth of bacterial cell in the presence of an antimicrobial agent to which that bacterial cell is usually susceptible.

Host range of bacteriophages: Diversity of bacterial strains that can be infected by a bacteriophage.

Solid matrices: As comprised by the present invention, solid matrices refer to any surface which may be colonized by *Salmonella*. Those solid matrices would include animal skin, surfaces of farms, slaughterhouses, poultry and swine barns and/or pens, crates used during animal transportation from farms to the food processing industries and other facilities used during the manufacturing process.

Products of bacteriophages: Any product synthesized by the bacteriophage with antimicrobial activity. Those encoded lytic factors are lysozymes, autolysisn or virolysins, also known as enzybiotics. All of them can act by: i) the formation of channels or pores across the bacterial membrane; ii) inhibiting the cell wall biosynthesis; iii) degradation of cellular wall or membrane; iv) depolarization and perforation of the bacterial membrane and v) the nuclease activity of some phage products (Bernhardt et al., 2002; Parisien et al., 2008).

Enzybiotics: Bacterial cell wall hydrolases (BCWH) that lyse bacterial cells from without. BCWH are enzymes that degrade the major component of the cell wall and cause bacteriolysis (Hermoso et al., 2007).

Parts of the bacteriophages: Any single part of the bacteriophage with antimicrobial activity, like the phage tail complexes or tail spike proteins (Parisien et al., 2008).

OBJECTS OF INVENTION

In one embodiment, the present invention refers to a bacteriophage-composition for the prevention of infectious diseases caused by *Salmonella* comprising at least one of the *Salmonella* lytic bacteriophages UAB_Phi20, UAB_Phi78 and UAB_Phi87 and/or parts and/or products of them.

In another embodiment, the composition contains at least two of the phages UAB_Phi20, UAB_Phi78 and UAB_Phi87 and/or parts and/or products of them.

In another embodiment the composition comprises phages UAB_Phi20, UAB_Phi78 and UAB_Phi87 and/or parts and/or products of them.

In another embodiment, the composition also contains other *Salmonella* lytic bacteriophages and/or products and/or parts of them. Those lytic bacteriophages do not include any known gene or similar gene to those involved in bacterial virulence. In a preferred embodiment, those lytic bacteriophages could belong to the Caudovirales order selected from a collection of lytic bacteriophages that infect *Salmonella*.

In a further embodiment, the bacteriophages and/or parts and/or products of them in the compositions are in the same proportion. In another embodiment, bacteriophages and/or parts and/or products of them in the compositions are in different proportion. In a preferred embodiment, the composition comprises phages UAB_Phi20, UAB_Phi78 and UAB_Phi87 in the same proportion. In another embodiment, the composition contains only two of the phages UAB_Phi20, UAB_Phi78 and UAB_Phi87 and/or parts and/or products of them. In another embodiment, the composition contains only one of the phages UAB_Phi20, UAB_Phi78 and UAB_Phi87 and/or parts and/or products of each of them.

In another embodiment, the compositions of the invention additionally includes a pharmaceutically acceptable carrier, solvent or pharmaceutically acceptable excipient.

In a further embodiment, the invention refers to the compositions of the invention for pharmaceutical use.

In another embodiment, the composition is in the form of a suspension, injectable and/or orally administrable dosage forms, sprays or aerosols, etc.

In a another embodiment, the injectable and/or orally administrable dosage forms are selected by the group comprising tablets, troches, lozenges, aqueous or emulsifier suspensions, powder or granules, emulsions, hard or soft capsules, syrups or elixir.

In another embodiment, the composition of the invention is in the form of an animal feed, drinking water, sanitizier or cleaning solution.

In another embodiment, the invention refers to an animal feed comprising the compositions of the invention. In a further embodiment, the invention refers to drinking water comprising the composition of the invention. In further embodiment, the invention refers to a sanitization or cleaning solution, comprising the compositions of the invention.

In a further embodiment, the invention refers to the use of the compositions of the invention to control *Salmonella* populations in food and solid matrices. In a preferred embodiment, food is selected by the group comprising vegetables, meat and eggs. In another preferred embodiment, solid matrices are selected by the group comprising skin of animals, surfaces of farms, slaughterhouses, poultry and swine barns and/or pens, crates used during animal transportation from farms to the food processing industries or other facilities used during the manufacturing process.

In another embodiment, the invention refers to the use of the compositions of the invention for the manufacture of a medicament for the treatment or prevention of *Salmonella* infection in an animal.

In another embodiment, the invention refers to the use of the animal feed, drinking water and sanitizer or cleaning solution of the invention for the manufacture of a medicament for the treatment or prevention of *Salmonella* infection in an animal.

In a further embodiment, the invention refers to the method of treatment or prevention of *Salmonella* infection consisting of daily continuous treatment of animals with compositions and/or animal feed and/or drinking water of the invention. In a preferred embodiment, the preferred daily doses per animal are selected between $10^9$ to $10^{12}$ pfu/day and animal. In a more preferred embodiment the dose is $10^{10}$ pfu/day and animal.

In a further embodiment, the treatment consist of spraying animal skin with compositions of the invention. In a preferred embodiment, the preferred bacteriophage concentration in the compositions is selected from the range comprising $10^9$ to $10^{12}$ pfu/ml. In a more preferred embodiment, the concentration is $10^{10}$ pfu/ml

*monella* bacteriophages of the present invention which are around 40 kb for bacteriophages UAB_Phi20 and UAB_Phi78 and around 80 kb for UAB_Phi87, as determined by PFGE technique.

Figure 3:
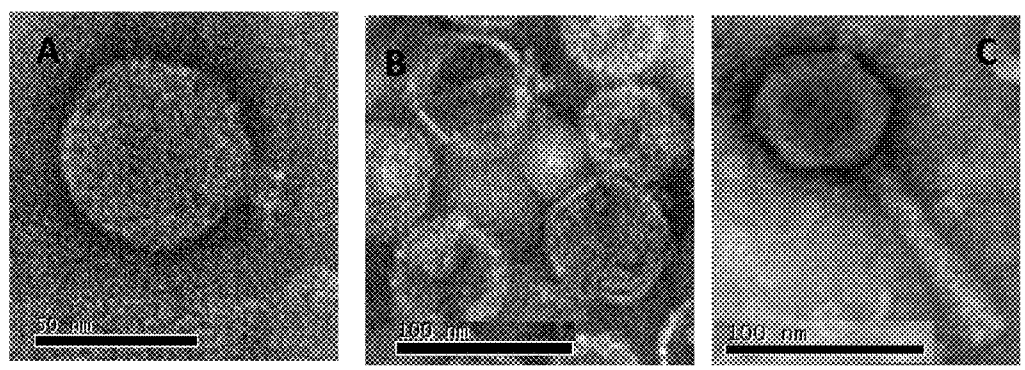

FIG. 3 shows the electron micrographs of the novel bacteriophages UAB_Phi20 (A), UAB_Phi78 (B) and UAB_Phi87 (C). Bacteriophages were applied to electron carbon coated grids and negative stained with 2% uranyl acetate. The preparations were examined with a transmission electron microscope. Electron micrograph images revealed that the novel bacteriophages UAB_Phi20 and UAB_Phi78 belonged to the Podoviridae family while the novel bacteriophage UAB_Phi87 belonged to the Myoviridae family, all of them of the Caudovirales order.

Figure 4:
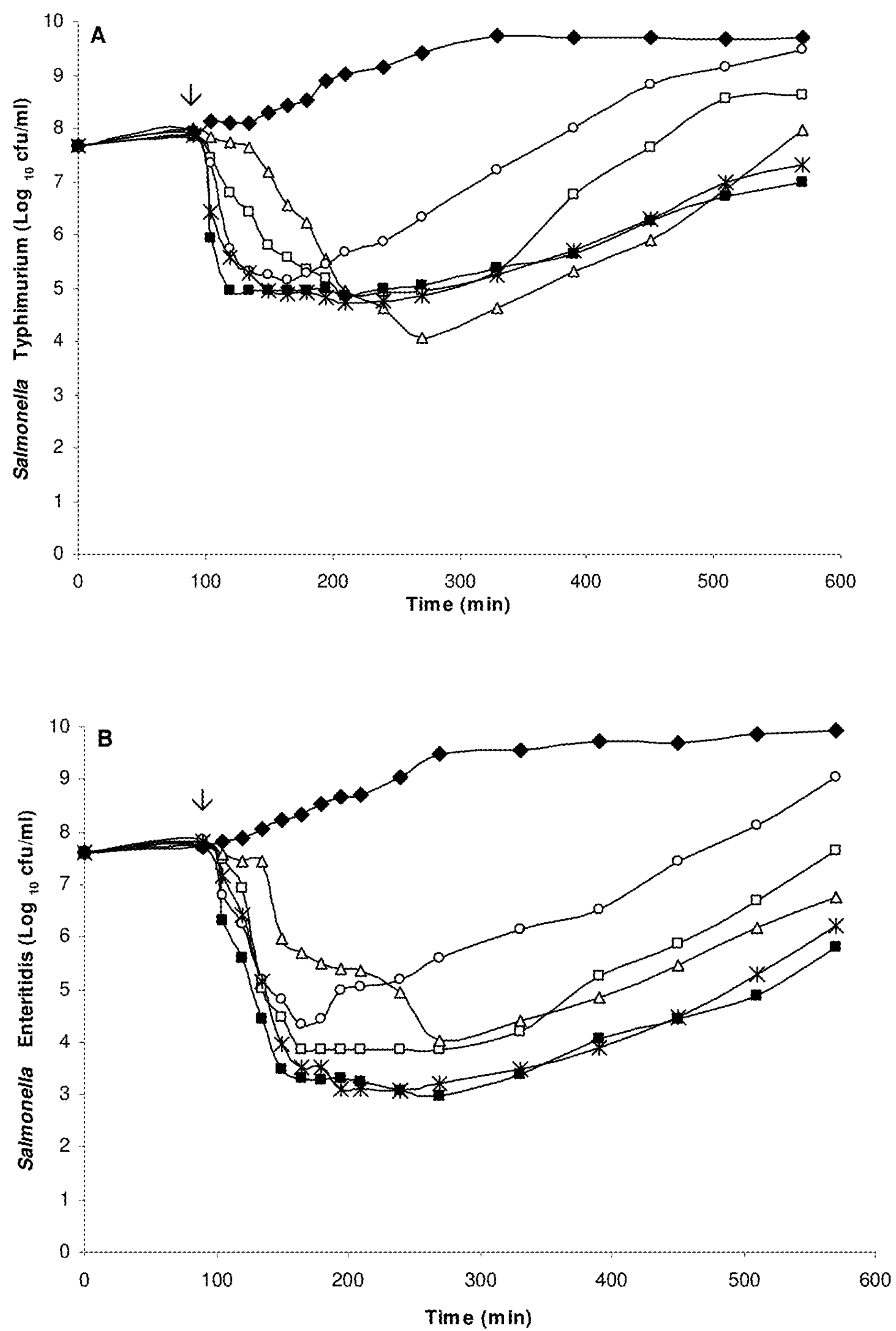
Figure 5:
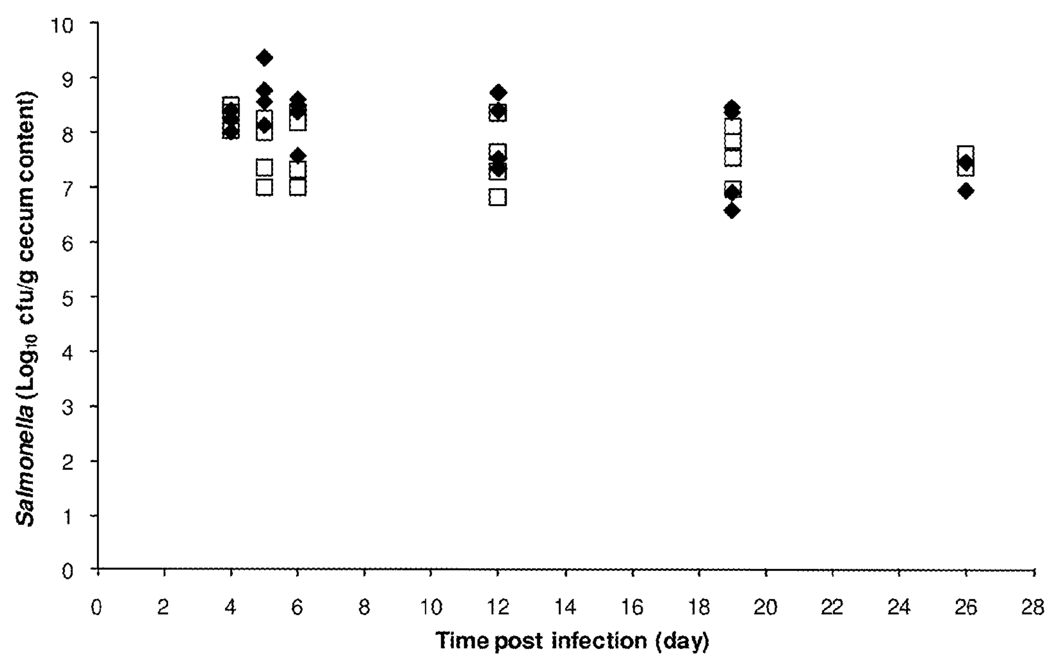

FIG. 4 illustrates the results of the in vitro killing kinetics when infecting *S.* Typhimurium (Panel A) and *S.* Enteritidis (Panel B) with UAB_Phi20 (□), UAB_Phi78 (○), UAB_Phi87 (Δ), UAB_Phi20 and UAB_Phi87 (concentration 1:1) (X) and a phage cocktail (■). The phage cocktail contains the UAB_Phi20. UAB_Phi78 and UAB_Phi87at a proportion of 1:1:1. Uninfected bacterial cultures (□) and the time of phage infection (□) are also shown. All killing kinetics assays are assayed using relation phage/bacteria of 1. In this experiment, the killing kinetics of the phage cocktail, composed by UAB_Phi20 and UAB_Phi87 or the three novels phages, over the time is better than those obtained with individual phages FIG. 5 shows the efficacy of the phage cocktail in reducing *Salmonella* counts in the cecum of the chicks. The cocktail herein used entails the novel phages of the present invention (UAB_Phi20, UAB_Phi78 and UAB_Phi87) at proportion of 1:1:1. In this assay, chicks were infected with *S.* Typhimurium by the seeder bird infection method. The phage cocktail was orally administrated to chicks when the digestive tract of chicks was fully colonized by *Salmonella* (values in the cecum were of $10^8$ cfu/g). The administration schedule of phage cocktail at a dose of $10^{10}$ pfu/animal was twice per day on days $4^{th}$ and $5^{th}$ after *Salmonella* infection. *Salmonella* counts from the cecum of individual phage-untreated chicks (♦) and phage-treated chicks (□) are presented as $\log_{10}$ cfu/g cecum content. Only, a decrease of *Salmonella* count can be observed during the two first days post-treatment. These data indicate that the treatment with phage cocktail have not a significant effect in reducing the concentration of *Salmonella* over the time when the digestive system of animals is fully colonized by this bacterium.

Figure 6:
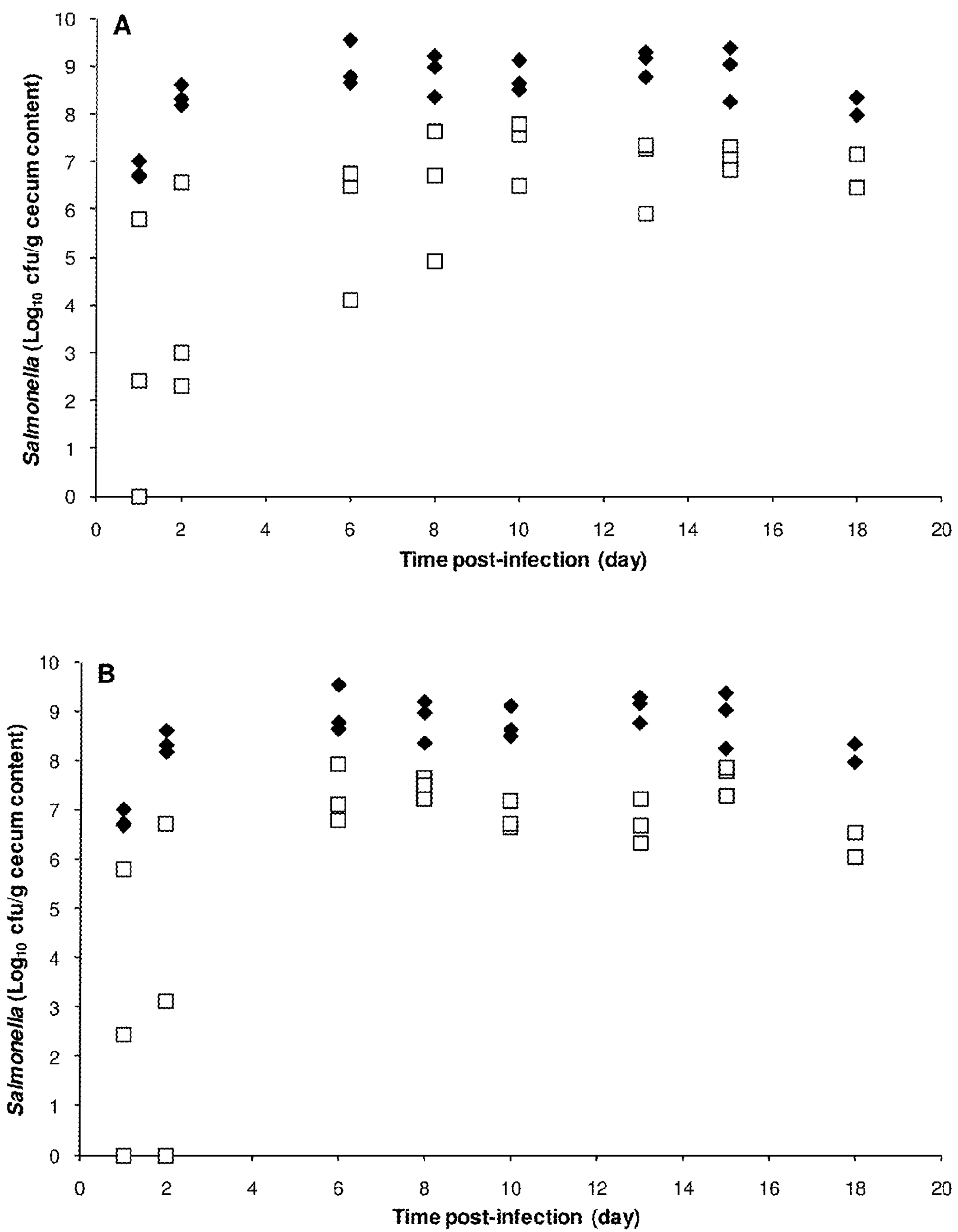

FIG. 6 illustrates the efficacy of the phage cocktail in reducing *Salmonella* counts in the cecum of the chicks. The cocktail herein used entails the novel phages of the present invention (UAB_Phi20, UAB_Phi78 and UAB_Phi87) at proportion of 1:1:1. In these experiments, each chick was orally infected with *S.* Typhimurium at a final dose of $10^5$ cfu/animal. The phage cocktail was administrated one day before (Panel A) and simultaneously (Panel B) to *Salmonella* infection. In both cases, the phage cocktail was further re-administrated twice per day on days 1, 2 and 3 post-infection and once a day on days 6, 8, 10, 13, 15 and 17 post-infection. In each administration, the dose of the phage cocktail applied was $10^{10}$ pfu/animal. *Salmonella* counts from the cecum of individual control chicks (♦) and phage-treated chicks (□) are presented as $\log_{10}$ cfu/g cecum content. A high reduction of the *Salmonella* concentration was seen during the first days post-treatment, indicating a high efficacy of phage cocktail in the first stages of *Salmonella* colonization. Furthermore, a significant reduction of *Salmonella* concentration over the time was observed with the administration schedule assayed.

FIG. 7 shows the different serovars and strains of *S. enterica* used to isolate and to determine the host range of the

*Salmonella* phages, including the novel bacteriophages and the bacteriophages of the phage cocktail herein described. In this table, the year of isolation of these strains and its origin are also included.

FIG. 8 shows the host range of the novel bacteriophages and the bacteriophages of the cocktail of the present invention onto the different serovars and strains that have been used to this purpose. As it can be observed all the serovars assayed are infected by the novel bacteriophages as well as the major part of strains of *S.* Typhimurium and *S.* Enteritidis.

FIG. 9 indicates the percentage of infectivity over the time of the novel bacteriophages (UAB_Phi20. UAB_Phi78 and UAB_Phi87) after exposure to pH values ranging from 2.0 to 9.0, simulating different environmental conditions. The infectivity of the novel bacteriophages herein described is only altered at extremely acidic pH values.

FIG. 10 shows the stability of the three novel bacteriophages at 4° C. in $MgSO_4$ 10 mM over one year period. This stability is measured as the percentage of infectivity of each phage maintained during this period of time at 4° C. These data indicate a high stability of the novel bacteriophages over long time periods.

FIG. 11 shows the stability of each novel bacteriophage in drinking water at room temperature and at 37° C. over one week. Again, stability is measured as the percentage of infectivity of each phage. This data is of interest for applications of phage cocktail in which the preferred carrier of novel bacteriophages was drinking water.

FIG. 12 illustrates the effect of a phage cocktail treatment for 3 and 6 hours at 32-33° C. in decreasing the *Salmonella* concentration in swine skin sections. The cocktail herein used was composed by the UAB_Phi20. UAB_Phi78 and UAB_Phi87 phages at a proportion of 1:1:1. A significant reduction of *Salmonella* concentration over the time was observed, indicating the possibility of application of this novel phage cocktail to decrease the count of *Salmonella* in swine skin.

FIG. 13 illustrates the effect of the treatment with a phage cocktail for 60 min at room temperature of romaine lettuce pieces, experimentally contaminated whit *S.* Typhimurium and *S.* Enteriditis. The cocktail was composed by the UAB_Phi20, UAB_Phi78 and UAB_Phi87 phages at a proportion of 1:1:1. A significant reduction of *Salmonella* concentration over the time was observed, indicating the application of a phage cocktail to decrease the count of *Salmonella* in food or in food manufacturing processes.

FIG. 14 shows the effect of the treatment with the novel phages UAB_Phi20, UAB__78 and UAB_Phi87, alone or as a cocktail, for 60 min at room temperature of romaine lettuce pieces, experimentally contaminated whit *S.* Typhimurium and *S.* Enteritidis. Data obtained show that individual phages as UAB_Phi20 can be used for the *Salmonella* control.

FIG. 15 illustrates the effect of a phage cocktail treatment during very short time periods (approximately 5 minutes) in decreasing the *Salmonella* concentration in chicken breast pieces, conserved during one week at 4° C. after the treatment. The cocktail herein used was composed by the UAB_Phi20, UAB_Phi78 and UAB_Phi87 phages at a proportion of 1:1:1. A significant reduction of *Salmonella* concentration over the time was observed, indicating the application of this novel phage cocktail to decrease the count of *Salmonella* in food or in food manufacturing processes at 4° C.

DETAILED DESCRIPTION OF THE INVENTION

The present invention refers to the novel bacteriophages UAB_Phi20, UAB_Phi78 and UAB_Phi87, deposited in GenBank under accession numbers GQ422450 (corresponding to SEQ ID NO: 1), GU595417 (corresponding to SEQ ID NO:2), belonging to the Podoviridae family and JN225449 (corresponding to SEQ ID NO:3), belonging to the Myoviridae family, respectively. Those bacteriophages are *Salmonella* specific bacteriophages from the Caudovirales order. The novel bacteriophages, when administered to animals, are useful for the biocontrol of different *Salmonella* serovars. The present invention also describes bacteriophage cocktails containing at least one of the bacteriophages and/or parts and/or products of the bacteriophages of the invention. Those cocktail compositions can also contain other lytic bacteriophages and/or parts and/or products of them. In those cocktails, bacteriophages and/or parts and/or products of them can be in similar or different proportion. Those lytic bacteriophages are selected between lytic bacteriophages that specifically infect *Salmonella*, wherein those bacteriophages do not include any known gene or similar gene to those involved in bacterial virulence. The present invention comprises the use of the novel bacteriophages and the novel bacteriophage cocktail compositions to control different *Salmonella* serovars, providing administration schedules and doses and different matrices on/in which *Salmonella* concentration decreases. The invention refers to the use of the novel bacteriophages and the novel safe phage cocktails as an antimicrobial for the biocontrol of populations of *Salmonella* in food animal therapy and livestock in general as well as a sanitization and sterilization composition to be applied on slaughterhouses, animal transportation, food processing industries and foods.

Characterization of the Phages UAB_Phi20, UAB_Phi78, UAB_Phi87

In this invention, *Salmonella* specific bacteriophages were isolated from cloacae or rectal swabs from broilers and pigs. Phages, UAB_Phi20, UAB_Phi78, and UAB_Phi87 were selected in the present study because they were able to infect the 94% of the clonally unrelated strains of *S*. Typhimurium and *S*. Enteritidis (67 of the 71 strains assayed) (FIG. 8, Example 3). In addition, phages selected infect the serovars Hadar, Infantis and Virchow (FIG. 8, Example 3).

Figure 1:
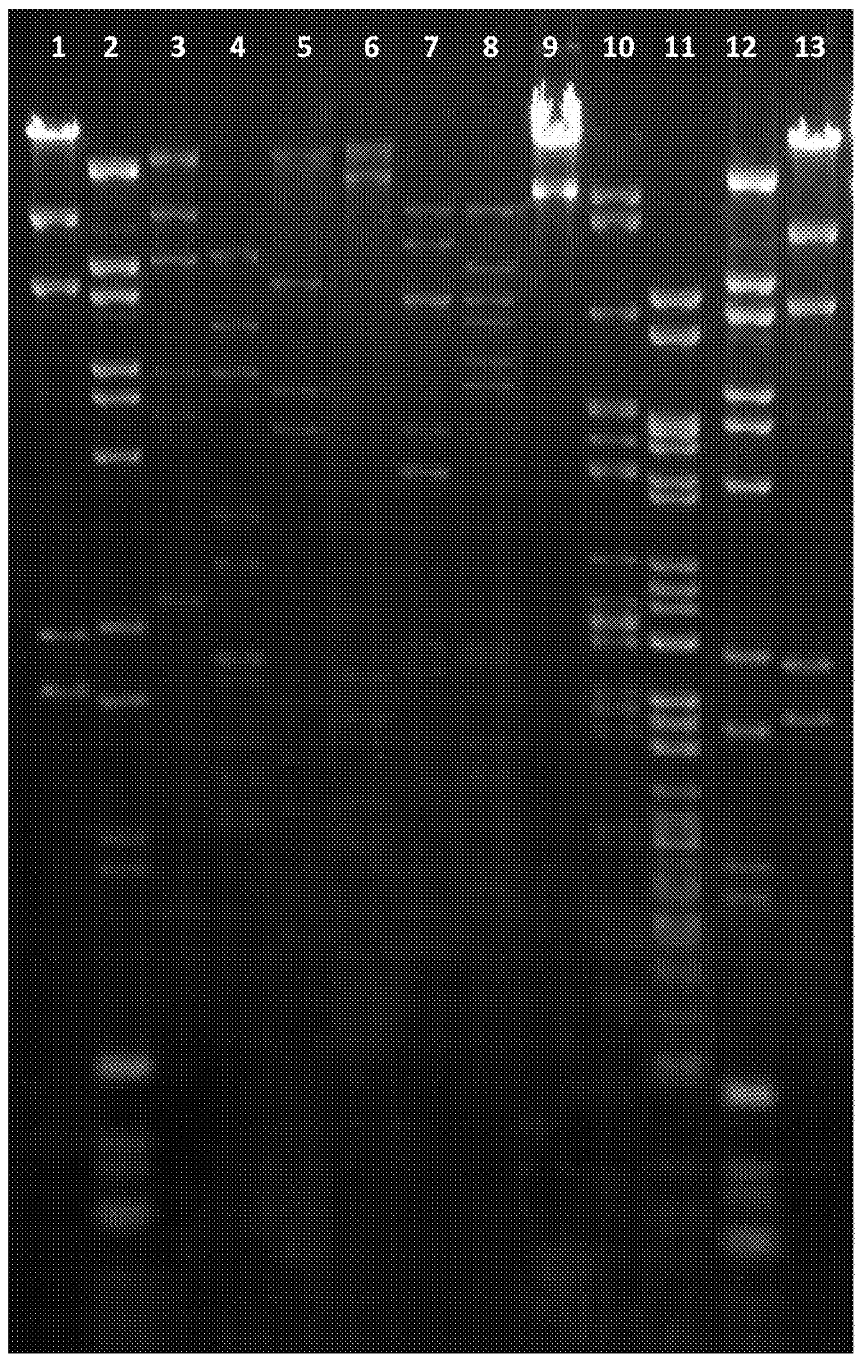
FIG. 1 shows the agarose gel electrophoresis of Eco RI (lanes 3, 6 and 9), EcoRV (lanes 4, 7 and 10) and HindIII (lanes 5, 8 and 11) restriction patterns of DNA of phages UAB_Phi20 (lanes 3 to 5), UAB_Phi 78 (lanes 6 to 8) and UAB_Phi87 (lanes 9 to 11). Lanes 1 and 13 corresponds to HindiI bacteriophage lambda DNA marker and lanes 2 and 12 to BstEII bacteriophage lambda and Xphi714 DNA markers. This figure shows the DNA digestion pattern of each novel bacteriophage of the present invention (UAB_Phi20. UAB_Phi78 and UAB_Phi87) with three different restriction enzymes (EcoRI, EcoRV and HindIII). It can be observed that each phage presents an own DNA restriction pattern.

DNA restriction patterns of the three phages were absolutely different among them (FIG. 1, Example 6).

Electron micrographs of negatively stained phages UAB_Phi20 and UAB_Phi78 revealed icosahedral heads and non-contractile short tails, indicating that phages selected belong to the Podoviridae family of the Caudovirales order. In the same way, the electron micrographs of UAB_Phi87 revealed also icosahedral heads with long, rigid and contractile tail, particular characteristics of the Myoviridae family of the Caudovirales order (FIG. 3, Example 5).

Figure 2:
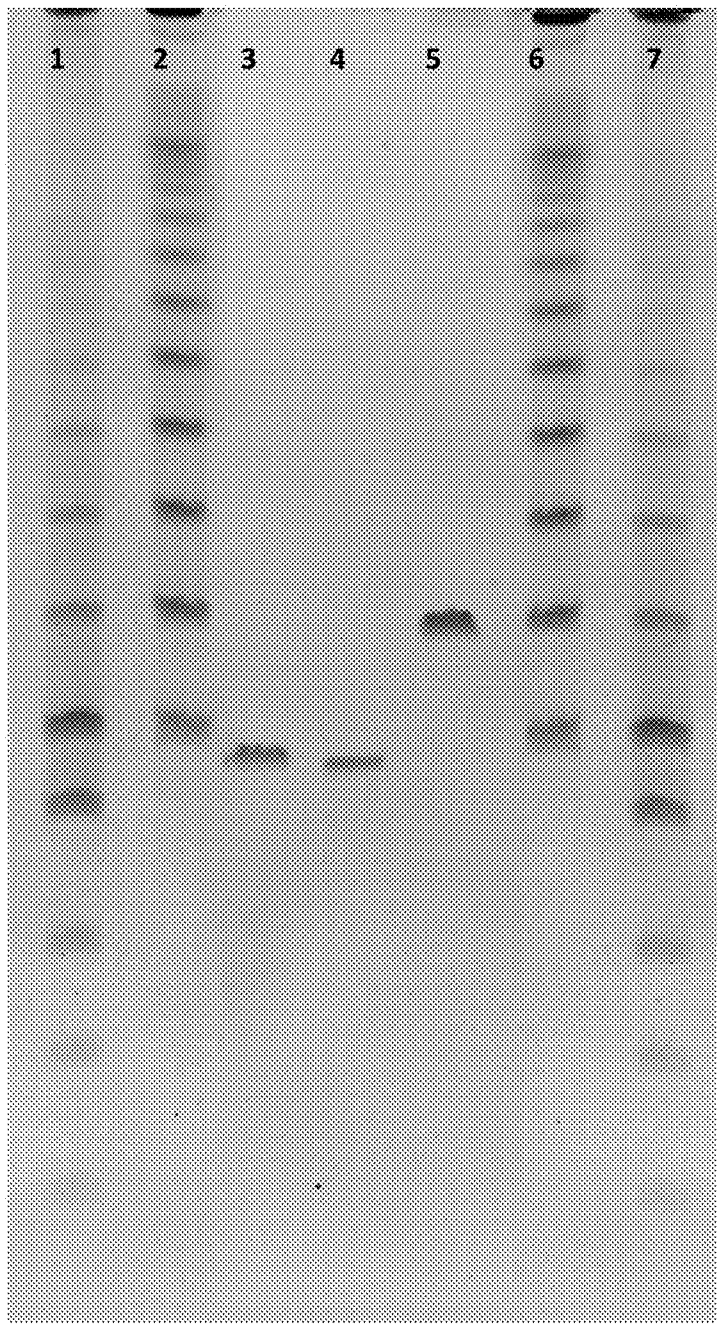
FIG. 2 shows the pulsed-field gel electrophoresis (PFGE) of DNA of phages UAB_Phi20 (lane 3), UAB_Phi78 (lane 4) and UAB_Phi87 (lane 5). Lanes 1 and 7 corresponds to lambda PFGE marker and lanes 2 and 6 to low range PFGE marker. This figure shows the genome size of the three *Sal-*

The genome size of phages UAB_Phi20, UAB_Phi78 and UAB_Phi87 is 44.05, 43.94 kb and 87.60 kb, respectively, based on PFGE of the genomic DNA of the three selected phages (FIG. 2, Example 6) and on DNA sequencing data (Example 6). The complete genome sequences of the three phages were deposited in GenBank under accession numbers GQ422450, GU595417 and JN225449, respectively. DNA sequences analysis indicated that no virulence genes are encoded in the genomes of the three phages selected.

Phage Stability to Different Environmental Conditions

The phages selected were sensitive to extreme acidic pH value (pH=2.0) (FIG. 9, Example 4). However, the fact they maintained a survival rate ranging between 60-80% A during 30 min of treatment at pH 2.0, implies their capacity to resist the pass throw the stomach, where the lowest pH value is reached. This data clearly indicated that phages selected can be orally administrated to animals.

The selected phages can be easily maintained at 4° C., because the percentage of infection was more than 95% over one year at that temperature (FIG. 10, Example 4). In addition, the phages selected are able to maintain their infective ability in drinking water at room temperature and at 37° C. during at least 7 days (FIG. 11, Example 4).

Phage Cocktail Compositions

As previously commented, lytic bacteriophages are the best suitable way to achieve a significant reduction of bacterial populations due its rapid bacterial killing, but it is not easy to find good candidates. In any bacterial population, resistant cells to phage infection can easily arise, thus it is expected to get better results if combination of different phages is employed. Taking this into account, the invention proposes cocktails to the biocontrol of different *Salmonella* serovars. The cocktails of the present invention comprise at least one of the bacteriophages UAB_Phi20, UAB_Phi78 and UAB_Phi87 and/or parts and/or products of them. Those cocktail compositions can also contain other lytic bacteriophages and/or parts and/or products of them. In those cocktails, bacteriophages and/or parts and/or products of them can be in similar or different proportion. These lytic bacteriophages are selected from lytic bacteriophages that specifically infect *Salmonella*, wherein those bacteriophages do not include any known gene or similar gene to those involved in bacterial virulence.

In one embodiment of the present invention, the cocktail comprises phages UAB_Phi20, UAB_Phi78 and UAB_Phi87 in the same proportion. In another embodiment, the cocktail comprises parts of UAB _Phi20, UAB_Phi78 and UAB_Phi87 in the same proportion. In another embodiment, the cocktail comprises products of UAB_Phi20, UAB_Phi78 and UAB_Phi87 in the same proportion. In another embodiment, the cocktail comprises phages UAB_Phi20, UAB_Phi78 and UAB_Phi87 and parts and products of them, all in the same proportion. In another embodiment, the cocktail comprises phages UAB_Phi20, UAB_Phi78 and UAB_Phi87 and parts of them, all in the same proportion. In another embodiment, the cocktail comprises phages UAB_Phi20, UAB_Phi78 and UAB_Phi87 and products of them, all in the same proportion. In another embodiment, the cocktail comprises parts of phages UAB_Phi20, UAB_Phi78 and UAB_Phi87 and products of them, all in the same proportion.

In another embodiment, the proportion of phage and/or parts and/or products of UAB_Phi20 in the cocktail is superior to the proportion of phages and/or parts and/or products of UAB_Phi78 and UAB_Phi87. In another embodiment, the proportion of phage and/or parts and/or products of UAB_Phi78 in the cocktail is superior to the proportion of phages and/or parts and/or products of UAB_Phi20 and UAB_Phi87. In another embodiment, the proportion of phage and/or parts and/or products of UAB_Phi87 in the cocktail is superior to the proportion of phages and/or parts and/or products of UAB_Phi20 and UAB_Phi78.

The invention also refers to cocktails which contain only two of the phages UAB_Phi20 UAB_Phi78 and UAB_Phi87 and/or parts and/or products of them. This way, in one embodiment, the cocktail comprises phage UAB_Phi20 and/or parts and/or products of it and phage UAB_Phi78 and/or parts and/or products of it. In another embodiment the cocktail comprises phage UAB_Phi20 and/or parts and/or products of it and phage UAB_Phi87 and/or parts and/or products of it. In another embodiment, the cocktail comprises phage UAB_Phi78 and/or parts and/or products of it and phage UAB_Phi87 and/or parts and/or products of it.

The invention also refers to cocktail which contain only one of the phages UAB_Phi20 UAB_Phi78 and UAB_Phi87 and/or parts and/or products of them. This way, in one embodiment, the cocktail comprises UAB_Phi20 and/or parts and/or products of it; in another embodiment the cocktail comprises UAB_Phi78 and/or parts and/or products of it; and in a further embodiment the cocktail comprises UAB_Phi87 and/or parts and/or products of it.

As comprised by the invention, any of the previously described cocktails (cocktails that contain the three phages UAB_Phi20, UAB_Phi78 and UAB_Phi87 and/or parts and/or products of them, cocktails that contain only two of the phages UAB_Phi20, UAB_Phi78 and UAB_Phi87 and/or parts and/or products of them, and cocktails that contain only one of the phages UAB_Phi20, UAB_Phi78 and UAB_Phi87 and/or parts and/or products of them) can also contain other lytic bacteriophages and/or parts and/or products of them. In those cocktails, bacteriophages and/or parts and/or products of them can be in similar or different proportion. Those lytic bacteriophages are selected from lytic bacteriophages that specifically infect *Salmonella*, wherein those bacteriophages do not include any known gene or similar gene to those involved in bacterial virulence.

The present invention comprises the use of the novel bacteriophages and the novel bacteriophage cocktail compositions to control different *Salmonella* serovars, providing administration schedules and doses and different matrices on/in which *Salmonella* concentration decrease.

In accordance with one aspect of the present invention, the bacteriophage and bacteriophage compositions may be administered into animals in a pharmaceutical formulation or as a component of the animal feed or in their drinking water.

Further, the compositions of the present invention may be administered in a typical manner via any route such as oral or parenteral routes, in particular, oral, rectal, topical, intravenous, intraperitoneal, intramuscular, intraarterial, transdermal, intranasal, and inhalation routes.

The compositions of the present invention may additionally include a pharmaceutically acceptable carrier and can be formulated together with a carrier to provide foods, medicines and feed additives.

A pharmaceutically acceptable carrier refers to a carrier or diluent that does not cause significant irritation to an organism and does not abrogate the biological activity and properties of the administered compound.

For formulation of the composition into a liquid preparation, a pharmaceutically acceptable carrier which is sterile and biocompatible may be used such as saline, sterile water, Ringer's solution, buffered physiological saline, etc.

Examples of oral dosage forms suitable for the composition of the present invention include tablets, troches, lozenges, aqueous or emulsifier suspensions, powder or granules, emulsions, hard or soft capsules, syrups or elixir.

For non-oral administration, the composition of the present invention may be formulated into injections for subcutaneous, intravenous, or intramuscular routes, or sprays inhaled via the respiratory tract, such as aerosols.

As can be deduced by the results of the present invention, the preferred administration schedule of the present invention for the treatment of animals consists on the continuous treatment of these animals with the novel bacteriophages and the novel bacteriophage cocktails to control different *Salmonella* serovars. This continuous treatment can be achieved by the administration of the novel bacteriophages and/or the novel bacteriophage cocktails by the daily drinking water and or daily feed.

In this way, in accordance with another aspect, the present invention relates to an animal feed and drinking water, comprising the bacteriophages as an active ingredient. The bacteriophage or composition of bacteriophages of the present invention may be separately prepared as a feed additive, and then added to the animal feed, or directly added to the animal feed.

The invention refers to the use of the novel bacteriophages and the novel safe phage cocktails as an antimicrobial for the biocontrol of populations of *Salmonella* in food animal therapy and livestock in general, as well as, a sterilization composition to be applied on a surface of a target in food processing industries and foods.

In this way, in accordance with still another aspect, the present invention relates to a sanitization and a cleaning solution, comprising the bacteriophages or composition of bacteriophages of the present invention as an active ingredient which can be used in solid matrices as surfaces of farms, slaughterhouses, poultry and swine barns and/or pens, crates used during animal transportation from farms to the food processing industries or other facilities employed during the manufacturing process.

In Vitro Killing Assays

To know the killing kinetics of *Salmonella* infected with the phages of the invention in vitro killing assays were performed, using *S.* Enteritidis and *S.* Typhimurium. As previously said, these bacteriophages UAB_Phi20 (accession number GQ422450), UAB_Phi78 (accession number GU595417) and UAB_Phi87 (accession number JN225449) were identified in previous assays carried out in the present invention. They belong to the Caudovirales order, and infect *S.* Typhimurium and *S.* Enteritidis. The genome of all phages does not encode any virulence gene and are stable to different environmental conditions. These characteristics make those bacteriophages useful for the purposes of the invention.

The killing kinetics of *Salmonella* infected with the phages UAB_Phi20, UAB_Phi78 and UAB_Phi87 followed a similar pattern for both serovars studied (FIG. 4, Example 7). As expected, the combined action of a phage cocktail, composed by UAB_Phi20, and UAB_Phi87 (1:1) and UAB_Phi20, UAB_Phi78 and UAB_Phi87 (1:1:1) in decreasing the *Salmonella* concentration was faster and prolonged along the time than the effect of the treatment of bacterial cultures with each one of the individual phages (FIG. 4, Example 7).

Thus, a decrease of the *S.* Typhimurium concentration of 3 log10 cfu/ml was reached after 30 minutes of addition of a phage cocktail composed by the three novel phages. This level of bacterial reduction was maintained during 8 hours, with a maximum of 4.4 log10 cfu/ml (FIG. 4 panel A and Example 7). Both values of reduction for *S.* Enteritidis treated with the phage cocktail were 4 log10 cfu/ml and 6.5 log10 cfu/ml, respectively (FIG. 4 panel B and Example 7). Regarding these killing kinetics the effect of a phage cocktail reported here on *Salmonella* is better than that described by other phage cocktail after 4 hours of phage infection (Toro et al., 2005).

Those results make the phages UAB _Phi20, UAB_Phi78 and UAB_Phi87 appropriated for the purposes of the invention.

In Vivo Killing Assays, Administration Schedules and Preferred Doses

After the in vitro killing assays, in vivo killing assays were made, that is, the effect of a phage cocktail on *S.* Typhimurium concentration in a chicken model (White Leghorn chicken specific pathogen free). In all assays, the phage cocktail was composed by UAB_Phi20, UAB_Phi78 and UAB_Phi87 (1:1:1).

Previously, the residence time of phages in the chick digestive system was determined by oral administration of the phage cocktail at a dose of $10^{10}$ pfu of each phage/animal. The results of the present invention show that the residence time of phages in the intestinal tract ranged from 7 to 9 days, but a significant decrease in the phage concentration was detected from the 4 day of phage administration to animals.

Two types of *S.* Typhimurium infection of chicks were experimented in in vivo killing assays. In one of them, *Salmonella* infection was performed by the seeder bird infection method. Whit this procedure, the *Salmonella* cecum content of chicks was $10^8$ cfu/g, approximately. In the second one, chickens were experimentally infected by oral inoculation with *Salmonella* at a dose of $10^5$ cfu/animal. In both cases, the effect of phages was assessed by measuring the decrease in the *Salmonella* concentration in the cecum of animals. The concentration of each phage in the cocktail was $10^{11}$ pfu/ml and 0.1 ml of that cocktail were orally administrated to animals.

The administration of four doses of phage cocktail to chicken fully colonized by *Salmonella* did not show a significant reduction of the *Salmonella* concentration in the cecum of animals (FIG. 5, Example 8). In contrast, chicks experimentally infected with $10^5$ *Salmonella* cells per animal and treated with the phage cocktail, showed that the best efficacy of phage cocktail was achieved when the administration schedule of phages was one day before (FIG. 6 panel A, Example 8) or just (FIG. 6 panel B, Example 8) to bacterial infection and successively re-administrated different days after the first doses. In these cases, the administration schedule of phages in reducing *S.* Typhimurium was significantly ($p<0.0001$). In both experiments, a reduction of 4 log10 cfu/g on the cecal content was reached during the first days post-treatment and a reduction of 2 log10 cfu/g was achieved at the end of the experiment (FIG. 6, Example 8). With this strategy the present invention achieves better results in *Salmonella* reduction over time than those reported by other authors (Toro et al., 2005; Atterbury et al., 2007; Borie et al., 2008; Filho et al, 2007). This result probably can be generalized to the application of phages to decrease undesired bacterial populations in the intestinal tract of animals As can be deduced by the results of the present invention, the preferred administration schedule of the present invention consist on the continuous treatment of animals with the novel bacteriophages and the novel bacteriophage cocktails to control different *Salmonella* serovars.

Taking all those results into account, the preferred embodiment of the present invention refers to the daily continuous treatment of animals with phages and/or cocktails of the invention. In one embodiment of the present invention, the preferred daily doses per animal may vary between $10^9$ to $10^{12}$, preferably $10^{19}$ pfu/day and animal.

This continuous treatment can be achieved by the administration of the novel bacteriophages and/or the novel bacteriophage cocktails by the dairy drinking water and/or feed.

Application of the Phage Cocktail to Reduce *Salmonella* in Slaughterhouses

As previously said, the invention refers to the use of the novel bacteriophages and the novel safe phage cocktails as an antimicrobial for the biocontrol of populations of *Salmonella* in animal therapy and livestock in general as well as a sanitization composition to be applied in slaughterhouses, animal transportation, food processing industries and foods. This comprises a sanitization and a cleaning solution, comprising the bacteriophages or composition of bacteriophages of the present invention as an active ingredient which can be used in the surfaces of farms, slaughterhouses, poultry and swine barns and/or pens, crates used during animal transportation, contaminated areas and other production facilities.

The pre-slaughter period is considered crucial for the microbial quality of the final products in the food production chain (Lo Fo Wong et al., 2002). In this way, animal skin with absence or minimal bacterial colonisation is essential for a safety food available for human consumers. In this sense, at our knowledge, there is not any report about the application of phages to reduce the *Salmonella* concentration in swine skin.

In this invention, swine skin samples (1500 $cm^2$) acquired in a butchery were experimentally contaminated with either *S.* Typhimurium or *S.* Enteritidis at a concentration of $10^2$ cfu/$cm^2$. Afterwards, skin pieces were sprayed with a solution containing the phage cocktail ($10^{10}$ pfu of each phage/ml), dried and maintained 6 hours at 33° C. This temperature condition simulates the skin temperature of pigs (Huynh et al., 2005) and the ideal lairage time (Warriss et al., 1998). In both cases, *Salmonella* reduction was extremely strong ($p<0.005$). In fact, after 3 h of treatment, direct colony count was not possible in both serovars (FIG. 12, Example 9).

The present invention is the first report showing reduction of *Salmonella* in swine skin mediated by a phage cocktail. For this reason, the results obtained cannot be compared with other studies. Overall, this invention could be used for reducing *Salmonella* on animal skin in the slaughterhouse during the withdrawal time.

Taking these results into account, a preferred embodiment of the present invention refers to spray animal skins with a solution of the novel bacteriophages and/or the novel bacteriophage cocktails in drinking water or in any other carrier for 3 hours at room temperature before slaughter (FIG. 12, Example 9). In one embodiment of the present invention, the preferred bacteriophage concentration may vary between $10^8$ to $10^{12}$ pfu/ml, more preferred $10^{10}$ pfu/ml.

Application of the Phages and Phage Cocktail to Reduce *Salmonella* on Food Processing Industries and Foods A relevant challenge for food production is to assure food safety by coordinated control measures applied in different steps of the food chain (from Farm to Fork). Foods are a source of *Salmonella*, and not only products derived from animals but also vegetables. It is well known the presence and the persistence of *Salmonella* in many vegetables, including lettuce (Wells and Butterfield, 1997; Kakiomenou et al., 1998; Weissinger et al., 2000; Natvig et al., 2002; Islam et al., 2004). In this way, another object of the present invention is the application of the novel phages and/or cocktails of the invention on foods to reduce *Salmonella.*

In this invention, lettuce samples were experimentally infected with either *S.* Typhimurium or *S.* Enteritidis at a concentration comprised between $10^4$ and $10^5$ cfu/g. Afterwards, lettuce samples were submerged into a solution containing the phage cocktail ($10^9$ pfu of each phage/ml). The phage cocktail was composed by UAB_Phi20, UAB_Phi78 and UAB_Phi87 (1:1:1). The highest effect of phage cocktail was found in reducing the *S.* Typhimurium concentration (FIG. 13, Example 10). A 3.4 log10 cfu/g and 1.9 log10 cfu/g reduction was reached in lettuce after 30 min of treatment for *S.* Typhimurium and *S.* Enteritidis, respectively ($p<0.0001$) (FIG. 13, Example 10). Phage UAB_Phi20 was the most effective to reduce *Salmonella*, reaching to similar values as the obtained with the bacteriophage cocktail after 60 min of treatment of lettuces experimentally infected with *S.* Typhimurium and *S.* Enteritidis (FIG. 14, Example 10).

The present invention is the first report showing a significant reduction of *Salmonella* in vegetables mediated by bacteriophages and a phage cocktail.

Furthermore, similar to what occurs with lettuce, the phage cocktail of the present invention produces a reduction of the number *Salmonella* in chicken breast pieces experimentally infected with $10^4$ cfu/g of *Salmonella*. In this case, reductions of 3.9 log10 and 1 log10 cfu/g of *S.* Typhimurium and *S.*

Enteritidis, respectively ($p<0.0001$), were obtained after the conservation in the refrigerator (4° C.) during 7 days of chicken breast pieces, treated for 5 min with the bacteriophage cocktail (FIG. 15, Example 10). Other studies of treatment of chicken meat with phages have been reported. However, their experimental designs were different that those here performed (Goode et al., 2003; Fiorentin et al. 2005b; Higgins et al., 2005; Bigwood et al., 2007). Therefore, a direct comparison among our experiments and those reported would not be adequate.

Taking all those results into account, a preferred embodiment of the present invention refers to the treatment of vegetables with phages and/or cocktails of the invention. In one embodiment of the present invention, the preferred way of treatment is to maintain the food submerged for 30-60 min at room temperature into a solution of the novel bacteriophages and/or the novel bacteriophage cocktails in drinking water or in any other carrier. In one embodiment of the present invention, the preferred bacteriophage concentration may vary between $10^8$ to $10^{12}$ pfu/ml, more preferred $10^9$ pfu/ml.

In another embodiment of the present invention, a preferred way of treatment of food is to submerge them for 5-10 min at 4° C. into a solution of the novel bacteriophages and/or cocktails in saline solution or in drinking water (FIG. 11, Example 4). In one embodiment of the present invention, the preferred bacteriophage concentration may vary between $10^8$ to $10^{12}$ pfu/ml, more preferred 109 pfu/ml.

REFERENCES

Ackermann H. W. 1998. Tailed bacteriophages: the order Caudovirales. Adv. Virus Res. 51:135-201.

Atterbury R. J., Van Bergen M. A. P., OrtizF., Lovell M. A., Harris J. A., Boer A. G. de, Wagenaar J. A., Allen V. M., Barrow P. A. 2007. Bacteriophage therapy to reduce *Salmonella* colonization of broiler chickens. Appl. Environ. Microbiol. 73:4543-4549.

Atterbury R. J., Connerton P. L., Dodd C. E., Rees C. E., Connerton I. F. 2003. Isolation and characterization of *Campylobacter* bacteriophages from retail poultry. Appl. Environ. Microbiol. 69:4511-4518.

Barrow P. A. 2001. The use of bacteriophage for treatment and prevention of bacterial disease in animals and animals models of human infection. J. Chem. Technol. Biotechnol. 76:677-682.

Barrow P. A. and Soothill J. S. 1997. Bacteriophage therapy and prophylaxis: rediscovery and renewed assessment of potential. Trends Microbiol. 5:268-71.

Bäumler A. J., Hargis B. M., Tsolis R. M. 2000. Tracing the origins of *Salmonella* outbreaks. Science 287:50-2.

Berchieri A. Jr., Lovell M. A., Barrow P. A. 1991. The activity in the chicken alimentary tract of bacteriophages lytic for *Salmonella typhimurium*. Res. Microbiol. 142:541-992.

Bernhardt T. G., Wang I. N., Struck D. K., Young R. 2002. Breaking free: “Protein antibiotics” and phage lysis. Res. Microbiol. 153:493-501.

Bigwood Y., Hudson J. A., Billington C. 2008. Phage inactivation of foodborne pathogens on cooked and raw meat. Food Microbiol. 25:400-406.

Borie C., Albala I., Sánchez P., Sanchez M. L., Ramirez S., Navarro C., Morales M. A., Retamales J., Robeson J. 2008. Bacteriophage treatment reduces *Salmonella* colonization of infected chickens. Avian Diseases. 52:64-67.

Callaway T. R., Anderson R. C., Edrington T. S, Genovese K. J., Harvey R. B., Poole T. L., Nisbet D. J. 2004. Recent pre-harvest supplementation strategies to reduce carriage and shedding of zoonotic enteric bacterial pathogens in food animals. Anim. Health Res. 5:35-47.

Connerton P. L., Loc Carrillo C. M., Swift C., Dillon E., Scott A., Rees C. E., Dodd C. E., Frost J., Connerton I. F. 2004. Longitudinal study of *Campylobacter jejuni* bacteriophages and their hosts from broiler chickens. Appl. Environ. Microbiol. 70:3877-83.

Datsenko K. A. and Wanner B. L. 2000. One-step inactivation of chromosomal genes in *Escherichia coli* K-12 using PCR products. Proc. Natl. Acad. Sci. USA 97:6640-5.

EFSA. 2009. The use and mode of action of bacteriophages in food production. Scientific Opinion of the Panel on Biological Hazards (Question No EFSA-Q-2008-400). The EFSA Journal 1076: 1-26.

EFSA. 2010. Analysis of the baseline survey on the prevalence of *Campylobacter* in broiler batches and of *Campylobacter* and *Salmonella* on broiler carcasses in the EU 2008. The EFSA Journal 8(03):1503.

Filho A. R. L., Higgins J. P., Higgins S. E., Gaona G., Wolfenden A. D., Tellez G., Hargis B. M. 2007. Ability of bacteriophages isolated from different sources to reduce *Salmonella* enteric serovar Enteritidis in vitro and in vivo. Poult. Sci. 86:1904-1909.

Fiorentin L., Vieira N. D., Barioni W. Jr. 2005a. Oral treatment with bacteriophages reduces the concentration of *Salmonella* Enteritidis PT4 in caecal contents of broilers. Avian Pathol. 34:258-63.

Fiorentin L., Vieira N. D., Barioni W. Jr. 2005b. Use of lytic bacteriophages to reduce *Salmonella* Enteritidis in experimentally contaminated chicken cuts. Brazilian J. of Poultry Sci. 7:255-260.

Goode D., Allen V. M., Barrow P. A. 2003. Reduction of experimental *Salmonella* and *Campylobacter* contamination of chicken skin by application of lytic bacteriophages. Appl. Environ. Microbiol. 69:5032-5036.

Greer G. G. 2005. Bacteriophage control of foodborne bacteria. J. Food Prot. 68:1102-11.

Hermoso, J. A., Garcia, J. L., Garcia, P. 2007. Taking aim on bacterial pathogens: from phage therapy to enzybiotics. Curr. Op. Microbiol. 10:1-12.

Higgins J. P., Higgins S. E., Guenther K. L., Huff W., Donoghue A. M., Donoghue D. J., Hargis B. M. 2005. Use of a specific bacteriophage treatment to reduce *Salmonella* in poultry products. Poult. Sci. 84:1141-1145.

Hudson J. A., Billington C., Carey-Smith G., Greening G. 2005. Bacteriophages as biocontrol agents in food. J. Food Prot. 68:426-37.

Huynh T. T. T., Aarnink A. J. A., Verstegen M. W. A., Gerrits W. J. J., Heetkamp M. J. W., Kemp B., Canh T. T. 2005. Effects of increasing temperatures on physiological changes in pigs at different relative humidities. J Anim Sci. 83:1385-1396.

Islam M., Morgan J., Doyle M. P., et al. 2004. Persistence of *Salmonella enterica* serovar Typhimurium on lettuce and parsley and in soils on which they were grown in fields treated with contaminated manure composts or irrigation water. Foodborne Pathog. Dis. 1:27-35.

Joerger R. D. 2003. Alternatives to antibiotics: bacteriocins, antimicrobial peptides and bacteriophages. Poult. Sci. 82:640-7.21

Kakiomenou K., Tassou C., Nychas G. J. 1998. Survival of *Salmonella enteritidis* and *Listeria monocytogenes* on salad vegetables. World J. of Microbiol. and Biotechnol. 14:383-387.

Lo Fo Wong D. M. A, Hald T., van der Wolf P. J., Swanenburg M. 2002. Epidemiology and control measures for *Salmonella* in pigs and pork. Livestock Production Sci. 76:215-222.

Matsuzaki S., Rashel M., Uchiyama J., Sakurai S., Ujihara T., Kuroda M., Ikeuchi M., Tani T., Fujieda M., Wakiguchi H., Imai S. 2005. Bacteriophage therapy: a revitalized therapy against bacterial infectious diseases. J. Infect. Chemother. 11:211-9.

Merril C. R., Scholl D., Adhya S. L. 2003. The prospect for bacteriophage therapy in Western medicine. Nat. Rev. Drug Discov. 2:489-97.

Muniesa M., Blanch A. R., Lucena F., Jofre J. 2005. Bacteriophages may bias outcome of bacterial enrichment cultures. Appl. Environ. Microbiol. 71:4269-75.

Natvig E. E., Ingham S. C., Ingham B. H., et al. 2002. *Salmonella enterica* serovar Typhimurium and *Escherichia coli* contamination of root and leaf vegetables grown in soils with incorporated bovine manure. Appl. Environ. Microbiol. 68:2737-2744.

Parisien A., Allain B., Zhang J., Mandeville R., Lan C. Q. 2008. Novel alternatives to antibiotics: bacteriophages, bacterial cell wall hydrolases, and antimicrobial peptides. J. Appl. Microbiol. 104:1-13.

Rabsch W., Hargis B. M., Tsolis R. M., Kingsley R. A., Hinz K. H., Tschape H., Baumler A. J. 2000. Competitive exclusion of *Salmonella enteritidis* by *Salmonella gallinarum* in poultry. Emerg. Infect. Dis. 6:443-8.

Regulation EC No. 1003/2005. Implementing regulation (EC) No. 2160/2003 as regards a Community target for the reduction of the prevalence of certain *Salmonella* serotypes in breeding flocks of *Gallus gallus* and amending Regulation (EC) No. 2160/2003. 30 Jun. 2005.

Sulakvelidze A., Alavidze Z., Morris J. G. Jr. 2001. Bacteriophage Therapy. Antimicrob. Agents Chemother. 45:649-659.

Summers W. C. 2001. Bacteriophage therapy. Annu. Rev. Microbiol. 55:437-451.

Toro H., Price S. B., McKee A. S., Hoerr F. J., Krehling J., Perdue M., Bauermeister L. 2005. Use of bacteriophages in combination with competitive exclusion to reduce *Salmonella* from infected chickens. Avian Dis. 49:118-24.

Warris P. D., Brown S. N., Edwards J. E., Knowles T. G. 1998. Effect of lairage time on levels of stress and meat quality in pigs. Anim. Sci. 66:255-261.

Weissinger W. R., Chantarapanont W., Beuchat L. R. 2000. Survival and growth of *Salmonella baildon* in shredded lettuce and diced tomatoes, and effectiveness of chlorinated water as a sanitizer. Int. J. Food Microbiol. 62:123-131.

Wells J. M., Butterfield J. E. 1997. *Salmonella* contamination associated with bacterial soft rot of fresh fruits and vegetables in the marketplace. Plant Disease. 81:867-872.

EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

Statistical Analysis

Non parametric statistics (Mann-Whitney-Wilcoxon test) was used to determine the significance of phage cocktail administration in the different chicken trials. Parametric statistics (Generalized linear model) was used to determine the significance of phage and phage cocktail treatments of food. The significance level was fixed at 5%.

Example 1

Bacterial Strains and Growth Conditions

Clonally unrelated strains of *Salmonella enterica* serovar Typhimurium and *Salmonella enterica* serovar Enteritidis, respectively, were used to isolate *Salmonella*'s phages and to determine the host range assays of the isolated phages (FIG. 7). These bacterial strains were obtained from the Laboratori de Sanitat Animal (DARP, Generalitat de Catalunya, Spain) and from the Hospital Vall d'Hebrón and the Hospital de Sant Pau (Barcelona, Spain). They were selected to present different pulsotypes as determined by Pulse Field Gel Electrophoresis method.

The virulent strains *S.* Typhimurium ATCC14028 (American Type Culture Collection) and *S.* Enteritidis LK5 (*Salmonella* Genetic Stock Centre, University of Calgary) were also used for the isolation of *Salmonella*'s phages. In addition and using the red recombinase system (Datsenko and Wanner, 2000), the ATCC14028 and LK5 virulent strains were respectively marked with a chloramphenicol and kanamycin resistance cassette in an intergenic sequence, generating ATCC14028 ΩCm and LK5 ΩKm strains. These strains were employed for efficacy studies of the selected bacteriophages.

Moreover, the strains 05S72, 10152 and 8546 of *S.* Hadar, the strains 05S44 and 1056 of *S.* Infantis and the strains 791/S and 9781 of *S.* Virchow, were used for the host range studies of the bacteriophages isolated (FIGS. 7 and 8).

All bacterial strains were routinely grown on Luria Bertrani (LB) broth or agar plates, and, when necessary, chloramphenicol (34 μg/ml) and kanamycin (150 μg/ml) were added. Growth was performed at 37° C. for both broth and plate cultures during 18 h.

Example 2

Isolation and Propagation of Bacteriophages

Samples (n=161) of cloacae or rectal swabs from broilers and from pigs, respectively, were taken from farms of different geographical areas of Spain from 2007 to 2009.

Bacteriophages were isolated as described (Connerton et al., 2004; Muniesa et al., 2005) or by an enrichment procedure. Briefly, 1 g of the sample was diluted in 10 ml of SM buffer (50 mM Tris-HCl [pH 7.5], 0.1 M NaCl, 8 mM $MgSO_4 \cdot 7H_2O$, 0.01% gelatin) and incubated at 4° C. for 24 h. Then each suspension was subjected to centrifugation at 7000×g for 10 min. For the enrichment procedure 1 g of the sample was diluted in 10 ml of peptone water and incubated at 37° C. for 18 h. After then, 1 ml of the enrichment culture was inoculated in 10 ml of Müller-Kauffmann selective broth and incubated at 37° C. for 24h. Following, each culture was subjected to centrifugation at 7000×g for 10 min.

The supernatants obtained from both methods were filtered through a 0.45 μm syringe filter. Then 10 μl of each filtrate was spotted onto the surfaces of *Salmonella* lawns by the double agar layered method. After incubation at 37° C., phage plaques were visualized and each different plaque was pushed and resuspended in 1 ml of sterile $MgSO_4$ 10 mM. Afterwards, 5 dilutions (1:10) were made and plated using the double agar layered using the same *Salmonella* tester strain. This procedure was repeated at least three subsequent times to purify the bacteriophages.

Bacteriohage lysates were obtained by infecting different *Salmonella* strains during 5 h at 37° C., grown in LB broth. After centrifugation of cultures at 7000×rpm for 10 min, the supernatant was filtered through a 0.45 μm syringe filter and the phage titter was determined by plating serial dilutions onto LB plates using the double agar layered method. When necessary, bacteriophages were purified by ultracentrifugation at 51.000×g for 2 h.

Example 3

Selection of Bacteriophages

The host range of each bacteriophage lysate was determined by spotting 10 μl of the lysate ($10^8$ pfu/ml) onto lawns of 76 strains of *Salmonella*. Plates were incubated at 37° C. for 24 h and bacterial lysis was recorded. Bacteriophages selected infect to the serovars Hadar, Infantis and Virchow and a wide range of strains belonging to the serovars Typhimurium and Enteritidis (FIG. 8).

In addition, DNA restriction profiles of the phage selected were also determined. To achieve this, a purified phage suspension was treated with DNase I (20 μg/ml) and RNase I (25 μg/ml) at 37° C. for 1 h. Hereafter, proteinase K (0.2 mg/ml) and sodium dodecyl sulfate (0.5%) were added and incubated for 1 h at 56° C. Following incubation, the DNA was purified by conventional phenol-chloroform-isoamyl alcohol extraction. The genomic DNA was precipitated in 2 volumes of ethanol with 3 M sodium acetate, pH 4.8. The pellet obtained was washed with 70% ethanol, dried, and resuspended in 100 μl MQ grade water. Phage DNA was digested with restriction endonucleases EcoRI, EcoRV and HindIII (Roche) according to the supplier's recommendations. DNA fragments were subjected to electrophoresis on agarose gel (0.7% and containing ethidium bromide) in Tris-acetate-EDTA (TAE) buffer at constant voltage of 80 V and visualized by UV light. DNA standard fragments of HindIII and BstEII bacteriophage lambda were used as markers to calculate the size of DNA fragments.

Phages UAB_Phi20, UAB_Phi87, isolated from cloacae broiler swabs, and UAB_Phi78 from pigs were selected for further characterization regarding their host range and their DNA digestion pattern (FIG. 1).

Example 4

Phage Stability to Different Environmental Conditions

The effect of pH on infectivity of phages UAB_Phi20, UAB_Phi78 and UAB_Phi87 of the present invention was determined at 25° C. in $MgSO_4$ 10 mM at pH ranging from 2.0 to 9.0. Phage samples were taken each 30 min for 2 h and were immediately serially diluted and plated using the double agar layered method. Plates were incubated at 37° C. for 24 h and phage plaques counted.

Phage stability in $MgSO_4$ 10 mM was recorded during one year at 4° C. In addition, phage stability in drinking water was also recorded during one weak at room temperature and at 37° C. Lysates titration was performed as previously described.

The effect of pH, ranging from 2.0 to 9.0 on the infectivity of the three phages was determined (FIG. 9). All three phages maintained a percentage of infectivity greater than 90% for 120 min at pH values of 4.0, 6.0 and 9.0, except UAB_Phi87 and UAB_Phi78 phages which have a percentage of infectivity of 85.2% and 87.8%, respectively, at pH 4 to 120 min. In contrast, the stability of all the three phages dramatically decreased at pH 2.0. The most sensitive to acidity was UAB_Phi87, while UAB_Phi20 was the most stable phage.

The stability of the three phages maintained during one year at 4° C. was also determined. The percentage of infection was more than 95% over the period studied (FIG. 10). Only, UAB_Phi78 showed a slightly reduction regarding the other phages. Likewise, all the three phages presented a very good stability in drinking water during 7 days (FIG. 11). No alteration of the infectivity was appreciated over this period of time at room temperature. However, slightly reductions were observed on the infectivity of the three novel bacteriophages herein described at 37° C. Nevertheless, the infectivity of them was greater than 90% after one week under this condition.

Those results demonstrated that phages UAB_Phi20, UAB_Phi78 and UAB_Phi87 of the invention can be easily maintained in some carrier as $MgSO_4$ 10 mM during a long period of time at 4° C. Furthermore, these carriers and drinking water can be used as vehicle for administration purpose of the invention. The high stability of phages to low pH values demonstrated that phages of the invention UAB_Phi20, UAB_Phi78 and UAB_Phi87, can be orally administrated and then used for the purpose of the invention.

Example 5

Electron Microscopy

Purified phages ($10^9$-$10^{10}$ pfu/ml) were applied to electron carbon coated grids and negative stained with 2% uranyl acetate. After drying, preparations were examined with a JEOL 1400 transmission electron microscope at different magnitudes. Phage morphology and dimensions were recorded.

UAB_Phi20 and UAB_Phi78 phages morphologically belong to the Podoviridae family of the Caudovirales order, while UAB_Phi87 belong to the Myoviridae family of the same order (Ackermann, 1998). Thus, electron micrographs of negatively stained phage UAB_Phi20, UAB_Phi78 revealed icosahedral heads and non-contractile short tails while the electron micrograph of UAB_Phi87 revealed also icosahedral head but a long, rigid contractile tail (FIG. 3). The head dimensions of UAB_Phi20,UAB_Phi78 and UAB_Phi87 were 60±1.5 nm, 66±1.7 nm and 68±2.7 nm, respectively and tail length was of 13±0.7 nm, 14±0.7 nm and 114±4.3 nm, respectively.

Example 6

Genome Characterization

Phage genome size determination using pulsed-field gel electrophoresis (PFGE) was performed as previously described (Atterbury et al., 2003). Gels were run using a Bio-Rad CHEF DRIII system in 0.5 TBE (Tris-borate 50 mM, EDTA 0.1 mM) for 15 h at 6V/cm with switch time of 2 to 20s during 10 h and 20 to 30 s during 5 h. Gels were stained with ethidium bromide and visualized using the GelDoc System (BioRad). Genome size was determined with Fingerprinting II program (BioRad).

DNA sequencing was done by Sistemas GenOmicos (Spain) using a shotgun strategy. Open reading frames (ORFs) were searched using the NCBI ORF Finder program (http://www.ncbi.nlm.nih.gov/gorf/gorf.html).

Potential ORFs were compared against the NCBI protein databases using the BLASTP nonredundant database (http://blast.ncbi.nlm.nih.gov/Blast.cgi).

Based on PFGE of the genomic DNA of the selected phages (FIG. 2) and on DNA sequencing data, the genome size of phages UAB_Phi20, UAB_Phi78 and UAB_Phi87 was 44.05, 43.94 kb and XX.XX kb, respectively. The complete genome sequences of the phages were deposited in GenBank under accession number GQ422450, GU595417 and JN225449 respectively. The study of DNA sequence of selected phages showed that UAB_Phi20 has a significantly homology to P22-like phages, UAB_Phi78 was similar to SP6-like phages and UAB_Phi87 has a significant homology to Felix01-like phages. These data are in agreement with those obtained by electron microscopy regarding morphological characterization (Example 5). The analysis of DNA sequences indicated that no virulence genes are encoded in the genomes of the phage selected.

Example 7

In Vitro Killing Assays

*S.* Typhimurium ATCC14028 and *S.* Enteritidis LK5 cultures ($OD_{550}$=0.2) were infected with the bacteriophages selected for the phage cocktail compositions at a multiplicity of infection (relation between the number of infective phages per bacterial viable cell) of 1 pfu/cfu. Cultures were incubated with shaking at 37° C. and both the absorbance of cultures and bacterial enumeration by platting of serial dilutions were monitored.

The viable concentration of *S.* Typhimurium was reduced 4.4, 3.4, 5.3, 4.3 and 4.4 log10 cfu/ml after infection with each individual phage (UAB_Phi20, UAB_Phi78 and UAB_Phi87), a combination of UAB_Phi20 and UAB_Phi87 (1:1) and with the phage cocktail (UAB_Phi20 and UAB_Phi78 and UAB_Phi87 (1:1:1), respectively (FIG. 4 panel A). In addition, a reduction of 3 log10 cfu/ml was observed after eight hours of treatment with the phage cocktail, which has a proportion 1:1:1 of the three phage selected. A greater effect of phages was seen on *S.* Enteritidis (FIG. 4 panel B). Thus, the viable concentration of *S.* Enteritidis suffered a reduction of 5.6, 4, 5.4, 5.9 and 6.5 log10 cfu/ml after treatment with UAB_Phi20, UAB_Phi78, UAB_Phi87, a combination of UAB_Phi20 and UAB_Phi87 (1:1) and the phage cocktail, respectively. In this case, a reduction of 4 log10 cfu/ml was obtained after 8 hours of the infection with the phage cocktail, which has a proportion 1:1:1 of the three phages selected.

The combined infective activity of the three phages into the cocktail achieves a great reduction of *Salmonella* over the time. This reduction is much better than that achieved by other phage cocktail tested only for 4 hours of phage infection (Toro et al., 2005). The fact that individual phages of the invention were not so efficient to maintain low concentrations of *Salmonella* over the time justify the use of two or three phages in a bacteriophage cocktail for the purpose of the invention.

Example 8

Experiments in Animal Models

White Leghorn chicken specific pathogen free (SPF) were used to assay the efficacy of the phage cocktail compositions in decreasing the *S.* Typhimurium ATCC14028 ΩCm concentration in in vivo experiments. In this model, animals are a reservoir of non typhoidal *Salmonella*. It is expected that animal treatment with phage cocktail diminished the *Salmonella* concentration in the digestive system of chicks.

White Leghorn chicken specific pathogen free (SPF) fertile eggs from Valo Lohmann Tierzucht (Salamanca, Spain) were used for these studies. Fertile eggs were incubated and hatched in level-3 biocontention facilities for animals (BSL3) of CReSA (Cerdanyola del Valles, Spain). Chicks of all trials were housed in air-filtered isolator cabinets. Feed and water were supplied ad libitum. In all trials, two chicks were euthanized before the experiments to check that they remained free of natural infection of *Salmonella*.

Previously to assay the effect of phage cocktail composition on *Salmonella* in chicks, the residence time of phages in the chick digestive system was determined. To achieve this, chickens were treated with the phage cocktail at a dose of $10^{10}$ pfu of each phage/animal. This cocktail was composed by UAB_Phi20, UAB_Phi78 and UAB_Phi87 (1:1:1) at a concentration of $10^{11}$ pfu of each phage/ml in $MgSO_4$ 10 mM and 0.1 ml was orally administrated. Afterwards, the phages were recovered from cecum by the enrichment procedure (Example 2) till the eight day after phage cocktail administration, but a significant decrease in the phage concentration was detected at the 4 day of phage administration to animals.

In attention to the results above commented, two experiments were addressed to determine the efficacy of the phage cocktail in decreasing the *Salmonella* concentration in chicks in which the phage cocktail was administrated to animals at a dose of $10^{10}$ pfu/animal. This cocktail was composed by UAB_Phi20, UAB_Phi78 and UAB_Phi87 (1:1:1) at a concentration of $10^{11}$ pfu of each phage/ml in $MgSO_4$ 10 mM and 0.1 ml was orally administrated.

In the first experiment, chicks were colonised with high concentrations of *Salmonella* ($10^8$ cfu/g of cecum contents) and only four doses of the phage cocktail were administrated. To do this, seeder infection of chicks with *Salmonella*, which simulates natural conditions of infection with this bacterium, was performed by using the methodology described by Fiorentin et al. (2005a). Two groups of thirty one-day chicks each one were housed on separated isolators. Both groups were infected with *Salmonella*, but only one of them was treated with the bacteriophage cocktail (treatment group). Previously to phage administration, both groups were infected with *S.* Typhimurium. To achieve this, three animals of each group (control and treatment groups) were orally inoculated with this bacterium at a dose of $10^8$ cfu/animal while the remaining chicks were infected by contact. It has been previously demonstrated that all chicks have been infected with *Salmonella* by contact after three days of the oral infection of the first three animals. Afterwards, two doses per day of the phage cocktail ($10^{10}$ pfu/animal) at 4 and 5 days after *Salmonella* infection were administrated to the animals of the treatment group. Three chicks of each group were euthanized and necropsied at days 0, 1, 2, 8, 15 and 22 post-treatment. Samples of spleen, liver, ileum and cecum were collected. Likewise, cloacal swabs of all remaining birds were also taken at the same days. Samples were subjected to *Salmonella* detection and phage enumeration. In all cases, samples from tissues were weighed, homogenized and serially diluted in sodium chloride 0.9%. *Salmonella* enumeration was determined by standard plating onto XLD plates supplemented with chloramphenicol and incubated at 37° C. during 24 h. At the same time, an enrichment procedure was also performed. To do this, tissue homogenates and cloacal swabs were incubated overnight on peptone water at 37° C. during 24 h. Following, 0.2 ml of these cultures were diluted onto 2 ml of Müller-Kauffmann selective broth and incubated at 37° C. for 24 h. Then, 0.1 ml were plated onto XLD conveniently supplemented plates and incubated at 37° C. for 24h for qualitative bacteriology. The administration schedule of the phage cocktail assayed in this trial produced a reduction of llog10 with respect to the control group during the first two days post-treatment (p=0.055) (FIG. 5).

In the second experiment, chicks orally infected with *Salmonella* one day after to the administration of phage cocktail and nearly simultaneously to treatment with phages. To perform this, three groups of 23 three-day chicks each one were housed on separated isolators and orally infected with *Salmonella* at a concentration of $10^5$ cfu/animal. One group was the control, the second one was treated with the phage cocktail one day before the *Salmonella* infection and the third one received the treatment of the phage cocktail simultaneously to bacterial infection. In addition, in the two last groups the phage cocktail was also administered twice a day on days 1, 2 and 3 post-infection and once a day on days 6, 8, 10, 13, 15 and 17 post-infection. Three chicks of each group were euthanized and necropsied on days 1, 2, 6, 8, 10, 13, 15 and 18 after bacterial inoculation. Sampling and culture methods were performed as described before. Similar results were obtained in both cases. Thus, a decrease of approximately 4 log10 was reached till the third day post-treatment and a decrease of 2 log10 was obtained from day 7 (FIG. 6 panel A) or 11 (FIG. 6 panel B) to the end of the experiment (p<0.0001). These *Salmonella* reduction values over time are better to those reported by other authors (Toro et al., 2005; Atterbury et al., 2007; Bode et al., 2008; Filho et al., 2007).

Results obtained clearly indicated that the oral treatment of animals with phages or phage cocktails was able to reduce significantly the level of *Salmonella* in the intestinal system of chicks before animals were colonized by this bacterium or when bacterial colonization would be in an initial phase. Furthermore, the administration schedule of phages or phage cocktails with this purpose must be almost daily, because the residence time of phages at the desired concentrations in the intestinal tract of animals is very short.

Example 9

Application of Phage Cocktail to Reduce *Salmonella* from Animal Skin

In order to simulate a practical way to apply the phage cocktail in animals before slaughter and thus reduce or extinguish the possible contamination on final product, experiments to assess the efficacy of phage cocktail to reduce the concentration of *Salmonella* in animal skin was designed. The phage cocktail assayed was composed by UAB_Phi20, UAB_Phi78 and UAB_Phi87 (1:1:1). Skin assayed was swine skin pieces (rear flank) purchased from a local butchery.

Skin pieces were experimentally contaminated with *S.* Typhimurium ATCC14028ΩCm and *S.* Enteritidis LK5 ΩKm. An inoculum of $10^6$ cfu/ml in 0.9% NaCl was distributed uniformly on each skin piece of approximately 1,500 $cm^2$ (2 μl/$cm^2$). After, skins were dried for 30 min in a laminar flow cabinet. By means of this treatment, we had previously determined that the final concentration of *Salmonella* was $10^2$ cfu/$cm^2$. After *Salmonella* contamination, the surface was divided in two equal sections. One of them was treated with phage cocktail and the other was the control. The treatment consisted of spraying the entire surface with a solution of phage cocktail with $10^{10}$ pfu of each phage/ml. The control was also sprayed with a solution of $MgSO_4$ 10 mM without bacteriophages. Following, pieces were dried during 30 minutes in a laminar flow cabinet. Afterwards, pieces were incubated at 33° C. and samples were taken by swabbing 6 areas of 25 $cm^2$ at different times. The swab (Copan Italia, Brescia) was placed in a tube with 2 ml of buffered peptone water (Merck, Germany). Following, 1 ml was diluted and plated by duplicate on XLD plates, adequately supplemented with chloramphenicol or kanamycin, and incubated at 37° C. for 24 h. At least, a 4 log10 cfu/$cm^2$ and 2.0 log10 cfu/$cm^2$ reduction of *S.* Typhimurium and *S.* Enteritidis, respectively, was reached after treatment with the phage cocktail (FIG. 12). In both cases, the reduction of *Salmonella* colonization was significant (p<0.005).

Results obtained show that the phage cocktail of this invention is able to reduce the concentration of *Salmonella* in skin surface when they are applied simulating the conditions of pigs in a holding pen in the processing industries.

Example 10

Application of the Phage Cocktail to Food and Food Manufacturing Process to Reduce the *Salmonella* Populations Experiments to assess the efficacy of phages and phage cocktails to reduce the concentration of *Salmonella* in foods and in food manufacturing processes were designed. The phage cocktail assayed was composed by UAB_Phi20, UAB_Phi78 and UAB_Phi87 (1:1:1). Foods assayed were pieces of packed romaine lettuce (Laetuca sativa) (ready to eat) and chicken breasts purchased from a supermarket.

Romaine lettuce samples were experimentally infected with *S.* Typhimurium ATCC14028ΩCm and *S.* Enteritidis LK5 ΩKm by submerging the pieces of lettuce in suspensions of those bacteria at a concentration of $10^7$ cfu/ml in 0.9% NaCl on a ratio of 1:10 (w/v) for 5 minutes and after air dried for 15 min in a laminar flow cabinet. By means of this treatment we had previously determined that the final concentration of *Salmonella* was $10^4$-$10^5$ cfu/g of romaine lettuce. After *Salmonella* contamination, 25 g of lettuce were placed in a Whirl-Pak bag (Nasco, Fort Atkinson, Wis.) containing 100 ml of a phage cocktail ($10^9$ pfu of each phage/ml suspension) in sterile distilled water. Treatment of pieces of lettuce with phages was performed at 25° C. during different times and shaking in a vertical shaker at 150 rpm. After phage treatment, for *Salmonella* enumeration, the suspension was discarded and 100 ml of buffered peptone water (Merck, Germany) was added to each bag and samples stomached at 150 beats for 1 min. Following, 1 ml was serially diluted and plated by duplicate on XLD plates, adequately supplemented with chloramphenicol or kanamycin, and incubated at 37° C. for 24 h. Sterile distilled water instead of phage cocktail was used as negative control in all the assays. In addition, a control without *Salmonella* contamination and phage treatment was also performed in parallel. A 3.9 log10 cfu/g and 2.2 log10 cfu/g reduction of *S.* Typhimurium and *S.* Enteritidis, respectively, was reached after treatment of lettuce pieces with the phage cocktail for 60 min (FIG. 13).

The same methodology was assayed but treating lettuce pieces with the individual phages UAB_Phi20, UAB_Phi78 and UAB_Phi87 at a concentration of $10^9$ pfu/ml.

These experiments showed that UAB_Phi20 was the most effective phage to reduce *Salmonella* (FIG. 14). Thus, the concentration of *Salmonella* in lettuce pieces treated with this phage was very close to those of lettuce pieces treated with the bacteriophage cocktail (FIG. 14).

Chicken breasts were cut and experimentally infected with *S.* Typhimurium and *S.* Enteritidis by submerging the pieces into suspensions of those bacteria at a concentration of $10^6$ cfu/ml in 0.9% NaCl on a ratio of 1:10 (w/v) for 5 minutes at room temperature and after the suspension was discarded. By means of this treatment we had previously determined that the final concentration of *Salmonella* was about $10^4$ cfu/g of chicken breast pieces. After *Salmonella* contamination, 25 g of chicken breast pieces were placed in a Whirl-Pak bag (Nasco, Fort Atkinson, Wis.) containing 100 ml of a phage cocktail ($10^9$ pfu of each phage/ml suspension) in saline solution 0.9% on a ratio of 1:10 (w/v) for 5 minutes and after the suspension was discarded. Following the phage treatment, the chicken breast pieces were maintained in the refrigerator at 4° C. during one week. Samples were daily taken and *Salmonella* concentration was determined as above described. A 3.9 log10 cfu/g and 0.9 log10 cfu/g reduction of *S.* Typhimurium and *S.* Enteritidis, respectively, was reached at the 7 day of conservation of the chicken breast pieces at 4° C. after phage cocktail treatment (FIG. 15).

Results obtained show that the phages of this invention and a phage cocktail are able to reduce the concentration of *Salmonella* in foods when they are applied in a suspension at room temperature during 30-60 min. Phages are also effective in reducing *Salmonella* in foods conserved at 4° C. during 7 days, after a very short treatment with phages before food refrigeration. In both cases, the reduction of *Salmonella* colonization was significantly ($p<0.0001$). These results indicate that phages and phage cocktail can be used for reducing *Salmonella* in foods and in food manufacturing processes.

Whereas, particular embodiments of the invention have been described herein for purposes of description, it will be appreciated by those skilled in the art that numerous variations of the details may be made without departing from the invention as described in the appended claims.

The invention claimed is:

1. A bacteriophage-composition for treating and/or controlling infectious diseases caused by *Salmonella* comprising at least two of the *Salmonella* lytic bacteriophages UAB_Phi20, UABPhi78 and UAB_Phi87 and/or parts or products thereof having lytic activity against *Salmonella*.

2. The bacteriophage-composition according to claim 1, comprising the following three phages: UAB_Phi20, UAB_Phi78 and UAB_Phi87.

3. The composition according to claim 1 which further comprises other *Salmonella* lytic bacteriophages or parts thereof having lytic activity against *Salmonella*.

4. The composition according to claim 3 wherein the *Salmonella* lytic bacteriophages or parts thereof are selected from the Caudovirales order.

5. The composition according to claim 1 wherein when one or more of the bacteriophages and/or parts or products thereof having lytic activity against *Salmonella* are present, they are in the same proportion.

6. The composition according to claim 1 wherein when one or more of the bacteriophages and/or parts or products thereof having lytic activity against *Salmonella* are present, they are in a different proportion.

7. The composition according to claim 1 which additionally includes a pharmaceutically acceptable carrier, solvent or pharmaceutically acceptable excipient.

8. The composition according to claim 1 in the form of a suspension, spray, aerosol, injectable and/or orally administrable dosage form.

9. The composition according to claim 1 in the form of an animal feed, drinking water, sanitizer or cleaning solution.

10. A method of controlling *Salmonella* populations in a solid matrix selected from the group consisting of poultry barns, swine barns, swine pens, poultry pens, crates for animal transportation, slaughterhouses, and production facilities in food processing industries comprising applying a composition comprising at least two of the *Salmonella* lytic bacteriophages UAB_Phi20, UAB_Phi78 and UAB_Phi87 and/or parts or products thereof having lytic activity against *Salmonella* to the solid matrix.

11. The method of claim 10 wherein food processing industries are selected from the group consisting of vegetables, meat and eggs industries.

12. A method of treating or controlling *Salmonella* infection in animals comprising treating with or applying into or onto an animal a bacteriophage- composition according to claim 1.

13. The method of claim 12 wherein the treatment consists of a daily continuous treatment characterized in that the daily dosage regime per animal per day is selected from the range comprising from $10^9$ to $10^{12}$ pfu/day per animal.

* * * * *

SEQUENCE LISTING

```
<160> NUMBER OF SEQ ID NOS: 3

<210> SEQ ID NO 1
<211> LENGTH: 44047
<212> TYPE: DNA
<213> ORGANISM: Artificial Sequence
<220> FEATURE:
<223> OTHER INFORMATION: Synthetic DNA for Salmonella Bacteriophage
      UAB_Phi20

<400> SEQUENCE: 1

ccgcataagc aaatgttgcg agcacttgca gtacctttgc cttagtattt ccttcaagct     60

ttgccacacc agggtatttc cccgatacct tgtgtgcaaa ttgcatcaga tagttgatag    120

ccttttgttt gtcgttctgg ctgagttcgt gcttaccgca gaatgcagcc attccgaatc    180

cggcttgtga ttgcgccatt cccatagcag ccatcacatc agtaccggaa agagagtcag    240

aagccgtagc ccgtggtgag tcactcatca tcgggctttt tggcgaatgg aatttagcta    300

cgctttcgag tctcatgcag catcgtctcc cgctggcttg ttcaatccaa tccggttcac    360

cagttcacgc tctcgctcat gcagataatc catcgccttc tggtgttgct ccgtcatctc    420

tctgacgctg cgtaattcag cctcgtcacg ttcacgctga tgttttgcct ggttaatgct    480

ggttacggtc ataaatacct ctcccgccct gatgaatcat taaaacgccg ttaacgatgg    540

cgtgatacct ggcttctttg tcgtacagat aacgcctgac tgtgttgcgg tggcacgata    600

agcgccgtgc tacttctgtc tggtttccat atgtctctat gagcatgtct ggaatggttt    660

tgacagtgtg tgtcatgcgg cctcccggat aacctgctca tgactcagat attgacccca    720

gcaactgacc aacaatctcg ctttcacagc ggctttctct tcgttgcacc acctgcagaa    780

ccagttaaca gcgccttcca tttcttgcct aaccttgccg gcattgtcga aatgcagcgg    840

atagacaaca tcatcgaaaa ttgccgcagt ggtcattggg tattggattt tgctcatgct    900

gcctcgcttc tgctgtcacg taggtcttta agcttctgct gatactccgc cttaatcgct    960

ttgcactctt cggtagtcca gcgatgccgc ttatggtcag attcgatttc gtctactgct   1020

gcaatcccta tgcgctcgat gagcatcacg cgataaggaa ccaggttccc gctcttgtgt   1080

tgattgcaca cgacgcattg cttatggata ttgcgttcat caaatcggag ctgaggtgcc   1140

gcagcggttg ttcggtaatg cccggcatcc cactgagcag acgtgagcgt tccgcacgag   1200

atacatggta agtcgcggtc tctttctctg atgaaggcgt ttacggcttg ttgggcttgt   1260

ttaatccagt aactgcgggg ctttaaggcg agttttcgaa tcttcagttt atctttctgt   1320

ttttgctcct ctcgtcgtcg tttcttctct gctgcttttt ctgctttttc gcgctctttg   1380
```

```
cttcgtcgtt cgagtgctat cttggttcca cactctggag agcaccacca ctgattagcg   1440
aatgcagggt gaaaccattc cctacattct tcgtttttgc atcgtcttcg cgctgattta   1500
gccatcgtct tcttcctcgt acattgagct attcggatcg ctcatcagtt ctgcgcagca   1560
cgcttcacat acatgaactt ccagcacatg cagcttctga ccgcagttag cgcacgttaa   1620
agcccgctcg acgctttctt tctggtattg aagggattgt gatgggctaa gcattattgg   1680
cgtcctgcat caggagaaag acaatcatgg cggcgcggag aggtctgata tcaaatattg   1740
gactcacgcc ttttgcatct acacaccatt cagttaactg gtctaagaaa gaaattctgt   1800
atttctcaat aatcggccat gcgtctgccg ggttattaca tgggtcaaac gcgcctattt   1860
tagttggacc tcttactatc actgcgctac aactgtcttc ttgtgtccct tgccatccca   1920
ggccgttaaa cttcttatgc cctgtcgcta tcgcgactcg cttgttaatt tcaaaatcac   1980
ttaactgtga ataatccatt gtcatttcct cgcacgatgt cttagccacc ggatatccca   2040
caggtgagcc gtgtaattga aggtttttac gtcagactct tttgggattg gcttgcgttt   2100
atttctggaa cgtttcgttg gaaggtattt gcagttttcg cagattatgt cggtgatact   2160
tcgtcgctgt cgtgccatac gtcctccttc gtctctggca gcgggaaatt acctactggc   2220
gaccgctcac atctgataca ccattggtgc caataaggtt gatttggccg gaatcgataa   2280
tcgtctttgc tttctccgca gcggtagcag tgtttcatgc ggcgtctcca aacctcgctt   2340
tacattccag tgctaaccgg gcttcgtctg accacttaac gccgcgctct gtaccgaatg   2400
cctgtataag ctctaatagc tccgcaaact cgcttacacg catcctgctg gttgactggc   2460
ctattaccac gaagccattc ccggcaaggt tagggacaac atcctgctgc tttaaggctg   2520
cggtaaacac acacttccag ctttcagcgt caagccatcg tccatgccag tttacctgac   2580
gtgagacatc accaaggcaa gcccaaagct tccgattttg gtctaagctg cggttgcgtt   2640
cctgaatggt tactacgatt ggtttggttg ggtctggaag gatttgctgt actgcgtgaa   2700
tggcattttg ctgatgtgct ggagatcgaa tttcaaaggt tagtttttttc atgtcttccc   2760
tctcccccaa ataaaaaggc ctgcgattac cagcaggcct gttaccaact cagtgatgta   2820
aatagtcata cgtcagcccc ttgtgcatat cgctttctgc gtccagcagg tgcatttgat   2880
gccgtgcaaa tctgtctggc ttcgtcctgg tcacatgcaa caaagtgtcc gttgcagaac   2940
cgctggtaaa ccgtaccaag cgagccaaaa cggtttttcg tcacgatgat ttcagcaaat   3000
ggcgcggcgc tactgttctc gtcatatacc gcttcccgat agagcatgat gattgagtct   3060
gcgtcctgtt caatgcttcc tgaatcccgc aaatctgcgt ttgtcgggcg cttgtttggc   3120
cgcttctcaa catcgcggga gagctggctt agggagataa ctggagtttt caggtctttc   3180
gccatcgctt tcaggctacc ggagatatgt gctatggcga ggtcattacg ttccgctttt   3240
ggtttctcaa ttagcccgag atagtcagcc ataatcagtg acagattagg atgctcctgc   3300
ttgtggcgtt cggaaatgga cctgatttct tcgacagaca aacgcgatgc gtcaactacc   3360
cacacatcca gctctgccag caacttcatc ccgcttgcaa ctctcgccca tccttcatcg   3420
tccatacgtg acgggttacg cagcacactg accgacatca ttcctgcgcc ggcaatccct   3480
ctctcaacaa cctgaatggc gctcatttcc atcgagaaaa tcaacacacc gcgccggacg   3540
ccagaaccag gaataacacg acttgccacg ccttcggcta tcttcagcgc cagttcggtt   3600
ttacccatac ctggacgagc agcaataatc acaaggtctt ctgcgttcat ccctccggtg   3660
atagcgtcaa gctcttcgat tccggtcttc agggtatccg actcttctcc gttcctcaga   3720
```

```
cgcctgtcaa gcgtgtcagt gtagtcattg atgatttcac ccagtcgcac aggtttaacc   3780
tcgttccgcg gcttcctgat ggatgacagg cgctttacaa gctcgtccat cgctctgcct   3840
gatgcgtcca gcgtgccgtt actgattggc tcccgcatct catccagtag ctgtaaaacc   3900
tgacgccgtt gataactgtc tgcaaccatt ccggcataac ctttcaggtt tgcagcgctg   3960
ggacatgacc gcgcagtcat catcaccgcc gttgcgtatt catccccgca ctcctcggcc   4020
accatcagtc catcaatcag gttcctgttt ctggcctgct ttcgaataac ttcaaaagct   4080
ttccggtaga gcggaattga gaatgcttca ggctccagtg ttgccagaac gtcactggcg   4140
gttggtgtta atccgccaat cagcaagcca ccgataacgc tcgcctcgat atcctgtctc   4200
atagtgttcc ctcacgaatt gctatcagta ctttcgggcg tagcagataa tcaaaattag   4260
ctacccagtc acggtcgtta tcaccgaaat ggaatggtct ggctgctgcc atgaacgctt   4320
tgacgtatgc ccggaatccg tcgatgtttt tggttgccag tgaatcaatc agctttttca   4380
acttgcgttg tcgttcagaa ttgacctcca ctgcatgtgg gagtctgtca ccaacaatct   4440
cgttgtaggc agcaagatat tcgctgtagt taatcttggt aggttttcgc ttttcaggtt   4500
tagaaccttc atcgcatccc cctttagggg gtaagggggt atttgtattt attgtctttt   4560
gtatattgtc ttttgtgttt gactgattcg gtaaattggt tttaccgat ttggtgaagg   4620
ttagttttac cgatctggta aatgttttac cgaatccgtt aaccttcgtc ttccactcgg   4680
aaatattttt attcatacca acctgacgcc ccacctgagt gagaaccccc attctgataa   4740
gctcgttttt ggcggtagaa catttggttg gcgccatgcc agtgagttca gcgaactgtt   4800
catttccgat ccaatctatt tttttgttat aaccgtatgt cttgcgccac acagccataa   4860
caatcagtag ctgatgttga gtaagcccag aaagcatgac agcttccagc agtgtatttg   4920
cagtccgggt gtagccatcg tcgagttctg ccacgcgatg ctccacaacc tccagatgag   4980
gttttatcgg tgtaactgtt gcaagattac tcatgacctt tcctcttcag tattagcttc   5040
actttctcca actcagcccg aaatcgacca ggctgtttga agctggataa gaaccgatca   5100
cgtagtatgt ttttgtgtaa tttgtcctgg tcaggactga gttgttttgg cataattact   5160
cctgtggatt gatccagtct ttctacatca ggcctcaaaa ctgttcccgc agtcttgagg   5220
cttttctttt gtcagcagat gcgcaacttt ctttgccagt tctgccaact cctcatcctc   5280
gacaccccac tccagaaccg ccaataacat ccccatcttc ggaatgaaat cgcctttcca   5340
tcgtgaaatt tgagattcgt taatgcctaa cgcatcagcg actttacgct gtccacgaat   5400
agctatccgg ttaaggatgc tgctggtaat tgcgttggct ttctttcgag tgcttgtgag   5460
ttccatatgt gaacattcct gtagttaata gttagttgtg cgcattcgtt gatgcgcttt   5520
gaaataggtt taccgcgttg tcggcggttc agattggtaa agagcgtttt gcttacgccg   5580
cttggcgata agcgttttct tggtacttca gggcgccagc tgtaacgatc tctaatcggt   5640
atgcgtcttt ctctgggata acttccttcc actgagagac cgctgcatcg ctaatgccta   5700
aagccttagc tactgcacgc tgggttccga agtggtcgat aacatctttc ttgtacatag   5760
actcgctccg aaattaaaga acacttaaat tatctactaa aggaatcttt agtcaagttt   5820
atttaagatg acttaactat gaatacacaa ttgatgggtg agcgtattcg cgctcgaaga   5880
aaaaaactca agattagaca agccgctctt ggtaagatgg tgggagtgtc taatgttgca   5940
atatcgcaat gggagcgctc ggagactgag ccaaatgggg agaacctgtt ggcactttcg   6000
aaggctcttc agtgctcccc tgactatttg ctgaaaggag atttaagcca gacaaacgtt   6060
gcctatcata gtaggcatga gccaagagga tcataccctc ttatcagttg ggtaagcgca   6120
```

```
gggcaatgga tggaagctgt agaaccttat cacaagcgcg cgatagagaa ctggcacgac   6180
accactgtag attgttcaga agattcattt tggcttgatg tccaaggtga ctctatgaca   6240
gcaccggcag ggttaagcat tccagaagga atgataattc tggttgatcc cgaagtcgaa   6300
ccaagaaacg gcaagctggt tgttgcaaaa ttagaaggtg aaaacgaggc cacattcaaa   6360
aaattagtta tggatgcagg ccgaaagttt ttaaaaccat taaacccaca atatccgatg   6420
atagaaatca acggaaactg caaaatcatt ggcgtagttg ttgacgcaaa actcgcaaat   6480
cttccataag ggcacccgc ccctcacact acattttcct ttaaaaatca aataaaaact   6540
taagtaacga taaaatattt aagttttctt caaaaataca cttgaccatt taattaagaa   6600
gtcttaaatt ttagccatca gcaggacgct ggtagccaaa cggaaaggca acgctcttta   6660
acttcgatga tgcgctgaca aagcgcgaac aaataccaaa cgagattggt ttggactggc   6720
gtgtggtgga gcttaggcct ctagctgtac cgatcgggcc ggactgagaa gccacttgaa   6780
atccggaaat tgagacaggt tccggcgcca gtaccaaagc catttcacat gaggattaaa   6840
tcatgacggt tatcacctac gggaagtcaa cgtttgcagg caatgctaaa actcgccgtc   6900
atgagcggcg cagaaagcta gccatagagc gcgacaccat ctgcaatatc atcgattcaa   6960
tttttggctg cgatgctcct gatgcttctc aggaagttaa agccaaaaga attgaccgtg   7020
tcaccaaagc catttcgctt gccggaacgc gtcagaagga agttgaagga ggatctgtac   7080
ttcttccagg cgtagcactt tacgcggctg gtcatcgtaa gagcaaacaa ataacagcga   7140
ggtaaggtat ttgtcggtta agtcgttatt ttttgagctg ttcgtcctgt acaataagtt   7200
cattcataag aatgtctgac ttcccggcaa atctcatgta gcactcatta aaatactttt   7260
ccgggataat aaaacggtca atatcaggat atccaatagc agaaggcaat cgagtgataa   7320
tcccttttt gagcaatgaa attgcttcag ggcttccctt ttctgtcttt agctggttat   7380
tagcggctac agcgaatgcc aaatacgctc tttctccaag agttaacgaa tcaaacaaat   7440
cccgaacgac tttttcttct ctgtccttac gccgctgagc agttgatgcc tcaattcttt   7500
cagtaacagc gtgataaacg gaattaacaa caccgttaag cacatagcta acgcagaaca   7560
acaggatgta atacatccag taatgaggaa gtatttctgg attatgcagg tttatccatt   7620
cttttacgct taccggcata acaataatca atacgatcag gatgattagc atatgaatca   7680
actgtttaag tgtcattcct tgcaggaaaa aacgcattaa ctcctgccac catgagttgt   7740
tcatcggcga ttctcttttt actctctgta ggggtgaata gagtttatcc gatttctcgc   7800
tgtaggggta cacgagaacc accgagcctg acgtggttaa aagacaggca caatctttac   7860
taccgcaatc cactatttga gatgagatat ggaagaagaa tttgaagagt tcgaagagca   7920
tcctcaggat gtgatggaac aataccagga ctacccatat gactacgact attgatacaa   7980
atcaatggtg tagtcgtttt gtgaaatgca aaggctgcaa gcttgatgct gaatgtatgg   8040
taaagcctga ggaaatggct ctggtgagag aagatggaaa gattgtcgat aaatgggcaa   8100
tcagaaccac ggaaatgatt gccagagagc tggaaaaact aaaggctata tagtctgtct   8160
tcttttggca gcaagccaca gaggtgaata tgaaagacat accgcattgg gatgttgatg   8220
aagattacat tgtcgatgtt actgaaggtc acattctgtt ttcagccgag aacgccaata   8280
agcaggaaat aaaattggca agtgcagctc ctgagcttct cgaggctctg ttaagcatta   8340
tcgatatgga acatgacgtg agcgagtggg acgctgtgta cgcgacggct cgcgcagcca   8400
tcggcaaggc tctggggaaa gagtgatgga gtggattaag tgtagtgagc ggatgccgga   8460
```

-continued

```
atccggaatt actgtgcttg gatattgtgt ttgcaattca aatttctcgg gaatttacac   8520
catgaggaag ccagtaattg aggcaaagaa ctcaaagcag gacacgcgtt taatcaagca   8580
tgagcgagtg actcactgga tgccattacc tgaatcacca agcgaataag cacctatagc   8640
agatttacga gtctgctatg tgagcaatat cgctcgtaac cgaatgagga cgaagactcg   8700
ttctggttat tggagaatca tcccttgata gtcttgccgc tctatatggg cggcattctt   8760
tttgcctgga ggaaatatga aattacgtgt ctggcatatc ccgcaagtcc ctatgaagcc   8820
attcattgta gaagtgggta gtgttgaaga aggtgtacga atgatggatg cactggctga   8880
ttatgacgcc tttcagtatg acaacaacat caagcctgat tactgcaacg ccaacggttt   8940
acagatgttt gacgagagcc ttaccgacca ggatttggaa gatatggaac tggatgatcg   9000
ctggattgat tggtatagcg agtgccagtg ttacgacgac ccgcgtgaat atctcgaaag   9060
cctgaaagaa gaaacgacag ccgcctgagt gcggcttttt catatccgca tctgagtgag   9120
tatttattca agtgctcagc ctcatgcaat cacacacaac ataaggaact cccatgatta   9180
tcgcaatcgc gggaagcgct cgcatgggcg tttcccagtt acacgaatca cttttagatc   9240
gcatcacccg caaattacgc gctggctgga aacggctggc agacatcctt aatcagcctg   9300
gagtgccgag ccatgactat tgtgcctgtt aacggaacca tccttgtgca gcaaggcaat   9360
cgtgagttta acaagctcta cgaagcatcc ttcccggata cgaaggaagg taacagcgcc   9420
gcatacgcat gggcatcatc aatcgcaatg ggctgggaag attgtcagga cgaagactgg   9480
aatcgaaatc atgcagcatg aatttagtga cgaagaattt atcgcgctta tctctcctga   9540
aattgaggaa gaggttgagc aacaaatcaa cttagccgca gaacggcaaa atccgattat   9600
tggttgggat gaatttgcgg ggtattactc atgaatctgg atctgttaga tgaaccgttc   9660
gctgctgaag atattgagtg gcgaatacag caaagcggga aaacacgcga tgggaagtta   9720
tgggctatgg tgctggctta tgtcacgaac agggcaatca tgaaacgcct ggacgatgtt   9780
tgcggaaagg ccggatggcg caatgaatat cgcgatattc caaacaatgg cggcgttgaa   9840
tgcggaatat caatcaagat tgattccgaa tgggtaacta aatgggatgc cgctgaaaac   9900
acgcaggtag aagccgtcaa aggcggtcgt tcaggagcaa tgaagcgcgc agccgttcag   9960
tggggaatag gacggtatct gtataatctt gaggaaggat ttgcgcagat atccagagat  10020
aagaaacaag gatggcacag ggcaaaactg aaggatggaa caggatttta ctggctccct  10080
ccatcgctgc cggactgggc catgccagca tcatgcaatc aaccatcacc agaaaatacc  10140
aaccagaaat ctccatcggt tgactgcgaa caaatcctga aagacttcag cgattatgca  10200
gcaacagaaa ctgacaagaa aaagctaatt gagagatatc agcatgactg gcaattattg  10260
gctggtcacg atgatgcgca gacaaaatgc gttcaggtaa tgaatatcag aataaatgag  10320
cttaaacagg tggcttaatg agaagattaa acataactcc agctgagatg gagtcagttt  10380
gcggtcgcat ggtagcttgc cgtgcagcag aacatctggg cctaaacata aatcagtttt  10440
attacatagc aaaaaaactg tcattaaaaa cggcattcgt taagccaaga tggagcgacg  10500
acgaagacaa aagaatgcag acgcttatct catcaggcta tacacaaaga aatgtagcaa  10560
aaattctcgg gcgaagtgaa gagtcggtaa aaagcaggct atcacgttta cgaaagaaat  10620
aaccctatac gtaccacatt attcggataa cctaccctgg agtaaattat gcctgcacct  10680
ctatatggtg cggatgaccc gcgcaactgc tccggtagct ccaagtcgga ggtgctggaa  10740
aatatcaaaa acaatctcga cgcgtttctt gctctgccac cggaaacaaa agcagaacgg  10800
aagtaccgac gcgatataca actcgcagaa aaacaggaaa aagaccgaat aaacgaaaca  10860
```

```
gcaatccgac cattccgaaa agccacttac accaaattca ttgaaataga cccgcgcctt  10920
aaaaattacc gttcgcgtta cggcgctatc agcaataact gagggattca tcatgagagg  10980
tttgtcctac gaccaaggaa tccttccatc ggaaatgatt attcgacacc gcttcaagcc  11040
catcaacgat attccacgcg aagaaatgct ggcgagaaag agttttccat cagtgaatca  11100
aaacaaatat ctgaatgcga tgtggcggag tgggaagaaa tgaaacaaat gacactaatt  11160
gagatggatg gatttctgaa aggtaaatgc atcccacgag atttaaaggt taacgaaaca  11220
aacgctgaat atctggtgcg taaatttgct gaagcggagg ccaagatttc cgcgctggcc  11280
gaagaccacc agagagcgat tgagtcaatt aagcaggctg attcggctgt taagttggca  11340
cacgagaagt tttcggcgct ggcttcggag aatgcggcac tgaaaaaatc agaggtcgaa  11400
ttcaacgaat attgtcgtcg cgagtgcgag gacgccagga atctattcca gcgggcgtac  11460
ttgttggagc cagtgtgaag ccgggcagcg cgcagaaacc ggagcgtata cgttgtacgt  11520
aagaatttcg agcactgccc gacctaaaaa tgatgaataa aatagatatt ttaaagaggt  11580
aatatgaaga attttttcaa aataattact gatttcatcg cggatatttc ccttgatcta  11640
tttgctatat ttttatgcat gttattcgta tacaaaacag gaccatcaat tggtgtgata  11700
tcattttta ttgcattaat tatttatatc attcttcatt ttttttactc atttcttgaa  11760
aaaatcataa aaaaaatatt caaataagta tttaaaatta ttgttttgag gtacaaattc  11820
agcgcaataa aacagagcaa ctaaaaaaaa ttaggcgtag cgaagtggaa aaggactgtc  11880
atgtactgga ccgtgagctg gtcgggagag caatgtacgg gaaagagcga aatactgtca  11940
ttgatatgag caggaatatc gatagccagt aaatcactcc tgtggtaata caggccactt  12000
gatgactgtg aaggtcgctt catctgaagc accggtgaag tccagcattt taagtgaaaa  12060
gcagccagca ggcgcttctg ctggtccata ttcctctatt ttgccagacc acactaaagt  12120
gccacacagg tatctgccag aacggtcctg agataataaa tataaaagca gttactgcct  12180
acctcaagaa gtatgcgctc atgatcattt aaagctcttt taaagagact gataataagc  12240
ttgtcaatat aatattatgc agtctctatt aagcgcctgg tttatttgtt ttgcataatc  12300
atatagttga cttttcgagt aagagttttc ttgcaaagac aaataaacgt gttttatatc  12360
tctgaataaa catacatcac catgaatatg agcctctata taattccctt catagccttt  12420
accataatta gaatgagcta aaaatttttc gtccttagcc attttaacca aactcttaaa  12480
gcaattataa ccaaaaaaat cattttgaca ggatgcaatc aggttctcca tatgccaaaa  12540
tgtagataat ttactcgtat ccaggccaaa tctgtggccg tagatatcaa aaggtgagaa  12600
tgtacagttt gtttttacat tatcatttaa ttcaaaaaat gatttcccat aggcgctggc  12660
acctccattt tcaccgttca gaaagtccag tgcagcataa attggtctgc ttgtagtgct  12720
aaaagttcta ctgttgggag tatatgctac ggaaaaaccg cctgtctgac catatggggc  12780
ataaggtgaa tctgcaagct tctccagttc aaatgcttta gtttcaactg aatcacgccc  12840
gacattataa gcaggtaaat ctcccggtct gcaacctaat gcataagagt tcagatattc  12900
tttattttt aagagagaga caaagtcaat ttttgctgca ttaaaattta ttgtcagccg  12960
ggcattttgt aaaatatcca ccatcttatt tagtaagaga gcgcaatcta tttcggcacc  13020
acactcacgg cttatccgcc tgagcgcttt ttctcttatt atgtcagcgt cgcgctgaca  13080
cctggaatga atatgcgcaa gtacttgttt tccaaaaagg cgaccataca cctttttacg  13140
ctcttcattg ctgagaccgc aaaacacttc gtcaaaagaa agcctgtacg ctgcgcttac  13200
```

```
agaacctctc gccgttctgc tttctggaaa tagcggaaca tcttcaacaa catttctaac  13260
ttgctgaatg tctgaagaca gtggagtacg tccggcattt ttttccttat ctgtttccag  13320
atattccgga acctttatac ttccactatg gcagataggt ttgagcatat gtctcctgaa  13380
tttttatgac taatatagca ttcactttcg ctgacgtatt ctttatcagg ctgatatttc  13440
aacacttctt agcagccttg tagaagagca aataaagcat gctaataatt ttataaaata  13500
cttaacctac ccactattgt agtcaataaa ccatcacttt ttattaaaaa attctcctga  13560
taataacaat aaatctggta aggcactttc aaaaaatagc caaatcacac attattaaga  13620
aaaccactac aatcaaaatc ggtaactatc agctttcagg ggggtctcag gttatcatga  13680
cgatcggggt aaaggatgaa ctactattgc ggtctgaatt gagggagttt tgataaagtt  13740
ttgataaccg ttcgaatact aataataaaa acggggacgt taagtccccg tttttgtttt  13800
taacaattat cgttattaca tattcgcgat aatcgcgtca ccaaactcac tacatttcag  13860
cagcttagcg ccttccatca ggcgttcaaa gtcataggtc acggtcttcg cggcaatcgc  13920
gccttccata cctttaacaa tcaggtctgc ggcttcgaac cactgcatgt ggcgcagcat  13980
tacattgcca aaaacatatc aaccatttga taaagttgaa attatcattc ttcctactat  14040
caaaaaaatc cagtaactgt cttttacaac tcattgatta tcaaaacgtt gattatagtt  14100
ttggggaaga gttttcttca agattccaat tttttcacgc cagtacattc aacatgatgc  14160
tactagtggc aaccccccaat agtgaagctt ctacattggt tgaggtcgct cgaagaaaca  14220
ccggaacagc cactcgcata tcctcttcta tactttcagt ctgaccgact ggaggtttca  14280
tatgtgtgga cgctttgcac aagcacagac ccgcgaagaa tacctggcat atctggccga  14340
tgaagccgag cgcgatatcg cttatgaccc tgaacctata ggccggtaca acgtggcgcc  14400
cggtaccaaa gttctgctgc tcagtgaacg cgacgagcaa ctgcatctgg atccggtatt  14460
ctggggattt gcgcccggat ggtgggataa accaccgctg attaatgcac gggttgagac  14520
tgcggccacc agcagaatgt ttaaaccgct atggcaacat ggccgagcta tcgtgtttgc  14580
tgatggttgg tttgagtgga agaaggaagg cgacaagaaa cagccgtatt tcattcacag  14640
aaaggacggg aagccgatat tcatggctgc cattggcagt acaccgtttg agcgcggcga  14700
tgacgcagag ggattcctga ttgttacctc cgcagctgat aaaggtctgg tagacattca  14760
cgaccgtcgt cctctcgttc tgtcacctgg caccgcgcga aaatggatgc gccagggcat  14820
aagcgggaag gaggtagagg agataattac tgatggtgcc gtgccgacag ataaatttac  14880
ctggcacgcc gtgaagcgcg ccgttggcaa tgtgaaaaat caaggggaag agctgatcaa  14940
acccgttacc tgactattgg cagatcggaa aatctggtcg tataccgagg tgaaagcatt  15000
tctcgcttca tagcccactg ttgcgacatc ccctacccgg cgaagtacag cgtccccttc  15060
ccgtcttttg cattaagatg gtccagtact tccatcaact tcgcactatc ggcgcgcggc  15120
gcgttatcgt cgaaaaggtt gagttgcgct acgccctgac tgaagaagtc tcccctgttt  15180
cacctgtgca tcatcagtgc tgtctgatgt tgtttgtcca ggaatatctt tgttcaccgc  15240
accacattcg cctggtgcgg tgaatatcgt gctcagttaa gacgccaccg ggctgtcaga  15300
tagctaccca gcacctcatc cacaagagcg cgcaggccat ccagaaattc ttttttcgca  15360
ctatccatcg cacttactcc gatagtacgt tctgcatcgg tatcgtcgac cagcccggac  15420
gatttcagca cttcgtcata cagcttccgg tacgtgtctt cataatccga tatttgcttt  15480
tcacgaagcg cgttaaagcg ttccggcact ttgcgttcca gcacgctgtg taacggcccc  15540
cactgcagta tccatttact gaacccgctg ttttcagcgg ttttcacctg aagctccgca  15600
```

```
gcctgaaggt ctgaaaccgt cacgccggaa acgtcaaaga aacgcatttc tgacgtcacg  15660
ctggtcagct caagtgattc cttcagctta ttctggaacg ccagatagac ctcaacgtca  15720
tcgactaaag ccagtgttcc ggctttttcc cgggcaatct gttccagtgt tgccaggcgg  15780
aacatctcac gccccgtgga aaccagcccc tggagattgt tgtcgtattc cccttttttct  15840
gcattatgta ccagttgtac gttattcatc tggtgcaggg catgtgtgac ccggtcctcg  15900
caggttgatg ttgcctctgt tgccatggca aaggtttttg ctctcagcgc agcatcttca  15960
gccagttgtg tcagccagga tgatatctgt gccttaaagc ccgcgtcttt tttgaagttt  16020
tccgtctcac gcagtctgtc caggaccagg ctgaaggcgg cggcgttatc ttccagtccg  16080
aacgcctgcc atctgtctgc ctgggccgct tccccctccc gtgcagacgt cagccagtca  16140
gcgaccgcca ggtgcagtgc ccgggcttcc cgggggacgg aaggccccgc catatcgaag  16200
tgtatcctga tgcctgaatg gccaatgatg tcccgcagag cctgcagagt gcgtacagac  16260
agtggattcc cgtccagata tacgcgtgcc gctgaagaca gacccgtgag gctttgcggc  16320
aggcgggtca gctggttatg agagacatcc agctcctgta gtcctggcga catctccggc  16380
aggctggtca gccgattatt ataggcccac agcttctgta gtcctgacgg cagcgccggc  16440
aggctggtca ggttgttacc agagaccctc agctcccgta gtgctggcgg catctccggc  16500
aggctggtca gctggttatt agagaccgcc agatccccta gtcctggcgg caacgtcggc  16560
aggctggcca gccaattatt ataggcccac agcttctgta gtccctgcgg cagcgatggc  16620
aggctggtca gttgtaggtt accagagacc tccagctccc gtagtccttc cggcaactcc  16680
ggcaggctgg tcagattatt atcaggaata accagtgttg taatatgcgg tggtaaacgg  16740
tctggtaagg tggtaagacc tgacgctccc acgttaagca ctggattgcc gttattcagg  16800
caatcacgca tttcctgtac cactgctgcg cggccgggtg actctcctgc tggtgcatcc  16860
ctttcccatt ttgaccagac agcatcatac tctgctgcct tctgtgaaac cgttgtggca  16920
gggcggaggg atgtcccgga tgccccctcc gcgaattctg tgcattcctc tcccggttct  16980
gtgtccatga tgaagtcatg tgcttcactg taccccctgac aattcacggt atagttcccg  17040
gcatcatcaa gagtgattga caatatctcc ttgctgcctg catccagaat acaaaactga  17100
tttataccat ccctgttaca ctgaatattc tcctcccacg cggggaaggt aagcgctttt  17160
aaacgcgcaa actggctgct gatatgatca ggcaacattc cccgggccgg atggcaaagt  17220
tcagcgagac actgttgcgc ttcttcgtaa ttttcctgcg ggaaaaaaac ctgaattttt  17280
tcccatacaa tttcttccgg agatgcctct ggtgccgctg caccagcaat agcctgcata  17340
cttacagaag gttgtgtatt gcggatatta aacatattcc actgcctaat ttacagcaca  17400
atgaaaagag attaacgcag acacacgcat caagccttca attaacgata tatatttagc  17460
aataaacgac aaataacata caattagttg tattagctca gacctgatct gacagttacc  17520
ggttatttat acaggtatct gtcagattac atctggctta aattcttctc agaccagatg  17580
cgttttccat caagtaacgt ttccatcggc gtccggccac agcacatttt tccctgatgg  17640
gttcgctcat tattatagtg aaccagccat tcatcaagat ccgattgtaa tgtatcaaaa  17700
tcgccatata actttttgcg gaacgtcacc tgataaaatt cgttcagtat cgttttatgg  17760
aaccgctcgc agatgccatt ggtctgcggg gacatcgcct tcgttttcgt gtgttcgatg  17820
tcatttatct ccagataaag ctgataatca tgatgttcca ctttgccgca atattctgta  17880
cccctgtctg tcagtatcct tagcatcggc aggccctgag actcataaaa cggcagtaca  17940
```

```
cgatcattca gcaaatcagc cgctgtaatc ggcgttttgg tgatatagcg cttgcagtga  18000
gccaccttcg agtatgtatc aacgaacgtc tgctgataga ttcgcccaac gcctttcagg  18060
ttgcccacgt agaacgtgtc ctgtgacccc agatatcccg gatgaacggt ttcaatctca  18120
ccacaggctt catcatcact ggctttacgc tccagcgcgg cgatctggca gtcagttcaa  18180
tgccatcgcg ggccactttt tcttccagcg ctttcaggcg ttttttgaag ttctcaaggt  18240
tgtggcgcag ccagacggaa tggacatcac taccggagat aaaaacgtcc tgtttgcgca  18300
gttcggtgct gaccatgggc cgggaacgca acggcataat caacaacagc ttgctcagtt  18360
gcctcatcgg tacggttctt aaggttaggt acgcggcgac tacgatttat cagcgcatca  18420
acgccgcctt catcggccag ttcacgataa cggtaaaacg tatcgcgcga gacgcccatg  18480
attttacagg ctttcgacac gttgctgagc tcttcagcca gattgagcaa accggctttg  18540
tgtttgatga cgggattggt agtatgaagc atgagagtta cctcgtgttt tgtataagga  18600
ttcgacaccc atatcaaaac cggtaactct caacctttca aggccatatg tcagatcaag  18660
tcgcgactaa tacatttaat aagagaaaac atattattac cctcatagta aacagtatta  18720
aataagccgg gatatatctg atgttcaatc agtccctcat atagggttag caccatagcg  18780
agttgttttc acaaaaaaca cagactgttg aaactttatt tatcactttg acatttgcaa  18840
tacatgacac atgattagct tcagccacca ttatagggaa agctccattt ccatactcat  18900
ttactcactt ctccctgcgg aaaaagaaat gcagtatagc cagcgtggtg cttttgctga  18960
aaccaggcgc gagcaacacg gcaatgatga tcggcgtcag aatgagttcg gaatcggcat  19020
tggcaaacaa ggcgcacagt cgttaatacc caccagcagt tccggcagga ctgcgacaat  19080
gtcgtaagag aggccttcag ccaggcaaaa cagcgctacg gtgcgccccg gcttgctgag  19140
gaagtgaacc tggggcctga ggtacaatgt aaaaacgata gcgtccagcc tgcgccgtca  19200
gggtctgcgg cgatctcagt ccggagcaat ttgaaaacca gaacctcgct taaggctgtg  19260
tccacaatac gcggacagga tcaaaactgt cagtgtggct ggcttacaaa aatgaagtga  19320
agttgattga tataacaaac actcctgata atgttaactg gcctgttcct ccgggggagc  19380
gagccagcca ggatttgaag agcacatgaa ctcactttca tatgaattaa tttacatggg  19440
aaataaaata taatagtgct tatcattttt atttaagtta aatattttat aaatggtttt  19500
tatttactca cctgatggta atgaataacg tttaatatct atagtaaagg atgctgtaac  19560
cgtaaggata gtgtgccaca atttaacagg taacatatta tgaaacacgt taagagcgta  19620
tttttagcaa tggctttaat attaccatcc tcactatatt ctgctcttac aatagcggca  19680
gactcccaag atcagcaaaa agcagaaaca attaagccca taccacctaa gatgtgtagt  19740
ctttggcctg cggacgtgcc cttccccgaa gattggttta aaatgtgtag aggttattga  19800
gtataaattt atatatacta accagtaacc atatcagtta tgacagacag gccttcttca  19860
tatttgctat aaataaggcc tgagctttcc tgacaaatta taaactactg gctggtttct  19920
ccggccagac aggctttaaa gtatcaacac ggtttacctg tacccggtac tttctccatg  19980
ccagaagaga agctttttct ttatcggttg cttcgtccag atccactgca tcctgtaacg  20040
gcgcgatttt ttcagatgct atttgcagga gcctgttttt ggtttcttcc gcctgacgaa  20100
gctgcgctgc tttttcagcc gcttcgtctt ttacccagac cttagcctta ccatcccatt  20160
tctggtattc accaactggt gaaactgatg tgacattttc gggcaacgga ccaggctcgg  20220
agatataaac ctgattgccg gttgttgtgt cgtaaaccgt ctcgccgcgg tgatcctcct  20280
gcagactcca cgtttgggtt tcagcgtcaa aaacagctat atgactggag ggaatatcag  20340
```

```
gaggggcgag atcagtacag tttgccggta atcccgtgtg cggcgggata tatgcatcac  20400
ctgcgccaat aaattcgttt gtatctgaac gaagattaaa aattttaatt gtctgcgcct  20460
gttcgctcat tttaaaagtc attatgccag cctcactatg tagttaaatg caatattttt  20520
aaccgtggtt tccgcattac cgtctgcgtc cacaataacg acgtgtccgt gtggaccgat  20580
atacatggtg tgctcatgtc ctccgatata aactgtatgt gcatggtcgc cagcggcctg  20640
tgtccatgca ccacctccag gctgaaatga ggtgtgattg gaatctcccc agtatgaatt  20700
gatataaccg ccgaactggt gagtatgatt gcccgtggta ttggtcgatt tcgtgccgta  20760
atcaaaggat gaggtagatt ttgcccctaa gtcagtatcc tgcgcccgcg cggtgtgcga  20820
gtgcgattta ttgccgtcca tttcttgcga caatacggca cgtccactga tgggcttacc  20880
ctttattgtc cagcctctca tgtcagggat aacgccggac ggatacgcta tagccagtaa  20940
cgggtaagca gatttatcga aggactgccc atacataaaa gcataaccac catccgggag  21000
cacatcagac ggccatgcaa tcgccgcccc tactggatgc gaatccggag gtgggtttag  21060
tgtggtgtag agcattgccc attcggacca ctcagcatcg gcggtatctc gatgactgcg  21120
aatatatgcg ggcgctggcg caccgtttgt cccgctccag ccaatgagga tttccccatc  21180
accggctccg gtcagacgta aaatatttcc gtattgcgtc ggatagccat tgttgtaaac  21240
ctcgcccatt atcaggccac tatcgctgcc tcttgtcgta ccagtcagtg ccggaagcgc  21300
gccgcgtgat gccagtctgt tcgctgcaac agccgtacct gatgcaggga gcgctccgat  21360
attttgtaca aacagcggct tttccggaat atcgccaccg ttctgtgatt ttagtaatgc  21420
atcggcggcg tgatttatgg tttcccgtaa accaacgtat tcgataagac cgtcaacgct  21480
ttttcctgac agcgccgtca gtgtatcgtc cagcggctgc ttgcccgcca gtttattcag  21540
tacagtggtg gcaaagttcg gatcgttacc cagcgcgtca gccagttctt tcagcgtgtc  21600
cagcgtttcc ggcgcagaac caaccaactg tgctactttc gcagccacaa acgctgccgt  21660
ggcaatttca atacctgcag ctgtggtttc cggagttggt gctgttggcg taccagtcag  21720
tgccggactg tccagcgggg ctttagcctg cacctcacct ataacggttt ttaccgcctt  21780
tggtgtggct gccagcgctt cgctgtcact gtccgtggca ctgcttaact taacgatacc  21840
tttttttcgtc aggctggcat cttccaggga aatcacgtcc gcgatgtctt ctgcccgttt  21900
tgcggcatct tctgctctgg tggctgctgc tccggcagca gtactgcttt gcgccgccag  21960
tgatgcgctg gtatcagatg cggcggcgtg agtggatgcc tccgatgctg atgacgaggc  22020
ggctgttgcg ctggccgctg ctgtacttgc tgacgttgct gcatttgtct cagatgtttt  22080
cgctgcggct gccgatgcgg ctgccgcctt ttccgacgct gccgccgcag tggctgacgc  22140
acctgcatca ccggcactgg aagccgcctg cgtttctgac gtcttcgcgg cggtttcgga  22200
tgctccggcg cgctctgctg atgtctgcgc cgccgtcgcg ctggcggctg cggcagcagc  22260
tgaatcgccg gcggcagtac gggaggcatc tgcattcgct tcagatgttt tcgctgcggc  22320
tgccgatgcg gctgccgccg ttctggctgt gtcagccgac gccgcgctgg ctgatgcctc  22380
cccggctttt gtggtcgccg tacctgcgct gctctccgca gatgctgcgg atgaggctgc  22440
ctgtgtggct gatgcttctg ccgctccggc tgcattcact gctgccgtgg cgctttccga  22500
tgcctgacct gctgatgtct gcgcctgttc agatgcctgc cctgcggcgg tggcattccg  22560
cgatgcctcc gatgcctggc gggcaacttc ttccaccatc gcctcaaaac gccgcagcgc  22620
ctccgggcgg acgtcgtctt ctgtcatggc ccccagaaaa tcattcaggg tgcccggctt  22680
```

```
tgaatcatcg taaaccgtaa taactccggc atgtgacggg ggatacccgt ccaccaggag  22740
cgtgacagtg tactgcccct gctccacatc catgctgtag cgcccggcgt catccggatt  22800
ttctgatgcc accgtattca cgaccaccgt cgtactggtc cggcaggcct tcagctgaat  22860
ggtgcagttc tgtaccggcg ttcccgtacc atccttcagt acgccggaaa taagtactgg  22920
catattgcct ccataaaaaa gcccgcccgc aggcaggctt cagattcatt cacatctcag  22980
cactgattat ccgggtcacg taaatatgcc ggcagagaac actggacgct ccgcgtgatt  23040
gtttttccct ttgcctcgcg gtgctgtttc tgcccacggt cggtgccggt ataaatccgg  23100
gtctggtttt caatattgct gttgccgctt cctcttccgt tatcggcaac ggcagcagtg  23160
gaaaataaaa cggacaggga aagccctgcc gccagcgaaa ttacgcgcga catagtcata  23220
tctgttcctt gttaaacgaa agagaccgga aatccggtca gtttgtgaag ttgttccccg  23280
accgggaaac catcaccagc ggccagacgg aagcagacgt ggtgtactgc ccacgaaccc  23340
tcagagaaac gctgatatcc acgacaggtg aagtggtgta gaccgaaaag acaacggtct  23400
gatacatggc cggaagccct gcggtatacg ggataacctc cgccgttttc acctggccgt  23460
taatatttat cgtgacggtg atggcaccgg agccaccgtt acgctcacag ttagccatca  23520
ccgtgatggt tttccctatc tgataggtgg cgctgtcggt ataccgtgtt gaggtgctgc  23580
gttcgtcgtt cgtcgccctg atgttcacgc cctgcatgac ttttgagccg cagatatcac  23640
cgacaaactc tcttgcttct atcacgccag aaaacttacc ggaggtggca ttgatttctc  23700
ccgtaaacga gccagataca gcgttgatat gcccgctgat atccgcattt ttcgcagtca  23760
gctttccatc cggcgtcagg gaaaatgccg gaggattccc gccactggta atggtcggcg  23820
cgctcagata tttcaggaac gcctcattca tgattatctg gtcgccctgc atgacgaatc  23880
cgggcgtctc gtttccgttt gccgggttaa tataagcaat gcgatccgcc gccaccagga  23940
actggcttat cttcccgtca ggcgtgtctt ccatgctcag tccaagtccg gccacataat  24000
atttgccgtc tttggtctgc tctattttga cgccccacat ggcgttccat ttatcgttag  24060
catcctgcca ctccttcgaa aactgctgca gtttgctggc gttatcctcc gtcagttcca  24120
ccttctccag cagttcctta cccaggtgac tttcagttat ctgccctttg aaaaaatcca  24180
gatagcctgc ggcatcgttg ctggcctgcc cggtcgcctc cacgaatgcg gatttaccga  24240
cctgatttac cgcccggata taaaaatagt aatccctgcc gggcctgata ttcacactgg  24300
ccgctatcca gtacagcgcc gttcccagat atcgtgcggc gttttccacc tgatggatat  24360
ccgtaatctg cgcgtctgaa aaccagaact catactgcac cgtcgggtcg tataccgcct  24420
gacgcggtgt ggctgtaatc tggaaatagc caggggtgag ttcgataaat gatggtgccg  24480
ccggcgcgga gatgctgaac tgtgtgctgg ccgggtctcc ctgttgtccc tggctgttca  24540
ccgccctgac ggacagggtg tagcgccccg gcgtcagccc ccggaaccgg tactgcgtat  24600
ccggcgttcc tgcgctgctt accagccggt cactgccatc ttccgccgcc acgttcaggc  24660
gcaaagaaaa cgaggcgccc ttaacgactc gcggtgtgtc ccagcgcgcc agtacctgat  24720
actgtccctc ctccgccaga atttctgtgg tcagatgctg tatcgccggg ggaacggtgc  24780
cgtgaatcgt tccgggttgc ggatcgaatg atgccccgtt gtccacgatg gactcttttt  24840
ccggcacatg ctgtacggcg gtgatggcat acgttccgtc gtcgttttcc cggacagcca  24900
cacaccggaa gagacgctgg cgcagcgacg gcagtttcag cccccagacg ctgtattccg  24960
ccacgccgtc cggtatccgg ctgacctgaa cctgcacacc gtcggtaaca gactgcacgt  25020
ccacgctgac cggcaagcct tcgccatcca tcaggcttat cagcgtggtg ccggacgacg  25080
```

```
gcagggtaat ctccctgtca agggtcagaa tgcggcgggc gcggtcaacg gacagaatcc  25140
gcccgcccag gctgatgccg gcataatcct cgtcgcaaac ctcaatcaca tcaccgggaa  25200
cgtggcgcag cccctccgca cccacactaa aatcaaccgt ctgggtttcc agcagctccg  25260
tttttatcag ccacagcccg gcgcggtgcg cctgcccgcg actggtacag ccaaacgcat  25320
ccatttttac cagattgcgt ccgtagtgac tgatggcgac cgtgtcttcc accagttccg  25380
tggatgtctg ccagccatta tcagggtcga tccagttcac ctctaccgca ttatggcggt  25440
ccttccgcgc actgaagctg taacggaacg gtgtgccctc atccggcatt accacattgc  25500
tgcgggtata ggtccagact gtatccgagg gcctgtcctg cacgaaggtc atcatctgcc  25560
cgttccacac cggcatacaa cgcatggcgg agcagaagtc ggtcagcaca tcccacgcct  25620
tacgctgctg tgccagatac gcattaaagg tcatacgcgg ctctgtcccg ccgaatccgt  25680
cagggaccat ctggtcgcag tactggccta ttgcatacag cgcccacctg tccacgtccg  25740
ccgcgccgat tcgctgtccc atgccataac ggggatgtgt cagcacatcc cagagacacc  25800
acgccggatt attgctgtat gcaggcttga acgtgccgtc ccagatgccg ctgtaggttc  25860
gcgctaccgg atcgtaattc gacggcacat gaataatccg cccgaaaaaa tggtaatttc  25920
gcgtcacctg ctggctgccg aactgctcag actccacctg caggccaatt acggcggtgt  25980
tgggatagcg ctgccggaca tcaataatct cggtatacga cgaccagacc gtgttgttct  26040
gtaactggtc agtggtactg tctgccgtca cacgtaccat ccggatacca aatggccggg  26100
gagggagatt atccactatc accgaggcca gatactgtgt ggttgttttc ccggtaatcg  26160
taatctcttt ttccaccacc cactgaccat agcgctcaag atggatttgc agcctgaccg  26220
atgtcggatt gcggtcgccc ttgctgttgg cctccaccag tgactgcacg ccgaacgtaa  26280
aacgcaggcg gtcaatattt gcagccgtga tggttctggt caccggattg tcgtatttga  26340
cctgtacacc aagcaccgtc tcggcgccgg acgattcaaa tccctccagc ggggtctgtt  26400
cctgctcacc gacgcggtat accaccttca cgccgtggat attcgtgtta ccgtcgcggt  26460
ccaccaccgg cgtctggttt accagaacac tttgcagacc gttcaccggg ccttctatcg  26520
gtccctcgct gatggcatcg atgacgctca gcagctgcgt ggatttaagg ttatccggtg  26580
cctcgcgggg cgtatgccct tttccgccgc cctttcccat ttattacccc gtaaaacgac  26640
aaaaccgccc ggaggcggtt ctgtctgaat ctgttctgtt gtcagcggcc aatcaccaca  26700
acctgaccac catctccttc atcagcggta ctgacttcct gggaaatcac gcgtgacccc  26760
acctgcatct cgccgtacag caccggcaac gtgttaccgt tggcaaccat attatccagc  26820
gacgagaaat acgtgttctg cctgccgtta tcggtctgcc tcatttcgga cattttaggt  26880
tttggtgcca gcatctgcgc cacaccgccc agaaccatcg acgccccggt catatacata  26940
ccggataccg ccgccgctcc cagccagcct gccgggttcc accaggcaac ggcaatcagc  27000
gccgcaccaa gcaccgcctg aaacaccccg ccagatttgg ccccgcccag acgcggcaca  27060
atatgaatca ccgcgccagg cggcagcggg tcatgcaggc tggttgtcag ggtatcagcc  27120
gtaacatcgt ctccggctat gcgtacctga taccagccgt cgttcagttt ctgccggaga  27180
ccgggcaact gtaccgccag tgcccggaca gcttcagcac cactggctac ctgcaggctg  27240
acgcggcggc aaaatcgttg cagatccccg taaaggcaga tgcgcgccat gcccggtgtc  27300
gccagatgga gtgcgtgcgt cgttgccatt tgtcggtata cctctcacgt ttactcagtt  27360
gttcaggaat atggtgcagc agctctccgt cgccgcagta aatcgctgcg tggttcggaa  27420
```

```
cggaggagcc aaagcagcaa atcaacacgt cgccgggctg cgcactggct gcgctgacac  27480
ggtaaaaccc cgtcgtctcc agattatcca gatagagatt gtcaccatgc cgccaccagt  27540
cgtcgtcccg gtgaaaatcc ggcatatcaa tccccgccag atgataggca tcacggaaca  27600
gcgtgtaaca gtcaaaaacc ccatgtttat aatgccgtcc ggtcaggtgt ggcacacagc  27660
ggaatttatg tacctggccg gcgcatacca gccaccacgg caggtcgctt tgaacctgca  27720
gcctgcggtc cacatcgctc agatacggct ggccgccagg atggctgtga accagcgcca  27780
caatatcccc ctgcgtttca gccctcagcc agtcctccgg cgccatacgg aaataatcct  27840
ccggcgcggc agaaatattc acacagggga gataccgttc tcccgcctgt gttctcacca  27900
cgaagccgca cgactccgca ggcgcacacc gtcgggcgtg cgccagaata tcctgttctt  27960
tcatgatgat ttactgtgaa agtttattaa tggagaggaa accgccaaag tttccggtat  28020
tgttacgcag ggcgcatccc cgggcgcagc ggctgcaggc atcttttgcc ggatcggcgg  28080
tagggttatc aaattcatct gcgacagctg gtcccgtata accgcattcg tcagagcggt  28140
atatccatgt acaggtattg gccagcataa ttcgcccggg gaagacacat ccgtccgttt  28200
cagtcggtgt tgccaggaca aatgtcgcac ttaccgccgt cagatcactg cactgctcga  28260
tcacccatcg gcttacggat tcctgctccg ggtcagcctc ctggttgccg ttttgaaaat  28320
tcacggcatc gagaaaccgg gcatatacta tcctgcggat gaccgtcgcc ccaaccaggc  28380
tatgcaaatc ctccaccatt ccggtcacca taccgtaaag attggatacc ttcagtgacg  28440
ggcgcgcagc tgcgcctttg ccgttcattt caaatccgca accgtctaca ggataaacgt  28500
catatttccg tccctgccag gtaaccgcct cccccttttc atttgcctcg ttacaaaaaa  28560
aataacgatc accgccagac tgtgtcagat cgatttccca caaagtgatc ctggcggact  28620
gcgccagttt agcggattcg ttcagcgtat cctgcgaaat gtcctgcatc actcctcctc  28680
agataacaac ctgttcaaaa gtcgtggtca cagtcaccca aagagagcca acgttaatcg  28740
accatttgcg gcaaatcacc cgaatttgtg tccaggtata aggcggcgtc cagagaaagg  28800
atttcactcc accgtggcgg gataaaaatg cctcaaggtt ctgatgttct cccttacgaa  28860
tccggaccgt tacgttatac ttcgccagat ggttgttcag cccggctgga cgccgttgtt  28920
catacccgtc acccagtttt atggaggtga cttttggttc tgattccact gtcatatcag  28980
ggcggatctt ccagttaaat gtttccattg ttatcgccct cctccagcaa taccccccgtc  29040
acgcgactgc tgttgccaga aatcaatggc ggcttttttt ccaatgttat atacggcctg  29100
taatgcctgc ggaccaatct gtccgttgcc ggcgtcgttg tggatttcaa tgttgtactc  29160
aggcgcaaac atcgccatcc ctcctgaacc ggctgccacg acacccagct taccgtcagc  29220
accacgacga agtggtaata ttgcctccgg tcctgcctcg cccatcaccc cggcaccttt  29280
ggcaaaagca aaaaatgtcg ggcgattaac aatgctgccg ctgtactggc tgagtcctgc  29340
cgaacggtac acgccgccgt ccgcattcgg aataaccgac agcgccgcag aactgtatgc  29400
ccctgatggt gtactgccgc ctgccgatgt gccaaagccg aacattgcca gcactgaacc  29460
caacagttta gaagccgcaa tacgtgcctc catttttgca aggtcagcca ggatggagac  29520
cgtcaggctc cggaaactgc cctttccggt cacggcaaaa ttcgcgatac tgtccgccat  29580
gccgttaaat gcgtttgtga aaacgttctc cgtcatgcct gccacattgc cgccctgcgc  29640
cagaaagtta tccagcgccc gcgacgcccc cagcgtccag tctccctgcg cagcgtcaac  29700
tttcgcattg taatccgccc actcagccag ccggcgatcg agactgccct tcagcgcctg  29760
ctccgcctga cgatattcgt cagaaccgta tgtccctttt gccttgctgt cgcgtttaag  29820
```

```
ctgctccagt tgttcctggt agtgctgctg aattttcaga cgctcttcgt atcggccacg  29880
ttgctgatcg cccataccca ttgtggccag cgccattgcg tgctgttgcc tgacgcggga  29940
ttcttcgtca gcgagctggc tggtcaatgt gagcgtcttt ttcttcagtt cattaagggc  30000
attctggtgt tgcaaatcct gttgtgagat atccagcttc tgtagcgcaa gcgcaatttc  30060
atccttatgt gccagtacgc tttgttcatc cgccgtcagt tttttaccgg acaaatcagc  30120
gatgcgctgc tgaaatgaca aaagctgctt atgcgcttcc gtcatttttt cggtcgtgga  30180
aagcttcgcg gcggtaatct gcccttcagt ctgcgcctgt tgctggctgt actgcaaaag  30240
cagtcgcctg gcctcgtcgt tgtggtaagt ctttggcttt ttcgcctgtt gtgacaacgc  30300
ctttttatga cgttcatttt cgcgctccag tgcggcattg cgtacagcag catcggcata  30360
ctgcatggcg gtaatgcgcg ccacctcccg ttggtgccgc agggattcag tttcattatc  30420
ccggttcagc gcggcgttct gctcgttccg acgtttctgc gtttcctgat aattacgctc  30480
tgcctgcgcc ttcgcatcca gcaggtcctt ctggcgtttc tgttcctgaa gttcgttcag  30540
ctgctgctga tcgtattcag tctgggaaga agacaccgtc cagggcgttt ttctgtcgcg  30600
cgcgattttt tcctgcagtg tcgcgatctt ttcatcgagc gtgtcttccc gcccgatatc  30660
cagcatccga tcccatgccc acttcgccgc atcaccgaca gcattccatg ctctttcaat  30720
ccagcccaga ttgtcgtgta cgtcccccat ccgcttattc atttcttccg aatacgcgga  30780
catggcaatt ttcgcggcat cagccactct tccctgctcg cccagtaccc tgatttgttc  30840
aagctgggtg gctgtcagaa aatgcagtgt cctgtccagt tctttcgccg cattcaccgg  30900
atcatcccgc aggcgtttaa actggcggat ggtttcatcc actgattgtc ccacgttttc  30960
ctgcattctg gtcgcggtac gggataccat tgccattgcc tgcccggtaa acgctccgct  31020
accgaccacc tgtgccagca cgcctgcagc atcgtgctgc gtgacgccat ttccggcgag  31080
cgacttcgcc atcgcattaa gctggcctgt ggtttttccg gcataactcc cggtcagaat  31140
aagctgttta ttgaacgtct cgctttcctt agcgccttca tagtaggcct tgcccagccc  31200
gtaaacagca gcagccacgc cgccagccag cccgccgagc atcatgccct tcggagacat  31260
cagttgctcg atccacccgg cgcggttagc gagcgtgata ccacttcccc gcagtgcccc  31320
gaaattccca cgggccagct caccagccag cacgcccagt tcacgacggg cagcagcgct  31380
tttcagtcct agcgtatggg tggcagttcc ggtacgctcc agtttacgga tataaatatc  31440
tgcggcgcta ctgacaccca gttcagccgc cttcacccgc agcagctcgg tacgggagag  31500
gccctgtacc gtcgtctgct ctttcaggcg gcgtataaac tgtgcttttt tctgcgtggc  31560
cagcgcttcg gcatcggtaa gctcacgggt cttcctggcg gtttcagaca ccagcgccag  31620
ataatcgccc tgtgagatat ctccgcgtcc tttcgcctgt cgtacctgcg cctggatacg  31680
ctgcagctcc tgcagaccac cgcttaactg ttttacactg tcaatctggc ggtaaaaagc  31740
agcacttgtc ctgtcctgtg ctgccgccac agccgctgac tgcgcctgtt cctcacgcag  31800
tttccttccc agtgcctcca cccgctgtcg cgtctgatcc acatccgccg ccagacgcgt  31860
actggccgct gcgcttttct ccacagcgga actgtacgcg gtactgctgg cagtcacttg  31920
ctccagactg gcggacgtcc ggcgcgtcgc ctccgtctgc ttatccagaa aacgctgcat  31980
ccgggccgct gaacgttctg agtcaccagc cgcatcgttc agcaattttt taatgcgcgg  32040
aacttcgttt cggaactctg cgctgtcgat acttaaatca atgaccaggt tcgctatctg  32100
gtccatagcg gacacctccg gtaatacctt cgcccaggat catcagttca tcatccgttt  32160
```

```
tttcgtgcaa cgactcagga tcagtgatca ggctgaacat ttctgcatcg tgatgcgtgc  32220
ctgtaaccag tccggaaatc agcgatttca gcgttgcaaa ctccgcatcc agcaacatgt  32280
cactgaagct gttcttcccg aaatgctccg cccactcacc cagctctgtc gcactcattt  32340
ccgccagcat ctgccgccag tctggtcgcc ggaactcacg cgcgagccgc atcacaaacg  32400
ccagctcccg gttcaggact tttccggcgt ggtcgtgtcc ttttcactcc cgctgtcgtc  32460
ttcctgcgat gccggaagac gcataccact cagggacaga accatatcag cgccacgtcc  32520
cagcgcctca taagaccatt ccagtctgac ggactcatac agggcgcggg cctcctcctc  32580
tttttgctt tcacacaggg agcgggatac cagccatgca ttaatatcca cccccatctg  32640
cataaattct gtctgacgct ctgcttccgt cagggtttca ggctgtgcgt catagtctgc  32700
cgtccgctgc tgaataaact tcagataatc cacacgttgc agggcagaaa gctcactgag  32760
cacgatggaa tgcccaccgt agttaaaggt gtctgtattg agaaacatga tgattttcca  32820
tagaagcccc ggaaccgggg cggactgata agagagggtt atgacgccgt cactgtcact  32880
gctgccaccg cgacaagact gccgtcactg ctgataccaa caatattcac gctgcccgcc  32940
ttcacgcctt taaccgtggc cacattatcc ttcagcgtga cggtggcgat cagcggatcg  33000
gcggtcgcaa cctgcagcgt tttatctgac gcgttatcag gttttaccgt aaatgtcagc  33060
gtggtggtgg ctccggcagc caccgtggca ctggccggcg caacggtcac gccggatacg  33120
ctgactacgt caggtgtatc ctcctccgca agagaaggac gcccgacgcc ggtgattttt  33180
acgctgcgtg tcatcacctc tttggacgtc acggttttac ccagtgaact cagccagccg  33240
cggaacacat caaccgtccc gttaggatac ctgatacgga aggcgcgaac ttcgccggtg  33300
tcaaacagct caaccagttt tttctgtccg gtctcaccgg gtttccaggc cagcgtggcc  33360
gtggtgtcac cgacgctttt ctgcccctgc gtagtgcttt tccagtcggc attttcatca  33420
tcaagatagt catcgtcttc cgcatctgca ctcatttctc cgggctgcag atccttaata  33480
cctgccagtc gcagccagtc atcatcagcc agtggatttt taaacgcatc gccgctgccg  33540
gtatacagcc agaatgtggt tccggcgcct ttcgttttta ccagtgggtt tggtgttccc  33600
atcatatcct cctcagttgg tataggtgat ccggtaagta atttctgcca tcccccacgt  33660
tgccatttcg ctgtcacgct ggtagtcata acccagcggg gtcatggtat cgataaggcg  33720
ctccagacca ctaacctctt ccagcgcagg aaagattttt tcttccatcc agatatcaag  33780
ctctgtatca ggagcctgag ccctcagaaa aactgccgta tggagagtag cctgccagtc  33840
atcctcatcg gtcataaggc ctgtatactg tgcgtctgtc agccagacag ctattgcggg  33900
taaatcttcc tgttctacga aagcaggaag tccatcaaaa agagtgacag gtgcgccagt  33960
cacggattcc agcttttcca gaacggcccg gcggattaat gtgtgtttgc tcatcagaat  34020
gcctcctttc ctccccggcc tgaaggccgg ggaggaaagg aggcggtttt ccggctaact  34080
gtcttttgca taatcacatt ttcctcttta atatgtgaag ccatgaaacg cgcatataaa  34140
taccggtttt accccacgac tgagcaggct gagcttttag ctcagacgtt cggttgtgtg  34200
cgtttcgtct acaactccat cctccgctgg cgtaccgatg cgtactacga gcgaaaggaa  34260
aagatcggtt acctacaggc caacgctcgc cttacggcgc tgaaaaagga gccagaattt  34320
gcctggctta acgacgtttc ctgcgttccc ctccagcagt ctttgcgcca ccaacaaacc  34380
gcctttgcta acttcttcgc cggacgggct gcatatccgg ctttcaaaag caaacggcac  34440
aagcaggcgg ctgagttcac tgcgagcgcg tttaaatacc gcgacggcaa gctgtacatg  34500
gcaaagaaca aaatcccctt agacgtgcgc tggagtcgtc cgctgccgtc cgtgccgtct  34560
```

```
accgtcacca tttccaaaga tgccgcaggg cggtactttg tttcgtgcct ttgcgaattt  34620
gaacccgcat cactgccgat cacctcttca atggtcggca ttgatgttgg tttaaaagat  34680
ttgttcgtca ccgataccgg attcaggtcc ggcaatcccc gccataccgc taaatacgcg  34740
gctcgcctgg cactactcca gcgccggtta agcaaaaagg ccaaaggctc aaagaaccgc  34800
gccaaagccc gtttaaaggt ggcccgactc cacgcgaaaa ttgctgattg ccgactggat  34860
gccctgcaca aggcatcccg caaactgatt aacgataacc aagttgtatg tgtcgaatcc  34920
ctgaaagtga ggaacatgat ccgcaacccg tcgctatcca aagcaatagc agacgcgagc  34980
tggggcgaac ttgtgcgcca gctccggtac aaaggcgaat gggcggggcg gtcagtggta  35040
gccattgacc agtttttccc gtcctcaaaa cgctgtagct gttgcggttt caccatgaaa  35100
aaaatgcctc ttgatgttcg taaatggcag tgccctgagt gcggaactga ccacgaccgg  35160
gacgttaacg cggcacgtaa tatcaaagct gccgggctgg cagtgttagc ccacggagag  35220
cctgtaaatc ctgaatcgct caaagcggct tagattcggc tcgttgaagt gggaatcccc  35280
gtccttcagg gcggggagca gtcaacgtga aagataaagc ctcagttgtt gtttcagggc  35340
ataccccagt tgcttcggca tttcctcgtc aatcaagctt tgtgtggcgc tttcgaatgc  35400
ctgagtcaat ggtccggaaa gaggaatttt cactacatcg attggataac ggtttttccc  35460
gttaacgcgt cgcataacat gccagcgtcc gttagccagt tgctgaataa aggcatcccg  35520
gaacagatat ggcccgattt taagcacact tccgcgatac agcagtttgc cctccgttt   35580
gctcatcctg acctgtgcag cgcccaactt tatggcggga aggtttcccc ggttaatccg  35640
tatccgggca gagcgtttac cgtctgtacc ggctttaaat aacctcaccc tctggcgaac  35700
cagcttcagc ggaagtcctc ttacctggtt atctccggcg acagtctccc gcgccacctt  35760
acgggttgcc actgaaacag ctttctgcgc cacgcgattc acagcccaga tactggcccg  35820
gggaaccatc tgtcggtcaa ggctgttcag attccggatc gcattttcaa gccctttcat  35880
cagaatgcct ccgggaaacc ccggccttta ggccggggag cagtcaaaca ttcctcccgt  35940
cctgcgccgg ttatccgtcg gcggcgtccc cctgcccagc agaataatac tgctgtctcc  36000
accagccgga gtgatgcgat ccacccagaa ggtgtcaccg agaatggtta gtgtgtccgg  36060
gcgcttcaga tggactgtca gggatgtttt gacaaaaaat gtaggcttgt ccccctcaat  36120
ccggacacct ccggcggcat acgacacact ttcaggatcg tcaaatacgc ccgtaagcgt  36180
ggcccctgcc agaacgccgg aggttattgt tgctaccgtt cccatcaccc ggaggatggc  36240
atcatcagcc tgagaaatcg cggtatcaaa caggttttcg gactgcgaca tatcgccacc  36300
cttacagttc aataataagt cctgcagcaa tcagctcgtc cacatcgtgt tgcgaaatac  36360
gcgccgggtt tcccgccata accatatcca gttcccggtt actgtccgga tcgatggcgc  36420
agatgtgtag tgtacgatgc gccctgataa gtacccgttc ggatctttgc ccgatcccgg  36480
gcggcactat ggattcatca ctgtcatttt ccacagcagg caaatgctcc gcctccgcct  36540
ccgcttcctc ttcccattcc atgacacgct ggctgagttc agcggcgctc ccggacacat  36600
ccggagcacg accaagccgc gtcgcaagct cccgcagacg ctgtatattc tcttcttttg  36660
ttgccataaa agatcctccc gcaatttgta acaataaagg cctgaatcag gccttttggg  36720
atgcttaacc gacagtgaca atgacaaact catccgggtc cggcaggacc atcagcggcg  36780
cagactgcgt catggtatat tcattcgccg ggtcccccac cgtcagccag tgtttgggat  36840
aacgggtggc ggcaacaata ccctccgcga gcgcctgtga atcctgaatg gcaccatagc  36900
```

```
agcggatacc ttctgccgcc gtatttccca gaaccagagt cccttcaggc aggtaacgct  36960
tttcggtccc gttatcagca acataggatg ttttagccac cacaatggcc aaatctccgt  37020
aataccccctt gaacgacacc acagccccaa ggtccttcac cgccgtttcc agctgagaat  37080
ttgaaccgcg gcgtgtatcc agtttttcac ggaacagctt aaaaccgttc agcagacgcc  37140
agactttccc gtccatcacg gcaatattga tcagaccgga tgcctggtcg cagtacatat  37200
ccagatcata agtcgggtca aaggtttccc tgtcctgctc tgaccatttt ttacctgtgg  37260
cctgaataat gttattcccg gcggagcgac caaaatccac ctccacggtg tcaaactgct  37320
cgccctgcat ggtgtatttc ccgttcagca ccgcactgac ggcctgcatc tcctccacct  37380
ggacgatggc cttctcttcc tgcttcaggt tatcggtcag aatgcgcaga cgacggtagg  37440
ccggatcgtt aagcctggcc gggtcttcac ccggcagacg ctcaacaacc tgcgcatagt  37500
taacttcatg cttcggtttg acataccccg gacgcagtac gcgcgtttcc ccgccgcggt  37560
tacgcagaac cttccctcca accaccggag atacataagc ggcaatcggt gtttttccgg  37620
taattttgtc cagcatgact tcctgggtag gaaatgtcac agtacggcga aaaaacaggc  37680
tcaggaagag tgggttaaat ttaactttct gctcggtata acccagcaac tggcgggtgg  37740
taaacaatcc cataaatggt gtcctccgga cgttaaatac gataaaggcc gcttcgcggc  37800
cttcttatta cggtaaagcg gcgtgactga cggcgcttcc ggcgaatgca tttgcctgct  37860
taatggcatc cacactcttc ggccatgcca gtgattctgt ggcaaaggtg ccgctcttcc  37920
agtacgtcag caggttttcc gacccgtcca gctcaagggc cagaaccccg accgccgttc  37980
cggccttctg cccgtcccag gccaccagtt tcccggtggt atcatccagc atcaggggcg  38040
tcagcatcgg tgtggccgcc gttatcccgc tgactcccgt tgcggtatgt gccggatcgt  38100
taccggcgaa aatgcggtta tccgcacgtt tctcaatagt ggtggtaaat gacatgctgt  38160
ctccttatca ggtggctgaa gtaccgggaa tactcatcaa caacgtcgtt tcggtatcat  38220
tactgtggtc tttaccgccg gatatggggc ccggggaatg agactgcatg aaagcatcaa  38280
atgcgttgtt catgctcagc cccgcattac cggatttgtc cggcgcggca gccagcaggt  38340
cacgggcctg atctgtggtc ataccaggca tgacagccag tttttccgcc aactcttcac  38400
ggcctttcgc ctcatcaagc gccatcacgg catcatgaag tgacgttgcc gcagcgatcg  38460
gcgatgctgc cagaatggtt ctggcctgtt ccaccgtcat ctccggcatg gccgccagtg  38520
tctgtgcgag tgtttcccga ccaccagctt cttccagggc aaggatacgg tcagcggtgc  38580
tggtcgtatc cgccggcgcg gcggcagcca gaatagactt cgcctgagca acgctcattc  38640
ccggctgccc ggccagcatc tgtgccagtg cctcatgccc cctggcctcc gggcaaccca  38700
gaattcccat tacgcgctgg ttttcctgcg tgacagcgtc agctgcactt aattcaggca  38760
tagtgcctcc tgtcttgtta ctgttgatag cttctgccat cacgccgatg gcgtcagcag  38820
cattcaccat tccatctgcc agtccggtag tgataatggc ctgcccgtca tacactgccg  38880
cctccgtcgc cattaccgca tcgacagaca accccgtgta ccgggccact ttttctgcaa  38940
acatctttct ggcctcgtcc attcgctgct ggtagtcggc atggacgctt tccggtaatt  39000
tctggctggg cgtcagatca gccttgtgtg cgccagaata gataagggtg atatcgatcc  39060
cttcctgttt cagtttttcg gcgtagctgg tatgcgccat caccacacca attgatccca  39120
ttctggacgt ctgggtcaca agacggtgcg aacaggctgc cgccagcaac atggccgccg  39180
aacaggctgt ttcatttgcc agtgcccaga caggtttctg ttcgcgcatc cggcaaatca  39240
tgtcagcaca gtcaaacgcc ccggcagcct gaccgcctgg actgtcaata tccagcagaa  39300
```

```
tgccttttac ctccggatct gaaaccgcct gttgtagccg ggcagtgata ccgtcatagc  39360
cggtcatccc tgaaaaggga cgcattccgc cgagtttatg aaccagtgtt ccggtcacgg  39420
gtaataccgc aataccgttc actacctgat aaaaacgtgc ctgcggcttt ccggtcgcca  39480
taaaatcgcc tgtgaccagt gccatatccg actgatccag actttcgtta ttaccgggaa  39540
tgtgcaggct gttaatgcct gactccctgc ccagcgcgca aaagaaaacc cgcgcatagg  39600
cgggttcaag cagcaacgga gcactggttg cctggctgat gatgtgcggg agattacgtt  39660
gcacgctttt cctcctccgt ctgacggctc gccgcgatct gttgttgata ggtatcggtg  39720
atccataccg gacgcgaaag tccggctgcc cgccgttctt cggattccct gacctgctgg  39780
cggaatatct cctggtaatc ctcgcccata atggcgagtt ctttttcata ggtactcagc  39840
ccggcctcaa tacgcatcac ggattcctga acctccttga gtccgtcaat cgccatacgt  39900
ccggcaccaa tccactccga gcggctccag ctggatcggg cctcccagaa ggaaaacctg  39960
gcccggggtg cccggataac tccccgtatc agcgcctcct ccagccagca ggaaaacatt  40020
tgtgtcgcca gccgtccggc aatgaaccgg cgccgcccca ggaaatagca ccaggactca  40080
ttggcagatg cgcgggcgct ggaatagctg acctgagaat aatcacgcga aagctgctca  40140
taagagaccc ccagcccggc ggcaatatac cggagcagcg cctgctccag cgctgaaaag  40200
ccattatcgg aatcctgcgc agtctgcaga ttcagctcat cacccgggta caggtgggga  40260
atttttacac cgcccagttt gatactgttg gtactgtaat agcgggcata atttgccagc  40320
atgttaacaa gaggcgtatc tttgttatct gccgccgtga tgtattcaaa ggctttctcg  40380
gaatcgagtt cgctttctat cgtggcggcg tacatggctt tgacaatcgc ggactgaagc  40440
tgcgttgcct gcagggtatc aagcatcttc agccgctcca tcacactgta aaactgattg  40500
gcaccgcgcg tctgtccgtc ctcaaccggc tcgaaaatat gtaacatcgc gggtcgtccg  40560
gacggcagaa aacgaggaat acgggtccag cgttccccac cagccaccgg ccagtcatca  40620
tcacagacat gataggcgag ggcttttcca ttccggtccg tttccactcc tgcgcgaagc  40680
tggcggtttc cgcgggcata ccccggcgtg tccacccgtt tcggactgac agccttgaat  40740
cgggtacgga aaacctgcgt ggtttcagcg tcccagacag gctggagaaa aatttcacca  40800
ttaaaggcgt gaacgcccac gccttcacgg atgaactctg taaaagtacg cttcccctcg  40860
gcatccattt cgccaaaaat accatcgcaa tattctgtcc atgcagcttc aacctcatcc  40920
acaaaactct tcgctgcgct ctcacgcata ccaagatagc gccagtttgg acgatagctg  40980
ataagaaaca ggtgtccgac aatatgatcc ttgtgcagcg ccaccgcatt tgctgcaata  41040
ccattattac ggaccagatc atcagcccgc gcattgccga ggcgcaacga aggcagcagc  41100
gcggcatcca cgctttccgc cgggggcatc cagtcagcca tctgtccgcc gaaaccgatc  41160
cccccgccgg tgtatcccag actttcccgc agcggcgtgc cgtgaacatc caccagaacc  41220
ggggtgcgct tcacagtctc acccccacag gtgcccggcg gcgaccattg cacagtgacg  41280
cctcaagttc cgcgacatat tttttcagat cccctaccga tgtcgcggta aattcaaccc  41340
gtcgcccgtc tttctgaacc gtcgccaccc gttttcccgt catcaggtca tgcagcgcga  41400
cgcgggcttc ctgtagctca gtgattgttg ccattaactc ctcctgccag cattgcggcc  41460
agttgttcaa gtgtcggggt atcctgctct tcgcttttcc ttgatgtcgc cagcgcctcc  41520
agatccagtt gccagcgctg cacagacacc cgtaacgctg cactggcata gacaagacaa  41580
tccagcgctt cgttacgacg tcctttggca tcccataaca gccggaattt tccgttaacc  41640
```

```
agtttctcca ccagctcttc ggctaccagt tgcttcgctt ccacctccgt aaaaacatcc  41700
ggattatccg gaaagcggat cgcataaggc gtggcttcgt cggcaggcgc agtaaccgcc  41760
cccattctgg cgtaaagcat ttctttggca gtatcagtac cgatttcgca caggaatacc  41820
ccgctctggt tgcgtttttt aggcatggta ataacgggtt ttccgtaaac ggaggcccct  41880
ttgacaggca gcacgcggaa aatgccgtgt ttttttgagc gtttatagac gatttctgca  41940
tcgataccgc cgatatccca gcagatacgg gaaatggaaa tatccgtccc gtcagcatga  42000
cgatattttt tattaatgac ggcatccaca cgctgcaggg tatcttcatc atcatgccgt  42060
cccatgataa tttgcttatc aataaggaaa gcctcttcgc ccggcgccca gccccagaca  42120
tacatttcat aacggttacg ctgggagtcg ataccagcgg tcagatacac cacccgctcc  42180
ggaaccggcg ccgcataatg aatcactttt tccagcaaaa gctcatggct gagtttttcg  42240
gccaccgcct cttcataagg ctcgcccaac gtggtgttta taaaggtttt cacaccattt  42300
ggatctttca gcgcatccag ccagtcataa ataatctgta tccaggtggt aaagggactg  42360
taagccgtcc agatatgaaa ggtaatggat cgtggcggcg gaacctcctc accggacgcg  42420
ctgaaataag ccagtccatc gcgtgtccac atgcctgtgt tatcgcaaat ccagcggcct  42480
gctttctgat caagttccga ttgacggatc acgcatccat tatgttcaca aaggtaatac  42540
accgtctccg gcttgctttt ctcccatttc agaccgaacg gcgtactgcc atcaccgaat  42600
ttaaggtact gttcttcgcc acaatgcgga cacggtacat gaaaacgcat aaaatgcgcc  42660
gattcatttg ccgccttttc aatctggcat gaccctttga cttttggtgt ggagccccga  42720
atggatttag gccagacaga accttcaata cgtttatccc ccagcagcgt cggcgaacct  42780
tctttctcga catccggctc aaaagatgac aattcgtcat agcagaccac atccaccgat  42840
ttttcacggt agtttttggc tgctgcaccg ccgaggcacc agaacccgac accggaagaa  42900
aagcgtttca gggtaagcgt gttatcacga tgtttacgcc cgaaccaggg ggccagctcc  42960
agcaatacag gaacatccct gatagtcggc tccacgtggg atttcataaa atcctcagcg  43020
gatgagtcgg tcggctggaa cagcaggctg ttgcgcgact tgtgctctat gaaatagcct  43080
tccacccca gcaacatttt ggtatagccc acgcgggcag acttaatgag gtttacaacg  43140
cggatcagtt catacccat cgcgttcatt atcgctacct gaaacggcag cgtttcccat  43200
ttgccggggg tgtaggagga ctcttttggc agatagtaat actcatcagc ccactgcacg  43260
gtggtaagcg gtacgggaat atgaagcgct atcagcccgt tagttatggc tctgttggca  43320
ttattcgccc tgcgctctcc ggaaatcatc ggtccacttc tccacatccg ctatcgtggc  43380
ggccctgcct gacgccctgg cgatttccgt tctgaccaca tcgatgtgcg actggcacag  43440
atcaggatat ttgcgctgta ataccagcgg tacccttgac agtatccctg ctatttcctg  43500
agccacccgt tgcaggatgt aggtgaacag ttcggtctca agaaccagcc cttcgcgctc  43560
agcattttta agttcctgcg catccgcctg ggcttttgtc aggcggtagc gctcatagtc  43620
gatggtgccg ggattaagat ctgattccgc agcggcacgt aaatcatcaa cctctttacg  43680
cagcttttca ttttcaatag acgcatcacg ctccgcgtac catgaaatcg ctgccgcggt  43740
gtcgaacact gcttcgttac cttttcctcc tccggaaaca agtggcagcc cctggctttg  43800
ccaggctgtg acagttctga cgtcacaacc aaaaatttca gccagttttt ttttgttcac  43860
gttcatggaa aagtctcccg gaaacaggaa aggatctgcg atcttcgttt ttaactaaaa  43920
acgttatcca gcagatcctt tctttttct aaaaaaacct ttaaaaacag gaaataaaca  43980
ataagaagaa cggatctggc ttttctctga aaattttcat aaggagtgaa atcctgcgac  44040
```

```
gctgccg                                                            44047

<210> SEQ ID NO 2
<211> LENGTH: 43931
<212> TYPE: DNA
<213> ORGANISM: Artificial Sequence
<220> FEATURE:
<223> OTHER INFORMATION: Synthetic DNA for Salmonella Bacteriophage
      UAB_Phi78

<400> SEQUENCE: 2

ctagggcggc ctgagaaggc ctgagagagt cgcttagtgt gggccaaagg gagaccggag     60

gccgaccgag agcgagcgag agggacacgc ggaggacgct tgacagcgtg tgcgggcgtg    120

ggctatctgt tcctttgctc ctcacttcgt ttgctccgct tacgctacgc ttcactcacg    180

cccttgtgta ccttagggac ttccttatcg tgtaccttgg gacagtctta gtaaatacct    240

tagtcacttc cttagtagct tccttagtga gtagcttagt ggctatctat tgctgtctta    300

gtgttacctt agtgattgca tagctacgct ataagatgcg aataggtcgc ggtcggtaga    360

ccgctaaaga aagagaagaa taataagatg cagtcggagg aacaccagaa cacaggccaa    420

cctatcctag ccttgtatct attgcttttt ccttggtcca acacgttaga caacctatct    480

tattcttagt gaggtaactt agtgttgaca aggtaggttt agtgtaatac tatgcatcac    540

gtaggcggtg ctgaggcacc tagtagccag ctagtaaggc atatgaagtg actagtgtct    600

acattgctct ttaataatct ggttgtgtct cgataggtca actaacaaaa ggtgaactgt    660

catggcttta attagtatga agaagttaaa cacgggagag gctcttaacc tatttaactc    720

cgaggagtgg gatctatcta aaggtgtata tacttgccct tgcttcaaac gaaataagga    780

aacaggtgaa gttttgcgtt tgcctgataa ggtaaaagta gattacttta tacatatgaa    840

aggtaatgct tctcttaaca gattgcacat acaaaagagc gcagctaaat ctatagcatc    900

tttgttgtgt aaacaattaa aggatataaa agagatacca aactattaaa gatatggtcg    960

gcgcaagctg gcctatcaag acacaaccta gctctttaac aatttgctta gtgtaaccta   1020

tgtaagccgt ggttaattac ttattgaatg aggaattaac tatgacaaga ctgtacaaag   1080

atgattcaag cggcgcttat tacacacttt gcgggaggac tttaatactt ctcaatggtg   1140

caacaggtag acgtcttatc tcttatcttg ctacacatag agcatgtata catagtggtt   1200

tgcagctagt tggtaataac tttaagagga agcaactatg atgaccttga accgtagaga   1260

agctagcgca gtctttacta tgttgtgttg gatgatacgt aacaacgaaa tgatgactga   1320

tgatgagcta gcgctttacc atcgctttcg taatgaaggt tgggatgata ctgtaaacaa   1380

ggaacgcaac atactgaagg agctaatcaa tgtttaaaca cacgatatac acgcaatgca   1440

gcatctccgc aggtcttatg aattggtggg gcaaatctgg gattaagtgc tacaatctga   1500

atgactctag cactatgtat gaggttactc tcatgagaag atacaaccat gatacgctgt   1560

tatgggtact atctgaatgg ggtatagact atgaagatgt gattacagaa gaaatctaaa   1620

ttagttgttg acaaccacgg cttacaaggt tacattaagc atcaagaagt aaagttcttt   1680

aacaaatcag gtgaactaag tcggataggt taacgcatag gaggcttgcg agtatcctag   1740

agggtaacct aactaactaa gaggatttaa ttatgtctta ctctaacatg acttacgcta   1800

acgtttataa ccacgcttac tccttgctgg atgagtacat tcgatatgaa gatgtacgcg   1860

attatgacga agcaactgat aagattcatg aggctgcgga taatgcggtt cccgtctatt   1920

acaaagatat tttctcagta atggctagcg gtggaatcga tcatgaattc gaagattcag   1980
```

```
gcttaatacc ggacactaag gatgtgacac gcattctaca agctcgcatt tatgagcaac   2040
tgactatcga tctgtatgaa gtggtagcag acttgcttaa tgaatatctt gaagaagtag   2100
aagctgaaga agacgaggag gaggaataaa tgtttgctgg taagctttat aacttcatgt   2160
tctccgatgg tatcatgctg aaatgctctc ttgctttcgc taaaatgcga gaggagacac   2220
ttggaactac atatacacta attatgtgac actataagag gcttaacagg tcatccttgc   2280
gagggtgacc gattaaacca acttaaagag gtgtaaacat gaaaactttg attaatgtgc   2340
tggcttgctt cctacttggt tctatcatct tgcttgctag tgctggcgtt aagattgaat   2400
ctcatcatta tgactttgga acttgcaaac atttgatggt aggcggcgca atgtggcata   2460
catggtatga gtgattagcc tatagctcat ttagtgggct atgtgatatt cacttaacta   2520
actaaggtaa gcaattatga ctactgaaaa cactgttgta tccgtccgtg aagctgcaac   2580
tgctgaaatc aaggtacact tagatacaat tggcaccgcc tatctgaaag ttggttccct   2640
cttgaatgaa ctacgcggtg actttgagaa tcaacgtgac tttctgtctt atgtagaagc   2700
tgaattcagc attaagaagg cacaatgcta taacctgatg aacgtagcgc gttgctttga   2760
cggtgacgag cgtttcaaag gcgttgccat gcgtgtcatg ctcgccctta tcccgttcgc   2820
tgatgatggc gcaatcatgg ataaggccgc cggacttgcc gctaacggcg aactagacac   2880
caaggccgtg aatgcacttg tatcgccgtc taagcctgtg aaggctgaag ccagccaatc   2940
acaagccgaa gacacaaaag ccgctgagaa ggccgctcct gtagaatctg aggcattaca   3000
aagcgtgccg catgaggtag caccggaagg cgacgaatcc gcaccgtggg aggatgcgcc   3060
agcgactacc gaggccgcag cgcctaagct agataatgct gagaacaccg agaacgcggc   3120
tatggctagc ctgctggcgc aaatcaagac gctgaccgag caactgaccg cagcaaacga   3180
ccgcatcgca gaactgacca gcacacgcga gaccaagaag gcagccgcgc ctatgttgcc   3240
tcaattcaaa tctaagtgct tctatgctcg cttaggtctg agcgcggagg aggcggagaa   3300
gaaaacagca gttaataagg ctaaacgtga acttgttaag cttggatacg gagaaggtca   3360
tgaagcttgg gatctgattc aagaggctgt taccacactt actgagaaat aatagttgac   3420
ttatagagcg tcattaagta agatggcgct caattaagtt atctagcact taacggagta   3480
aacaagatgc aagacttaca cgctatccag cttcaattag aagaagagat gtttaatggt   3540
ggcattcgtc ggttcgaagc agaccaacaa cgccagattg cagcaggtag cgagagtgac   3600
acggcatgga accgccgcct gttgtccgaa cttattgcac ctatggctga aggtattcag   3660
gcttataaag aggagtacga aggcaagaaa ggtcgtgctc ctcgcgcatt ggcattctta   3720
cagtgtgtag aaaatgaagt tgcagcatac atcactatga aggtagttat ggatatgctg   3780
aatactgatg ttactcttca ggctattgca atgagcgtag cggagcgcat cgaagaccaa   3840
gtgcgtttta gcaagttaga aggtcacgcc gctaaatact ttgagaaggt taagaaatca   3900
ctcaaggcta gccgtactaa gtcctatcgt cacgcgcaca acgtagctgt agtggctgaa   3960
aagtcagtag cagaaaaaga cgctgacttt gaccgttggg aggcatggcc caaagaggct   4020
caattgcaaa ttggtactac cttgcttgaa atcttagagg gcagcgtatt ctataacggt   4080
gaacctgtat ttatgcgtgc tatgcgcact tatggcggca agactattta ctacttacag   4140
acttctgaaa gtgtaggtca gtggattagc gcgttcaaag agcacgtagc gcaattaagc   4200
ccagcttatg ctccttgcgt agtccctcct cgtccttgga aaaccccatt caacggtgga   4260
ttccatactg agaaggtagc tagtcgtatt cgccttgtaa aaggcaaccg cgaacatgtg   4320
```

```
cgcaagttaa ctcaaaagca gatgccaaag gtttataagg ctatcaatgc cctacagaat   4380
acgcaatggc aaatcaacaa ggacgtatta gcagttattg aggaagtgat tcgcttagac   4440
ctcggttatg gtgtgccgtc cttcaagccc ctgattgaca aggagaacaa gccagctaac   4500
cctgtgcctg ttgaattcca gcacctgcgc ggtcgtgaac tgaaagaaat gctctcccct   4560
gagcagtggc aacaatttat caactggaaa ggtgagtgtg cccgcctgta taccgcagaa   4620
actaagcgcg gttcaaagtc cgccgccgtt gttcgcatgg tagggcaggc ccgtaaatat   4680
agcacctttg aatccattta cttcgtgtac gcaatggaca gccgttcccg tgtatacgcg   4740
cagtctagca cgctctctcc gcagtctaac gacttaggca aggcattact ccgctttacc   4800
gaaggacgcc ctgtagacag cgtagaggcg cttaaatggt tctgcgtgaa tggcgctaac   4860
ctttgggggt gggacaagaa aatttttgat gtacgcgtgt ctaacgtgtt ggacgaagag   4920
ttccaggata tgtgccgcga catcgccgca gaccctctca cgttcactca atgggccaaa   4980
gcggacgcgc cttatgaatt cctcgcatgg tgctttgagt acgctcaata ccttgactta   5040
gtagaggaag gaagggccga cgagttccgc acacacctgc cagtacatca ggacggttcc   5100
tgctccggta ttcagcacta tagcgctatg cttcgcgatg aagtaggggc caaggctgtt   5160
aacctgaaac cgtccgatac gccgcaggat atttacgggg cggtagcgca ggttgttatc   5220
aagaagaatg cgctatacat ggatgcagac gatgcaacta cgtttacttc tggtagcgta   5280
acactgtccg gtgcagaact gcgagcaatg gctagcgcat gggatagcat tggtattacc   5340
cgcagcttaa ccaaaaagcc agtgatgacc ttgccttatg gttctactcg cttaacttgc   5400
cgtgaatctg tgattgacta catcgtagac ttagaggaga aagaggcgca gaaggcagta   5460
gcagaagggc ggacggcaaa caaggttcat ccgtttgaag acgaccgtca agactacctg   5520
actccgggcg cagcatataa ctacatgacg gcattaatct ggccttctat ttctgaggta   5580
gttaaggcac caattgtagc gatgaagatg atacgccagc ttgcacgctt tgcagcgaaa   5640
cgcaatgaag ggctgatgta caccctgcct actggcttca tcttagaaca gaagattatg   5700
gcaaccgaga tgttacgtgt gcgtacctgc ctgatgggtg atatcaagat gtcgcttcag   5760
gttgaaacgg atatagtaga tgaagctgct atgatgggcg cagcagcacc taacttcgta   5820
cacggtcatg atgcaagtca ccttatcctt accgtatgtg aattggtaga caaaggggta   5880
actagtatcg cggtaatcca cgactctttc ggcactcatg ccgacaacac tctcactctt   5940
agagtggcac ttaaagggca gatggttgca atgtatagtg aaggccatgc acttcagaaa   6000
ttactggacg agcacgaaga tcgttggatg gttgatactg gcatcgaagt gcctgagcaa   6060
ggggagtttg accttaacga aatcatggaa tctgaatacg tgtttgccta atagattaat   6120
aaacatacag gtcagccttc gggctggcct tttctttcac ctactacttg taacatttca   6180
ttaacaagtc taacgtgttg gacacgatgc ggatttaagg gacactctag gactaaccgt   6240
cggagacgga aagtaatagg tagtaatagg aagtagtagg taagtaaggt aactataggt   6300
tacttaggtt acttcttcct attacctcct tcttaatagg gagggcagac actaggttgt   6360
ctaacgtgtt ggacagaacc tatttacgtg acactattga acaagattaa actttcaagg   6420
aggtaacatg cgtaaatcat tagctcaaat ggtagagcaa gcaggttata ctatacatgc   6480
agacggtact atcacaggta agcgcggaaa tatcttgaag ccttggcttc agacttccgg   6540
ctatcaggtt gtgaacattg tgttcaagaa gggaacaaga accacaacac ttgtgcatcg   6600
tattatcgca agtaaatact gcccatgctc agatcaacta gctaatgatg taaaccacaa   6660
ggacggagac aagaccaata acgtctcctc taatctggaa tggattacac gcagacagaa   6720
```

```
ccgcaaccac taccttgggt ttgaagatta catgacactt acggcaaacg atgcccgtag   6780
aaagaacaat gagcgtacta tcgctcgtcg taaattactt aaacaactta ataagtgagg   6840
aataaatcat gcgtaccaac ttcgagaaaa tccgtaaagc taaccgtgac tttgacatgg   6900
aagttaaggg gaagaagttg aacaaagtca agcgcgaccg ttctgctaaa cgtgcgtgga   6960
tggaggctgc ataacatggc gattgtgaac aacattcctt gccctgagtg ccaacgcaac   7020
ggacatgata aatcgggcaa tcacctcatg atatttgagg atggcgctgg ttactgtaac   7080
cgtggtcact tccataatag tggtcggccc tactaccaca aacccgaagg tggcatagaa   7140
atcactgagc ttcctattac tggcaacatt aagtatacac cttcacagtt ccgtgaactt   7200
gaaaaggaag ggaagataag cgaccctaag ctgcgcgcca ttgcacttgg cggtatgcgt   7260
atgaaagatc gttgggaggt gatgaatgac gaagaaaggg cggagcaaga agcagaatgg   7320
cagcttgacg ttgagtggtt ccttgaactt aaaaggaaga accttgtatc acgacacatt   7380
cgcggagaca tttgcgccct ctatgatgtc cgagtcggtc atgatggaga aggcaaggtt   7440
aacaggcatt actaccctcg cttcgaaggt ggcaaacttg taggcgctaa gtgccggacg   7500
ctacctaaag actttaagtt tggacaccta ggtaaattgt tcggcaacca agacatgttc   7560
ggcatgaaca caatgtctaa cgtgttggac aagggacgcc gtaaagatac cctgctcata   7620
gtaggtggtg aactggatgc cttggccgca caacagatgc ttctggattc tgccaaaggc   7680
acgaagtggg aagggcaacc ctatcatgtg tggtctatca acaagggcga ggcttgcctt   7740
gaagagatcg tgcagaaccg tgagcacatc tcacaattca agaagattat gtggggcttc   7800
gacggcgatg aggtagggca gaagctgaac caacaagcgg cccgcctatt ccacggtaag   7860
tcttatatcc ttgagtaccc tgctggctgc aaggacgcta acaaggcgct tatggctggc   7920
aaatctaagg agttcgtcga tgcatggttc aatgccaagt cgtcagatga ggtcttcggt   7980
agccagatta aatccatcgc atctcaaagg gataagctga aggctgcacg accggaaccg   8040
ggattgtctt ggccttggcc taagctgaac aagataaccc ttggcatccg taagcatcag   8100
ctaatcatcg tcggcgctgg ttctggtgta ggtaagacgg agttcctccg cgaagtagtg   8160
aagcatctca ttgaagaaca cggtgaatct gtcggtatta tctctacgga agacccgatg   8220
gttaaggtct cccgcgcatt cattggtaag tggatagata agcgtattga actacctcca   8280
accaatgacc caagggaaga tggctaccgt gaggtattcg actacacgga ggaagaggcc   8340
aacgctgcta tcgactacgt tgctgacact ggtaagctgt tcgtggctga ccttgaaggt   8400
gactattcaa tggagaaggt agagcagact tgccttgagt tcgaggcaat gggtatttcc   8460
aacatcatca ttgataactt aacaggaatt aaattagatg aacgaaattt tggtggtaaa   8520
gttggtgcgc ttgatgagtg cgtcaaaaga atcggcacta tcaaagaccg acatccggtt   8580
actatcttcc ttgtctcgca ccttacacgt ccttcggggc aacgtacctc acacgaagaa   8640
ggtggcgagg ttatcctttc tgacttccga ggctcaggag ctatcggatt ctgggcttct   8700
tacgccttgg ggattgagcg taatacaagg gctgaaacgc ttgatgaaag gactaccacg   8760
tacatctcat gtgtcaaaga ccgagaccaa ggcatctaca ctggcactaa ggtgatgctt   8820
aaaggcgatg ttagtacagg tagattgatg gaaccgacaa gcacgtacta ggtcatttga   8880
tacaggcgct ccaaaagagc aagctgtacc tgatgaatta ggtgacacta tagaagataa   8940
cacacaggag ttttaaatgg atgaactagg cttttggttg ttcatggttg tatgtatcgt   9000
tatgattaac ctagacaaac ttgccatgct aattaagtag tgtccttatc agggcttgtc   9060
```

```
caacatgttg gacaggctct tattaagcac attaactaac tggagattaa ctatgaagct   9120
taacttaaaa gtaggtgaac gtgtacgtaa tattcgtgtt ggatctgcac gcgcagggtg   9180
gcaaggtgcc gtcatcgttg taacagagga ggagtacgaa gttcgatggg attgcggaga   9240
gaagcaggct tatcttcgtc gcttctcaca caagaacctt gagcgcacac atgtagcaag   9300
caaatgcacc tgtgtacacg atgaactgtg tgaccgctgt gctcgtcaag tcagtaaggc   9360
actgacattc atggagcggt atggtgcagg tcacaagaca cttgcggaag cagcgtggaa   9420
tgtgctcacg atcgaacgct ctaatggttg gcaaggtact gaagcgtgag cgtcgtaatg   9480
tgatcacagg ccagacacaa gcagaaatgc aagcacagta cgggccagca aagggcggta   9540
tcatattcaa cacccgtaca ttagggcgca gtacaggtca agccttttcg catcttaggc   9600
gaggccatgt gtaatcctgg tattgctata cgttatgaag atgtagacca tgcaatatct   9660
gaaggtacga gtaatagagt tgtattgaac agacactttg aacaggtgtt acgtgacact   9720
ataggtgagc gcaagggctt tacctttgag cgcggccatg ttacatttaa ccctatcgtt   9780
acggaggaaa cctatgtcac gcaatgacag caagcacagc ctgaagttcc ttgagcagca   9840
tgaagacctt gcagcaaagg taactaacca agcattcctg tttgcacaac tcacactggc   9900
tgaagctaag aagaacagcc ttactcgtga acagattatt aaggaaggtt gccgtggtgc   9960
aactcgtcgt attaagaacc acagaagtgg tgctcgctag ttaataagtc gtggcttgtc  10020
taacatgttg gacaggtcac tatcatatta attggaggaa ttactgtatg attaattacg  10080
attctgattg ggattacgaa gattcattac agcctgaacc ggagacacca gactacaagt  10140
ttgaaacgga ggcaatgtat gaagactatt aaactaagta aagtttgctc ttgcggtaaa  10200
ggttatcgca gtcgtataga tggtaagtgt gggcattgca gatctaagaa agaggctgct  10260
ttgtttgata agtaccacca tgaattagcc tataactatc ctcatctcac acctaattct  10320
ttattaggaa ttggctatag ggttaaatac tttggagcag tctatgaaat caattgattg  10380
gaagagggag gcggaaggtc gtatcctagt gatggatgcg gaagctaaag gtctgcttga  10440
tgctatccgc tacgggcatc gtgaagatgt gcatatcatt tgctgcatgg acttgcttac  10500
taccgaggag ttcctcttct ttgacccata tgagatgcgt gaccctgaag caagagaacg  10560
cctgaaagag tgggaaggcc atcaagatgg tgacttggtt gatggtgtta acttcctgaa  10620
gtactgtgaa gctatcgtgt cacagaactt cttaggatat gacggcctgc tctttgagaa  10680
agcattccct aatatctgga aaggctttaa ctacacagag aagcgcggca agggcaggct  10740
ccgtgccgac ctgtgtcctg tgcgggtcat ggacacactg gtgatgagcc gcctgttaaa  10800
ccccgataga cgcctccctc cgcaagcata cgccaaaggt atgggtaacg tcgcccctca  10860
ctctattgag gcgcatggta tccgtatcgg tcgctataag cctgagaacg aggactggtc  10920
taagctgaca gaccacatgg ttcattgtgt acgtgaggac gtggcgatcg gtcgtgacct  10980
gttcctgtgg ctatataatg gcgagtggat ggagcacaag cggcgtgtgg gttgtgactt  11040
gataggcctt ggcattgaga cggcctttca catggagtct attgtagcac tggagatgtc  11100
ccgtcaagcg gagcgtggct tccggttgga tatagacaag gcactggcac gatgccagga  11160
acttgaccag aagatcgacg agacggttgc agcattccga cctcacatgc caatgcgtat  11220
caagtctaaa cccttcaaac ctcaagagaa gcaggagcag gtagatgcag caaactcatt  11280
tagtttacag aatcagattg gtgttacgct tggagccgat gctttcattc atgccgagcg  11340
gcgctccgat aggaagactg tatggtcagt cactactaag tcaggtgatt ggtcggctac  11400
tgtcaagaaa gacttccctc acatccgagg aaacatcaat gatactccga gcattaaaca  11460
```

```
catcgggcca tatacacctg tcaccttcga agatatcccg cttggcaacc gagataccgt  11520
taagcaggtt ctgtatgact ttgggtggcg gggtgttgag ttcaacgaca ctgaacaatc  11580
ttatctggac gagcatggag tgttgcctaa accttggagt ggaaagataa atgagaagtc  11640
ccttacttta tggcaggaaa gggctgcacg tgaaggtaag tcagtccctg attggtgctt  11700
gggtatcgct gcatggtaca tactcgtttc ccgtcgtggt cagatcctca accgtggtga  11760
tgttgaaacc ttcgatgcaa cggggcgttg gccctcgcaa gctggtgtac gaaagtgtcg  11820
cggccttata cctgtagcct ttaataagga gctaggtatc aatgcacaga cgtactacga  11880
aacgtatggc tactggccta cgtccgataa ggatgacgga gagtggcgtg ttcccgctgt  11940
tgctatttct attggcactt ctacgttccg tatgcgtcac aggaatgtgg ttaacatccc  12000
cgctcgtggc ctttaccctc ttcgtgattt attcatagct ggtaaaggta agatgattct  12060
tggttgtgac ggtgcaggtc tggagttgcg tgtactctcg cacttcatga acgaccctga  12120
gtaccaagag atcgtcctgc atggtgacat tcatacacat aaccagctca aggctggcct  12180
gcctaagcgt gatatggcga agacctttat ctacgcattc ttgtatggct caggtattgc  12240
caacctcgct gcggtatgtg gcgtaactga agatgagatg aaggaagttg ttgcacgctt  12300
tgagatagag ctaccttcat tggcaagact tcgtgagaat gttattgcgg caggtaatcg  12360
atatggatac ctccaggcac ctgacggtca ttggggccgc atccgtatga gcggtggtgt  12420
acttaaagag cacaccatgc ttaacgtatt actccagatg acaggctcat tgtgcatgaa  12480
gtatgcattg gttaaggcct ttgcagtcat gcgccgtgaa ggtgtggcac tagatgacat  12540
gggaaatccg tgtggcgtgg ctaacgtaca cgatgaaatc cagatggaag taccagaaga  12600
ggaggtgttg taccttgact atgaattgcc tttcacgctg gaaggtttcg aaaatgagaa  12660
gcaagccatc aaagctgtgt tcgaccctga agagaaacgt gtgcatgtgg actcagaggg  12720
tcgtatgtgg tctgctgcta acttggttga agttgatgct gctgctggtg tgctgcgttg  12780
tcagcgtcgc taccacaggg ctggtcatat tatcgctgac gccatgactt gggctggcaa  12840
gtatcttaac atgcgctgcc ctatggctgg cgaatataaa ataggtgcaa gttggaagga  12900
gacacactaa tgcaaacagt tattatcata ggagttgtat tattattcgc ggtagtattt  12960
tgggccttct caggtactga cccagattgt gatggtaatt acgattaagt tagattcacc  13020
taaattcttc ttacttgatt taggtgacac tatagaagga cagccaaggt aatctaggtt  13080
attaaggcag tataggtaat taggtaatat aggagaataa atatgtctat ggtaactatc  13140
cttgtagcaa tgtctcagta cctgcgtagc ctgtctgttc gtatgaagaa caaggctatc  13200
aaggcaatta aagatcgcat cgctgtagtt gaggcggagc aggtagagtt agaagagagc  13260
cgaagcaatc gcatggttga ttgccacaag cgatactatg catcttatga agaccttcgt  13320
gctcgatacg tcaaagaggt ggctgagtta ctggagcgtc atgagacgga gcagcgtaat  13380
ctgaaggcag actttgaaga gaacaagcgc actattgcac ttacctctca ggctgcatct  13440
aatgaactga agcgtgaact tgtaatgctt agttctgaac tggataacct aaccaagtaa  13500
ttaggtgaca ctgtagaaca ataggtcgat taagttcggc ctatgattgt atcgtgtaac  13560
caaaaggagg aattaattaa tggctcgtaa tgaatttaac tttggtgctg aaattgccac  13620
ttcaactggt ggggtattca agaacccaga tgttggcgac catgaagctg ttatctcagg  13680
catcattcat gttggttcct ttcaagatat attcaagaaa ggtaacacta ctgaagtgaa  13740
gaagccagct aactttgtac tggtcaaggt tgtgctgatg ggcgatgaag acaacaacga  13800
```

```
tgatgactct cgcatggagc agtggatggc tgtgccgctg aagtcaggcg acaaggctac  13860
gcttaccaag ttcctgaatg cagttgaccc gcgtgagcag cttggaggtt tcgatgactt  13920
cattggagaa tgcatgaccg taagcatggt tggcgatgac aaaggtggta agaatgaaga  13980
tggcaccttc aagtatgtta actggaaggg attcggcggt atgccggata agctgaagaa  14040
gctggtactg gctcaggttg aagaggaagg tctgaccatg acaggtcaca tcaccttcga  14100
caagctgacc aaagacatca tcgactctat ccctgcacac cttgtccgtc agtacctgct  14160
aaatgagaca cctcgtggca agaacctgtc agtagctggc tctcacgtag agactatcat  14220
tgctgaagct cgtgccgctg accctgagtg gaagaaggcc aagaagaaag acaatgacgc  14280
tacaccggaa gaccgtaagc cgctagacac cggcgctgct gttccgcagg aagtgccgga  14340
agcgcagaat gccccggcac ctgctatgga tgaagatgct gagtattaat taatcaagga  14400
ggtttaatga aagtagaagc agtaacccta cacttcaagc ccggcgtaac gtcgctgggc  14460
ggcacgcagt tcatttcttt tagcgagggc aaggcatacc aagacttgca ctacattacc  14520
cgtgaagggc agcacgtcgt gaattatagc gacccggtga ctggcaaacg tcacggcatc  14580
ggattcccta tgacggacat ccgtcagacc aatacgattc tgtaagtcta acgcgttgga  14640
caaaatggta tcctcttatt taggggacac tatagaagag agaattttaa tcggcgataa  14700
tgccaccatt aacagaagga gaatttaaat atgttcacta tcgaaactat cgtaaaccgt  14760
gttgttaaag gcgctaccct ggtatccgtt gagtctttca ttatcgtcga tgaagctggc  14820
tcgctggtag ctggtactaa ggcttatgat acccgtgaag aagctcaggc taagattgac  14880
cgcatgggta actttgctgc tggtctggag ttcgcacgtg cttgcttccc ggagcaggct  14940
gacaaagctc agattggtaa ggctaacatc gtagctgaat atctggactg gattgaagca  15000
ggtaagcctg tgaaagaagc taagtctgct gaagttgttg aagctgctgc cgaagaagct  15060
ccggttgctg ctcaggtgag cgaagaagaa gagttctaat taacatgccc tgtctgcctt  15120
agtgtaggca gggcttttgc gtaatagata ttggagaata aattatgccg tctattgaat  15180
ctcgtttaaa agcagactat gaaagctatt atgaccatct aaccatgaca tcttatttaa  15240
atgtgtatat taaactggac gggagcttgt tccatctcaa gaaatatact cagaaagagt  15300
tgtttgagtt aggttattgg atttggtctt atgaagagat agctgaaaag gttctgcttg  15360
aagttctcaa ggagtggcct acatgtcaag accaaacttc gagttcggag ctacagtgtc  15420
ggaagacagt agtatcatcc tgtggccgac tgaaggtaag agaatcgctc tcatagatgg  15480
ggacatgatt ccctacatca ttggttacac tatcaatgag atgacacttg tccgagctat  15540
gactcgtgtt aagtcaggac aagtagagcg cattgaagat acacctgagt gtaagcaagc  15600
ttgcgatcgc gtaaactcca tgcttaactc ttgggtgtat ggcgcagaat gtgatgctgc  15660
acgcatcttc ctcacaaagt cagatgctaa cttccgctta cgcttggcct tcaccaagcc  15720
ctacaagggt acacgaaagg cagacaaacc tccattcttc tatgagatgc gacaacattt  15780
gataagtgtg catggtgcag aactggcaga tggagaggaa gcagatgacc ttatgagcat  15840
cgcacaatgg gacagtcatc gccgcttctt gcaagaggta ggtaacgagt tctcaatagg  15900
aagccctgag cataaggtgt tctccgatac tgttattgta tctgcggata aagacctaat  15960
gatagtaccg ggatggcact tgcaaccggg aagcgagatg aaatgggttg aacctatggg  16020
ctggcttgac cttcgccgta aggctaacgg gcaggtcaaa gaccttaaag gtgcaggcct  16080
caagttcttc tatgcacaga tgattatagg tgacgacata gataactatg caggcatccc  16140
cggacgtggg gccaagtatg cttataacct ccttgatagt tgcaagactg agaaggaact  16200
```

```
ctatatggct gtgcttggtg cctacaagtc taagttcgga gaaagtcaag tcaagctaaa  16260
gaaccataga ggaacatacc gcatcggcaa ggcttttgat cttatgctag aatgtggtcg  16320
cttggcccat atggcaaggt tcaaaggcga catctggcgt gcggataaga atccaattgt  16380
gtggggagat gatgattcat ggcaatcaga ttgaaggctt cggaggtagc tgactacaag  16440
aaggagttac ttgagaagca gaaatggaaa tgccctttat gcggttgtag cctcaaggct  16500
gtcactgcaa ttaaccgtgt acttgatcat gaccatgaga caggcttctg ccgtgcagta  16560
gtttgtcgag gttgcaatgg tgcggagggt aagatcttag gtgttatttc tggttatgtt  16620
aaggcaggta acaatcgcta cttccaactg aagtggctgg agaacttgta taattactgg  16680
aagttacatc aaacacctca cactgataag ctgtatcata agcataagac tgaggcggag  16740
aagcgcgagg ctcgcaatcg caaggctcgc ttggcatacg caagaaagaa ggagggtaaa  16800
gttgggtaag ctacgctcac tgtataaaga ctccgaggta cttgatgcaa tagagcaggc  16860
taccgacgag aaaggtaatg ttaattataa cgagatggct aaggtattgt ctgctcatcc  16920
ggtcggtaag aagattacac gacagcttgc tcgttactgg catggtcaat tcatgcatac  16980
caagaagaat ggtgactact accagactct ttctcaggag gataagcgac tcaaagaagc  17040
acgtaagctc aggactcctg accgctatga ggatctggct attgtaccat tgcctgactc  17100
gcctcataga agtgtactgg taatccctga cactcatgca ccttatgaac acccagacac  17160
cttggagttc ttggcagcag tggcggcacg cttccgtcct gatacggtgg tgcacttagg  17220
tgatgaggca gacaaacatg ccctgtcatt ccacgatagt gaccctaacc ttgactccgc  17280
tggtatggag ttagagaagg cccgtgtctt catgcacaag ctgcaccgga tgtttccggt  17340
catgcgcctg tgccactcca accacggctc tatgcacttc cgcaaggcaa gcgccaaggg  17400
tattcctgtc caatacctgc gcacctaccg tgaagtcttc ttcccgcatg gaggcggaga  17460
tcagtgggat tggcagcata cccatgttct ggagttacct aatggagagc aggttgcatt  17520
caagcaccag ccagcaggtt ctgtgttagc agatgcggca catgagcgaa tgaatctggt  17580
gtgtggtcac ttgcatggca agatgtcagt agagtatgcg cgcaacaccc atgagcagta  17640
ttgggctgtg caaggtggct gtcttattga tgagtcatct cgcgcatttg cttatggacg  17700
tgagtccaag tacaagccag cactaggttg cgtggtgatt gtagaaggtg tacctcagat  17760
tgtcccaatg cagaccaatg cagaaggccg ttgggttgga aagatttaag tgacactata  17820
gaacaaaggg ctaggtaaga ctttacttgc tggcgtatcc aaacggtatt tcactagacc  17880
ttgattgtat agtgaatgga ggaattaata tggctaaatt taaagtaggt gatgaagtta  17940
agcgtaaaga agatgactat agtgaagcat ggcttgatgg atgtagagag ggtagattca  18000
gtccaaacga tgtcatggtt gtggaaaagg tatcagtatc tggttctttg attacactcc  18060
gaggtgtgac tggggcttgg gttgctgaga gttttgaact gtttcataag aaggaagact  18120
cttgtgacat ggtaatgaac cctaaacact atgaattctt cgaaggagta gaggcaatca  18180
caatcattgc ccgtagcatg accgagaagc aattcgctgg ttactgtatg ggtaacgctt  18240
tgaagtatcg tctacgtgca ggtaagaagc tcaatactga ggaagatctg aagaaagcag  18300
actactacaa agacctgttc cagaagcatc gccatgaatg tatcgatgag gatctctaat  18360
gaacatattc gaattcctag gactacctga agatcatcgc cccaaacctg ttatgctggt  18420
taagcatagg gatgaagtgc cagaaagcaa acttacactc ccggtttacg cacaggtgaa  18480
acgggatgga atctttagtg ctacagttgt gcgttctgat gggactgtag gtgtctttgg  18540
```

```
tcgtactggt aaaaagctgg ctaacgtcga acaactggaa gcatctttta caggttggcc  18600
tgctggtgtc tacctaggcg agttgcagtc tatggctgtt gatatctacc ttgaggcgct  18660
ttcaggtgtg gtgaatccaa acaggactga gcctcttgac ttcataggcc agcagattaa  18720
agataactta tacattgact tctttgacat gctgactatt aaggcattca ttgaagggca  18780
gacggatgtt acattcttaa agcgatacga agctctatgt cgtaggttga agaattgcct  18840
tccacctaag aatgcaatcc taactatcac accttgtcac accgagcaag aggtggaggc  18900
gtttgcacag aagcacatcg atgcaggaag agaaggtgca gtcttcaagt tagactgtga  18960
ctatgaatct ggtcacaaag gattccgaca aaccaagatt gtacgcatgg tgtcctatga  19020
cttaacatgc attggttggg aagaagggaa aggtaaatac aaaggtaagg tagctaatct  19080
tatctttaaa tggaagggtg gcaagacaat caaggctatg cttggtcgtg gttggacaca  19140
tgaagatgct acccgtatgt atcacgatat taaacacggt ggtgaactga acgtcatcgg  19200
taagatattc gctgtcaagg cactccaaga atctagcaag ggagtcctgc gacttcccaa  19260
ggctggagag ttacgccatg ataaggagga gcctgatgtc ttttgattca atgaaagcga  19320
cgaaggcagt tgaggtagca gaagctatct ttgatatgct gtcttgtggg attgaagtcc  19380
cttatacact tctgtctgat gcagaagatt taggtctgtc tgtggaagct atccgcgaga  19440
aagtggagga actgtatggc gacgaccaag aagaagccga ctatcaatat tgaaggttgg  19500
gatatgctgg agaatattat cctagctcca tcaagaccta gaccagataa gtcacacgaa  19560
gagttagtat gggatgaagc caatgcgtat caagtctaaa cccacgcgct gctgtttgtg  19620
gtgcatccat gataagacag gcttgcttgc tagatatccc tgagataatt accttaggga  19680
acagatatgt agaagaggaa gtcaaggtag ttaagcacca ttcagctaca tgggatgcag  19740
atcaaagcgc acatcacctt tgtgcatccc ttaccagtaa ggatttattc ttatgggtgg  19800
ctgtagaaga tggtgttatc atagggttcc tgtgggcggc tgcacacatc atggcacctt  19860
ggtctccggc acttgtggct tctgacctac tcttctacat cataccagaa aagcgagggt  19920
ctcttgctgg tgtgcgcttg ctcaaagctt acaagtcttg ggctaaggaa cgcggctgca  19980
tagaggcaag actgtctatc gcatctggta ttaatgagga acgtgttggg cggatgtata  20040
atcgattagg gtttactccg ttcggtacag tgtataactt gaagttttaa ggagataaca  20100
tgggtgtagt taagaaggca tttcaagcgg taggtctggc acaaaaggcg cctcgcattg  20160
aggcagctaa ggttccagca cagcaacttg agcggcagac tgaggttaaa tctgaagaca  20220
tccagattgg acaagatgat gatgctgcgg catctgctaa aggtaagcgt ggactcgttc  20280
gtcctgtagc ctctagctta ggagtttaat atgcaagaca ctatacttga gtatggtggt  20340
cagcgatcga agatacctaa actgtgggag aagttttcta agaaacgcag cccttacctt  20400
gatagggcaa agcatttcgc taagttaaca ctcccatacc tgatgaacaa caaaggagac  20460
aatgagactt cgcagaatgg ctggcagggt gtaggtgcac aagccaccaa tcatctagct  20520
aataagctag cacaagtgtt attccctgcg caacgatcat tcttccgtgt tgatttaaca  20580
gcaaaaggtg agaaggtatt agatgaccga ggactgaaga agactcagtt agcaaccatc  20640
ttcgctcgcg tagaaaccac tgcaatgaag gcactggagc aaagacagtt ccgcccagcc  20700
atagttgaag tgttcaagca cttaatcgta gcaggtaatt gcctgttgta caaaccaagc  20760
aaaggtgcga tgagtgcagt acccatgcac cattatgtag ttaaccgtga cactaacggt  20820
gacttaatgg atgtaatcct tctgcaagag aaagcgctac gtacattcga cccagcaaca  20880
cgcatggcga tagaagttgg catgaagggt aagaaatgta aagaggatga taacgtcaag  20940
```

```
ctatacaccc atgctcaata cgcaggtgaa ggtttctgga agattaacca atctgctgac  21000
gacatccctg taggcaagga gaaccgcatc aaggccgaga agctaccgtt cattccactg  21060
acatggaagc gcagttatgg tgaggattgg ggccgacctt tagttgagga ttattctggt  21120
gacttgtttg ttatccagtt cttatccgag gcagtggccc gtggggctgc gctgatggct  21180
gacatcaaat acctgattcg ccccggctcc caaactgatg ttgatcactt tgttaactca  21240
gggacaggcg aggtaatcac aggtgtagag gaagacattc atattgttca gttaggcaag  21300
tatgcagacc tgacacctat cagtgctgtg ctggaggtat acactcgacg catcggtgtt  21360
atcttcatga tggagaccat gacacgccgc gatgctgaac gtgttactgc cgtagagatc  21420
caacgcgacg cgcttgagat tgagcagaac atgggtggcg tatactccct gtttgccatg  21480
accatgcaga cacctattgc tatgtggggc ttgcaagagg ctggtgattc cttcactagt  21540
gaactggtag atcctgtgat tgtaacaggt attgaagcat taggtcgcat ggcagaattg  21600
gataagctgg ctaactttgc acagtatatg tccttgcctc aaacatggcc tgaacctgca  21660
caacgtgcaa tccggtgggg cgactacatg gattgggtac gtggtcagat atctgctgaa  21720
ctcccattcc tcaaatctga ggaggagatg caacaagaga tggcgcagca agcacaggcc  21780
cagcaagagg ctatgcttaa cgaaggtgtg gctaaggctg taccgggtgt tattcaacaa  21840
gaaatgaagg agggttaatt agtggccttt gaatttgtag aaccgaccaa tgaaactaca  21900
gctgctccgg ctgctgaaga gaacaaggag gtaacgaatg atgttgctgg tgctgacgct  21960
ggtactactg gcaggggatc ctctaagagt cggacccccgc aagggccaca gaatccggga  22020
agcaaaaaag ctaatcaggg ccggttggag aatttaggta agtctcaggg ggaggttaaa  22080
atattttctt catacctagg tgagccgaaa atccagcatc tggggtttga tattccggct  22140
agaaaagtaa ggaggaaaaa tgcgatcggg gaaccttctc cggtttagcg tgcggaagag  22200
taagaaagac gaatcgcagg gccatcttca agtataagcc caggttgagg aagaagtacg  22260
gataacacga gatttttctt tggacgctac aggtttttag gattcgcaaa ttgctggcgc  22320
gcagtccaat gaattcgata tcagtacaga ttggatggaa ggaaggcgcg agcaatctgg  22380
aggagtgggc gcttgatact ctttctgatg aagaactgga agcatttaat gcagtgatgc  22440
agtcaggcaa ccagtacctc cagcagtacg ctgtgcgaga gttagaaggt cgccgtaagg  22500
ctgcacaggg tgacgacaag cccaacctga ttgaaccaac ggctaccgct gctgcatcgg  22560
aagacaatgc tcccctaagc cgggagcagt acatccgaga gattgcacag ttaggccaga  22620
agtatggacg tgaccgcaaa gggatggctg aagcacaggc acgtctggat gcacgtcgcc  22680
gcgcaggtat ggctcgcggt ctttaattgc ctatttaggt gacactatag aagggaggta  22740
cgcctcccta acatatcaac ttgatttata aggagattct gttggaactg tggcttccag  22800
ttaaagggta tgaaggccgc tattctgtga gtaacagagg tgttgtcgtc agccatttga  22860
caggcaagcc actgacacag agttgtaata ccttcggata taaacaagtc agcctacaca  22920
aagatggtaa gcaagtgagc aagactgttc atagacttgt agccgaggtt ttcattccta  22980
accataatag cttgcctttc gtcaatcaca aagatgaaga caagacaaac aacgacgtta  23040
gcaacctaga atggtgtact tgtcagtaca atacctagta tagttgcgcc aaagagttca  23100
cattcatatc gccagaaggt aaggtggttg atgtgtttaa tttgtcttcc ttctgtaaag  23160
caaacaaact agataaagct gcaatgcaga aggtgagcgc tggcctacgt aaatcacaca  23220
aaggctggaa gtctactaca taaggaggtt tatacatgag taccccaaat aacctgacca  23280
```

```
acgttgcagt ttccgcttcc ggggaagtag atagtcttct cattgagaag ttcaacggta  23340
aggtcaacga gcagtacctg aagggcgaaa acatcatgtc ctacttcgac gtacagaccg  23400
tcactggcac caacactgtg agcaacaaat acttgggtga aaccgagttg caggtactgg  23460
caccgggtca gtctccggct gctacctcta ctcaggccga taaaaaccag ttggtaattg  23520
atgccactgt tattgcccgt aataccgttg ctcacctgca cgatgtacag ggtgacattg  23580
acagcctgaa gccgaagctg gcaaccaacc aagccaagca actgaagcgt atggaagatg  23640
agatgctgat tcagcagatg atgttgggtg gtattgccaa cactcaagct aaacgtacca  23700
acccgcgtgt taagggtcat ggcttctcta tcaacgtaga ggttgcagaa ggtgaagcac  23760
tggtgaaccc gcagtacgta atggctgctg ttgagttcgc gctggaacag cagttagagc  23820
aggaagtgga tatctccgat gtggctatcc tgatgccgtg gcgctacttc aacgtactgc  23880
gtgatgcaga ccgtatcgtt gacaagacct acaccatcag ccagtcgggt gcaaccattc  23940
agggcttcac cttgtccagc tacaactgcc cggtgattcc gtccaaccgt ttcccgaaat  24000
actctcaggg ccagtctcac cacctgctgt ccaatgagga taacggctat cgttatgacc  24060
cgctcccggc aatgaatggt gctatcgctg tattgtttac ggctgatgcg ctgctggttg  24120
gtcgctctat tgatgtgact ggtgacatct tctatgagaa gaaagagaag acctactaca  24180
ttgacacttt catggcggag ggtgcaatcc cggatcgttg ggaggctgtg tctgttgtta  24240
caactaagcg caatacgacc acgggtgcag tagaaggcaa cgatggtgcg cagcatacta  24300
tcgtcaagaa ccgagcacag cgcaaggctg tatatgtcaa gagcgctaac ccggcaggtg  24360
ctgctgctgc taacctgtct gctgaagatc tggttgctgc tgttcgtgct gtgatggcta  24420
acgacatcaa gccgactgca atgaatccga ccaagtaata acctatgccc tatctacctt  24480
gcgtaggtag ggttcttttg tttaggagga ttcatgcctg taattcaaca atcaagtgat  24540
gtaggttaca tcatgtccga tgcaagcttt agcatcattg atagcaagct agaggccgtc  24600
aacctttgta tgcgggccat tggtcgtgag ggtgtggatt cccttgactc aggcgacctt  24660
gatgctgaag atgcgagtaa gatgttagac attgtatccc agcgcttcca gtacaataaa  24720
ggcggtggtt ggtggtttaa ccgtgaaccc aactggcgca tcgtgccgga cactaatggt  24780
gaagttaatc tacctaataa ctgcctagct gtgttgcagt gttatgcatt aggtgagcgt  24840
aaggttccta tgacaatgcg tgcaggtaag ctgtattcca catggaacca cacgtttgat  24900
atgagaagtc atgtcaacaa agacggtgcc atccgtctga cactcctgac ttaccttcct  24960
ttcgaacatc tgcctactag cgtaatgcaa gcaattgcat atcaggctgc ggtagagttc  25020
attgtgtcca aggatgcaga taagaccaag ttagctactc atcagcagat tgcagcacag  25080
ttattcattg atgttcaatc ggaacagatg tctcagaaga gacttaatat gttagtgcac  25140
aatccgacac agcgccagtt tggtattatg gcaggcggtt cgcagaacgt accagcatac  25200
tcacattcgc cttacgatgg ttatccactt aaactttggg agagttatcg ctaatggaag  25260
ttcaagattc tttaggtcgc cagattcaag gcataagcca gcaacctcca gcagtgaggc  25320
tagatggaca gtgttcagaa atggttaaca tggtgcctga tgtagtggag ggaactaagt  25380
cccgcatggg tacaactcat attgccaagc tcttagagta tggcgaagat gacatggcag  25440
tgcatcatta ccgtagaggt ggtgaaggtg aagaggaata cttcttcata atgaagaagg  25500
ggcaagtacc tgaaatcttt gacaaacaag gccgtaagtg catggttcaa tcccaagacg  25560
cacccatgat ctaccttagt gaggtgacta accctagaga ggacgtgcag tttatgacaa  25620
ttgcagatgt cacttttatg cttaatcgca agaaggtggt taaagcaaga ccagaacgtt  25680
```

```
cccctaaagt aggaaatact gccattgtct tcatggccta tggtcaatat ggtactcatt  25740
acaaaatcat tattgacggt gtggtggccg caggctacaa gaccgctgat ggtgccgaag  25800
ctcaccatat tgagactatt aggacggaga gtatagcgta caacctacat cagtcacttc  25860
aaagctggga taaaattggg gattatgaga cgcaattgga tggtacatca atctacatta  25920
caaggaaaga cggctctact gacttcgata ttaccacgga agatggtgcc aaaggtaaag  25980
atttggtagc aatcaaatat aaggtggcat caaccgacct gctgccttca cgtgcgccag  26040
aagggtacaa ggtacaagtc tggcctactg gcagtaaacc ggaatctagg tattggttgc  26100
aagcggaaaa gcagaatggg aacattgtct cttggaagga gacactagcc gccgatgtgt  26160
tgatagggtt tgataaatca actatgcctt acatcataga gcgtacaggg tttgtcaacg  26220
gagtcgcaca gtttaagata cggcaaggag actgggaaga ccgtaaggta ggtgatgacc  26280
tgactaaccc tatgccttcc ttcattgatg aggaagtacc tcagacatta ggtggtatgt  26340
tcatggtgca gaatcgtcta tgtgttactg ctggcgaggc tgtaattgca actcgcacat  26400
cctacttctt tgacttcttc cggtacactg ctgtatctgc tgtagcaact gaccctttg   26460
atgtattctc agatgctagt gaggtttatc agctcaaaca tgcagttacc ttggatgggt  26520
ctactgtctt gtttgcagat aaatctcagt tcatccttcc tggtgataag cctcttgaga  26580
agtcaaacgt attgctcaaa cctgtaacca catttgaagt taacaataat gtcaaacctg  26640
tagccacagg tgagtctgta atgtttgcta caagtgaagg tgcttattca ggcataaggg  26700
agttctacac agactcttat agtgatacca aaaaggcgca agcaataact agtcatgtca  26760
ataagctgct ggaaggtaat gttatcatga tgtcagccag tactaatgtg aacagattgc  26820
ttgtcttgac cgacaagtac cgaaacatta tctactgcta tgactggttg tggcaaggaa  26880
ccgaacgggt acaagctgca tggcataaat gggagtggcc attaggtaca ttcattcgtg  26940
gtatgttcta ttcaggggaa cacttgtatc tgctcatcga acgtggtagt acaggtgtgt  27000
accttgaacg tatggatatg ggtgatgcgc ttgtatataa cctgaatgac cgcatacgta  27060
tggacaggca ggctgaactt atctttagac atgtcaaagc ggaagatgtc tgggtatctg  27120
agccgttgcc ttggcaacca accgatgtgg ccttgcttga ttgcgtgctg atagacggct  27180
gggattctta catagggggg tctttcttgt ttagctataa ttcaagagat aacaccttaa  27240
ctacaacctt tgatatgcac gatgataacc acgtgaaagc taaggtagta gtaggtcagt  27300
tatatcctca agagtttgaa cccacacagg tagtcatacg tgataaccaa gagagggtgt  27360
cttacataga tgtaccaaca gttggcttgg ttcaccttaa tctagacaag taccctgact  27420
tcaaggttga ggtcaagaat ttgaagagtg gcaaagtgcg aaatgtattg gcctctaata  27480
gaataggtgg tgccagaaat aatattgttg gttatgtaga gccgagagaa ggtgtattca  27540
aattcccact aaggtctctt agcaccgaca cagtttatcg tgtgatggta gaatcacctc  27600
acaccttcca gcttagagat atcgagtggg aaggttcgta caaccctact aagaggagag  27660
agtgtaaatg gcaataggta ctgcccttac agcaggcttg tccagtgtag caggtagtgc  27720
tgcatcgggt ggcttcctgt cttcgttggg tggtgctatt ggtgcagaag ggataatggg  27780
ttctgccatg agtttcttag gtggaaccac tggagggttc tctaatgctg gtctcctgtc  27840
ggcaggtatg caaatgctta acccgatagg ggactacttc acgcagaaag aaacagcgaa  27900
ggcgatgaag aaggcacaag aggagcaatg gcgtcagcag ttgatagcca caagagaggc  27960
ttatgcttcc gtggctaatg ctgaaaggtc ggcctctaaa caatatcatt ctgaactaat  28020
```

```
agacaatcag gtatccttat tacagcaaag agcacaagtt gccttacttg caggtgcgag  28080
cggcacaggt ggtaactcta tcacttctat gctgaatgac ctgacaggtg aagctggtag  28140
gaaccaagcc accattattg acaactatga aacacagcag attaactttg ctaaccaact  28200
caagtctatc cagaagggtg gtcagatgat gatgcgttca tttgagaagc cgtctgcatt  28260
cagcgcacta gccaaaggca tgtctggtgt aggcgaggct tacctgtctg gtcatcagaa  28320
aggtacagca cttagcaagg cttggtctga ttctaggaca tattcatcag gaacaagagg  28380
agtttaaatg gcaattgaac gtcaagctgt acagggctta cgccgagtgc agtctactgg  28440
tgggccaagt gctgctagtt ttgcgactcg tcaggttggg gtgcaagaga ctagtgcatc  28500
tggtagccgc tttcttgaag accttgtaaa tgctgctggc agtttggcga ctgtcactac  28560
ttctatcctg aaccaaaggg tggaagatga taaggtacga caatacaacc gggcgttaac  28620
tggcctgatg ccaactgaag atgcaacggt tggtggcgct cgcgcacaca tgcttgtcag  28680
cttacaaaat gacatcatcg cgcaaaccat gcaactgtcc gatgatgcac agcgttttga  28740
tggtgatgac agccaatggg aagatcacgt tatcaacgca cgcatggctg ttcaagaccg  28800
cctgtgggat acctaccctg aactgcgtgg agataaggag tccatgcggg tagtaactaa  28860
cgccttcatg gagcagcaac ctaagatctt tgcagcaaga gagactgcca agttgaagca  28920
ggaagctgaa tctcgtatca agtctatgga atctcgcatt ctgttggcta cacgtgatgt  28980
tcctggagaa gctatgggtg atgccttgaa tcagttgcag aaagaagcta tggctatgca  29040
aatcaccaag caggagtttg atgcgctggt ttctcagttg gcatctaatc gtgcagctat  29100
tggtgatgat tctatgattc aaggaaccaa ggctctcaag gatgagaatg gagtgtcact  29160
ttatgaccga gtaggtcagt tgcagacagg tgagattcag gccaaccgaa catgggcggc  29220
gcagaaccaa gtggcgctct ttgagaagaa ggatgctgca atcaaagcct ttgaggctgg  29280
acagcttaac cgtgagcagc tacttcaggt tatgcagaac cataatgaaa tctcaggggg  29340
cactgcttgg tctgatagcg agatcaaatc tttatttgat aggcaagcta aggttcgtgc  29400
tgagtctgcc aaactagaag acttggtggc ccgtggtgaa catggctctc ctttaggctt  29460
gcaagacatc agcaaggaag accgcaaggc gtatgctggt gcattggttg atgcctacac  29520
caagttggcc aatgacgaga taactcgtac cggagctact ggtgaagaag ctgaggccat  29580
ccgtggacgc tatgagcaga tgcgatacgc caagctgggg cagcagttga ttgaagaccc  29640
catcatcaaa gaacgatatg gctcgctaat gcaactatct tctgccaacc tgaaagatat  29700
gaaggttgaa cctgaagcat tacagactat tatgcgagca cgtgattcta tcccggaaga  29760
tgcacgccgg gcggtgatgg gtgacaagga gtatgccttt gcggagaact atgacttggc  29820
tacacgcatg ggttatacgc cggggcaggc catagagttt gcacagaatg catcgcgtgg  29880
cgataagctt cccggttctg ttatgaaaga attgaatgat gaagtcgatg gtgtagttag  29940
cgatgtggct agtggtagct ggcttacgcg tggcgacaac atgagcgaca tgggacgtga  30000
tcttatgtta gaagaggcaa accagattgc ccgctctatg aaggttgcag gtcataacaa  30060
tgacaccatt aagcgacatc ttaaatcttt cctacagaat cagtacactc aactatctga  30120
aggtttcttc actcaaggtg ttctggtcaa aggtgatgtg agaacgctag gtgacactat  30180
aggcaccaac caaggagacg tacctacggt attacgtcag taccttgaca accataagca  30240
agccttgctg gatgcatctg gcggtatgga agaaggagac ttgtactttg atgtagactc  30300
taagcgcggt atgtttacaa tacgtgctgg ttctggtcgt gtaccagtta ctccagctat  30360
gcctttgtct gaaatcaaag gacaggactt actgaaggag cactacgaga aggcagtgaa  30420
```

```
agagcgcgat gaggctaaga agaactttga agctaatcag atgcgtatgt ggggtgctgg  30480
cgggtatcaa gctcctgcac cagaaaagac tacagctaag actgtaggtt cccgtggtat  30540
cgctgacttc ctcatgtcac cagcctttgc atcaggtgag aatctacctt ccaactttga  30600
attcaactac aagaggaata acatggactt ctacaattat gtagctaaga ccgagaacgg  30660
ggccaacgta gggttcgacc gagtagctgg tgtatacact ccgtacaaag atgcacacgg  30720
tcaatctgtg ggctacggtc acttcctcac ggaggaggag aagaagaatg gatacatcac  30780
tattggcgaa gataaagtac catttgcacc gggacaatct cagttaacac ctgagcgtgc  30840
aatgcgcctg cttgagcagg acatgaagag tcacgtacct agcacaaagg attgggctgt  30900
acctttgat gcaatgcatc cgggagtgca acgtggcctc atggacttgt cttataactt  30960
aggcaaggct ggcatcaaga atgcgccaaa ggcttatgca gcattcaagg ctggcaagtt  31020
cactgatggg tttatcgaga tgctgtctac tgcatctact gaaggtaagc gcagttcagg  31080
tctgctagtt cgcagggcag aagcctataa ccttgcacaa agcggaggtg ctgttcctaa  31140
gattagcgaa gtggagacga gggaagatgg ctccatgtac gttaggttct caggtaacat  31200
gtcagaagca tttgtgagca agtctatcct tggcaagata ggcaaagatg ggtggatgga  31260
agtctaccag cctaaagcag gagcacttgc aagcggcacc aaagtgggtc gcattaaact  31320
gtagtgtcat actcaaggtt gtctaacacg ttggacagcc tttatgaatg acattaacta  31380
aggaggtaac atggctgacg atattagcca aagctgggtg acggtatctc aacgcaggtt  31440
gccgcctacc tttgcacaag tggcagaagc cgagcgtaag cttgaagaac aaagagctaa  31500
cgataaggtc atgcagactg cactggaaag cgaatgggcg ctatacggtg gtcagcgtgc  31560
tattgaacgg catacaacgg agtttgccga acaagaaggc tacacagttc ctgagtcaac  31620
aaaagatgaa ctgtcaaaga ttcatggttt tgaaattgca caggatattg tgaaggatgt  31680
taagtcacca gaagaattgc agttccgtat gtccaatgcg atggcagaca aggagcggtc  31740
ggagatactt gcacgtaatg gatttacagg gtttagcgca cagttagctg ctggtattct  31800
tgacccagtt ggttgggctg cttctatggt tgccgcccct gtagctggtg cagtcaaggt  31860
cgcccgtgtc ggtcgtatca taaagacggc agcagtggct ggtgccgaga acgcagcatt  31920
ggaagccatc ctagccagtg gtgattacca gaagggcgca gatgatgtgc tggctgctgc  31980
tggctttggt atgataatgg gtggcactat cggggcagcc acacgtgaac gcatcgccag  32040
aaagccggga gtacaaggcg tgaatgatgg tgctgaagca gtggtagatg acttggatac  32100
tgtcgtgaaa ggtgctgatg agtttgatgc atctgcggcc aaggctgtgc gtgaggctat  32160
ggagtatgac gcttacatgg ctgtgcgttc ctatgaaccg ctgaaggcta aggaagtgga  32220
tatggatgtc gcaatcctct cccacttaga tgacctgaag gcgaactcta gcgtgcgtat  32280
gagtgcctcc gagaagggta aactgaagga gcagatacgt cagcttgaag cagaagccgc  32340
cactatgaaa ggtaagaagg tagatgccgt ggcagaagct gctgctgcta agggtgcgcc  32400
taagtctgct gctgacaggc tggacttgga tgttaagaag aaggcactgg cacgtcgctt  32460
tgatgagccg cttgccgaca tccaaacaag actcgacgag cttaatgcta aactggcccg  32520
cgtggagaac gtaggtaagt ccaaggagga gctgaagaga ttctctagct taactagaga  32580
gcagcaaatc aaggagctag ggttagatgc tccggctcgt aaagtggaga tgacaagtgc  32640
ggtacgggaa gctcttgcgg ctatacgtgc tgagaagaag aagacaccaa cgcaggccca  32700
tgccgaagct aaagcacagg ctgaagagga agtacggcag aagcgagatg attctatcgg  32760
```

```
cgctaaacgt gtagaggatt cggaaattgc aggcgagcag tttgacctgt ctgatagcat  32820
ggaagacctt atggacgacc ttgcacgcga agcctatcag tctgaagtta gacctgtgaa  32880
tctcaagggt cttggttctg tgtcttccgt gattctgaac tcaaagaacc ctgtgtttcg  32940
tggccttggc ttgcgactgc tggaaaacgc acaaggtggt gcctaccaag gcaagactgc  33000
ctctatctta tctaacgtat atggtaactt gattcgcttt gcggagaaga accgatacaa  33060
tgatggcttc tctcagttca tcaaggataa caacctacgt gctgttgatt acctgaaccc  33120
tgctgttacg agagacttta ataaccagat ttacactgct attgtcaaag gtatacctga  33180
tgatacacca cgtggtgtta agcttgctgc tgaaggtatc gcagataaac tggctaagtc  33240
ccttgaaatt agaaaggctg ctggtgagaa aggcttcgaa gatgtcaagt cagcacgtga  33300
ctacatccct gtaatctatg atggtatcaa ggtaactgaa gcagtcaata ggctgggtag  33360
cagcgaggcg gttattgccc tgttgtccaa aggttatcag actggtaagt ataagatggg  33420
caagaaggca gcagatgcac tagctaaggt tcagtatatc cgcgcctccg actcaacctt  33480
atcaagtcgt gtggcctttg acagggtagt atcgcagcaa caacaagcac agcttattga  33540
agacctgaag aaggcaggtg tgcctgataa catcatcgat aacttcattg aaggcactga  33600
gttgcaagag atggcggagt ccgtatctaa ccgagctaag gcaagcatgg gtatcaatac  33660
tcaggctgaa tatggcggga tgaaggttca ggacttgctc aacactaacg taggtgagtt  33720
ggcggagaac tacggcaaag aggcagcagg cggtgcagct ttggcggcga tgggcttccc  33780
tacccgtcag tctgtattga atgcgattga cgcagcagaa cgcgcaggac gtaatatggc  33840
gggtgctgac gccaaggcaa tcaaacagct tagggcggaa tcagaaatgc tcagggactc  33900
cgtgaagctc atatacggca acactatcga cgcagaccca aatgctggta ttgtccgagg  33960
gactcgccgt gtacgtgaaa tcactggcct gttgcgtttg ggtcagatgg gctttgcaca  34020
ggtgccggag ttggcccgcg ccattaccaa gatgggagtg ggtacagtgc tgaagtcgat  34080
acctgccacg aagttcttac gctcccgcgc tggacgtaag ggtggaacag cacaaggtga  34140
attacttgag cctgaactga gggagatgga agaactcata ggctacatcg gagaagacaa  34200
ctggctatca ggttggaacg taaggcacga tgagttcggc gagaccgctg acaacatggg  34260
gcgtctgtcc gccatcatcg ataatgggct agctatgggt agccgtatta acacatggct  34320
gtctggtttc aaggcaatac agggtggttc tgagaagatt gtagcacgct ctatcaataa  34380
gcgactcaag caacatttga tgggtgagcg ggagctacct aagcgtgacc ttgaagaagt  34440
cggtttggat gaggctacca tgaagcgact caagcgccac tttgatgaga acccgatgta  34500
tgccgactat aatggtgaga agattcgaat gatgaatttt gacgctatgg agccagactt  34560
acgagaaacc gtaggtgtgg cagtacgccg tatgtcaggt cgtcttattc agcgtaactt  34620
cattggcgat gaaggtatct ggatgaataa gtggtggggt aaggctctta ctcagtttaa  34680
atcattctct attgtgtcta ttgagaaaca gcttattcac gacttgcgtg gtgataagat  34740
tcaggcagca cagattatgg catggtcttc cttgctgggc tttgcatcat acgctacaca  34800
gatgcagatg caggcaattg gacgagaaga ccgagacaag ttcttacggg agaagtttga  34860
tacacagaac atcgctatgg gtgtattcaa taaacttcca caagtagctg gctttggcct  34920
agctggagat gccttggcaa cattcggcct tatgcctgac tccatgatgc aggcaccggg  34980
tcgtatgggc ttccgccagc aaggatttgg cgacttggtg gctggtgctg gtgtcataag  35040
tgatgctgtg aacttgtcac aggctttagt gaagtacgcc aatggggacg acgatgtttc  35100
cactaggcag ttagtagata aggtacgacg tcttgtgcct ttggcaaata cgattggtgt  35160
```

```
aggtcagatg accaaggcca gcgtagactt attggaggac tgatgagtta tactttcaca  35220

gaacacacag cggtaggttc tcagacgact tatccgttta gctttgctgg tcgcgacaag  35280

ggttacattc gcgcatcaga tattattgtg gaagtgtttc atgaaggaga gtggagtatt  35340

acacatggtt gggtgctatc tggcacccac cagattacct tcaatgtagc actaccagaa  35400

gggactaagt tccgcatacg tcgagatgta gccaaagagt acccttacgc ggagtttgat  35460

agaggtgtgg ctcttgatat gaaatcattg aacaactcct tcattcatat cttgcagatc  35520

acacaggaga ttcttgatgg cttctatcca gaaggttact tcgtcaaaca gaatgtatct  35580

tggggcgggt acaagattac cgacctagct gatggcacag accctcacga tgcagtgaac  35640

aaaggtcagc ttgacgcaat agacaggaag cacactgagt ggaatgaaca gcaagatatt  35700

gcaattgctg gactcaaggc aggtatgaca tcaggcatct ctcaccgaac agtgccttgg  35760

gttacggtag cggctggtgg agagcaagtc attagaccac cttacatctt tgaatcggcc  35820

ttggttttcc ttgatggagt gttgcagcat gaactgtcag gtgcagttac tatagctaac  35880

agcactctca ctttctccga gccactacgt cgtggcacag aagtgtatgt attgataggt  35940

agtcgtattg caacatcttc accgggtctg catatggagt tcaacaagga cttagatgca  36000

ggaactacgg aggttaggat tggtatggcg ttctcccata ttgatatcta ccttgatggc  36060

ctgttccaac ctaagtcaac ttatcaaata aacggcgatc ttgttacatt ctccgagggt  36120

gtaccagctt gccatatgtc agcggatgta gtcactttat aggaggtaag atggttgatt  36180

ccgaactggt tagcggcggg atgaagttag cgccatctgc cttagtctca ggtgggtact  36240

tcctcggcat cagttgggac aattgggtac tgattgcgac attcatttat actgtgttgc  36300

aaatcggcga ttggttctac agcaaatact cgttatgtaa ggagaagaaa cgtggcaagt  36360

cataacaaac acgccgctac ggaagatgag gtaggtaagc tacatagtgc tatcaccaat  36420

cttttcaaca agaaagctgc tgcaatcctc gctgcggtag aggaagaccc tgatgcagca  36480

attgcgctgg tgtcaggtaa ggacatgggt gccatgtgta agtgggtgct agataatggc  36540

attacggcta cacctgctgc acagcacgaa gagtctgcac tgtctaagcg ccttgctaag  36600

atcaaagcag catctcaagg taaagtaatc caatttgcta aggaggctta atggctagag  36660

caagggagtc acaagctgaa gcccttgccc gttgggaagc cctgcatgag ttacagcaaa  36720

cttttccgta cactgtagca aggttactct catttgctca ggttgtaatt aatactttaa  36780

tcactggcaa cccagacctg aaccgggtac aagcggatat tctgaaattc ctctttggag  36840

ggaacaaata ccggatggta gaggcacagc gtggtcaggc taagacaacc attgcagcta  36900

tctacgctgc gttccgtatc atccacgagc cacataaacg tatcatgatt gtgtctcaga  36960

cagcgaagcg agcagaagaa atcgccgggt gggttatcaa aatattccgt ggtctggact  37020

tcttggagtt catgttgcct gatatctacg caggtgacaa ggctagtata aaaggctttg  37080

aaatccacta cacattgcgt ggtagcgaca agtctccatc cgttgcttgc tactctattg  37140

aagcaggtat gcagggtgcg cgtgcagata tcatcttggc ggatgacgta gagtcgttgc  37200

agaactctcg tactgccgca ggtcgtgctc tcttagaaga ccttaccaag gaatttgaat  37260

caatcaacca gttcggtgat atcatctact tggggacacc tcaaagcgta aactccatat  37320

acaacaacct cccggcacgt ggttatcaga ttcgcatctg gcccggtcgc tatcctacac  37380

tagagcagga ggcttgctat ggagacttcc tagcgccgat gattcgtcag gatatgattg  37440

atgacccaag cctacgctcc ggctacggca tcgacggtac acaaggcgca ccgacctgtc  37500
```

```
ctgaaatgta cgatgacgag aagctcattg agaaggaaat ctctcagggt acagctaagt  37560
tccagttgca gttcatgctg aacacacgtt tgatggatgc cgaccgctat cctcttcgtc  37620
ttaatcagct tatcttgatg agctttggta ctgacgtagt gccggagatg ccgacttgga  37680
gtaacgactc ggtaaacctt atcagcgacg cgccgcgctt cgggaacaag cccacagact  37740
acctgtatcg gcctgtgccg cgtccgtatg agtggcggcc tattcagcgt cggctgatgt  37800
atatcgaccc ggcaggtggc ggtaagaacg gcgacgagac gggcgtagcc attgtgttcc  37860
tgctgggaac ctttatctac gtctacaaag tcttcggcgt accgggcgga tactccgaat  37920
cggccctcag tcgcattgtg agagaggcaa agcaggcgga ggtaaaagag gtcttcatag  37980
agaagaactt cggtcatggt gcgtttgagg cggtaattaa gccatacttc gaacgtgagt  38040
ggcctgccga gttgaaagaa gattacgcca ctggtcagaa agaggcccgc atcattgaga  38100
cgctggagcc gcttatgtcc gcacaccgca tcatcttcaa tgccgagatg atcaagcagg  38160
atgtcgatag cgtccagcac taccctcttg agattcgcat gagctacagc ctgtttgctc  38220
agatgtcgaa cataaccctt gagaaaggat gcctgcggca cgatgaccgc ttagacgcgc  38280
tgtatggcgc tatacggcaa ttaacctctc agatagacta tgacgaggct aaccggataa  38340
atcgtctcag ggcgaaggag atgcgcgaat atctggagat gatgaccgac cctctacgtc  38400
gccgggagtt cttcacagga caagaccacg gttatcgaaa acaagtgaac acgtcagtgg  38460
caatgcagcg ccgagtctac ggaaatgcgc cgacgatgag aatcaagtct cgaaatactc  38520
tttcttcaag aatatcaagg acttggtaat taggggacac tataggagga ggcccagaga  38580
ataagagaaa taacaaggat aatataggtt aacctaggtt atataggtta ctatagtatg  38640
ggtgtactcc tgtacaccct attccttact tccttactat acttacataa taggagagag  38700
aatgtctaat agctatagta cacaacctct tacaggtaag tctgctcgta agcaggtaca  38760
acctgtgagt gaagcactaa tgcttcctgt aatctcaaaa gaggaggcta gtaagaaaag  38820
caatgttatt aatgatgcca ccaaatcagg caaacagaaa ggagccatgg tgtgtcttga  38880
ctcatctggt gcattaagta ttgctattgc agttgatgac aaagaagatt ctaattggct  38940
gtccgttaca gcgggcactt ctattacccc agcttaagaa gaggaggatt acatggctaa  39000
atatggtgaa ggttctgtta ctggtcaggc ttttcgagta aaggcagtac aaactattgc  39060
aacggcaatc cccatgcctg ttgttgctga agcagacctt aagaagaaag atcaccctat  39120
caacattaaa cacctatctg gtaagcagaa gggtgcgatg attgctgttg agaaagaagg  39180
cccaaccctg tatattgcta ttgcacgtgg tagtgaacct actgaccctt gggatacaac  39240
cactatggag ggagaccctg tcactccaac aggggactaa taatgcttaa caagtacttc  39300
aagcgtaaag agttcgcttg ccgttgtgga tgcggcacat ccactgttga tgctgaatta  39360
ctacaggtag tcacagatgt gcgtgagcac tttggtgctc ctgtggttat cacttctggg  39420
catcgctgtg ctaagcacaa cttaaatgtt ggtggcgctc gtggctccaa gcatctgctt  39480
ggcattgctg ctgacattaa cgtgaagggt gtatctccta tacgggtgcg agagtaccta  39540
tgcaataagt atcctgacaa gtacggcatt ggtgcttaca cgaacttcac acacatcgat  39600
gtgcgctcta acaaggctag gtggtaatga agggttgcat tgcatactgt gagcgtaagg  39660
taaaggaggc cagtgaagct ggaaactaca ctgacttcca gaactatacg caccttctga  39720
acgaatggaa agtgagggct ggttgtgaaa ctgttaaaga gtaagaaggt agtagcagca  39780
ctggtaggtt tggtggtagc gttggtttct gtcggcatgg gtgttgagtt tggcgctcag  39840
actgccgatg cagttaccag tgttgtctgc caagccgtag gctgtgaata aacttcttaa  39900
```

ggtgctggca ggtctacttg gcctgctggt tgcctacaag cgagaacaag agcagaagga 39960
ggctcaacgt gaagcgaatc atgctagcga caatcctgct gattggttcg ctgatcactt 40020
ccgggtgcgg gacggcgtta ccagaacgcc caaccaagcc gacgctgacg gcagtgtacg 40080
aggtggacga taaggtctgc ttcagcaagc ctgatgctac acaacttgga ctgtacattt 40140
tatcgctaga acgcggctac aattaataca tagtcttatg tatcatacac ctacgattta 40200
ggtgacacta tagaagagaa gtatagtgcc gttcttttga gcggcctatt actcaccagt 40260
cttcatgggg atggctggat attaatagga ggtttaatgt cattaactaa accacgttgc 40320
ttcaggaagg caagctatct aagtcagtta ggcactttgc agaatctagc taacactgga 40380
gatgacgtac ttgttatcga tgttgactac gagttcacta acggagagac tgtagacttc 40440
aaaggtcaac tggttcgtat agagtgcgaa gctaagttca ttggtgatgg tgctttgatc 40500
ttcactaata tggctagtgg ttctgtggta gaaaagcctt tcatggaaag caagtccaca 40560
ccttgggtta tttacccttg gacagaagat ggaaagtgga ttacagatgc acaagctgtt 40620
gctgctacat tgaaacaatc taagaccgaa ggatatcaac cgggagtcaa cgattgggtt 40680
aagtttcccg gacttgaagc attgatgcct caagaggtga aagatcagta tgtagtatcc 40740
acactggaca tccgtgactg cgtaggtgtt gaggtaagac gcgctggcgg ccttatggca 40800
gcttatttgt ttcgcaactg tcatcactgt aaggtgattg attctgacac catcattggt 40860
ggtaaagacg gaatcataac ctttgaaaac ttaggtggtg aatggggaat cggtaactat 40920
gccataggtg gtcgtgtaca ttatggctca ggaagtggtg tgcagttcct tcgaaataat 40980
ggaggtgcat ctcacaacgg tggagttatt ggtgtaacct catggcgtgc aggtgagtct 41040
gggttcaaga catggcaagg ttctgtaggt gcaggtacat ctcgtaacta taaccttcag 41100
ttccgtgact cagttgcact gtctcccgtg tgggatggct ttgacttagg ctcagatcta 41160
ggaatggcac cagaagagga cagaccggga gacttgcctg tgtctcaata ccctatgcat 41220
cagctaccta acaaccacat ggttgataac atccttgtta tgaattcatt aggtgtgggt 41280
ttaggtatgg atggtcgcgg tggatatgta tctaatgtta ccgtacaaga ttgtgcaggt 41340
gcaggtatcc ttgcttatgc attcaaccgt accttctcta acattacggt gattgactgc 41400
aactacatga acttcgattc agaccagata atcatcattg gtgactgcat cgtgaatggc 41460
atccgcgccg ctggtattaa acctcagcca tctaagggta tggtcatcag tgcacctaac 41520
tcgaccctta gtgggattgt aggtaacgtg ccaccagacc gtatccttgc aggtaacatc 41580
cttgaccctg tgttgggtca tacaaggatt aatgggttta atagtgactc ggcagaactg 41640
agcttcagaa tccacaagct taccaagacc ttggatagtg gtgctattcg ctctacgctg 41700
aatggtgggc cgggtacagg ttctgcatgg acggagatga ctgcaatttc agggtcagct 41760
ccaaatgctg tctcgttgaa gattaaccgt ggagacttca aggcaactga gatccccgtg 41820
gcacctactg tgcttccaga tgaagcggta agagaccaca actctattgc gctctatttc 41880
gatcaggagg ctctttgggc tttagttaag aaaccaaacg gaagtcttac acgaatgaag 41940
cttgcttaat ataggcagcg cgttagcgct gctttcacgc gaacttttct taaaggttat 42000
catagtggta gcctttcaga aaaggaggtg acatgataca aagattaggt tcttccttag 42060
tgaagatgcc aaatggtctt acattgacac agtggttgca gcctgcaaac atcatcaagg 42120
tagatgatgc accgtacaat ggagacctta ttgctgcata taatgctgtt ccagttacag 42180
gtaattatgc tttggttctt accaaccaca cttacaatgc agttggcttg ttcgatgcag 42240

```
gtcgtaacac gaagcctaac atcaccatca ttggtgctgg tatgcctcaa cttgcaggag  42300

acagatcgtc atttgttgca ggttcgggta ctatcattaa gggtgcagta aagaactccg  42360

ccaagggttt ccagattgct aacctaggta ttgattgtgg taacacagtt agtcgtacag  42420

attaccaacc tgcacgcttc gaagacccac tacagatata tgggtgtggc gctaatgcta  42480

acatcttcat cgataacgtg aaatgcctta gtgcagtttc tgtagatgaa cgaccgggaa  42540

cacacagcat tctgcttgag cagactgaag gtgtcaccat cggctatgta gagtgcattg  42600

gtggctttca cggcctaacc atcaagtgcc gtaacctacg tggtgggatt gcacattgct  42660

atggtcagta tggtgatggc ttcatcatca agtccgatgc tggtggtgca gcgagtcaca  42720

tctacatgga gcgaattcag gtaggacacc cagatcagtc tatgtggcct gatgtgcact  42780

tgggtggtat ctacgatgcg cacgatggtg taaccattga tagtgttagc attggtgagt  42840

tgcatgttgt acgaggaact tggggtctga tacctgctga taacgccact ggcaatatca  42900

ccaacttcca tattggacat tatgagtgcc accttactta cggcaaccac tactcccttg  42960

ttatcaacaa caaggttgta ggttggacta tgggtactca caacatcacg acctgctcag  43020

gtggtatcaa ggtagaccct gcatcagtgt atgtgaacat aggtactggt cgctctacaa  43080

acaacactga aagtgggtac tctcttggtg gcaacacctt gattcatggt gaactgattg  43140

cagatgcgaa tggtaagtat ggtgtagagt attctggtgg tctaggtctt gatgtaagta  43200

agattcatgg attccagaat ccacttggga cttactcagg gtactcttct gctatccaat  43260

ccctactgtg gcctgacgct gggtttgaag ctatggtaac aggtagaact gtgactttac  43320

gtggttcact cactaaaggc tctactgcat ggtgcggtca ggtgcttgat gctgttaagc  43380

ctacacgaga cattcgtatc tacgcatggg ctgttggcat tggtggttca atggttcctg  43440

tggaagcatg ggttcgttct gctactggtg ctatagatgt cgtaggcaag gattcggttg  43500

gcgaagggca gattgttagc ttcactggca gctacatctt caagtgaggt atgtatgccc  43560

ttagtgaagt ctatcaagga gaaggctgta ctccagaaca cagaagagct aatcaagtcc  43620

ggtcgtgacc ctaagcaggc ttatgccatt gctaaggatg tacagcgacg tgccttgaag  43680

aagccttctg catcttagtg taaccaaagg gctggcctag gttggccctt agtgtaatca  43740

aaggagataa catgtatatt ccaatggaag cagtagtagg tatcgcttgt ttgctagtag  43800

ggtttgtcat aggtttgata gcacaataat ggtggtcaca aagtagccaa agtcaaaatt  43860

ttgatatagg cgtgtgtcag gtctctcggc ctcggcctcg ccgggatgtc cccatagggt  43920

gcctgtgggc g                                                      43931
```

<210> SEQ ID NO 3
<211> LENGTH: 87603
<212> TYPE: DNA
<213> ORGANISM: Artificial Sequence
<220> FEATURE:
<223> OTHER INFORMATION: Synthetic DNA for Salmonella Bacteriophage UAB_Phi87

<400> SEQUENCE: 3

```
cttcagagac tgctgcattg ccagttatgc tataccgcta aaattggtac tccatatcgg     60

attcgaaccg atacataaca cagattttaa gtctggcctc tctgccaatt ggagtaatgg    120

agcattggcg gggatgttg gaattgaacc aacttcttcg atttcaaaga ccgaggtttt    180

aaccttgtaa actaatcccc tttaaatctt tactttctta gtggatgaat aaagaatgcc    240

aacataactc tttcccttga aaatgctctt tcttctggga caacactttt aagtttccat    300
```

```
ccaacataaa ttctccagta aaattgttta ccaaagattt tgattgatgg tacaaaagcg    360

aataaccccc aagcattact gttccacatt aggagataac ctgtctgatt atcttcaggg    420

ttagaactta cattgatatt acctttccac ttagtaacat ctttcacatc tcttcctaac    480

acatggtaag agaagttata agctttgttt ctccagagcc atccaactct ctgcatatag    540

acaccaagct taccaatctt tctaatctta gcccatcgtt cgacatgacc tttatcacca    600

tcaattgggt tgtcatatgt ctccatccat ctgaatccaa aagggagatg tcctttcttc    660

tcactgtaga atggaactac aaagggtgct aagataactg ctaggattgc tgcaaatggc    720

tctaacaaag ctaagaaaat ccatgaaaca tattttaagt atctcattgt ctaatcctcg    780

taaggaggta agcattatta tttgtttctg agttttctgg taacattgtc tcaaaattga    840

cgcttttaag ttgtcttcca ccaaagcaat gaccaataaa tttttctact tttattgggt    900

cgcactccca tccaactttc aagaaaatgt gggtatctat agtgggaacc cttacaaact    960

caatactatt ggaattttca tgttcaacga cgattaatgt ttgcataaat tcctctcact   1020

tatctggcgc aggataaggg attcgaaccc ctattaacag cttcgtagac tgttgctcta   1080

tccatttgaa ctaatcctgc aaaattggtg ttccaagacg gattcgaacc gtcactagta   1140

caaggtttga gcttgcatcc tctgccaatt gggatactgg aacatggtac tcactaaagg   1200

acttgaacct ttttcttcat cttgtaaggg tgatgtttta ccatataaac taagcgagta   1260

ttaaagaggt ctgaagttgt gccgctaact caactccgtg gaatttgtta cggtcttcag   1320

ttgacaccag cggtctttca cttgacctct gaattggtgc tcccacaagg attcgaaccc   1380

tgataagttg cttacaaggc aaccgtaata gccaattata cgataggagc attaatttgg   1440

agcatccaga gggaatcgaa ccctcaacct cagtttggaa gactgtaatt ttcccgttta   1500

aactatggat gcactaattg gtggagtcac tgagaattga actcagttcc caagtttgca   1560

aaactcgaat tttaaccata taaactatga ccccattgtt tggtacaggt ggagggaatt   1620

gaacccatcg tcttactgat taagagtcag ccgcataacc attttgctac acctgcatta   1680

atttggtagg agacaaggga ttcgaaccct caaacaccaa cttctaagga tggtaggttt   1740

accaattacc gtcaatctcc cattaaatct ttttagagaa cttctaagaa cctaagcaac   1800

aaggttccac aacaagctgt aataacctta gaagccctct aaaaagacct aatttggtct   1860

ttgcatagtc ttgtttaatc cggtgactag aacctttgga gagcttgata ttatctcttc   1920

tccgtgacac ctactaggtg ctttactgtg cgtgtacgac aatacacgag ggataccaaa   1980

gcaacatccg aatgaagctt ggctttaaat cttattaggc ggtaagtaaa ggagtcgaac   2040

cctcaccgta tctctacagt ggcaactgtt ttcaagacag tttggctacc attagccgct   2100

acctacccct aataagactt tggcatggga cggaggagtt gaacccottt gaaacggttt   2160

tggaggccgt tgctcatgcc ttagagtctt aacatcgtcc cacactataa ttctaagctt   2220

accgtatttt cacaacactg taaagcccct cctcagatta tttacatgtt ctggaaaaca   2280

tgagatacag accacctcct tacacggaga cccgataagg tcgtctaagc aatctgctaa   2340

ctatttggca caccctacag gattcgaacc tgtaactaac gatttagaag accgttgctc   2400

tatccaattg aactaagggt gcattaatct ttaaagactc tcttagaaag cccttaaaga   2460

tgcccacatt attaatcata ccgtgggcga gtacgccaaa ttctttgatg agggattgga   2520

agacctcact ggtgtttagc ctatcaagct actgccagaa aaacattgtc gtttgcattt   2580

attttaaatt tgcaaaatag acgctacgca acgaaaacta ttcagaatat gtacaacaaa   2640

tttccccaca ttgtgttacg tctaacgctc atgtattggt gtttgaatta tacatattat   2700
```

```
gaagtatttt agttactata aagtggtcac atctcaatgt caacaacttt attgaaattg   2760
gtactggtag gtggaatcga accaccgatg ttcccttatc aggggagtgt tataaccttc   2820
ttaactatac cagcttggag gttcagatgg gaatcgaacc cacattcata gggcttatga   2880
gacccttgca ttaccttatc tgcgactgaa ccatattggt agaagtggag ggattcgaac   2940
ccatcgcctg tcagattaaa agtctgccgc atcaccattc tgctacactt ccattaaatt   3000
atctttgtag ataagctacc cagacttgct taaggtctgt agcgatgtgc cttgttgggt   3060
ttaaatctag aatttaccct ttcacccttt gtggtcgcat actcacaggt aagcttaata   3120
acttatctac aaagataatt accagaccgt tgtttatcat cttaagtgct accattacac   3180
caactcgaca tctgccgagt gaaggaatcg aaccttcgcc ttttctttac cggagaaata   3240
gattgtttaa gttttgctgt aaacggtctt ctgtaaattt gttgagccag accaagtttt   3300
aaatttttc aaaattaaat tggcttgaaa atatcatacg tacttgctga atttggtctt   3360
ctgctccttt aaagaatact cgtaagaact ctttaaggga ggggctaaat aaccctctca   3420
aaacatcatc ttgaaatact tattataatt tggcggttac gaagggattt gaaccctcat   3480
catctcccgt gacaggggag tattttaacc agttaaacta cataaccttt atttggtgtg   3540
ccgtgtagga gtcgaaccta ccgagtctca atgacaaggg atttacagtc cccaccgcta   3600
ccatctacgg gataacgaca catttaaatt tggcggttag tcagggattc gaaccctgtg   3660
ccattcgctt aacaggcgac cgcacatacc ttatgtgctt cctaacctta atacattgcc   3720
agaccgtgtt ttttctttta tccgcaaaaa gtagtttgtt gctgaatacg gtcttctgca   3780
aaattggagg cgggtgcagg agtcgaacct gccgatacca tgctaatgag acatgtgaga   3840
cgccctttct ctatacccgc aattcttaat gaccagacca aatatcttct ttgtccgatt   3900
tcgtgtcaga tgaataagat taagtttgct gcaattggtc ttctgtcaaa actggcgttc   3960
cagaagggat ttgaaccctc aaatatccac tttgaaagag tggtgacttt accgttttgt   4020
ctactggaac attaatttgg tctctgttgg aggacttgaa cctccggcct taccgcccca   4080
aacggaacgc tctaccaagc tgagctaaac agagataaac tttccaaact ctatgtaacc   4140
actttaacat tattttttag tggttgtcaa gaactttttt aaaatatttt tcagtatctt   4200
agaaaagctc tcatttcgtt tctatgtaga acatattaaa gggtatcaaa cacattgtca   4260
ataccctttt taaaactttt taccagatgt aacggtcaat cattactgct ttgagcatta   4320
cgctggttgg gtcaaacttc tcaccaccaa gcagagcttt taaagtggct ggagagaacc   4380
ctgataccat tgctacacca ttatccttaa cagatacttc gcaagtacca ttacggtttg   4440
ctaagtacca gaatactagt tgtggcattt cgtatccagc ttttttgtac ttactctgaa   4500
ttgcttcaaa gtttgtacga ccatttgcac catcaacctg attaaactcc atatcagaga   4560
agataataag cttacttggc atatctttct gagtcaagtt gtttctctta cctacctcaa   4620
gaatacggtc aaaagctgct tgtaagttag ttgaaccata ttcaacatga cgcattacct   4680
gacgatgacg gtttcgtaaa tcaccactca gttcaatgaa atgagggttt gttgaataga   4740
ccattaactc atctttaaag caacctgtat tgcgttctgc tacatacaag gcaagtgata   4800
caccaatatc aagggcagtg attgaaccaa gattcaccca agacattgag cttgaaacat   4860
cagtcataca caagatgttt tcaccttctg ccatccagtt tggaagtgct ttccactgct   4920
cattagcaac atctgcatta ccatacttaa tagatttaat cacatcatat gggtaaacag   4980
caccagcatt aatcttaacc tcaccctttg ataatgattc gatgtaagct ttgtaacgct   5040
```

-continued

```
ctccatcttt acggttaaag agcttttggt aacgtgcagc agcgagtgaa ggaatcttgc   5100
tgtagtcaat cttaccaaac tcattagcag agatttttttg ctcaaccgta tcagacagtg   5160
cagatagcag tgtgcgatac tccttctcgc ttaagtttgc aaacttacag aaacgtttta   5220
caaactgttt gtggcgtggt tttactcgtg gcaaccactt agctgctaaa cctgctgttg   5280
cagggtctag taatgctgct tctaaatgtt tgaaggcatc tgtctcgaaa cgagtaccta   5340
cgaagatttt gaagtcatca aaacgaccaa gttctgcaat cttatccata atgcgaagaa   5400
cctgtgtagg ttctaaaacc ttatcttcaa tcgcttgaag taaaacagtt cggaaagctt   5460
tacgctcacc catacccttct cgtacatctc gcatatgcag taaaatacga actgcaacat   5520
caacatcctc acgcaaagct ttgtagaaca ggtctggtaa gatttctaca ttgctacggc   5580
ttgagccagc ggctttgtag aagtctacca gagcagacat tgatgaagta tggtttacag   5640
caccattttc agttcgacct gcatgaaggt gcgcatgttt aaataactcg ctcatatttt   5700
actctcttct ctcattgttg tttgatgtga cagactttag agcaactttg tagagtctgt   5760
caacaccttt taaaattatt ttttgagagt cgctacagca gagaacgttg gtttgttatc   5820
tgtctgttgt tgaccaccgt tatcaggagt cttcttagtg tctgctgcaa gtgctttcat   5880
ctcacctgct gagtgagtaa agatagtctt accgacctca atcatgctct tgatggttac   5940
gtcatctgtg tttaacccga actctgcaag cttagcagcg tcccttgtaa caatcgcttc   6000
aaacagcttt gcagcaaact cagcagaatt atcaatggtc agttgagctt ttacgagtga   6060
gcttttgtta cgagagcctt ttggtcttcc agatgggttt ccagattggc ctttttttaaa   6120
ctggcctttg tttgttctgt ttttcattgg tatgcctctt ataagacctc ttaaaaggct   6180
tttaagataa aagatagata tccagaaaga tatctgttta aatagccttt ttagaggaac   6240
cttttaagtt atcttctaag tatttataag cctacacctt gtcaagtact ttgtcaacaa   6300
ctttttttaac ttgcaatagt tcttgacttg ttgtatggat tactgtacca tcttacttaa   6360
agctgtaggt ctgccttgtt ctacaaagga gacttaatga gaaaatcaaa caacccgaag   6420
aaaggtaaaa ataccaatca ctgtaaggaa tcaaaaaggg tagagttact ctactattca   6480
tcctctgaaa ttggtctgta cctgttcttt caaaattaca gaagacaaga ggattatcta   6540
tgtgtagttc ccaattagaa atcgcagata ttatagattt atataaaact gcaaagagtc   6600
atggctatat aacctcaatt ggaaagaata gtcactacga tgctttgact ggaatgtatt   6660
tcagggcaat ggctcaacct agtgaacaac acttaatggt ttcttccagt gagtttactt   6720
cgtttctcta ttgcagcaaa atcataaatc gcaggagaac tgaaaaatgt taacagtaag   6780
ttttaattat aatagtgatg gctctgtatc aattaattca ccatatgcaa atgacctatt   6840
gaaagagcta gttaatcagt gtgatagagg tcttcactat gtcccaaatt ctttcaagca   6900
gaagactatt gctaataact tgatgcgtgt gacggttaca acatcaaatc caaactatga   6960
cattgatagt gaaagccctt actctttagt ggctcttggg gaatgcagtc aattcaaact   7020
tgtatgccac gactcagaaa catttcttaa ggtattttcc agccttattc acaataataa   7080
gtatgggtat gttgatggga gtgttaactt ctatccagcg aactacacct gtctattgat   7140
tgataaatatg agaagtagca agcaagagcc tacagaaatt tcatttgatg tgaactctag   7200
tccagacgca gaaacaagta ataactttga tatgagttac gcactatcac ttagtaagaa   7260
atccgagttc attgattatg tcaatggatt tggttttaag tttgacgaga gcatgaatct   7320
caaaaaactt aagaacctac ttaagaccaa agcttaagta taagcagggg ctgatgcccc   7380
tttatctgtt tataaggata tttaatgaag gctaagagtg caaaagactt ttattgcttc   7440
```

```
ctacaatcct atatccactc cgtggagaat ggtgaaagat acaatcttaa cgatgttatt   7500

gcatcacctt taacatggag aatgagtaaa tggcctgaag aggatattac accaacttcc   7560

gaacaaccca cctataaccc agaaattaaa ctcccagatt cagataagtt gctataccca   7620

atgttccaca ttgttgggct tggtacgttt cttatggata tccagtatgt aattggtaag   7680

ggttataaag ttgaaggtat tgttgttagt gatgtgtctc cacaacataa aggctatttt   7740

agattaaacg cacgtttaga ggctaaaaag aaatgattaa agcaaagact tacccagact   7800

tcaaagaatt tgtaaatggt ttcattgcaa atgtaaaggc tggtaagagg tatgatttta   7860

gaacatatca agaagctatt ttaccactta cctatagttc atattggcct gaagctgata   7920

tcgcagaagt tgagaagttt gactacaaac cagactacaa agtccctttt agtgatgatt   7980

tgctttacag catcggtgct caaatgagaa cttctgactt cttcatggat ttacaatacg   8040

caattatcaa tggtaaagac gttgatatag tttattgtga atggctggca agagttaagc   8100

ctttctcaat gttgaatgct aagctgaaag atgctattaa gccaccagca attactcagc   8160

aaccaacagg ccaaacagtc aatgagggcg gtacactcac tctaagtgtt ctagcaacta   8220

acgccactgg ctatcagtgg aagaaggatg gtgaggacat ccccagtgcc acttctgcaa   8280

cttacacaaa acaatccgta gcaccttctg acgctggttc atacacttgt gttgtatctg   8340

gagagggtgg aacaagtgtc acctcagatg cagcaacggt tactgttaac gcactgcctg   8400

tgattacaca gcaaccttct agccagacca ttaatgaagg tggaaacatc agtctatcag   8460

tgactgcaac aggtgcaaca ggttaccagt ggaagaaaga tggctctgac atcccttcag   8520

ctacaaacgc tacctatagc aagtctggtg cactgccagc agatgcaggt tcctatactt   8580

gtgttgtaac tggtgctgga ggttctgtta cttctaaccc tgcaacaatc acggtaaatg   8640

ctttgccagt tatcactcag cagccaacca atcaagaaat cactgaaggt gataccttga   8700

cactaagtgt tgtggctact ggtgcgacag gttatcagtg gaagaagggt gaggaaaaca   8760

tcctagacgc aactactgca acttacacca aagaaggtgc aaccactgct gacgcaggaa   8820

gctacacctg tgtagttact ggtgcaggtg gctctgtaac atctaatgcg gcaacagtta   8880

cagttaaccc agcaggggag gcataatgca actctcaaga aaaggtttag aagctattaa   8940

gttctttgaa ggtctgaagt tagaggctta cgaagactct gccggaatcc caacaatcgg   9000

gtatggtaca atccgtattg acggaaaacc tgttaagatg ggtatgaaaa ttactgctga   9060

acaggctgaa cagtatcttc ttgcagatgt tgaaaagttt gtcgcagcag tgaataaatc   9120

tatcaaggtt ccaacttctc agaatgagtt cgatgcactt gtaagtgaaa catacaacat   9180

cggtatcaca gctatgcagg attctacatt tatcaagcgc cacaatgctg gtaataaggt   9240

aggttgtgca gaagctatgc agtggtggaa caaggttaca gtcaaaggta agaaggtcac   9300

ttcaaacggc ctgaaaaaca gacgtagaat ggaagctgac atttatcttg acagtgtata   9360

tccaaagtaa tatcttcata ggctccttcg ggagcctttt tattttctaa ggagaaaact   9420

atgaagcttt gggctagtga ctttgggact tttaagtata ctcgtaatgg ttcgcttgta   9480

cgcattgtcg gaaacaatgt ggtttcaaga ggcgacaagg tgtatatacg atttactgta   9540

gagcttgttg aactgtcacc tattgagtct gtgaacaatg gcttgttcaa gtttgagact   9600

tacaatgtca atgaacatgg acaattcaac cctcttggtg aaagtggact tgatattatt   9660

tcagaacacc cgttgacaaa agaacaactt gcaggttatt ataaaactgt tcttgaaagg   9720

cagttagcaa cacatgaaca agaagctaac taccatttac aacattgcga aattttaaga   9780
```

```
gaaaaaatcg aacaagcaga gagaggtttc tatgaataat aacagccata tccatgttaa   9840
agttgatgtc agccgttaca gcgaaaatga ggaactagac ctgcaagatg ctcttctctt   9900
tgagaagaat ggtaatctcc atttgcattt tgaaggtaca aatacatatc tccacagatg   9960
ccgagatgat gtagatggtt gtcctgtttt tgcttggtac aatttagagt ttcctcttta  10020
tgcaatccat tatccagatg gtggagaaga ctggacaact caatcaatct ttgatgagct  10080
taatggtatt cctgttgagc aagaagaaga agaagaacct gttgaactca ccttcacttt  10140
tatcaaagaa gagaaagtag gtgaattgtc cgtaactgaa gcaattcaag tcacacaggt  10200
tatccgttaa tgagtaaagt acaggttatt ttccctattt gtgacttctc actagagcgt  10260
gaacttgacc tgtacgaaga aattactgac gaaatcatct ggtctgttgt agaagaggct  10320
atcaagaaac tgtatagtgg cctcttaaat ccatcaagca agaagttaag cactaagcaa  10380
gtagctgacc catatatttc atacgatgcc tacaacaaac cttttgagaa tacctgcttt  10440
gaccttatgg taggcaatag caaagtcaac tatttcttcg tcagagagtt taacgatgag  10500
taagctccat gtcacagtgt acaaaaactt ctcagatatc aaagagtctt taacaaataa  10560
gcttgactta caacgtaaaa ggctcttttt aatgtatgat atcgacaact acaaccatcc  10620
taaagagttt aactacaaag atggtacgaa ggtcgttgaa tttgaagatt ctgtaacggt  10680
gtatgtcaag catgacttac cagcaaaata cataggaatg ttagagtatt acatattcaa  10740
acatactggt atgcgtggtg aatctgttaa gatatcttct atagaggttt ttgagaaacc  10800
taacacacaa cttaaaaagt atttaatgag gaaactgtaa tgtccgaaga gcaacaggat  10860
atcattccac aagtaacact tgtacaacac tttgggaata ttgaagggtg tgttgcactt  10920
tttcaaccaa gcatcaattc ccctgcaaaa gtttgcaagt tgactatgaa tgttaataac  10980
attagtgttt gccttgttga tgaagtccag tacttcaagt ttaatgacag agaggttgat  11040
gctgcactgt tgaagtatcg agcaagcctc gaaaaagaca tcgaccacaa agaacttgta  11100
acactgtttg gtgaccttca caaacttctt gaaaaagtta tgaagcgcac atactacatg  11160
aacaacggtt caattatcac cactttaatt ccaccatgta tttcagagcc aattttaact  11220
gatgaaggtg gatactacgt ggtggcatca gcagattctg actggtggat gaagaacacg  11280
gcacttaaga cggttatcga tgctatccgt gaacatatac cttcattcag cccgtggaaa  11340
ggtaaaagtg acgattttat cgcactattg agtgaagaga gtaacaagcg tagcgcatta  11400
ctgcctaaaa aatactcttg accaagtata caatattaac tatgatggga gctatcgaga  11460
ggtggttccc tttttagttt ctggagaata gatatgccta aagtaaaaga acacgataaa  11520
attattttgt atgtgaaaca gaacccttcg aagagtgttg aggctgttgt gacacatgtc  11580
tcgcatactg gcacagttta ttttcgacca ctgaagaact tagactttga cataacacca  11640
aaccacacat ttagtacctc tgcaagactg tgcgcaggga ctgtatactc aactgctgag  11700
attgagtctt tagctttcac aggtgcttac aagaacttta tagggattgc tttaaaggac  11760
tctgaagaat cttttaaatt tttcatggat gctgctaaag gtggtcatac acatctcatg  11820
ccagtattta agagagttga tacagaactt accagtaagt gtaaggagct acatagcaac  11880
ttagatgaac ttaaaacatc agttacaaag actacttata ttattgaaga gaatcactta  11940
gagcatcttt tcagacatat gttaaaagct ggctttactc caaacgaaat tacaagagag  12000
actcaacgtc agttcagaaa cgctatggtg aaagaatgaa aaaactaact acagttgaag  12060
attactacaa tctgtcctta ttagaacaat accgtagaag ccagaatatc agaaaatgtt  12120
atggtaaaca tgctgaaggt gacttttacc gttgctacga tgcagattta aaaggtgtaa  12180
```

```
cacctagagg gaaagtcctg caaagacttg ttgaccttga gtggaacaaa cgattgagag  12240
aggttggaaa atgatttacg aagaaagata caagatagat tatcaggata ctcgccatca  12300
tacttcccta agagtaacta aaccaaacgg ggatactggt atcatagcac actttggtgg  12360
tgattattgg tacggtacag gttgctttga aggctacaat aaagaatact tgaaagcttt  12420
ctacagagat ttcacaaatg actacaacag ggttgttgac gaaaagaata agtgcattaa  12480
gcatgaatac catgccagag gttgtctgag tattgctatg atactggttt tcttcttagc  12540
aacattacta gccgtatcag caattagtta catagctcaa gacttaacca ttacacagat  12600
taccgcaaag gtatatgatg tttggtactt gtatgctgtc cctttagttg gtatcatcat  12660
cgcactaatg agattcagag ttcataagaa acgtcttaag gattctgagg ttaaacttga  12720
agaggtaagt aaagaatgca acctacaatt atagctgtat gtgttcgttt tgcaatcgct  12780
gaaatgatta acaaggcaat cttaaaagat gcctatggag aaactaagta atgattaaga  12840
cacctgtacc aatttttgga ttcccttcta ttgaagagtt taaagtttat cttgacaaaa  12900
acttctacaa tgagcagcct gttactctgc tgaagagcga cttatcagag cttcttgata  12960
tggttatcaa ggcaacttct gagaaggaac ctgagcagaa agctgagaag aagactagta  13020
agaaatccga taagaagact gaaaagtctg agtagtaact tgaggggtta cttgataacc  13080
cctttgtaga aacttagagg gtagcgaata tgcaaatcat tgctggtcaa gaacttgaca  13140
tcatagatgc aaaaacacag aagtatatcg caacagtgaa ggctatagga gttagggatt  13200
ggaatactga ataccccatt caatgccttg tgctggaaaa gtttaaagtg aatggtatac  13260
acttttatca tggtaactac atcagcttta acaaggacgg ctattggcgt ggtagtgacc  13320
atcctcaagc aaatgagttt gatatgtgtc tagtgatacc acaaaaagtt aacccacaaa  13380
acgtaaaaga tatccttgta gaagcctatg aagaaggtat aatagatgtt gtgcatgatg  13440
ttgaagaagc tttaaagctc attatgccac atttagaatc tggaaagctg actttagaga  13500
tgcttaatag ggttattcgg agagcttatg aaaattaaag aagtcgttca aaaagccatg  13560
cttaacaatt caactaaaca tgaaatgtac atagagattt gtgataagct gaattgttca  13620
agacatgctg ctaaggttct tgtaagttgc tttatctggg aatgctcaga ggcttatatg  13680
caacatgtag cttttgatag ttctcactta ctaggtgatg tagaagctgg tgagaaactg  13740
aaagaacctg agatgaaaac agttcctaaa gttggtaatg tataccctct taaagatttc  13800
aagactggag aggttgttgc aaaaggtgta gtagaatctg tttatcacga tggtaaatac  13860
ttacttaaaa tatttgagta tgatagccac tacacacact tatgtgggat tacattctta  13920
gtaacagaag aagacctcat taagaacaat ggcaacaagt ttgcagtccc agcttaccaa  13980
gttttacgat aatggtgtga tagatatgga aaaagataac ttaaaagatg ttgaaggtaa  14040
ctacctagta cttgattgga atgatattcg ggaagcacta tccgaagaaa gccttgacct  14100
gctagagcaa cttatcttct cagtacgcca taccagaggt attgtaaacg gtaaagagcc  14160
acttgaagga atctttgtag agaagtctta tccgttctat gaagacacct tgcagaaagt  14220
taaaatgtac tttaagcaga agaaccgtaa agtagtcact atggtttctc ttggtggaca  14280
aaagatgtca gtgatggaag acatcaaccc taaaagacca aataagggtg tatgtatcaa  14340
aatcacaggt aaagaagatt acatcacaga aagtgacttt aatctgctat gtactggttc  14400
tgcaacattt catggtttcc attacatcat ccatgtattc ccaatcaagg gagatgatat  14460
tatgatacag atacatgatg gtgatagtgg atttactcat ttttatcaga ccactaagtc  14520
```

-continued

```
gtcattacga acaatccttg aaacactgat ttaaaatatc tagagcctcc ttaattgggg  14580
gctttttaat tttataaaat tttatcggtt gttccaacct ctgggtcacc atgatatgtg  14640
aacaaaatat ctacccttct taacaacctt cttaatctta ctctctatat agttatatag  14700
tactatatag tatcttagta actatttagt ggtcttaata gaccatctgt atagcccttc  14760
taaatatcca tctaaacact cttctaacaa gccttcttaa caacctatac aatcacctta  14820
accacctctc tataccctct tagaagcccc tatacacctc ttaatctcta ggttagctat  14880
gacactctct ataggtgttc actaggtatt actaagcctc tatatagact gttttaacaa  14940
acttaacagg aatatcttca cagaccttat ctcacaaggt ctaacacggt actaacaagg  15000
tatcttataa gcctgtttat gcctgtattt ttaaaagact gtctaggtaa ttattcagaa  15060
ttttaaaatt tttataaaat aggactatca agtcattttt tagggtcttt gaaggaactg  15120
aaaaatatct gtctaggatg tatatctgct tggtagccct taacatccct gtaacatccc  15180
ctttgcagaa ttttaaaata tcattaacaa tctcttaaca actctctcaa gctcttaaca  15240
tctcttcaga tgtcttaaca gattcttaac agaactaaca aggctgtaac aagttcttaa  15300
cagtcgatac atggtcttta tagtctctta acagatgact aacaagagct aacagggatt  15360
ggtaacaata ccaattagtt aatttttaag agttattttg ttaagataat taacaagttc  15420
ctaacaagtg tctaatcttt ttaacaagct attaacatgg tcactatccc ttttcttatc  15480
gttccctttc ctttcttagt gattccttaa acataccttt taaaagcttt ctatagctct  15540
ttgtaagccc ttttaagcct ctccctagta gttacacccc aactgtacag acaccttttt  15600
atagagcttt acaggagctt ttaaggctat gtcaaagact cttacaaggc ttttacgttg  15660
tcttaacaga gatttaacaa ggggctaaca agttgctaac aagtgcctta aaagcataac  15720
tatgtaggga ttgttaagaa attgttaaga aaatgttaag ggggctagca tttacgtaac  15780
ttttaagcaa ctttgaagtc acttcatagc ccctataaca tacttttaag acactaacaa  15840
taggattcga tagattccta tctcatagcc ctttctagat attcacaaga aactaacgag  15900
atgataaagc ttacaccctt ataagattct tttaaggctc tgagaagctt tataaagggc  15960
ttttaagggt gagttaatgc aatcccttaa gttaggttga taaggctgtt atagagcttt  16020
atagagcgtt taaacggttg cccttccctt tcgggttatg ggcttatatt taagttgatt  16080
tgataagagg ttatagagta gactatagag ttattgcttt taaggtctga taagattctg  16140
gaaaggtgat ggaaagagat tgtataagga ttcgatagat gtaaaaaagc ccctttaaat  16200
aggggctgtt gaggtatctg gggctaaata gccccgctgc gtcgattagt tataatcttg  16260
tttgttgtag tacagggaga cgattttttc tccccaatag tgataagtat aaccatcctt  16320
gagaacttct tgttttgttt cctcccagaa ctcatccgaa ggattataat ctttgatggt  16380
ctgactgata agacctttca ccatttcaaa ggcgttatca gtgcctgcaa tgtcaaattt  16440
aacatccaga gagtaaaaac caaattcgtt aacagtagcg cggatagttg ccatttttga  16500
atctcctagt ttaagggttt tatgtagtgg ggaggttatc cctcccgttg attgacaatt  16560
tacagacttt tgattgtctc gtcaatatct ttttcaatat cttttaaagt tttttctaag  16620
ttcttgatat tgaacgttaa accttcaccg agagtcttag agtaaccgct agtgcgtaaa  16680
tcatacagct tgatttcttc cacttcaaag agactcaccg cctcaccatt tacagcatag  16740
gccattgaca cagtattttc aggtgcgttg taaaacttgt ttaaggactt gatagaacgt  16800
tcataagcca ttttataact gtttaaaagg tttttaacgt gattgtgaac gtttttacac  16860
tcatctaagt aaagacctaa aaacatcggg agaagttccg cgacagcttg cataaagtga  16920
```

```
gaaactacaa cagtagaaac attacgacga tggacgtaat aagccccgtt ttctgattta  16980
gtgatggttg caaagtgtac accattgcaa cgaaattcat aggtatcttt aacaggcttt  17040
gacattacag catttgaacg aatgaagttg atagcttgaa atttgttcat tttagaatct  17100
ccagtttagg actttattta gtggggaagg tcattccctc cccgttgatt agtaatttac  17160
ttgttttgat atctgattgc aagcaatttt ttaagtttat ctataaagaa tcttttaagt  17220
gaatcccttt aagataaacc ccctcgaaca aagttaccaa tgtcaagagg gattgtcaac  17280
actttttag aagtttttg taagttcttg attaactgat gaatattttt tcaggtttta  17340
cgtagctgat acgctgattt tttagcaagt catcccagat tagcgcggca atatgagaat  17400
aaccggattc acgtaatagc ttcattactt tacatctcgt ttcaaatctg gttgtatagt  17460
gctcactatt taaaaccgtt ttaatccctt cattacttac atggataatc tgcatcactt  17520
gaaaggggct gatatcctcg cccttgttcc attgctcaaa gtattttagg cactgcatag  17580
gtgtcatctt atcgcttact tgagttgacc aagatgaatc cgctttatcg gtaattacag  17640
ttacataagc catcttttga atctcctagt ttaagggctt tatttagtag ggaaggtcat  17700
tccctccccg ttgattgata atttacagac ttttatccgg attgtctatt ctttatcaat  17760
gataatttca tattgaccat caacgctgtc aaaataaacg ccgtcgctgt cttctgtctt  17820
aaagtaacat tgaatatcat cactggcggg atagtcttgc cttgctatct ggcaaacctg  17880
aatagcattt tctttactcc ctgtaaactc ttcaagccct ttaaaatcgc atgaatgacc  17940
gttacaaatg gaaaggatga ggtaaacggt tgtaagcatg atttaagcct cctaaaagcc  18000
cctagaaggg gctaatcagt gtttataagg tgattgtata ggttattata aaaagccctt  18060
taaatctctt tctgcgatgt ttcccgtcag cgtgtccatg atgtcacaaa aaacttgaat  18120
actgtcggac tgttgaacgc ttttagcgag aagttccaga gactcgtcaa tatagtttaa  18180
attcgggtta tccagtgaag gcagacaaaa tggtgaaaac atagcattaa attcagtggt  18240
gtaaaccttt ttaatccagt ttaaatcgaa atattctgta aaacttgcca cgccagacat  18300
attatcacaa gaataatcat cgtttaactc atcttctgga atatcaagtt ctaagataac  18360
aatattttgg gttttcatct ggaaagctgc ggtgatagcg gcattgccca gagcttgctg  18420
gataccttca gagattatct cttcctcatc gtcgccatag attttatttt ctggataaac  18480
gtaaaaattc ccatccatat ccgaacaatt ccatgcacct gatggcttat caccgttatt  18540
aatcaggttg atgaagtttt cttgagtagt accgtgaaag catttcattt ttgaatctcc  18600
tagtttaagg ttgttgataa atctctttat ctggggctta agatatcatc ttttaagccc  18660
cttgtaaagt actttatctg ttatttttga caacttttaa aactgcaagg taacctaagc  18720
aatatgaatc accgaagaga gtccggccca tgaatgaatc ctctttgata tcttttgcag  18780
tgacggtttt ttctacgccg tgaaaaagga ctacatcacc gaccttaata tctttgatgt  18840
gagtagtttc aatgtttaaa ccgttgataa tagccatctt ttgaatctcc tagtttaagg  18900
gttttactta gtggggaagg tcattccctc cccgttgatt agtaatttac ttgcttttaa  18960
aaccaaaatc aagagaaatt tttatagttc tgcataaatt gcatcgcaga tatcacgaaa  19020
atcgtgattt gttaaattac gttgtaacca tgttgcgaaa aagtcagcga ttgcaaaatt  19080
tgcaccatac tcgacggaca gccatacttt cacggcaaat ctaaacattt ttaaatcaag  19140
ctccctattc attaccttag atttgcctaa catgtcggtc atttcatatt gtgcaccgtt  19200
tagcgtgata cctgctgcaa cgtcagtcag tgagtttttt acgctttcaa cgtctaagat  19260
```

```
aacactttga atcttcccga taatgttttg cagtgtctcg tctggtgctg atgatgtaac  19320
agcattaatc cggttaacgg tcaaacgtgc ttttaagatt gataattcac ggctattaat  19380
agtcattttt gaatctccta gtttaagatt aatgtggtaa aactctttat ctggggctta  19440
ctttatcgaa ctataagccc cttgtaaagt actttatact aaatgcagct tttacctttt  19500
taccatgatg taacttgttg cgctattgct gtaaacatcc tgataaattc tgcgcaaacg  19560
tccttcgtag tatactttcc aactagttgg aatctttttc ccgtatccgg tagcagtttt  19620
ttggaatcct gcaagttgcc aatctaagat atgttgttca gcttgtaaat cctcgaagtg  19680
cattacaccg ttcacatagt ggcgtagggt tacatttaag gtgcgaccgt tgttagtagt  19740
atacattttt taatctccta gtttaagggt tttacttagt ggggaaggtc attccctccc  19800
cgttgattag taatttactt gcttttaaaa ccaaaatcaa gaggaatttt ttcgtttgtt  19860
taattcttga acaattacag cgtaatagtc ttttaagtca ctgatattta aagcatttat  19920
cagtgaatta taatcatcga ctaactgaaa atcatctttg aagatgtcac ttatctgata  19980
ggttttcgct ttatatctga agctcatctc tagccgcttt atttgctcat cactgaggcg  20040
ccctagaaag ctttctacaa ggctattgtt aacctgctgt gtgattgcct tatctgctag  20100
attataggct ttatatgcct tatatagcgc gaaaatggca atgattgcag tgataccagt  20160
cattaacatg gtgtttcctc tttacgtgat actttgccat ttacagttat ctcataggat  20220
tctaataaat cgcttttaga ctttacagga cttttaaaag tatcatcata gatattaact  20280
tgcaatacag gtttttttata ctccctgcaa ctgttccata agcaaatcac tacacgacgg  20340
ccttttattt tgccgtgtaa ccattccata acatcatgac tattccttga tgtttcaatg  20400
aaatcaattt tgttgagtaa tttgcttaga ttttcacgca cttgatttga taatttcatt  20460
ttagaatctc ctagtttaag ggctttattt gataaatctc tttatctggg gctatcctac  20520
cagcttgata accccgtgta aagaaatcta ttcagttctt aaagatattc atcactgaat  20580
cttttagtga ttccaaacgt tctaatactt cagattctgc gtctgaattg ttcacctctt  20640
cttttagtct atcctctaaa tcatcgccgt cacgataaca ccaatcgaaa gcataaccaa  20700
gataaaaact ttctaaaacc gtgttaccgt ttgcatccac aactttcgcg gcaaggttgt  20760
actctgaagc ctctaaatct ctttctagtt ctttctgtaa gcttgcgtaa gcctcttttg  20820
atggattttc ccggccttgt tttgcatagt cactagaaag ctgtttaagg ctgtaatgta  20880
aagggattgc atatttaaaa tcattacgct gacagttggg gtttttgata gtcacgccgc  20940
cctgatgggt gtctgtaaac ttccaattat caagattatg gcttgcttca aagcaattga  21000
cagcttcgta aataatggtg aatttttctt ttacaacttc aaaggtagcg tctacagttt  21060
tcatttttga atctcctagt ttaaggattt agtggtaaag ctctttatct ggggcttaag  21120
atatcaactt ttaagccccc tgtaaagtac tttatcagat taaattgcca gttaatgata  21180
agtgcatttt gtaaccttgt ttagtgaaaa cattcacttt accgagtgtt tttacacctt  21240
taaaaaggtt atttgaactg cgttttaggg ttaactgttt atcagccttt acgccccatc  21300
ttacagcaga ttgtttcccg ttgtcaacca ctttcccgca taactttttta gccataacgc  21360
gagcgtcatc acgagttttt gcagcaatta caacgttttt gataatagcc atttttaagt  21420
tctccaattt aggattgagt ggtaaagctc tttatctggg gcttacttta tcgaactata  21480
agccccttgt aaagtacttt atttgttaat tttgaagata gttacataac catcgctgcc  21540
gatgatttgt gatgctccag ctttttctac ttgatagccc atattttcaa gatggtaaac  21600
agcatcatca taaccatatg cgccgccctg ataacgtctc ttatcacatc ttactaatac  21660
```

```
ctttccacgt cctgccagtg catttagtac ggctttttca cttgaaagtg taccatctaa  21720
catggttgcc gtgtaatggt tgattctatt cccgtttaca tcatacttaa aattgaatgc  21780
gtgaacaacg ataatgttac ctttaaaatt ctcatcaagt gacttctcca gtgcgttgcg  21840
aaagttgtct ttgttgatga atttaggtgc acgatatgcc atttttgaat ctccagttta  21900
ggactttatt tagtggggaa ggtcattccc tccccgttga tgcaaatact agataaccac  21960
gttcaaagag tcaagaaaaa attttaaaaa tatttttggc aaaactgtaa tgaaacgggc  22020
gcacacgact accacaaaac agaacacaaa tcaagaatta tttttcaatc cgctacaaat  22080
ttttctcttg acttttgggg agagggggag taagaggggg agaggggttg gtctggctct  22140
ctataaaaac ctacctgcac aaatctaaaa tgatttttct tgcccgacct gagcggggtc  22200
tgcacgtttt gaaaatgaaa aagctctttg gagattatct gcacagtttg aaaatgaatt  22260
ttctctttgg agttcaatat tttctctaca ggtttctcta tagaaatcta cctgcacaat  22320
tctgaaatga aaaagccctc cttacctgaa aaatttacca gataagaaag gcttggtcta  22380
ttgtgaatat tctacagagt ttcttagttc tttgcgtcta agaaggtaac ttctggtgaa  22440
gagaagatta actcaatatc ctcatcagtt cttgcataga tataagcatc tgcatcactg  22500
ccaaatgtta ctgcaatcct gtgattgctc ttcgacaggt gggtaactag agcgttactc  22560
agagacatct tttcaaccgg agggttactt tgatgtatct taccttttct tcgtctgaag  22620
agggtaactg cgttatctgt gaacactgct acacctgcaa agtattctgg ttcacagtag  22680
ttcttccaac ctgagcgtaa cttgtggtat atttctcctt catagacata tagataaaca  22740
tctacactct tcatcacctg attgatgata actgtgacag cttgagggtc cagcccaccg  22800
atacctgcac caatcatagg taaaccaact ttcttcaact ggttaacttc acagtatctg  22860
ttaagctgtt tcaaagatga ctctaaagca ctgtatcgtg catctttacc agtcttaagc  22920
tgagtgtaaa ggttagctat acggccttgt tttaaacgtg ctacagagaa attacccagt  22980
aaattttcac agggtttgtg gcctatacca cctgcatata gataaacttc tgtatcggtc  23040
tcatatgctt ttgggtaaag tttagaaatc ttgtcagcga tacctgcacc cattaaattc  23100
atacagttgc aaccgtgacc aatgatgtca aacttacctt tatcaaatgc agcaaagata  23160
tcaccattga tgatttttac aatacccatt taacatctct cccaagattc tttatcttct  23220
gaaggtttta cacgctgacc ttcatggtct acccagatgc acccacaacc ttcacatact  23280
actggcattg catagccagc tttaaagtca tcttcagtga taagaccttt taagtcacct  23340
gtatcacgtc cgaacatttc gatagaacaa tctttgcaga agtcagccat tgataattgc  23400
ctcttgaatg atgataccct taccacaacg acttttgaag tcttccaatg gttgtgagat  23460
gaagccacgc aagcaataac taaatgctaa tttttccctg taggctatca catcatttgc  23520
tgtaaatgga atcactttat ttcttccaat gaatactgct gaccggataa ttttccgtgt  23580
ctttttatct ctggctagaa ttactctcat aatttacctt ctcagtcagt tcatataaat  23640
caacatgctc aatactatca atgttgatat caatcttttt gaagcgttct atcacttcgt  23700
tgtcagtcat ccatatcaga caccaatgat tctggatgga ttcttcaaga aggtcaacac  23760
aatctttaaa ggtttttgta tcacttcttg ttcctactac tgcgattgtt ccatatagcc  23820
acttaccatt gccataagat acttgtgcta cgccaacttc tttatctttc tcgtagtaaa  23880
cggctacaaa gtctcttcca ttaatctgca tttgtaagtt cctctgttgg taattcacca  23940
ttttcagcaa agtattgaag gtacggcaac agctctttta cctgttcttg attgagcttc  24000
```

```
attctttgat tacctacaaa atctttacca actaatgctg ggatatcaag tgttttccag  24060
ccattatcta ggtactgaac agagacctct ttagcaccta accagataca tggttcgtat  24120
gatgaactct cttgtaaagt acaaatttcc cctttagcgt ctttaaattc tgcataagaa  24180
aatccacgat ttgttggctg gaattgcata atcatttcct cgttttaaga actgctaaga  24240
tttctttaga gtctggtaag aaccatgtgt agtgattctc tttgatttct ggatgagtgt  24300
caacctttat tttgcactct ttaccaacat gcttaagctg tgctgtgaca ccttgcataa  24360
agatatgaca catcacatta tccataatgg ttggtaagaa atcaattcgc atataagttt  24420
cttttggtcg tggcaacagt aagtaacctt ctacatagaa agtatcttga ttctctgtca  24480
ttgctgctta ttccctaata aaatcatgtc aataaggttg ttagctttga ttgtgcactg  24540
gtaaaagccg tcacgataga actcaagggc tgctgctaca tcgctgcctg tgttgccttt  24600
gatgatatac cgtgattctt cttgagtgta cttatcactc tcacttactt gggagttttt  24660
gaatgtactg ttcactttgt tcgttgaaca ccctgacata attatcagta acacaaacat  24720
tataaaactc tggcttagtt ttttcatatg ttagtacctc ttttgtgtgc ttattcttag  24780
caagcacatc tttcaaatca tttttgtaat tggtgctcag tgtaactaat ccttcctgat  24840
aagcatcttt agcaacactt atgagctttt gattgtttag ctcagtttca gcaacttggt  24900
agtctctgta agagtaccct ccccagacac ccgccccaac taagaaaaca attatgaaag  24960
tagcttgaca gaactcttta aatgtcattt aacaatctcc tgaaatgaaa aaggctcccg  25020
aaggagcctg tatcttaacc ttaaccgagg actttagcaa ggatattcgc agccatcgaa  25080
gaagcttttg cagcagcaac tacgccagct ttgacagtgc tatccttaat agcagatacc  25140
gttgcagcat cagtaaagag ataagtgatt gttttggaac cacttgtaaa ggaaagcata  25200
agagtagttt ccagattgaa agagcgatac ggagcacctt ctttaacgat accttcagca  25260
cctaactctg aagccttacc catatcatag atagtcatca ggttttcttt gtgtgcagtc  25320
gttgaaccaa caccttttac gtgcttctta acgttcaaca atgcacgata ttcacgaatg  25380
ctaccatcag cttttacatt aacagcacgg aaaattttac cttcaaagtt accttgaatc  25440
attttacgaa ctacttcaga tttgtttgcc gtatcgtcca gtgctaccgt aatgatatta  25500
ttcataagtt ttctctcaat gtttaactaa catggtttta atgtgtggaa ggattctgtt  25560
caccttctgc acattcttct ctgtatcttc tataaagcat actatattaa agtaaggcag  25620
aatgcaagac tgaatcatcc tcactttcaa actttctgca cttatagagt tagtcccaaa  25680
accacgcata aaaagcatgt aatcatgctc tatgtaatgc cttaaaaaca tctcagtagg  25740
tattctctga gattcacctc tcgctgtcaa gagtccaatg gcggcatgat tagcaattgc  25800
atcaataata ttgaaaacat acgttggttt tgctcttaca gagtcaagca aattagtgta  25860
ctgtgaaaat gacccatcaa tcaattccgt tgagcaatct tcgtgattaa aatttgtaag  25920
aacaccatca atgtctgcta agataaggtt accttttttct acaaggtctt tattgactat  25980
gactaagcta tcacgactta cgcctatagt ttgtccagtc tctttatcta caacattcac  26040
aattggctct gatgtgtgga actcttcgag tgaacataca acttctcttg cagtgtcttc  26100
aaaatcccta cactgttctg gagtccatac acaggaatca agacctaact catgaggatg  26160
taagtcgtaa gcatgacaca gtacttcatc agactttttt aatttttca tggtttacct  26220
tagaaatgtt tgttgcaaat tcacattgag cgataacttt catattgtta tagacatctt  26280
gagagtattt cttagcttta gggattttgt acgaataccc agcattatat gatgctaaaa  26340
ctttttgtaa agtcttcttt gactttgggt gaccatgtac ctttgtccaa aactcaagct  26400
```

```
ctttgtgagt ttccttcgca gcataatcaa agtctcttaa gagtttcttt ttagccacat  26460
tagggctaat tttgttacgc tttacaacag tcttcaagtg attctggaaa ataccataat  26520
catgtgtctt tttattctct accttcagac ctaactctga ctcttgtaag gctatagcag  26580
ctagagtgat accccaacct ttacccatat tattctcacc atactggtaa gcttttaaca  26640
tatttacttt ttggctaatt gatagctctg ggcagtcgac tgcataagat aagtgtgctg  26700
taaacattaa gcacaaacct agaatcaatt tcttcattgg ttctcctgtt tagtttatcg  26760
tgacaacaat tatacagcac tctgcacaaa atacaaataa aaaaggccgc cggagcagcc  26820
ttttaagaaa ttacttatta gatttcacgt ttacgttggg agataagttc tccagcagta  26880
ccaacgatga catgtaaagc ttcagtcttg ccatcccatg ctttcagcac tttacgttga  26940
ttatcaacga ttgctgcaac ttcataacga gacgagcgca tcttcatatc gttgtaatca  27000
gttggtacgg atacaacgtc tcgtggatgg acacgaacct tcagaattgt atcacctgag  27060
aaacaacgaa cataatccca agcaccaaca tgaagacctt gagagcaagt cacgttacgg  27120
ttattatcaa ccatccaacg tggcatttct acaatgttac ccaaatcatt aggtactctg  27180
taggtgtggg agtcaaccag cttgccttca cgagtagata ctttcttcca accaatgatg  27240
tagccttctt catcaatttc aacatcaagg tgagatacga agccccaaag ttgttctacg  27300
gaatctttag atgggttttc catcagtttt tcgaagaaca tcacaaggcg ttcgaaacct  27360
ttatctccag tcttcatcat gtgaagaata cggtcaacca gagtagaacg catctcaaca  27420
gcaccgtaga ataacttgtc acctttgatt gtgatagcac cctgagtgaa gttttcgata  27480
gacttacgaa tgttcatcag ttcaaaggct ttcttaaact cacctttcac aacatgaact  27540
acaatctctt gatagttcgg atgagtagac tcaacaattt cagattctga accgtaagtc  27600
ataattacag agtcaccagt aatcatgtac tcaatcttgt catctttctg catagcttcg  27660
tgcagtttat ttactggagc tttctgtaca gcatctttaa caatcttttc aactggtttg  27720
tcagctttct ttttaaaggt cttagcaact tgcttcaaag tcttcgtagc tggtgtagaa  27780
gtcgcctttt tattcccttt taaggttgct tcatgacgct ctacagcacg accgactgaa  27840
cgggttgagg tattaaattt ctgtgcaata gctgttttag tcagcttgcc ctctttaacc  27900
agtttgtaaa tttctgcgtc aatctgtgct ttagttttgg tagtcatctt attactctct  27960
cttgttagtt aataaatcat tttgtgatgc tattctaagg ggcttcaaag ccccttgtca  28020
aacactttaa tcgtaaattg tagtcccttc tggaacacac ttcacatcaa agcctaagaa  28080
cttactcact tcgataggtg acactttatc ccaatctaaa tgagaaagca agaagttttc  28140
ttgttttctt tttgaaagat agtttgtcac cttaatgacc atacggtcac cagctttctt  28200
gattttcttg tacagctttg tatcgttgtc aaggcattct ttcaaagttt gcaacctgct  28260
aacagtgtaa gtgtatgcaa acggtgcagc aacgtattgg attttaccga agattgcctc  28320
aacagcatct tcattacctt ctaggaagat agttttgttt gtatctcgtg aatagcaatg  28380
gccacgagaa atcttcctgt tattgaacgt aaagtttctg gcaataatcc agctacttgt  28440
aaggtcaaga acaccattca tgtagatgcg tgtcatatac ctgttatgat taatccaatg  28500
aacatcagtt aagctgtcgt tcaagagttt ctcatctact tcaatccagt cttctggtat  28560
ctttttccaa tttgcttttc ggaaaacata gactgtcttt ccaataacat tagcaactga  28620
cttagctaca tcttctgggg atgagcaaaa acattcacca tcaactgtgt caccaattgc  28680
cttaatgtaa agctgaggtt cttcaattgt atcaaagtcc tctgaaacct ctttatagga  28740
```

```
agctacacct tctgctggaa cagctttcca gagttttaca acacctctta cagcttcttt  28800
acgctgataa tggtgttcct tatcagacat cttcacaatc tttaacaagc ttttatcaag  28860
tttgtgtaga ttgattaggt catctaactc tttttcagtc gagaatacaa agacaatacc  28920
attgtatctg tgaaacagac tagactcact ggcatagtct cgacatgcac cacgcaagat  28980
ttgattgcgt cctacagtct tctcagtacc atttttattg cgacggtcat ttataacaaa  29040
caaaaactgt tcaatttggc ttttacgcat tgcaccaaag atattgaaca tacttgcctc  29100
ttgagtgtag gaaagtgctg ttgcacgaat cttactctct aaagagttga acttgacata  29160
agcaactggg tcataaagat aatctacttt aggtatattg ttcccgtttc tatcaacctt  29220
aatattgcct ttaccgtcac gttcataaat gactgagccg tcttctgcgt agataattcc  29280
acgacgaatg tttagcaatt cttcttccag agaatcaagc ttaacgccac cccactctag  29340
ctttggacac acagcattaa acatctctcg tgagttcaaa cgtaactcag cataagcctg  29400
tgcagcatcc atgagtgtag gttggctatt aactttcttg ataacatcct ttgtaatggc  29460
ttcagttatc tttttagtag cctcaatgat aacatttttt gtcgtgtcat tcatctgcaa  29520
tgcttcacga gaagctgcga tagcaactga accaataggc atgtagatgt ttacaaggtc  29580
tacgctccta cggaaaaatt ctggcaacac tttgaagaaa tcatcaccaa gtaatgcttc  29640
catgttaaca gggtaggcaa tgttacccat caccacatta aactctgtcc tgttaccact  29700
agaacgccag ctttgcttat gaatcatggc atcataaaca ccctcttcac gggcaatgac  29760
gttcatatct gctaatacat cgtcgtacac aatattactt tctggtttta cagcaaagta  29820
tgagtataca ttgccagcct cttcaaagaa ctttgaaata cggtggtcag caactgccac  29880
acgtacagct aaaccattag gttcttttgt tgggttagtg gtcagcttag ttacttgagg  29940
gataccattc tcaagataaa cagagtactt attaacaaca ccgtcaacat agctagacac  30000
tgtgaatgac tgagcaattg caaatgtgga ttttgagccg atacccattg caccaatgta  30060
gtcattagag tcattcttcg tagaagcccc gtaatttaga tacaaactca taactttatc  30120
atgagtcaat ccagttccaa aatcacgaac ttcaaagtaa ggctcaaaac gagtaggtaa  30180
atgcacatgg aacgggatat tctcttttcc agcttctttc tgagcatcta ctgcattaca  30240
tgacagttca cgaataactg ccctttcttt aaaggtatat acaccagaac tcaaaaggct  30300
gaacatttca ggtgtcattg taatctgtgc ttgagacgtc tctaaagaag ttgaactctt  30360
aatcacttct gcgtggtcgt ttaccatgcg cataatactt tcctctcagt ttactgttaa  30420
attacttatt aaacatttta ccagaaccac cacacatagg gcaacaacct gcccttatgt  30480
acccctctcc gttacagtag ccacattttt tgtgctctgc aaagtactta caaagaaggt  30540
aaacaaatac tgctacacta ccaagtgaca gtaaaatttc tatccaatat gcttgcatga  30600
ctcacctctc atatttttgt aaaggataaa gcttctgtca tgtacgatac ttgtagacac  30660
tgcaaagtta ctttcaagca tctgtttgtt tggattgtag aagttttctt taaactcgtc  30720
aagtgcaaac tggtgatgtt gtggaagacc ttttacacaa acctttattg tgattgctgc  30780
tgcaaccttt ccagtcagtt cttctttagc tgctactaaa attttgttga ggaacttatg  30840
accatcttca ggcttcttga tgttctccca acgttcttct aagacaatgt tgatgttcat  30900
ttctttgatt ttcatagtct tctccagaaa ttaaaaaggc tcccgtagga gcctcttatc  30960
atatactttt aaagctgctt gtcaatatta tttcgaatat caccaagagt tgtgtaaccg  31020
aactgctcag agttgctaaa gactaaacgt aaagcacaag ctggatggtc aagtgcatct  31080
gcaaaactct ggattccgag tccatctaca gctttcagct tatcaccatc ccacataggt  31140
```

```
gctacaccac caaaagcaga cttcttaaca ccactatctg ttttagggtc ttttgcaagc  31200
ataatctctt taccaccaat gcttgcaaga gttgctttga cagcaaatgc aaaggtgtca  31260
cgagtcatgt actggtaagt gtaagagcct acaccaaaca ctacgttaga gcttgcaaaa  31320
cccatttcat acagacgctt caggatttcg tttgcacgtt ccagcgtgat agagtcacca  31380
tagataaggc cgatatgctc atccattacc ttaaaccctt tagagttaat agttccccca  31440
aagatgttgt acagtgtctt aatagctcca tcaatctccg ctacagggcg tgttacaacg  31500
tttgcagagc cgttgatgta agcatctttc agcaacactg tatcggctac ttcaaagtct  31560
tctctgtcaa ccaccatttc atagccttct gcacgtaacc acccagccat aacatagtta  31620
atatcttcaa gcttcatgtt caggacggtg ctcagcattg tatcactagc ttccagcttg  31680
ctaagatgtt cataataagc cttcttagca cactctaagt ggattgcttt ataacctgtg  31740
acaatatgta cagggtctcc agagtcagga cgaattacca gtttaccgtc acgttccata  31800
atttctttac ggagtgctgg taagatttct gacacagttc tccagaagtt ataagtatct  31860
gaaacaacac ttgcaatacc agttgggtaa gtttctgtta agaagtgacg gaaggtttgt  31920
aattcacctt taaagcgtct ttcctcttca atcaactcat taccaccttc ccaagcaatg  31980
tttgcacaca ttacagagtg ttcagtggct ggtacagaac taccaatatc agaaattggg  32040
taagactgac catagattcg tttagccgtg tatacagcag ggaagctatc agttccttta  32100
aagctggtta agtgacctac agcgttaaat gcgtcatcag taaagccgga cataccacgc  32160
atagcaaagt cgtggcactg ataaggtaaa tgtaggtcgt tgtcacaagt aaggtcagcc  32220
cacttcttac agatgcgttt gtagtgcaat gcaatagtcg caatggtgca agccttccaa  32280
atctcagcag agaaagcatc ttccagataa cctgctaccc aatggaaacc tgaaacagtg  32340
ttctggaaga caatcattgg gacacgcatc gggacaactg tgccttcttc tacagtgtat  32400
acttcaactg gtagataacc taagtcgtga agtgcttccc aatgctctcg accgatagca  32460
tctttaccca gaacaccatt catgacttct aagatttcgt caattgcttc tttttatca  32520
cgttcaaaga aagtggcgtt ccaatggtct accaagtaat ccttaacaaa acgttgaata  32580
ccaaaagcca ctacaccatc aattgccaaa gggctgttaa accatttgtc actacgtggt  32640
gtcaggttga acatcaagta ttctgttgca ctagggtact ggtaaacatg accagatttg  32700
taagcatctg catttaaacc tgctggtact gcataaagtg atttagtcat cttttaatct  32760
ctctcaaaat ggggctgtca agcccctata aagtttcaat caatggttgc tacagtaact  32820
tgtgcgtaat gtgttaagcc acggtcttta gcttcaccca aagagtttgt agtgtagata  32880
tggtcaatgc cattgtcaag taagttttca acacctttag agaaaatacc atgagttaca  32940
tagagttcca cacgttttgc acctgcttca cgaagatgtt tagctgcctc tatgaaggtt  33000
cgcccaccat cacaaatgtc atccagaatc atgacggttt tatctgtcaa atcaacatca  33060
tcaaggattc gcataccagt aatttcacca gtcttaaggt tacgcacttt agacattgtg  33120
atatatggtt tatccacctc tttagcggcg tcttcagtct tcttagctgc acctgcatct  33180
ggggctacta agaaatcaat gcgtgggtca cttgcaaagt gtactgccac atctttttgc  33240
ttcatgctct gaaaacactt aaataagttt tctgcaacat tactgtgagg gtcaagagca  33300
catactgcat caaaacccat tgcattaacg aggttagcaa agactttcag tgctgctgca  33360
tcacctttga acatgtggcg gtcgtatcga gcatttggta agaacccgaa aacaacggtt  33420
ttcatcgctg atttctgggg aacaagactg tcaacggcat ccttagccaa agctaatgca  33480
```

```
aacagtgtat ctttgtcata cccctgtaca gtaaatataa cattatcaat cttaccagca  33540
ttacgctcag caaacttaac aaaatcttca gagaagtttc caccaatttc tccagatggg  33600
aattggatga tattaaattt ttctgtgtgg aagagtctct cttgtgcggt gatgacggct  33660
tcaataacag ttttcatagt tttctctcta tctcaatcaa aggttatgtt tgttactgcc  33720
attgcagatt tgcattttac agggtctaca acgtggtaaa gtacactaca gttacctgtg  33780
ctgtctggta caggtttaac ccattgatgc tttatagttg gctctcccaa atctttgtaa  33840
gagccatctg taaaattgtt taccatctca agtgcaattg gttctgggac atgaccacgt  33900
atcatgtaca tatcacaacc gttaccgcct tcactcacta atggtaaaat ttcccacttc  33960
tctttagcca ttgtaagttg ccctataaac tgtcttgaac ttcaacagga gagatattgc  34020
caaatctgta tagttgttgt caagcacatc tggcatatta tttttgatat atttctcttg  34080
ctcttcatag gtcatcttag gggtgcttag aaggctatct ccttgcttct ggttatcagc  34140
tttagtttgg ataaaccagt tcgcacagtg gtgttcacca ccttttgtaa taggtttgtg  34200
gtggcctaat gtgaaggact ggttacctgt gtatctacaa agcttgttga gcactgcaat  34260
ggtgttcttc acaacaaaac attcatacag attatctatg gtgtagtgtg ggtaatatcg  34320
gaatagtact ctttcacgag tactgtcacg attccagaga atcatgtgat ttgagttaga  34380
agggtcgtat tggtgggagt caatgaactc ttgacgttcc ttaaagctga gtcttagaac  34440
tgacattgca gccgaacgtt tcaggtttga cagatacata ttatctccaa aataaaaagg  34500
gaacctttgc agtcccctta tagtatctgt ttactgagct actttcaaga tgcttgtgaa  34560
tgagatttca ctctcatcca taaactcttt tgcttctcca gtaactttta caaagttatc  34620
taggcagata atcttcttat ctttcttgct gtaggttagc ttaacctttt caatatcttt  34680
cttagagctt ttctcttcat tgaagagttt tacagcctct ttgaatggta gatatgaacc  34740
atcattatca ctaatgaacc ctgtaccaca atagtagtag ttatactctt tagccataaa  34800
ctggcacagt acgaaaatct gtaatttacg agtgttataa actttactca tgattattta  34860
gccttcttgt tacgtttacg gttacgagct tttttagctg cacgtttaat tgctgctgca  34920
ccagttggtc gatgtgcttg ttttttacca ccttttccac gacctacata gatgcttttc  34980
ataatctcat tagccagcct ctcatccatc ttgaagttct gcataaggtg agtcacatca  35040
acaccagtga gcatacctaa tgaagctagt gctgctttta cttttgattt aaaactattc  35100
cagagtccca tttcatatct ctctcaatct tttcacaaaa tgttttaagt tctttttcag  35160
tgacacaaac ggttaagttt gttctgtaga acattgtaaa gtacccttta ccgataacct  35220
actttacgac gagacttact cggctctcca ttgacaatcg ccttgccacc catactcttt  35280
tctccagagg ttttggttat cagaaccacg atatggttta actgttggtt tagatgaatc  35340
atacttacca tcaatcacca cgtcaacata tttcattaca tctaggtgaa ttttttcgtg  35400
taactgaaaa cctgtccaga gccatatagt cttctctggg taaacagttt taacacgttt  35460
gcatatgtct gtaacctctt gaatatttct atcatccaga ggttctccac caagtattga  35520
caaaccactg acagcattat cacccattag ctggatgatt ccgtagaggt ttgcataagt  35580
aaatacctta ccagcattaa acttccaaga ctccctgtta aagcagcctt cacagtgatg  35640
cttacaacca gctacgaata ggcttacacg aaccccttca ccattagctg tgtcaaatgg  35700
tctaatctcc atgtaattca tctagttacc tcaccaatac atataaacgt tctttaaacc  35760
ttttcttcga attgttttac tcattcaaac accacctgac aaggaacctg tttagtaata  35820
aattcttcac agtgctcttt aatgaagtct tgtaatggta cacaatcttg tgcgcaagtc  35880
```

```
attagcataa tgtactctgg attcatgatg ttttcaagac tgtagaagac aacatcgtca  35940
gataattcat gaccgtcttc ttcagaccaa gttccagtga ctatagctaa tttgtcaagc  36000
aattcattag gcaacgctac accatcttct acggaatcac ttagaacgtt gtcacctatg  36060
tacaatgtaa agactgtatg gaatgttgag tatcttacgt gattcttttc gcaagagcca  36120
cactctgagg cgtaatcttt aagccactct aactgttttt ggtttaactt aatcataatt  36180
tcaccttagt cggtaatgca ctgaatgcta tagctaaccc taaaaatggt ttgaagcatg  36240
accataaatc catctgacca tgatatgaga aaccccattg tgggtctgaa aaaccccata  36300
ccataacact aaccccaaag aagaagatta gaatgtggag tatgtatatc atcgtttttg  36360
atatcttaaa cattttaact tatctctcaa ttcacaataa gagagtccta aaaagaaccc  36420
tagtaagaca gaacctatga acaacccaat aatattctct gccatgtcta acatccaata  36480
aaaaaggtga tgtaagccta tcaagaccca caccaccttg tcaagtttta catagaaatc  36540
ctgtcacgaa tctcagcaat ttttgcatca ttcattcggg attcaccttt aatcttagtc  36600
cacccaagat acccacacac tctgttaatc acagagatgt catgtgaatg gcaaacctca  36660
cattcttcaa catcagcctt tggtctgttg ccacaatgtt cgcagattgc taagtcaaag  36720
ttaagtccct gatagaaacc tttcaacatc cctcttgtaa tacaactttt aagtgctgtt  36780
aagttttctg ggttagctac ccttacatac tggattctgc cgcctctaca gatatggaag  36840
aatggttctt ctaagtcctg cttctcaaat ggtgagatat ctgctgcaac attcatatgg  36900
aaactgtttg taaagtattc cttatcagaa acacctttga taacgccaaa catatctctg  36960
aactgtttta gttgagtccc acaaagtgat tctgctggag taccatagac ggcatataag  37020
aagccatctt cattcttaaa ctcttcagtt ttcatgttaa tgtatgccag aacatcatat  37080
gcaaaactat agcttccaac ttcatgaagt cgtttaccct cagcaagaac agacaactca  37140
tcaagagcag taaccccaaa agaggctgtg aaagacttca caatatccca gccaaccttg  37200
tcagtaggtt tcttagtccc tttgtacaga ccaccttgtg tgaatgcaag agggttagaa  37260
cttgctggca tattagcaat catctcgtag cgtttcttgt ggaagctgcg aatcatctct  37320
aggtacttat caagctcttt ccagaaatct aaaccattct ctttagaata ctggtaaatc  37380
attggtaagt tcaaagatac agcaccaatg ttagcacgac ctacataaaa ctcttcacca  37440
tcttcgttat ggtatggtga taaaaatgct ctacacttgt tgttcaggta agttcgctac  37500
gcttaccccg ctttatccaa gctgcttact gtcaccagta agtccagact atatcttcta  37560
cttatttcta agtagcgtac catttcgagt cgcttgaccc tacaccgcta cattcatcac  37620
ggttagtcgt tcggcattta gatgtattca aattcatgtt caaagttatt atgctctttt  37680
acacccttca atattgaaga gatagtcttg cgattatatc cgagtatatt ggataactct  37740
cgtattgact tagcaacaat aacttctttt gtcactttgt gtgtagcctt cacagcatat  37800
gaacgcttac aaaacttgta gcaaccattc tcataacctt ctttaacatt ctcagaatga  37860
gttccccatt ctaagttaga agcatggttg ttcagtttgt tatcatcttt gtgttttaca  37920
attggaagat tgtttgggtt aggtacatat ttctcagcaa ctaacctatg gacatacatg  37980
tcacgattct tcttaccgta aaactttact ttcatatacc cagtgttgga tttccactgt  38040
gtaagctcta caccattttc tctaaagact cttccgtctt cagtaacatg ataatttggc  38100
atgtaatact cctatgttat atagtttctt acatcttaca tcatttagca caggattgtc  38160
tacatctgta gagtttccct gtttaggcac gttttagatg agctatagag cctgttaacc  38220
```

```
catcggtgaa ataaccttac cagaacgctc aaaagcctct gctacagcac catgaccaga  38280
tacacttaag aagtctggat acattgcttt agagcaacac tcaatagctt tactgtacag  38340
gtgactttga cagatatttt catcatgtct cttctggtca taaatataaa ccagtttagg  38400
gaatacaaca ggtttcttgc tcttaccttg accattcata cgaacatcta ggagggtact  38460
tgcaatcata tattgcagtc ggttatcttc attggacata tctgagtcaa gtaacccgaa  38520
tgtcaaagtt gtgaatgcaa aatccccacg gctacaaggt acagtgttta gtttcatttc  38580
aagtgactgg aaaccttgag tcagttcaat ctgtagctgc tccatgacat aattgtggta  38640
atgttcttta ggaataccat aagatgctgc tttctcagca tgatagcgta gagacttctt  38700
agcatacggt acaagtacct tatcaatctc tgctaaagta aagccaccaa attgctgtgc  38760
agttgctgaa agaactacgt caccaataac ctgtaaggct gacagtacag actttggttc  38820
acaatattca atgccagaca tttcaaagcc acctttcagc actttaccaa tgtcaaacag  38880
gcaacagttg ataccaccaa aaattaggtc tcttaaatca tggatataga taaacccttt  38940
ttcaatggct tcaagttcct ctggtgttaa atggtactgc ttaaagattt ctttagtcag  39000
ataaccacga ataattgaac cttttgtaga aattaaactg ctgtcaaagt tagcattctc  39060
acggtcacct aagaagagcg tgtctctagt cttttggtaa agctcatccc agttttgagc  39120
aacttcttta cggtaatttc tatatgttga gtaagactca taaatctcgt gattgacttc  39180
tgccaaagca ccctcaacaa tactgtgaat atcgtttaca gaaattagca aattattctg  39240
cttagtggac tttaccagaa tcctcataaa tgctgactca agagcttgag taacatctgg  39300
tggaagctct ttataaccaa ctctgttagc tgactttgtg acggctgcta aaactttttt  39360
gatatcgggt tcttcaagtg agccgttctt tttaataatc tgtactttgt tcattattgc  39420
ccctttacat actaaaaagg tctccgaaga gaccctttca ttttaaatct ttttagaaaa  39480
cttcgcaaag agttctctta gtttttcagt tatacctaac tgtatctcta atatttcgaa  39540
gataacccat agtaacatgg ctccaaacaa tgaaccttgc tcaaagtcag taaataggtt  39600
aacaataagc ataccaatca caatagctgg tgcatcaaca accaaacctt cccaaatgcg  39660
tttaagcatt attcacctct gccataaaat tctgtagcgt cccaacaggt tttaggtttt  39720
gtccatcagt tttcatgatg aacggcatct gacgaactgg catctgtgca atatccgtca  39780
ggtctgatag ttcatagtcc tgccctaaca ttctcacaat atggtcaata ccacgagctg  39840
ttgcaaaatt ctttgcagtc tcacattgag ggcatccagt tttggagtaa attacataag  39900
tcattaagga acctctaaaa atccactatt caaatcatct acaacagtat tcaacaggta  39960
cgcaccgttc tgttgctcct gattagcatt ctgctcttta tcaatttcca tcttcttaat  40020
catgtacttc aaaggtggtt ctttaggagc tacaaaatct ctgggaatgc caaacatatc  40080
atacagtggg gcagcattat agtaaaccca ctcatgaaga agctttgtat ttaatccaac  40140
tacagcacgt ccttcggaga agatataata cgaccatttc tcttcacttt caactacttc  40200
atctaagatt actttaatct ctggaagaat ttgttgaaaa gctttctgcc actcatcatc  40260
tcttaaagtt tcttttaaaa cttcaatatc aattttagtg tgaaggattt cgtcaagcat  40320
aattttctgt accgcttgag caataccctg aaatttatct tgagcatcaa gtgcaaaagt  40380
acatgcaaag gatgccataa aagatatacc ttcaagtgca gtcactgcaa acagcccttt  40440
cagaatcact ttatggaagt gtaaagggtc tttgtccaga agtgagtcgc gcacataact  40500
caggcgatag tttatacctt catccagtaa ttcttcaaga acacgattca cagtttttaa  40560
tcggtcttgt acagcaacat tctggttaat ctcatctaag attgtttcag ggtttttaat  40620
```

```
acattgcctt acaatctctg agtaagtaag agcatgtagg ttttcaatct cagactgctt  40680
cataattgca gttgcataga tgtcatcaga gataaatggt gcaaaggcaa atgccaaact  40740
cttagcaact tgagtatctg cttcccactg ccacttaaga atctcaagca ttacacctga  40800
cattgatgct ggaacactct caaaatcaag acgtgattgt tcaaaaggga actcatcttc  40860
tgaccaatct tgtgcttttt gttgtttata aagctcaaag atttttgggt agtgtttatt  40920
aagtgagtca aaagtttttc tctcaccacc taaaaagatt gggtgctggt taatcatagc  40980
gtgatttctc ctttctttat catttctaag gcttgttttc tgtctaaaac ttcccaattt  41040
tctttgttga acatctcata aggtcttgcg tagattttac catctgctgt agagatgtaa  41100
gagataccag caacccatga gtcatccttt tgttttatca tcatatctgt gctactcaca  41160
tagtacatcg ttttccgagg cttgtggagc aagtatatag gtcgctcatg tttttctatt  41220
aaatctttca tggtctctcc aaagttaatt ttagagggtc ttttacgacc ctcatagtta  41280
ttaaaactaa acaccacaac cctcgcaata agcatcttgc agtgcagatt tacctacacc  41340
aatgcgactg ttaaggtagt acatggtttt catacctact gagttggcat aaatcatgta  41400
cttcaaagct tgagacaatg ataccttctt agcttttgca tagtcaacat agaaatctga  41460
agagatagct tgaccagtga acttttgaac aattgcataa caatcaatca ggtcaaaggt  41520
gtcaatatcc caagcaattt catagacata cttcaactct tcataatctg gaacaataaa  41580
cagtacgtta ccagttgcag actttttagt taaaataaag tcacgaattg gatacaagcc  41640
atttgtcgta ttagttgcca gtgaagaact ctcattaggc atgtaagctt ctaatacaga  41700
gttacggatt ccaccatttt ctttaatacg ttgtgctaag tcatcccaat catatcttag  41760
ttttgcatca tgcttctcat caatcttctt gttagctgtc ttcggaggaa cccaaccttc  41820
aggatactta gtgaacttca tgtattcagg tacaccgcgc tctttagcaa gtcttagaga  41880
agcttcatgc agatagtaag agtgcatctc tgcaagttcg tgaagctttg tctttcctgc  41940
tcttgaagag tagttcacgt agtttttcgc aaggtaatga gccacatttg taaggccaat  42000
cccaacagaa cgacgcttct gaacatggtt gcgcatcgac ggatacggat aatccataag  42060
gtcaataacg gagtcaacca ttgcaagagc ataataagca acgtcagcgt attcatcttc  42120
tgaaattctc cctgcaacca aactagctag gaagcaaaga gctacctcac catcctcttt  42180
cacagcatca tctctgtaaa ggtctgtctc tttctcaaag ccgtacactg gcaacacaat  42240
ttccatacaa agatttgaca tcttcaaagg ctctttaaat ggcgtatgtg tgtttgcatt  42300
atttgtgaag aatggataca cacggcctgt tgcataacgc tgctggataa acagtttagc  42360
aatttcacga gcctttactc gtctgtgctt aacacctgaa tgtactgcat gaccaactgc  42420
catagcaaac tcatcagcag atgctgtgta gaacatgtca tagagctttg gtgcatcctt  42480
gtaagagaat agcaaccaat ctgtatcata ctgaacacac tgccagaaat aatcatttgt  42540
accaaatgag tagtccatct cgttaatacg tttagaagga accgttgtag ggtgcttcaa  42600
acgtagtaaa tcttcaatct gcgggtctag agcagtgtag aagttgttag ctgaaccacc  42660
acgactcttc tgtttatttg cctctacaga tgaacgtaca agcttgtaat aaggtagttt  42720
acccatgtgt tcgatagtgt tttgacggat accatcacca atagtgcgag tctccatcag  42780
cataccaata ccagcttgct ttgtggtcat atcataagca acctttgcag caataccaag  42840
tgactcagca gtgtcgtttg ctttaatcaa acagcatgac gcataacctg atttagtagc  42900
tcttaaacca ttcagataag gcgtaggagc attaatctta aggtcagata ggtaagtgta  42960
```

```
tagcttgata acatcttgca gtctacggtg ctttggttgc ttctcaaagg ctttcatagc  43020
catacccata aacataaact gtggtgactc aaaaagtctt cccgttttaa tatcacggat  43080
accatacttg tctctgaact gtttcaggac tgcataacca taagagatat cttttgagtg  43140
cacaatgtat ccttgcaggt attcaagctc ttcctgagaa tagtccatct tctcccaaag  43200
tcctgctctc tccatatttt taacgaaggt aaccagcgta ggaaccttag taaagcctcc  43260
aaaggcttct ttgtagataa tccccagaag tagccgtcca gccatatctg agtactcttg  43320
agtttgttta tcaacacaaa catcaatcat ggcttggtgc atctcttttg tagtgcaacc  43380
ctcatagaca cgtttcatgg cttccatagt gacttctgac cagataattc cacgcttatc  43440
tgcccatgat gcccacttat tcagtctttc tgggtcaaag cttactactg taccgtttga  43500
ttttttaatt gtcttaatca tttttgaatc ctacaggtga aaagagcctc cgaagaggct  43560
ccctagttta aatcttgaaa atttgctcat tctgccacat atcgtaaaac ttatcactta  43620
cttttgtgac tgaagaagtg tgcatacaat tcagtgagaa ccatgatggt gtattatcat  43680
ccataattgt ttcaagtttt tgtgtaacgt tcacatccat gtctgcaaca acataattac  43740
ctcgcatctt gcaaacaatt cttccaaaca agattgcact tctacctctt cggtcatcac  43800
agtacataac tgtgtctccg tgcttaacgt cttgtccgat actgtcaaca cctagcttag  43860
cacctgagat aatgtcatca taagatagct tttttgcttt agacacggta tttctccaag  43920
tttcttttta gatataacca accgtagtca gtcctttcta cacccataaa aagtggagcc  43980
atcacaactt taccaaaagt atttctgtgt tggcagattt caaaggaata ctctttctca  44040
atatcaatcc cgtatttgta caggactgct tttaaaactt gttcattatc cagaagtgta  44100
tctggagtct caccatactt ctcaagtaac gggtcattca taaacaccgt catagagata  44160
ttgtagtttg agaagtggct cttctgagcc acacattctt tattaatgtt ctgtgaatcc  44220
attataacca accccttta accagcactt caggttatta gcatcataat tcagtttcgg  44280
gtatgaggtt atatggaact gctcaccatc gtagtagaca atatctgcaa tccatagtcc  44340
attctcttta cagaaatctt tatctgcttt agaggtaatt ggattaactt ctacaaaacc  44400
atctacaccc aaatccttta agctacatac aatacctttg cagataacgc atgtatcaga  44460
tactaccaca aaaagttctt ggctttcaag ctctacaatg tattcaccaa gctgtacttt  44520
agggagattt gattgcttca taatcttccc atcggctgca cggacaatcg cataccactc  44580
tttaccatca accactgaca ttctgatgat acactcttga ccagtacgct tctcaatatc  44640
tgcaagacgt tttaaagctt cttcatagtc atctgtgtac ttcaggtcat tattatggca  44700
aacagctttc atagcaccgt tatggtcatg ttgtgacaga taaatcagac catcaagaac  44760
atattgcaaa tctgcctgag catccagtgt ctcaatgggg tctttttctt caattgcttt  44820
tacaagctct tttgcttctt caagcataca cagagactgg gattttaaag attcccaata  44880
ctcatcactg taaggttgct tttgagtgtt tccacaacga agattccagt tttttactgc  44940
ttctcttgag ttaaacattt ggactcctta aaaatctgtt aacctttagc tctcgtgttt  45000
caatatattc cagatgctca cgtagctctt gacgtttaag cattaggtgc tgcatttgag  45060
actcaacagc ttcaacttct ttaattattg actctctggc atttgcaaga attcgctcaa  45120
gttcttcaat cttgctgtca acttttgcta catgactcac agctttactt ttgttaaaca  45180
ttttattctc tctcaatagt tatcaagcac aatttgcttt cattacctta tggattcttt  45240
tttcagcatc ttcataagtt tctttagtaa taaacttaat tgctgcaata ttggcattgt  45300
agaagagtct gagcttcgag tcaatccttt ttgtcattac atcgaattta tgttgaaggt  45360
```

```
ttgcttcacc atagactagg ccaccttttg tgtagtaggt ctgaataatg taaaagtcaa  45420
aaaattcttt tccaaagctc tcaatatctt ttttaatata ctcagaagaa gtctcgtaag  45480
tcatccaatc actctcctta gtgactacct tcttccgagt cttcccagca acttttcttt  45540
ttgtcacact gttaagttgt ttctttccta tataatattg tccagtcttc ttacagtgta  45600
ctaaatagac aaagccaaaa tgtttagtgg ggtcaacttc cccacataaa gatacccaat  45660
gaccgtaggt agggcaattg ccaaatcctt taatcttcat tcatacacgg ctcccaatta  45720
tatttcttga aagagaaatt gtcttttgga tttctctctt gatatgctat ccagaaatgc  45780
tgttccatta actctaacgg tgtctttgta acagtctgtc catcccatga cacataggta  45840
taagagtctt ttttagcata gagttcatag atagcatcaa gacactcttt gtaggtctct  45900
ttaccatcta aagcattcat cacagctact ttaccagcac cttttaggcc gaagtagttg  45960
tctgcattat ctccagcaac agcctgataa cacaagaatt taaaacctac accaactgtt  46020
tttgcagctt ttggttttga tttgatagga caatcccaga tatcaccaac attgttgtca  46080
gcaataaaaa ttaatggtga tttttcataa gtcatatcaa tacaataagt cccttcagct  46140
tgtcgaaggt ctttgtcaat actcataaga gcagctttct tacccatctt ttcagcttta  46200
gcaattacga ttgaatcggc ttcgaagccc cccccttaaga gcttgaactc tggtcttgat  46260
aggagatact cacgacaagc aactaagtgt gttggtgtga cagcatcttt acggttccct  46320
tgatattggt gctcaagacc tttaatgtct ttatgtttat gcacaccttt ctctgttaaa  46380
taacctaccc aagttctttc tttaccaaca accttaagcc attcctgaag aacctgttga  46440
gtagccatga tagcttcttt ttcactctta gcttctttcc aagtctgtct ttcccattca  46500
tcttcatcaa atgctaggcc aagctcttct acaaggattc tctggtctgc taaccatctt  46560
gcagcatctt ttgcattatc aaatgattca gattcttctg ctgtgagttt attgacatat  46620
ttatattttg ctttctcaac tacacaagca cctttatagg caatactgtc agagtcaata  46680
aagacatgtg taactgaatc gggaagtttt tttaatgtgt acttctccat tgtgactctc  46740
catatgaaaa agccccatac taagtacagg gctttaaagt aacttttaga gattagtctt  46800
ctgtatcgaa gtcttcatct tcttcgtcat ctgggtctgg caagtcttca tcgtcaccat  46860
catcagaatc attcgaaggt ttgtggtctt ttgcgtcttc ttcagtgatt tcaccgttat  46920
cttcaacacc atcaagacca agcatagcca gttcgtcttc atccagttca ggttcgccat  46980
tagcaccgtt accaccagtg taaggtacaa gagtatcaat gataaactgt tcctgaatag  47040
gttttgtcag aacattgttc tcaaaagtgt agaagtgagt agaaagaatc acactaccaa  47100
aagaaccgtt accgactgca atatctggat gaattacatc atagttcttg tcatcttcat  47160
gtttgtcaga tgcttgagct ttgattttct tcatcggctg tttaacagct acacgcttac  47220
catttacttc ttcaataagc ataacaggga atgactgttt agctgtccat acagcaccat  47280
ctttataagc tgctgcacga cttactttca agatgtagta agtgtctgct tcaaaaggtg  47340
gtttacaacc aaacttctct tcgaagtcgt ctgcatcaac tgcttcagta gtgactttat  47400
cccaaccttc tgggtttttc ttagacttag taaactcttt aaacagcttg ttaccatctt  47460
ctgccagaat tgaaacgctg tagttacagt ctttgcctgg gaatttctta tcaatggact  47520
tgccttttcc cggacgtggt gaagtgttca ggtaataaaa ccagacatct ttcagaaggt  47580
aacgcagagt ttgacgttca gtaccgttgt acttctctac cggagctttc attttaacaa  47640
ctttagacat tatttaaacc tctatctcaa tttatgaaga gtaccaattc tagtttgttg  47700
```

atactctatt gtcaaatact aattactgga agttgtgctt atctttagaa gctgctttac 47760
gtgcagtttt tccagttctt acacgttttt cttcatagta ttttgctggt tttccagcag 47820
tggcttttaa ggaatcccca aaaacttttt caaatgcttt agagtgtttc atgatattct 47880
ccgatatact tgatattcaa acacattttc tttcattata aacagccaac taatattatg 47940
ctgaggcagc gcaatgatga ccgtaatcat gctctggtgg aaatcttgtt ttatctcaac 48000
ttccccatcg catttcatgt ggagcattct atagaaccta tcaatccttg tcaaacactc 48060
ttcatgaaat ttatttaaac ttttttcttc aaaggagggt gtgaacccct ctcttttata 48120
actatcactc agtttcgaat gggcagtcat ctgcatcctc acttaataca ggtggaatcg 48180
ctgagctttg acgctgctca tcagtataga cttcaccagt ctcacggtca aacacttcat 48240
cctcataatg aggcaaagag tcatcataat ggtcttcagc ttcaccaata ccaaactgtt 48300
gacgaatatt ttctgctgca ccatcaatat caacaccaca tccagaagct ttgataagac 48360
gtcctgtatc tggattgtac caagtatggc cagcaatacc tgttgactta ccatgacgac 48420
gacacttagt taacttgatt tttgtcaagt ttttcttaac agggtctggg tcaaccttgt 48480
tacgcattaa cagaatgttg ttcatagaaa tctggaaata cgcaccagaa cctttgatat 48540
cctcttcaga gatatctcca ccttcggagt tagccttctg accacctgca ctcttacgaa 48600
cgtgacagac gttcacctgt gcatactggt agcgcttgca acgacgcaat agctcagaca 48660
aaacttcctc ttcatccgta tctgaacgtg acagagccaa cgtaataggg tcaagaataa 48720
taatcttaca gtctaaacta ttaacaagat agtcaacaaa ctccagcaag ttatcttggt 48780
caatcgcccc ttgatggtca acgatgtgga tacgacgacc tttagacagt tctgcgtgtg 48840
ctacttttaa ttcatcccaa tcacgttcgt cataaggaat ctcagaaatc tgcttactta 48900
ggtggattgc acagagcatt tccataagtt cttcataggt atcttctaca ggaattacac 48960
cgatattata atcagtttct ttccaagctg aataaatcat ctcacgagtg taagctgact 49020
tacctactga agatggtgct gcaatagttg taatctcacc taaaccataa ccaccataag 49080
ttaacctgtt gaggtctccg aaagattctg ggaaaggaat caatggaatc tgaccacgat 49140
tcttcattgc ctcaaaacca tctgcgaagt tcttgatacc agcagggcag taacggggtg 49200
cattgtagat acgctgctta aacccttcaa gaactgtgtc tttctcttta tagaactttg 49260
tccaccactc gttaaggtct ttcacaccct ctggatactg gaataaacga accttctcga 49320
tagggagaat gccagcagcc tctttggtag ctttagcacc tgcttcatcg ttatcaaagc 49380
acaagtaaat ctcatcaaat gatgtgatgt actgatagtt gtctttgata gacttaatgt 49440
ttgcacctga tgggacagat acgtgacagt aattcttacg acgagacttg tccttaatcg 49500
caagagaagt catatagatt gctgtcgcac attccatctc accttcccag atgaatagac 49560
ggttaccacc ttctggagca atccatgaac cgaacattgc cagttcacct ttaatgtctc 49620
caacaccacc tgagaagtct tttagcttac cacgtaggtg ttcttttgga tggtcttcgg 49680
gataacggtg acgaacacgg tagccaacat gttctagctt gccatcttca ttacgtttgt 49740
aagttgggta gaaatgtgcg tcaatttcac cgtcactatc aatgtcaacc ttgatgccta 49800
aacgttcaag gacttttgca ggaatcttcc tgtctttcaa gtccattgct tctaggtttt 49860
cttttacgtc atctaaatcc attccacgga aagtacggtt tttattatct gaaccagtag 49920
aataagtgct cacgatttgt cctttatcaa aatcccactc tgggaaacct ttattacaac 49980
taaagcaagt catcgaataa gaatcatcat catgatggta gattgaacca gcatctgatg 50040
agccacaacg tggacatgca caatgaccaa taaactgacc agcctctttc aatttacgac 50100

```
ctttagacat tagcacctct tcgttgtagt tctgccttca atccattttc aatcttgtcc  50160
agttcatgaa tttcatctgc aatctctttc cttcgtgatt caactctctt cagacgttca  50220
atcattacct cattggaaag agatgagagt tccactaaac ggtggtcaat aactttaaaa  50280
ttgtctttta ctctcatctt cattctctct tttaaatctt caggatagct cttagcttgc  50340
tctcaaggtc tgcaagagta ccattattat gaataatgtc acgctcatat tttgtagaaa  50400
tcccattttc tgaaacatgt gatgaaactt tgtccacatt gtctcttttt acttcaatag  50460
tttggtgtgc aaatctactc agccactcag cttcagagtc aaatcttaaa tcactgatta  50520
aaacaacacc ttcttgattt ctaagtgagc aaacgtcaaa gaaatttacc attcgttttt  50580
caaggtcttt agcccagaac ttgtcaccca taactttacg gataacttca gtgccccaaa  50640
tctgttgaat ctgtcttgat gagaatttat acttcttgct aaatcccaga cgtgtcaata  50700
gagttggttt agcaactttc ttaagttcca tgattaatcg tccggttaac tccgacataa  50760
gcttaaagtc catatggtaa cgttcatctc tgaaggtgaa ctccatagct tccgtaactt  50820
tagtcataag ttcagagtat gataaatcaa aaacctgtgg agtctcttta gtttcaccat  50880
acaggtcatt ccaagtcagg tcaaatatcc ttgatgcaga tagcttaagg ttgtctgcat  50940
aggccattac tgcaacattg tagccgtact catcctctaa gatgttcttc acaatagagc  51000
acgaggtgtc ttttccagaa cgtgcctttc cagtaaatgc gataatattg ctcattttat  51060
ctcccttaat tactaaaaag cccccaacta aggaggcttg taagatttta taaagactta  51120
gtgtagttgg tcagcagact ctttttcagc catagctgag agttgcttca caaaatcatc  51180
accgaagtta atgcgaagtt tctcttcaat gattgaagca ccaatattca ccaaaacatc  51240
attgattgct tgcatactaa caccaccagt catctcctca atgaactcaa tactcatacc  51300
catcatctgt gacagttgga ttagtgcaac gatattcatc atcgtagaga tagctggaat  51360
catcagtgca actttcacct gaagtggttc tatatcagct acagagtcat tttcaacagc  51420
ttcttccaaa gactctttag tttgctggat aatctccttg attcgtgggt ttagttcttc  51480
tacgccccaa tcaagttttt catatcgtga aagtttctct tccatacgct tctcaagagc  51540
agccataaca gcacttgttg atgagataag cgtatcaata atgaaatcag tgtccttagt  51600
cagcaacagt tccttatctt cgtctgacat cctgatatag tcattctttt gcatttcata  51660
aaaaatgaac tcagcaagtg catcaacacc aaccgcaata gatgccagag caagtgtagt  51720
gtctgtcaac atcatgttaa cctgttctgc aaaagcaccg ttatcagact tgtcttcagg  51780
caagttatag cttgcaggca taaactgttc tgtgtagttg ttcccacgaa taatcatagc  51840
catgctttct acggcattga ttaaaaacgc ttcgtcaata ccttttttctt caagcatctt  51900
ttctacatca atattcatat tatttctctc tcagttggtt aagtttcttt ctagaacatt  51960
ttaagttttc ggatgaagaa aagtcaagtg tcttttcaga acgtggataa tagtgcctat  52020
cccaagaagt ttcaacatcg ttaatcagtg acgatagatt acacaggtct gtaccacttt  52080
gcaacctctt tttaagagaa tctagtaaag caactgtgtc tttagcttta cgtctcgctg  52140
tagcaacatc tttcatatgc tcaaacacag agcattttaa gtcatcttca tagttttcag  52200
acaactctat ttcatgttgt atatcaacca ttctcctgtg atggtgagca tattcccgtt  52260
gagcagcaat gtcaagttct tccaacttct gcaaagctct aacaaagtca gctatgtctg  52320
ggtgaacaaa cattttctgc atgtaagcct cttttaagta actattaagt tttaatcttt  52380
tatcttaacg tattctatac gttatacttt aaagcttttt aaaagctatt aaataatctt  52440
```

```
ttaagaattt taaagtatct gtatagttaa actgttaagt aaccttttaa gtaaaaccca  52500
cttcgcaaag attaacacct tgtcaagtac attgtcaact tgctttttat aatttttttgc  52560
agtaatgtat gaggttaatg attttagagg gagtaaaaat ggaaaacgta gattttaaaa  52620
acttacattt ggttggtgat acagaaactg atggtttact ccttgagttc actaaagttc  52680
acgtaatggc ttttgcagac tataaatctg acgatgaaga gccacctgta tgggtcttca  52740
cagatgagcc tatcctcggt cacaagtaca ctaagtacat taagggtggt ttacgtgaag  52800
gtgttgagtt tgcgttaaag gcaaaacgac tttgtatcca taatggcctc ggttatgact  52860
ggtgggtttt caatcacatt gcaccggatt tatggaactt tgataatcca aaatgtaagc  52920
cgtggagtaa tttctttcag gattctctta ttcagtctcg tgttcagtgg atggatagac  52980
caactccaaa gggttataaa ggtgctcatg gtttggctgc atggggtgct cgtgttggtg  53040
ttcgtaaacc agagattgag cattggggtg tatggaatgc agaaattttc actcgtgttg  53100
tagaagatat ccgtattaac gccaaaacta aacgggcact tgataatgag tatctcaagc  53160
ttaagaagtg tggcatagac acttatgaaa cctacatgcg agctaaagaa acatctttct  53220
ggatgagtca acaagctatt aatggctgga aagctgataa agagcttatg gagttccatg  53280
tgaaggaact tgacaaattg actaatgagc ttgcttcaga ggttgaacca catcttcctc  53340
caactattaa gaccaaaggt aaagtgactg gagaagagtt tgcaaaagct tggaatgagt  53400
atgttgaaac atttggtcat gcagatggac tgaagagaat taccaagtac cctaagacaa  53460
agtatcgtca gcaggtgcgt aacggtgaga tgcagactta tgaaatcaaa ccatttggta  53520
agccaactac aaagattttt aacattgaaa agagaaattg ctatacacca accaacactg  53580
taactggtga agagtacaag gaaggctttg tagcaatgaa ggatgctcgt gcaatttgca  53640
atgagttgaa tgcaaagatt ggtaagaaat gcaaagactg gaagccagta aaaacagtca  53700
aaactgtgaa gtactataac agtcacgttg ttaaccactt tgaacttgag tcaagtcgct  53760
acacaggttt gattgatgca ccgtatacac caattgagtt tgaagtttct cgtatgactc  53820
aggtagcagt tgttaaagac tacttgaaat cagttggttg gattccagat gactggaact  53880
acaagaaaga ctcagatggt cgccctgtca aagtttgtcg tttcaaagac aacaaaaaga  53940
tgattacaaa gcatcctaag tggcaggaaa tggttgagcg gtgtggtttg agttatgttg  54000
agcatgaagg tgtccagtac attgagcata actggtctgt gaagaaatac acagatttgc  54060
ttgagccttg cttaatccgt acttcaccaa aacttaccga atcatcctat gatacgattg  54120
aaggtgagct tggacagaag attgcgaaat actacacttt gatgcacaga cgcagaacta  54180
ttgagaactc aaaggatgat gaaaaaggtt ggttgaacca gattcgtcct gacggtcgcc  54240
ttagtgctgg tgcaatggtg tttggtactt caactggacg tatgacacaa tatggtattg  54300
taaacgtacc gtctggtgct gctgtctatg gggaaccaat gagggcagtg tggatttgtg  54360
aagaaggtac taacgttgtc tctgtagaca tgaactcagc ccagctagtt ctcctttgta  54420
actttatggg tgacaaagac ttcaccaaag cggtaacgca aggtaaagaa gagattgagt  54480
ttattcgtca agaagatgga cgctattact gcaaacactt tgatgagtac ctcaacccag  54540
agattgataa gtaccttcgt tatgactctg agaatgacct gtacgttgtc tattcaggga  54600
ctgatgcaca tacactgaac agtatttact ttagcttgaa cgatgagcag gacatcttga  54660
cttgtcgagc tactcaggat gagaatcttc ttcatgagat tagcaaaggt cgtaagaaag  54720
ctaagaatgg tatctatgca ctgctgttcg gtgcaggtga tgagaagttt gctaagacga  54780
ttaaggctgc aactactcag gagggtgcgc tgactaaaca gacttacttt atccgtttgc  54840
```

```
ctaaaattaa gaagctgtta gatgacttgg aagctgacta caaagcaact aaaaaggcac  54900
ttgaagaggt gtttggtaag actgctgcaa tctctaaagg gggttttgta aaggttgctg  54960
gagcttggtt gtggtgtaaa tctccacata agttattgaa ctatttgctc atgggttcag  55020
aggctcagat tcaaaatgag gcaattaacc ttgcttgtcg tcgtatgatt gacgaaggtt  55080
tgatgaagtt aaatgggcgt aaaccagcta ttggtgctcg tttgctctgt gcatatcacg  55140
atgaaacgag ttgggaatgt ccagaaagta tgacggcaga ggtgaaagca gttactgact  55200
ggtattatgg acaagcttct aagaacttag gtcttaagaa agaaacactt gttacaggta  55260
ctggtaaggt tggtaaaagc tggtatgagg tacactaatt agtattgaca aggtgctcag  55320
ggaagagtac cttatactat atcttgtata ggaggtcaca tgacgctttc agagattgaa  55380
gttcagttgc aatgtgcagg ttattctcaa aaagagattg aagacatgct tattgttctt  55440
tgcagtggtt ctagaaattt gaaggtaagt cctgaatttc tgcgtagagt agatatcttt  55500
attgctggag gtaaaattgc aaaagacaag acagggtact taaaaggtga acgtgtagac  55560
attgagaatt tactatgagc caccgtggaa gaacccatgc agcgatgatg aaaggtgctt  55620
caaaggaaac tatcaagaac cgtaagcaga agttgtttga gagaatgaac aggttaattg  55680
acaattcatc tctttcaggt tctgagaagg ttttcttgaa aggtaatctg aaaagtattg  55740
cacaagaact tattgacatt gagtattgga gacaccaaaa atgacacttg cagacgttat  55800
tcatcaactt catgacaatt gctacacccc agagttgatt caggaaatgc ttattgtagt  55860
gatgcctagc aagttcttaa aaggttttaa tcgtgaggct ttaaaggtcg cgcatatcct  55920
tatcgttgac ggtaagattg caagagaccg tacaggtgtt cttaaaggtg aacgtattga  55980
tattctggag ttgctatgaa gaaaatgtac agtctctggg gaagggttgg taaaggtttt  56040
gactggacac ttcttcgttc aaacgttaaa cgtagtgaat taccagaact catcactcac  56100
tatttaaaaa catacagaga ggtagactat cgtgaacaat aaggttaaga gttgtgtgaa  56160
aacaatggtt gcacttggag taatttttct ggctggctgc aacccatctt atgaaaacaa  56220
agatgcttct tacagcctcc caccagagat gcaagattgc agagtctatg agttatatgg  56280
tgatactaca agtagagata ttattgttgt aagatgtcca aactctcaaa caacaacatc  56340
ttatgagtat ggcaaaaatg gccaatcaca tactacggtt attgagtgag gttttcacga  56400
tgaaagtcct agtaaactat atctatcgtt atgatgttgt tcactccact acaaccatag  56460
ctcaacgtaa tccaatcgtc ccacgagaag gtgagttggt tcgcattgct ggttggactt  56520
acactgttga gagcatcatt cataagtttg atgttgctgg tgatgttcaa gttatcgacg  56580
tagagattgg tggtaagaga aaatgactgt agaagataaa tttaagaacg cagttcttac  56640
agaagatggt gagcttgaaa cattcattct tcgtgttgat ggtaagctat tccggtgtcg  56700
ttgtgggtca aactgtttcc ataaaccaga taaaaatgac ttagagcttt acgcatgtaa  56760
tgcttgcaat acttggtatc actcagaggt taaaaatggc aatcctatac aaacaaaata  56820
aagatggttc cttcaacgtc tggtcatgcg ttgctgtagg tgacaaagtt atcacaacct  56880
atggtaaaga aaatggcaag atgatgtttg aagagtacac agcagagcct aagaacatcg  56940
gtaaaaagaa tgagcgtaac gctgaacagc aagctctctt tgaagttgct gctaagtata  57000
aaaagcaagt tgaccgtaaa ggttatgctt acacaaaaga gtctgcacag aatactgaga  57060
aggtaggtgt acagcttgct catgatgctg caaaggttag tcatgcaaag tatttgaagt  57120
tccctgctga tgctcaacca aaacttgatg gtgtccgttg taggatttca agagatgctg  57180
```

```
attcagttag tttcacagct tattctcgtg agaatactgt ttacaacgtc ccagcagaac  57240
taatcccaga tttgctttta ttacttaagt tacatccaca agttgaagat tttgatggtg  57300
agatttatgc tcatggttgg gatttagaag atattgtatc tatgattaag aatgctgaca  57360
atccagaccg tcaccttctt aaattctact ggtatgatat ctgtgacaat tcaaaatctt  57420
ggcctgagcg tcgtgaagtt attgataact cacctattgt tgagtttggg gatacctgta  57480
gagttgttcc tgtacagact atccgtgtaa attcttggga agagtttgat gaagctcatg  57540
ataaatgggt tgaagctgat tttgaaggtg caatgtaccg ttcaatctct gaagactcct  57600
tctatgagtg ttgccaccgt tcatacttct tgattaagca caagaagatg cacactgaag  57660
aatttaaagt gactggtgta aagactgaca aacgtggtca tggtaagttc gttgtagaga  57720
ctcttcctaa cgtctttgta gatgtctcat ggaagactac tcatgagaag aaacagtatc  57780
ttgctgagca tcctgatgag tttatcggga agcctttgac ggttcagttc cagaagatga  57840
ctcgcaaggg ttctttacag ttccctgttg gcctcgttat tagggattat gagtaaacta  57900
tgctaagcat aatcatacta tttgcattag ttatctttgt gttgtcttac atcacaagta  57960
agcttttgga cacatctttt gcaatgggtg tcttgtttac aatcttttgt ttcgtgacgc  58020
atatagctat cagaactttt ttataaaaag ttgttgacat agaaaatttg gtgagtatac  58080
tgagcagcat aaaccaacgg gtactcacca gcatcactta agagtcttct aagagggttt  58140
ttaagtgatg tttggtaaag tatggttctg tccggtaatg cgatgtatgc tatggtttgg  58200
tgtgggtagt tagtctcagc tacataaaaa tgagacttac ctttttaaaa ggtctttaag  58260
agggtctttt aacaaggtat tgtatggttt agcttggttt ggtatggtag ggtgcggtaa  58320
agtaaggtat ggaaggatgg cagtagcctt ataaaaaatc tgccaaataa gctataaaat  58380
ctgttgacaa gtcaggtgtt atagcttatt tttatactca atgtaataca aaatttaata  58440
taactttgag gtcattatga aaaagatttt attagctgct gcaatggtta tggcaatgaa  58500
ttcaccagtc aatgcaacag aacttccaaa tgtggactta tcaggtgttc cagaagacac  58560
ttgccatatt gtaaaaggtg ttgctctagc taaaggtgag ctacttaaac caatctctga  58620
agaatcttta acagagatga ctgataaggt aactgactat caatatcgtg ttcttgcaga  58680
gtatttcctg caatctgcaa acattaaaga gaaacaccat gatgatattg atgtacaggc  58740
tatgctcaac catcgtatcc agtttaaaga agatttgatg caaaaagcta tgtatggtgt  58800
tgagtatttc ttagaaaaca gaagctgcac aggtatctga tatggctctt aaaaagttac  58860
atcccagaag cggttatggt aagataattg atgatacaga cggctttaca gtctttacag  58920
ttatctgtca agatgattca cagattgaaa aggctcttga tgattacctt aacgatgaac  58980
gtgaaaaggt tagggctaca aacatagatt cattgattga cactccacgc aaacggagga  59040
agaaagatga atgaggtttt tgacccttat gctccacaag atgattggga ggctgacaga  59100
gaggctgaaa tggagagtta tatttgtcca atggatgtag acgaaatgag agatttcgtt  59160
gcacatcgtt ttaagagaga gattaaatcc agaggtcttt ctcaagagca agttgctaaa  59220
atttgtggta tctctcaggc tcgtgtatcc aacataatca atctcactgg taatgtctcc  59280
cttgagttta tgttggaagt atgtgaaaaa tttggtgtta actttaattt aaggctggca  59340
gattaatatg aaacgtgaaa acattatcca ctctgaaaac ttcgcattag gcttttatgg  59400
tgtacctact caccttgaaa agtattatgg tgtaaagatt ctttccaatc tcattatggc  59460
ttacaaagat ggtaagatta agcatactga gaagaaacgt gtcatgggtt atatggctgt  59520
aggctcagca atctcaaaca ttaagctgga aacaactagc agccagattg tgaaagacca  59580
```

```
cttcatcaaa gaactttacc acaatcttga tggtgtagat gttcaggctg tttggctaga  59640
tgttgatggt cacaactaca caagttttgt cttcaaaaac gatgacatta agtgtctgtt  59700
cccataatag gtgattaact atgattgatg tctacttaca agatgctcat gcagatttcc  59760
ttaaagagat gcttaaaaag tttatggctt cacagtatga gaatgaagca tcttttaaaa  59820
tagttacatg tggcgatgaa gctggttttg ttgagattga acatgaaagt actggaaaga  59880
ttgtttgtaa actacctgac agtatgttct ctagtacgtt cttaacaaag actagtataa  59940
atgttaagct tgtccctcag attgaaacat actctggtac agattaccct aaaggtttta  60000
aatcgctgat gaagtacttc ttagatgact ttgtgggtaa tcttctgagg gaggtaaaag  60060
aaagtcgtac agtgttgact gtagagaaca tgggaggaac tatcaaggtc acttctgact  60120
gttttgttat gagcctcttc gacttcgttc ctaagaactt tgatggtatt ctggatgaag  60180
aagatgactg tgtagacttt atattggttc ttgaaccagt ttttgaggtt aaatagatga  60240
aaattgaaca ctgctatgag tctgatggaa cacctatccg ttgtccacat tgtgggtgta  60300
cagacttaca aggtgaggta agtgaaatag tcaacggtca tattgctgaa gaaagtaccc  60360
gatgcacagg gtgtaatgaa attatcgctt tctgggctta tggttcatac caaccctctc  60420
cacattttat ctaccatcat agtaaagttg tgaagagtgt catcaactgg ttcattaaga  60480
aagggtttac aaaatgatta agctaatatt tgcaagtggt gaaaacggtg aatttggtac  60540
tccaactggt atgccgtggc ctcgacataa acaggacatg caagagttta agagactcac  60600
taaaaataac ttagtagtca tgggtaatga gacttttaag actctgggta gtaaaccttt  60660
accagaacgt gcaaacctca tcttaacaaa ctctgtacca tacttaggta tagactttgg  60720
caaagatgat gtaatgtatg ctaaagccag taaagagtca tttggagcat ttttgaaata  60780
tcttgatagc tctattgatg aagatgtctt tgtaattggt ggtgcaggtg tccttgtcaa  60840
tgctttaccg tatgctggtg tggtgttcca tacagtcttc cataaagtta ctgaagaggc  60900
cactgtgcat ttacctttg aaaacttttt tgagaagctg tatgataatc gtgtatttac  60960
aaaggtacag tcaaaaccat cagaggatgg taaagcaact tttgaaattt atgttccaca  61020
agtgaaagga cacttttgat atgtcacaag cagatacaag ttacaaaaat atcctgaacc  61080
atgttttatc cgttggtgaa ctgcgtacta cacgaactgg agatgttatc tctgcatttg  61140
ctccacctca gtttcgtttt gatatgcgaa ctggtttccc gctcttaaca tctaaacagg  61200
tgtttacacg gcaagttatt ggggaagctt tatggttcct gaatggtgag aataagcttg  61260
gtgaactccg ttaccgcaca tggggtgaaa atgacggaga acgctggact atctggtcag  61320
atgattttaa acgctggtta agctctaatt attcttctga acaagattgg ttagaggatg  61380
caggtggaag aatctatggg gttcagtgga gaaactttga aggtcataac ggttgtgttg  61440
tagaccagtt agagacctta gtaacgaaga tgaagggtga tatcacagac cgttacatgc  61500
ttgttaacgc ttggaatgca gcagatattg cagcaaactc aatggctcta gcaccttgtc  61560
atgttctgtt tcagatttat atcactaatg aaggtgaagt tgacttacaa tggtatcagc  61620
gttctgtaga cacctttta ggacttccct ttaacattgc gtcttatggt tttattctgg  61680
aagttctttg caagatggct ggatacactc cacggtactt gataggtgtc tttggagata  61740
ctcagattta tcagaaccac atgaagcagg tttatgaact gatgaacaat gaagagttcc  61800
atgcaccaac ttttgagatt ggtatcccac ttaacacttt aagtgactta aaacatctca  61860
ctgcaagtga ctttattggt ggtattaaca attaccaaca tgcaggaaag attgaagcac  61920
```

```
ctttgtcagt aggtaaataa aacaaaaagg ctccttttta cgggagcctt aaactttact  61980
tttcagtatt ctttgtgttc ttttcagtaa tagcttggag ggctgatact gattgagcca  62040
gattgttcac actatcagag aatttatcaa gagtcttagt aagttttgcg ttctcaccct  62100
taacattctc taactggact ttctggttct ccatccctag ctgaagcagc ctcatatcag  62160
actgtaaatc acgaatagct gaatagttac ttttggaata attatctagc tgctgtaact  62220
ttgttgtgac agacacttct tgcttaccac ttgaaacttg catcgtggta tacatcccaa  62280
taacactaaa aataccaact acaattgcac caatattatt tttaaaagca tcctctagcc  62340
acttcattta ttctccccct taaaagcttt ttctaagtta tctacgaact catcatcaat  62400
aggtgtgtct gtcttactcg caagatatct tgcaagctta aagaacactt tctcaatcat  62460
gtattcactc agaagggata aaatgagttt ccagaagaag ctacctagat tttttagaag  62520
aattgctagg attgtaggca tttaatcacc tcatcagcca agatggtgag aatacccata  62580
aagaatatta acaccatctt aacaatcagt caataaggat taagcagttc ttacccaagc  62640
cattaatttg tagaactggt tagtaatact aaatgccgaa ccagagcctg tactaccagt  62700
gttaccacta actgtatggc tgtgagcacc aataccaact gtgtgagcat ggtctccgtt  62760
agaggcagca gtaccagaca cagtgtgtga gtggtcacca gctacactgg aaacctgagc  62820
agtccctgag gcctgaacac gttgtttacc accaatagag tcaccaccat aatgaccacc  62880
aactgtatgt gtatgagcac cagtgttgtt agtagaacca ctcactgagt gggtgtgagc  62940
accagtagta tcagtggttt tagtaccgta gtcaaagcta gaggttgtcg cagagaaact  63000
atgagtgtgt gaaggtaagt ttccaactgc taacgtaaca gaatctgaac ctccagttgt  63060
agcaacatct gaaccgtttg ctgctgcaat tctaatagtt ctaccaacac cattgttcag  63120
atacgtccaa gttaaaccag ggagtgctgt attagggtta acattactgt taaaccatgt  63180
cacaatccct actggataga ttttattcag gtctgtagag tcacttactg cctgtgcaat  63240
cttctggtca gtttctgctt tagtgtatgc accgatagct gaaggagttg gcttatactt  63300
ctctgtataa atttgtgtga agtcctcttc aaaaccaaaa ccatcccttg atgacctata  63360
ccaaaaaccc ccattcctgt agttgaattt taattgagca gagggagtag agcttgcacc  63420
ctgatacatt tggaaaacaa gctgtgttga gcctccacta taacctgtaa cattatacag  63480
tccagtttta gcattccaag caatgccatc actatcacct acctctgtac cagtacctgt  63540
ggaacctgca tacataaatt tctgattagc tactgattgg gtaaaatatc tggcatctaa  63600
gttagaccaa tctgaaggtt taacctgtcc agtgattgct aaagttgcat tcatttcgaa  63660
tgttgagccg atggtaagcc ctttacctgt tttgtagtta aacagcctta agttattatt  63720
gttatcggca tcgccattac caacatacca cttggctgtc ccatcagcag ctaaccctct  63780
aatgaacaat gtcgttgcag tttttgcttt taacgcaaga gcttcaccat cagagttgat  63840
aacttgtcgc acagaaaatg tattggtcgc attagttctt gcaattgtac ttaatgttgc  63900
tgccggaata tacctagagt caatgttagt ccaatctgaa ggttgaactt gtccagtgat  63960
tctgacattt ttatttgctg atactccagc agcatctaag accaaagagg tgttagtggt  64020
atagttgtag atagttacac cagcacctga actaccttta ccaagatacc ataagtttcc  64080
accttcataa tcttttgcaa gtagatacag ggattcgttt gctgatgcac attgcagtgt  64140
gatagcagca gcatttgaaa taacactcat agtcctaaat gtgttagcac ctgtaaaagt  64200
attattgcca gctaactgtg caaatctctg attagcaact gtctgagtga agtatctagc  64260
atctaagtta gcaaaacttg aaggctgaac ttgaccagca atttgaagag ttctgttgac  64320
```

```
tgtcaccaaa ttttctgaaa tagcaattga aacgtcagtt tttacattct tcaatacaag  64380
gttatgtgtg cccctattat cattacctag ataccatctg ttagtgccat ctgcatcttg  64440
accacgaaga tagagtggtg tgccttgagt gatattttta ataatgagtg cttcattgtc  64500
agagaggata gcttgagtac ctctaaaggt attattcaca gcaagtcttg catatcttgc  64560
atcattctct tcattagttc tcataccaag ctcattagga cttggcttat tcagagtatg  64620
ataaacagtt gctgaccttg aagcatctgc aatagttagt ttaagaccat ttgcgttaag  64680
tttaaaagtc tttaaaacat cccccatagt aatctcagaa gagcctgtag ggtcaaagac  64740
tgccttacca ccataaagta acttaacaat ccctaagtca ccagtcatag tactaccagc  64800
aatctgaaca aatctttcaa gcttaaaaga tgctaagaaa tcttgatagg tcattcgacg  64860
gtcttcatca cccagcattt caggtctctt tttaaccctg acatgaagaa ggtcatctga  64920
acggattgta tcgattgagt ttaattcact caacttgtaa tctgccatta tttttgtcct  64980
ctagaaagag ggctatacag ccccctgtaa aagaattttt aagcggttct ttgccataca  65040
taaaccacaa aggatggttg ttcaacgcta aatgcttgac cagcacctgt agtacctgta  65100
gtacctgagt gagtatgctc agatgactgc aaagttactg tgcctttatg ggtatgagca  65160
ccaattgcaa cagtgtgtgt gtgagcacca attgcaacag tatgtgtgtg attacctgtg  65220
gtatttgttg aaccgctaac agtgtgtgag tggtcaccag ctacactgga aacctgagca  65280
gtccctgagg cctgaacacg ttgtttacca ccaatagagt caccaccata atgaccacca  65340
actgtatgtg tgtgattacc tgtggtattt gttgaaccac tcactgagtg ggtgtgagca  65400
ccagtgctat tagtggtctt tgttccataa tcgaaactgt ttgtgctctt attgccgtaa  65460
tcaaagccat caatagtaat agtagcacca tgagtatgtc caccaccagt tagatagact  65520
gagtggctat gtgatggtag attgttacta gataagctaa cactacttga gccaaagtta  65580
ctaccaactg gcctagaagc actatcataa cctacaagtg ctcttcctct tgaaactaac  65640
tcccaagtac ctccacaaat taaatatgta gaagggtttg caggattcat agagagatgg  65700
atagtaccta ctggataaga agcctgaaca gccttgtaca agttatttac tgctcttgct  65760
gtagcgtact tatctgcatc ttcattataa aggttggatg ttgtccagtt ctgaacatta  65820
cttaaaccaa cctgtgcttt agttgtattg tgtggattac tcttatcatt aatatgctgt  65880
tggacaaggc tattaacctc ttctgaagac ataatctgta gatttgctct tgcctcatca  65940
acattagtaa tgtctgataa attatttgca gcaactaact gaagagcatt gataacgtta  66000
tctaaaccaa tttgtgtttt agtaacaccg tgggggttat ttcttaggct tgagtgtgga  66060
gcaagtaatt gctcaagagt acatctctta tcctcaatac cctgcttaag atggaagata  66120
tcactaaggt caattggtaa ggctgcttga ggcaaggcac taatttgaat ttcacctact  66180
gccattatta agctcctaca aattcataag tgtaaaggtt ttttgtactt gttgatgcag  66240
tacctgtttc ggtcttaata agactccagc cattagctac taaatctggt tgctcagtgg  66300
caaaagacct tacttcgcca acagtaccat ttgctttctt caggagatag tttaagatat  66360
agttaaacca ttgtcgtccc ataggctcac cccttaataa accagtggcc tgaatttctg  66420
gtggtggtaa tacttttagc tggttaccat cagcatctac ttcatctgta gaccaattta  66480
aaaatgccat taagaacttc cttcttgctg tgatttatct tttctacctt tgatgatttg  66540
agctacttca gccataacac cataatcacc acctgctaca gtttctttac caacgatgta  66600
gttatctgta gcgttgtaat ttttattaac ctttaagtaa tctactgagc cactattagc  66660
```

-continued

```
cgttctgtca accctaaaat aagcgtccct gacaccagca tctgctaaac tacctagtaa  66720
gttcttctct aaagaaccac ctgtgttgtt agtgacaaga cccttgttag catctgtaac  66780
gaaccagtta tctttatcat caacaattgc taaggctgag tcagccacct ctacaggcgt  66840
ccaagcagta ccattcagag ttacgtctct tagaataact gctgaaccaa tggttgttgc  66900
agcaattttt gccaatgtgt acgctgtatc aatgacgtta tttcttgtat taactctgac  66960
tacaatacca gcagtcacag gtgcaatatg ctcaaaaatc tgtgaaaatg ttgcattata  67020
cagagtcatg atggcattct gtaaaaatgt tggagttgta tcagaacgtc ttaggaaaat  67080
ctggatatac aacattgctc tgtatgtttc atcatcagca ccaagtggtc gtggtacttt  67140
aattaatgaa ccaatgttgt caagttgctg tccaacagct tttctgatat tcctttcagt  67200
gtgcatttgc catgaaacat cttccaatgt ctgcaactca tcagtgatag ctttcagtaa  67260
actcgtgtag atgaatttat ctttaaactg tgtaacagtt ctttcatcaa gagttttata  67320
ataaacatta tcaatttttct gaaacattat tactccttag taatggtgta ctggctactt  67380
tcccatacag tatattggtc accatcaaca gtaattcttg ctgtagtata ctgtccatca  67440
ctaggaggta ctgactggtt atttgaaaga gctactttga tttcattaat ctcaacacct  67500
ttaatgacat cataaatgta tccatagatt ctgttaggaa taacatcatt accaactttc  67560
agagttctgc cgtaagcgtt aataccttga acaatactat ctctgatatc ctcttctggg  67620
attgtcaagc tctcttcatc atataaagaa taagatactt tgacaaaagc atacttgggt  67680
gttggtctgc taaaatagac attatgagct aaattgccta agtcataagc tgtcccaaag  67740
atagctccat aagccctgat accagcaggt ttggtatccc agattgcttg agcaacgtta  67800
tcattttgac caccaactac aacaatcttg aaagattttg gtggaagtcc ttctgaattt  67860
gtctcttcag tatcattttc cacacctgaa gcatctgata caccctgaac ccttttaacg  67920
gcagctacga ttgcatcgag agttcctaca ccagtaactg ccaaagattc taaatatctc  67980
tgacgaagct ctgtatcggt ttcttcattt ctacctgttg tcaggtcata tcggttgtat  68040
acactgtcaa ggccatctac agttgtttca atttcgataa gtgttccagc taatgcaggg  68100
attgcaccaa cttcctcagc aacaacatca tggatagttg taatttttgt gaatgtaagg  68160
aacgtcgtag cagtcaccac catagggttg attcttgcaa taatgtcacc ttcatctttg  68220
taaactcgta atgctgaacc ctcattgata acttcggctt ttgctacgat accaccattg  68280
attgcatcgg caagttcagt taatagcact gtgattgtat ctgaagattt tggctgataa  68340
gagaaaatag tgttatcaat aataataaca taatttgcat cagttcgtaa agagttaact  68400
tcaagaacag cttcaacaca atatgatggt gttaatgtaa tgtttgaaac tggatagaag  68460
atattaccag cagtgcttct tagtctagtt gtagacggaa ttgttgcacc agttgcccca  68520
gtaaactcta cttggcctct tgtagcctga gccacatatc tgtatacagc gtttaaagct  68580
gtaatatcat caaggttaaa accttcagct ttatcaattg ttccaccatc ataaatttct  68640
gacaggactt catgagtgtc tgctaaagac cttgcaattg aagccagaaa gagacctaat  68700
tgactatctt cagaaacgtc aaggtttggt gaaatatctc taagaagtct cgatttgata  68760
ttatcaaaaa tttcctgata tcttagagtt tgtaatcctg ttgtagttaa tcctgccatt  68820
agatattaac ctcttgcgta atgtctgtta aaatatctgt tgtagtagtt gcatcaaaat  68880
taacagtcac ttttctctga gcattatcca ttgaagaaga atagttatag atgttggata  68940
catctcttgt ttcaacaagg taggctttca tgtaattatc aaagatagaa gttttctgtt  69000
taaatttggc aagttgtaaa tatgggaacc cagcagatgt attaaagaag acttcaccag  69060
```

```
cccttaaaag gcatctaata tgaagtcttt gagcaacctg agtagcttta tcatcttctg  69120
ggataattct aatttggtta ccagtaatct ttaaatctcc atgagccaca tacactgaat  69180
ctgaacctaa agtggcaaca tagtcaccac ctagatttaa tgcaaaatct gttttcatta  69240
ttgtgcctct gtagtatcag cctcaccagc agggtctgtc cagtaataat ggtgcgtgtg  69300
ttcattaaag ctcacaccag ttgtgtcact gataaaatct gagccatgta cttcttctgt  69360
tacatacaag tttttagaaa tgtgtacatc accttcaaag tagaagttac catcatcagt  69420
aactcttaac acagagtcac cgaaatgaag tctaactgct gttgggtctg gtttaaaatt  69480
ctgtgttctt gtgcagatgc ctacgaaagc tacacagtct gaaatatcat gtgtccttct  69540
catgtttgtt tccatctgaa cattcttgtc attgacaacg aagtcatcta aaggtaacat  69600
tgagaaagct aaccagcatc tgtcattagt ttttacgggg aatgttaaag atgctccacc  69660
accacttgga aattgaacag gtacaccagt aatctctggc ataggtaaac cgttaataga  69720
gtaaagtggc ttaacagtgg ctgtttgagt ctttgaatcg aaagactgaa taatggctgg  69780
taatccagta tacagctctt ttctaaattc atcaagacat tctgaaacat acccagacat  69840
tctagtaact ggtgacttca ttactccacc ttctctaaat ctagttcagt tgtccaagca  69900
ccaccagtaa agtcaagatt atgagaaaga cctttactc gatactgacc ttcaaaatct  69960
tcactttccc taatagtgat gttatcaccc atcttaattc tcccatctaa atggattttg  70020
caacgaactc cagttttaac tttaataact gtcttattct ctttttaag aacctttcta  70080
gttcttctgt agtaaccttg caaagagtcg ataacgttat atgggtaaat ttcccaagaa  70140
agttgtctgg ccttagcatt aaaaggtact actcggattt gcttattaaa tgtataccaa  70200
cgtagactac tttcttcaca aacctttgta agtgcctctg caacacttcc ccagacacta  70260
aaaccattct tgtaagtgta accatcaata cttgaaaggt cttcatcaat aagtgagaag  70320
cctagtctat tgactaaatc tctgattaca tttttacgtg ttgttcctgc tttataagaa  70380
attgatgtct taatcgtggt tctttccatt ttatcattgg aacagataac ctttgtaatc  70440
atatcaacac cacgcttata tgtataagca tactcaatag tgcctagata aattaatggg  70500
agattgtcat actcaataat aaggtcaccg ttcgcatctc ttttaaagcc agtggtataa  70560
cctgctctaa gcataactgt tgcaccaacc gttttaaatt tggctctcat ctctttattt  70620
aggttgtaga tttcaaaagt ggtatcatca gaggttactt tattcttctg agacgtataa  70680
gacacattac aagtgaattg taagttgtcg aaatagtcca tttgcataga atctttagca  70740
tggcttgtag gtttatcatt aaaggctgta gtttcactac ctacagccaa ttgatagcac  70800
ctaaaagaag ccccagcagt gctatctttt acagacatta taaattctcc attaatctca  70860
tatcttcttg agtgtaataa ttaagctcaa atgccttttc tcttccgaag ttatttctgg  70920
taggttgtaa atcagtacca tacattcgtt caacaaaaag ctctccagct aatgaaggaa  70980
ttacatagcg tcctgtgatt gactggtctg caaggcattt cttttcagat aataatacat  71040
taccatcaac atcagatagc gtcaagaacc atctgtcaag cctctcttta tactttaact  71100
caattacaaa gacagtacca tccagagtta cagtttgtgt agaccattct gtatcaggaa  71160
caggaatata ttgtgacatt aataagtccc cttcttattc ggattcactg agtgcttttg  71220
taatgccttt ccagttccag cagtattatt atttaacgct gctccagcat ttctttcagc  71280
ctcttcactg aatgtagtaa caccttttct tgtcttcgca gacattgagc attttgcaag  71340
agcattgtct tcagcactag tgagttccct tacaccatta gcatctaggt caaataataa  71400
```

```
ctgacagttt aatttaccat tacctaaact tgttgtagtg ttccctgtat tctttttact  71460
ggtagcaccg ccatcattag tagtagcagt cttgcctgtt gcagccgaaa tatcagtctg  71520
acccacaatg gctttgaagt taatttcctg aaaagttagc tggactctta gaccatttga  71580
aataccaaca tctttagaag ctttaaaact cgtaataatg gaatcatcaa ttttaattcc  71640
gtccttacag ataaccgaaa taatttgctt ctggtcacgc cagctttcaa gagtgtcaat  71700
gaagttttct actaattgac cctgacgagt taataacaag cttccttcat agccaactac  71760
aacgacacca ctaatagtga ttgttctggg tgctctttga acattatctg tgacggtttg  71820
ccctgattgc atgttctgtg tagtaacctg catagggctg tcaaattcca tgttttcagt  71880
tgctgataag gttaagaagg catctacatt atctcttaag tggaaataga tgccatcttt  71940
gccactatat ttgatttgca tattagaatc ccataacatt attcttcctc tggatagctt  72000
gaacttagaa gaatgtcttc ttgattcttg tcagtaatat ccaccatctt agtagcaatt  72060
tgtttaccat caagattgaa agtaacattc agggtttgtt tagtctgcat aggtaaacca  72120
gaaggtgtca tcatcattgg tgtctggtta aacttattgg caaaattatc aatagatgtt  72180
gatagcttct ccatgataat ctcccaatta gatagaccat tatcaattaa ctttctgttg  72240
ccttcaacgt cttgagtgta ctgtgcaaac tgaagttgac cattctcatc aaagaacatt  72300
ggcctttttg ggtttgtaat atttgcaaca gcattttcaa atggttttgg taatgtaact  72360
tcactgtagt ttttagcagc atttgggtct gtggagcctc ttagcattaa tgctgaacca  72420
acagtaccaa gtgccattct cgttgctgta actccacctg ctgctgcggc tgcttctccg  72480
gctgctgctg tacctgctgc actaacacca agtctttgta agattttacc aaagataccg  72540
ccaccaacca aaccacttag gagcttgact gcttttgata ctacagcaac tgcaccacca  72600
attgtgacaa ctgttcctaa aaactcacca gcacttttga ttagtttttg ctgactgttg  72660
tcaaggtctt tataccaagc tcttgcatag tagtataatg cagatgttct gtacatgaag  72720
tctgtaacga agtctagcag attactagca ccttttaaca ggtttccaat cacaacaccc  72780
aaagcctgtg tactacccaa agaaccttgt aagaacattg caacggagtt agataactgt  72840
gaaatgccct cactagaatt gttaaacagt gctacaagtg tgttatccca catagccttc  72900
gcttgaccca ttgatgtagc agtctgcttg gacacagcat tcataccacc tgcttgcttg  72960
acaagttcag ccattctttc agatacttta ggaagaacgt cttgagcaag aagtttaccg  73020
tcttgcatca tcttatcaag ttcttgtgga gtcttaccaa tggcatcagc gaatagttgt  73080
acagcacctg ctaaacggtc acctaactgt ccacggagtt cttcagcctg aactttaccc  73140
tttgatgcca tctgctggaa tgcaaccatg atacctttca agtcttcatc agtagcaccc  73200
ctgatacggg caaacattgc agcattctta tagaactctt gagtaccctg aaaaccaagt  73260
gttggttgag caccagcagc gaagtttgag tactgcttca tagtatctgt gtagttctga  73320
ccaatctgat gtgcgaatga tgcagcgaac attctggctt gctgggtatc tgctccaaag  73380
atagctgtgg aggccaactg tgcagactgt ctttttacac ctgcttcgat agtcttttgt  73440
gatagttcca gtaaagcata agctgaaaca aatccaccaa ctaattgacg taatgatgag  73500
ttagctctgt cctgtagcca agctgattct ttaactgatt ttaatctagc attttctgca  73560
ataacccaac gtttggttac gtcgatgagc tttttaactt ccatctcata ctcaccaacc  73620
ttaccagtcc ctttgtatct gttgtagata ttttgcaagc tccctctgaa agaggctgcc  73680
atttggttac cttgaccacc gattgtttcc agtctacggg ttaaccctga atagaagttg  73740
ttgttaaaca ttctttccat ttgtctctga gcaacatcta ctctcggacc tctgggtgct  73800
```

```
ccaccaccac caacaggagg gatactctgc ccacctctac ctctacctgt tttgatagtg  73860
attttaccgt caaccttcat agcatctctt aaggacttgt taatacctt tgcagtcttt  73920
tttgcttgag tttcaagttt cttaagagat ttaacacctt gtgaatcaag gttcaaggaa  73980
ctgttgagtg ctttattgat tctgcccgaa gcagactgag catttttac aattctatta  74040
agtgcttcct gagaactctt attaggtttc acatcaaagg ctttattaat atttctctca  74100
atacgttgag cagcttgcat agacatcttc tcaactcttt gcaaaccttt aattaccttt  74160
tcactgaaac caagttccac aatgaagcta tcaactgtat attgtgccat tacatttttc  74220
ctgctcttct aagttcgttg taagcaattt cctctttata cgacctctga atttcaagaa  74280
attgtctcaa tgataataaa tcagagaatg tcatagcaaa gagttggtca agtgtttctt  74340
tacacccttc cataccataa atagcaagca caaatttcat ctcgtctgct tcttcatagg  74400
ttgcctctac agcagcatca gttagtggtg tctgtagagt gttacccatg tttactgaga  74460
agttaggctt ttgaaaatgc ttgcttcgaa aaaacttccg aagtttgcct ccagcgcaaa  74520
tgctaagtaa tcaataaact caccgtagtt tgcttggaag tacgtatcaa tattaagtgg  74580
gaagtcatca acagttgccc cttgaaatag taaggtagcc atttcttcaa ggttaatttc  74640
ttcaattctg tcaaaacaag cttcaacaag ctctttaaat ggaaccattg gagcttcttt  74700
cttacccttg tcagtcagac ttgatagcat ctgtgcaaaa gttggaacaa caattttacc  74760
caacttcata gacatcttaa taccatctct tgccccaagc agaacgatat tcactttctt  74820
accattaatt actctagatg ctgttttcat tgtgattcct taatactttt aaaagaaaca  74880
aaaaagggga agacctttta aagtctcccc cttataggat ttattaaaca cttgacgctg  74940
gaattgttga agtgtagtct agcttctcac aaccaaaaat ccaagtttta gagttctggt  75000
cacgaccaag ttcaatctgt ggtagttcct gcaaccaagc attaataccg gttgccagaa  75060
cagagcctga tgggtcgtag attacgaagt tagaagagat atcttcttca agttccatat  75120
tgtcttgttt agcttgaatt gcagaaagca tctggttaga gagagaagtc tgcattaact  75180
caatctcaat agtacctgtc ttgtctgcat ttcttgtcag agcaacttga ccacctgcac  75240
ctacaactgg tgtcacaagt ggtgatgttc tctgtagacg caagaatgag tctggggcaa  75300
agccttcaat ggcaatacca ttccagctac atacaacgtc tttaggggaa tattgctgat  75360
acatagccat tccaatttac ctctattatt cgtaagccac tgtacctttc aagtcaacat  75420
ccaagatagc ccctgctaag atacctgcga aggtaacgtc tttcaggata cgcgctttct  75480
tgtctgctaa agcaacttga gaggctttag gaacattaac tgtgtaagat gacaggaagt  75540
ttctgttgac tgctctttgc agagaggttt caatgacttg acgaatacgg gtaataccag  75600
tatcatcata agtaatctta ccacccttct ggttaattag caagtctctc agagaagttt  75660
tcaggtctga ttctaaccag tcaacaccac ggacgatatc aatccattcc ccaccagaag  75720
taatccctct acgaaccact ggaacaccac catcaaggtc aataaagtta cagtgacgtg  75780
catctaaagc tgacttctga atacttgtca gaggtctttt attagctggc tgtagagaag  75840
cagctacacc agtcaactga gcattacccc aagcaattga ccctgcatcg tatggagcac  75900
cataagcaat gtatgccatc tctggatagt cttctgctgc tgtgtgatgc cacaagcaaa  75960
ctgtgcgagt atacatactc ttagcaagtt gtgctggaac atcgtttgca ctgtttaatt  76020
ctgtaccttg tagtgctgat acatcagagt tagcagtgaa gaagattttc ttacgagcct  76080
gaatctcaga agccattgct aagacaaact gttgagttct gtcttctact gcaatgaaat  76140
```

```
accagtcggt agaataagct tcaatggctg ccagagcagt tgatgctgta tcggcagttg  76200
tacttgcaat atacacagtc tgtgctgtag ttgttacttt cacaaagtca ttatcaccag  76260
ctttggtaat aaccattgtg gcagaaccat tgctaccagt tacattcaca gaaaccttat  76320
ctttgattgt tgggtcagct tcaatctgtg ttttaaactg ttgcaacacg ttctcagcag  76380
tgtctgaatc ttgtgctgtg tactggtatg gttgagaaat tccaccgcca gcagctacag  76440
taattgaata gtcagtactt tcagtaacgg catcaggaat tgatacagtg tactgcatag  76500
cacgtctacc aatataaagc tgagttactt taggagtctg actccaaagt tgtttagcag  76560
ccttatatgc agcagagttt tcatcgaaat cttcagcaac ttcagttaag gaagtgtaac  76620
cacggactct ttcttcaaag ttatctgttg aagctaagaa tagtggcaaa ccaaaacctt  76680
ctcttgtagt tcctgcggtg ttcaatgtaa tatctacatt aacaattgga ttccacattt  76740
attttacccc tttggagtct acatctagat ggatagtata ttctggtggc tcttgtcctt  76800
cttcataaac caactcacca tcaacaatga cacgctcaat aatacttcca cgttcatctt  76860
tcaggactga gtttttaca agagttacaa caagaggtgc agaattttcg aaatctgtat  76920
tgagataagt gtaatcattt gggattgctc cagtgtccag tactgtagct cctgtttctt  76980
caaggattaa atctctgact gaactcatct ctaatctttg tttaagctca agcataatac  77040
tgtgagcacc tttgccattt accgtaatta atactggaat ctgaaaagca attctgtagc  77100
aaactacatc atcctcaaca aacttatcaa gaacccaacc ataaggtgtt gcggcatctt  77160
gacaatatac ggtaataaat ggctggtcag gttttaaacc tttgtcattt gagttatcag  77220
aagggtaagc tctaattacg tttggtctat tatttttatc acgagctagt ctgtgaccaa  77280
taacatccac taaggttcta actagacctt tttcaagttc tgctgtttct aactgcattc  77340
attttatccc ttctaataat gatatattca taatgggacg tatgggctaa ttgctgtgac  77400
caatccatag tcataaatac ttcatactca tgaccatcaa tcataacaat atcagactca  77460
ttccactcta catcatctga agttctaagt ttatatgtgg tatacaggat tcttgtatcg  77520
gtaagtctaa taccttccgg taaagcaatc tgtgtaccat tctttacaga acctttgata  77580
tatggctgga tattaccttt acagttaacc tccacaatat cttgtgaaga tacccaatca  77640
ccatcatcgt tataataacc gtcttcagag actttacgct ttactacaaa gctgtgtctg  77700
tttaagagtc tcatttctta ataccccttct tagtagaaat tttataagca aggttatctc  77760
ttaagtcacc tgtctcaaca agaggtgcgt taaagccttt tttcttgact gtggaaggtg  77820
cgttaggagg gaggatagca gaattaccaa aacctctttt aattgccttt tgagcattct  77880
ttgcaaatgc ttctaaggta tttgaagggt ctgtgttgag actgctaagt tgcttatata  77940
gattcttctt agtctgctct aacaaggtct gtttgtttag catcgtagtg atttcaaaca  78000
acctacgata tactttacca gaagctgaag gaaccccaat aacttcttgt aaatacatta  78060
aagcaggata agaaaaacca gagctatgtt gaccttgttc ttgaaaatac ccaacttgag  78120
cattagccgt ttgcaagttc ttcatagccc cgactaattt tgctctagcg gggtgaataa  78180
ccctttttaac cattattcat ctcgctcgat aataaatacg ccattaacac ggttgcagta  78240
atctctgcct tcgtatctgg cagcatcacc atattctgtg tatttcttga cagagcaagg  78300
attctgacga cgcatgtcaa tatcacactg attaatacca cctgcatagg gtagtcctga  78360
aacagagctt ttaacaaggt cgtcataaac agctttcaga gacttgaatc tggaagagtt  78420
acgtaaataa acaccaccaa ccttctcatc tcccatcttg gctacttgaa agagtaaata  78480
tttaagagct ttgatggctg ctttcttttc atcctttcca gattctagat agaaccactc  78540
```

```
tagcacagac tgctcaataa gaatttcatc attattagtg tctgtgcaga ggattcttac  78600
tctatcaaga gggttattgg ctgggtcgcc tgtataacac attcataacc ctccttaaga  78660
atattagtct ttggcgtcag aacgaacatc taccagcaac tgaggacgag tacagtatgg  78720
cagcatgtaa gagtgagctt caaagtcgat accttcgtca cggtcttttt cgtattcgaa  78780
tacgtacagt tcctgaccaa gtgtatttgc ataacccatc ttaggacatg gaccatatgc  78840
aacttcgaag atgttgtttg cttcacccag catagaaacg ttagggaaag catgaccaac  78900
accaacagtg tctgctacgc tatcaatgct caccagagtg tgaaccttac cacgcttgtc  78960
tttgaactta ccgttgtact ggacaaactt aacaccaccg tagtagaaag tgttcatatg  79020
agcctgaacg ccgtcagtac caccagttct cagagaacca gtaatctgtt gccaagccag  79080
tggagtctgc tgtgcaagat aagcatcacg aatcttaggg tgcttagtca gtttgctgaa  79140
gaatacacgg tcaacaacta cgtgaatttc ttcaccgttg attacagtgc cagtcttagc  79200
ttcatcttcc atgtgcatac gcagttcttc aatagaagca tcgatgtcag cattagggtt  79260
gtcaaggtcg aagtaaatag tcttcttctc aacgtcgaac tgcttgtaca ggtcagcgta  79320
cagagtacca cgagcatcaa caactttacc cttcagagct tgcataaaca ggaactcacg  79380
agtaatatcg aacttggtac gaatcttcat cagcttcttg gcacgtacta cagcttcagt  79440
agtcagttcg tttgcagtgc ctggctgacg tacaccctga atttcatcag gagtaatgct  79500
ttcaacttct ttgaagtaca tcattgggaa gctgatttga cgaacacgct caggtgcgct  79560
agtctctgct ttacggctat cacggtctac cgcatcaagc aagctaacat cccaatcagt  79620
caagtccatc aggaaagtag tttgggtgat tggtgctgaa cggaacagac ctaagttgga  79680
aatataccca taagtatttg ggatagactg gacttcacca gtcaggtcag caaggaaaaa  79740
tctgcttttt tcagaattag tcaacattgt aaaattctcc agaatgtctt attattgtta  79800
ttacaggcca gttggtacga aatcaatacc tttggcagcc agagctgtct tgactgcatc  79860
agcatcaaca cctgattcaa gagtaagcag gtcttttagt tctgcgtcac ggtaaatacc  79920
aaccactttc aactggccgt ggtaagacag ttgcaggtct gcataaaagt taacgataca  79980
tacagaatca gcctgagctt cttctcctgc tgcaacttta gtaccatttg ctttcagaac  80040
ttcacctaca cggtattctg ttgaagcaac tggggtgtac tctttgcgag agtggcctgt  80100
tggggtaacc tgttcccaaa gaatgatatc attcagaggt tctcttttac ctaacttagt  80160
aaaaccttga tatgccatta ttgtgttcct tatttgataa gagattttag agcattctgg  80220
agagccagtt tgcgttgttc agcggtgtct tcggaagcat tcttagctgg ttctttttct  80280
tcttcaacca aatcagcttc gccgtcatta cccatttctt ccatagcgtt ggagtgttca  80340
agaacagcac cagcagtttc tttcagcttg gtaatttctg attctttttc ttccattgca  80400
gaagcatggg acgcgatagt ttcattaagt ttctggttag caccttccat agcattcata  80460
aacagaacgc tcagagggtt atcaagacca gcacctaaaa tagtcgttgc agcttctttt  80520
gcatcaaacc caaaagcttc agcagaagca gaaatcttat tagtcaaatc tgacaaagca  80580
gcttcctgtt ctttagcttt catttgagca acctgaagac gcaaagcttc tagttcttgc  80640
ttttcttgtt cagtcatttc ttcacctgaa ttgttaacgt ttaaacttac aggagcctct  80700
tcagaacctt gtaagtaatt taagaaatca tcttgagaca tgattgagtt aattaaacca  80760
agttcaagag cttcctgagc agaataaaca ttcgcctcag tattctttac agcttcttca  80820
gagagattac gagattcggc tacaaaacct gtaaaggttg cgtaggtatc attaattctc  80880
```

```
ttttgaagtc tttctttgct ttctactgag agtgcttgga atggtgaacc cataccttta  80940
aactcaccag ctttgatgac gttaattgtt acgccattct tttcaaatgc cttagttaat  81000
tcctgatgaa ccataattac accaatagaa ccaacatctg catctggtga tgcaataatt  81060
tcttcagcag aagatgcaag agcgtatgca gcggaacaag cgaactcatc tacataagca  81120
ataattttct tttggcctct tgaagccata atgtgacgtg ctaattcaaa gcaacctgaa  81180
gcttcaccac caccagaatc gatgtgcaga acaatagtct tgattgactc atctgctaaa  81240
gcttcgtcaa agcctctacg caaaccttca taagaactta atccacctgt acacattgca  81300
tcaatgaatg tcatacgatg ggttaaacca cccataatag ggataatagc aatgtcatct  81360
ttcactttta aaagacttct tgcttcacct ttgggtttat caaagtttac tgctgcttgg  81420
acatcaccca gcaatctgtt attcacataa gttgctgctg agtgagctaa tgattcagtg  81480
gctagtaaag gttggttgaa taatctatca gcaagtctga agatattcga actcattttt  81540
actcacccta tttgtttaaa tctacagaga ctgaagagat aacatagata ccttcttcag  81600
caaagaattg aggtttgcta agagcaccag ttgccacgca tttatcgtta gcatcccaca  81660
agctatagtg tgagaccgtt gcagaagctg gaacagtaat attaactgta tcttctgagg  81720
caattaagcc attatccggt tcagaaaaat aaataaccac tggctgagta accttatttg  81780
ctgtagggtc tgccgttggg tctacattgt gtaaaataat agtcgttggg gttagcgtgg  81840
cgaggatttt attcttacca tcaatagtta atgttcccat taattaaacc ttactttttg  81900
tttaaggact gttgaatggt taccagattc atctaccaca tttacaatca tatcatatac  81960
tttacctttg acaagtactt tgtaatcatt ttgtgaaaaa atgtattcaa gtctgtttgt  82020
ttctttatta actgtcattg gagattgaaa tgcagtgtcg agggtaatga aagcggcttc  82080
aatgctttta acattgatac gtttattctc gcagttatat aactttacac ccaaaaggca  82140
tgaactgtca aatggaattt taacaatttc actacaattt cctgaaataa acggttttcc  82200
actcattggt gcatcaagta acctgcaaat agtgaaaacg tcagagactc caccatcact  82260
aacataacct gaaaggctga cccttgagcc agcctctaca gataacttat cagtaatgat  82320
aaggacaccc ctatacgaat gcactcgtgt agcatttgaa atagagataa cttcagccat  82380
tatttatttg ccttatttgc tgtgcttggg tctttcgctg aaggtgtctt tgcagtacct  82440
tctccagcgg tcttataacc atctcctgaa cggctttggc tattcggaga aagcttttca  82500
gatactggct gagactcatc agcaggagga agaccaatat gctctctaag tttgttagat  82560
agctctttgt caacttccaa agcacctact gcaacagtct tctgaatata agaaccaatt  82620
gcttcaaggt ctggagtttc gatatcatca tatgtgattt gtacatgttc ttcatcatcc  82680
cacatattaa gagcataagt ctgtgcaact aaatcacggt taattacgtt cttaatttgc  82740
ttcagcagaa tatcgactga cattgctaat aggcttgtct tagaatctgc aagagagaat  82800
gaaccatatt ttgactgacc catagcaaga acatctgaca taaatgccat cataatttgc  82860
ttggaatatc tgtcaatgat agaacctgta tcatatgctt tagcaccctg tctagagact  82920
aatgagaact caaagatatc ctctttagta tctgggtcga tatatctagg ccagattaaa  82980
cctgctctgt cattagcaat catatcatta acaacagttt tgcagtattg tacgaaagct  83040
ttcttttcag gttctgcatt ttcatccaga taatctggtg gtaaaccaat ctttggcata  83100
cctactaagt ctcttgaaac accaacagct tcatactctt caatctgtac tttatacttc  83160
cacggtacat aagcattaag caatggtgaa cgaccttctg ggttaccata ctcatcatca  83220
tacttaaaca gcatgaattt agctcgtgga agttttcttg ttagtggtct ttctccaaga  83280
```

```
ttgattgctc cagcaatatg tgaaacattt ctcagattct gtcttacacc agtaactttt  83340
ctaaagtctt cgtcaaaata ccacttatca agtgttgact ggtttctgat tggtaattta  83400
gcccacccaa ttagaccatc atcaaatttt gactggtact ttcctttttt accctgacgt  83460
ttcttataaa ccttttcgtt aacacagaac ccataagtgc agaatgacat tacagagtta  83520
ataaaatctg cccaatcatg ctccatgtca tccattaaag aattaaagaa gtctgctctt  83580
tcaagcattt tagggtcttg ctcttttccc tttggaggta cgaatctcca gttgactttt  83640
ctgacaaaca tcttaataat atttacagat gctgctacag cagggtcacg catcattaat  83700
tggaaagttt taatactttc agggaacctt agtgcctgac gaggttcttc atagattcta  83760
ccattcttaa ccttcagacc caaagaacct acttcaccca ttctaaatgg tggtaagctt  83820
tcttgtgttt ctgtaatttc tgccattctt ctcacctagc tatcaacgtc taagcccctc  83880
atatgggttt cctctcacta agtctgtgtg agcacccatt gatggtggct tgaataattt  83940
aacttcgtta agactgttga aagcatcact ggtagcatcc acttggtcat ctttagtttt  84000
gccgtcacca caaaaacctt caagttcttg gaagtaagct tcgttccaac tacctctcaa  84060
gacttttaca agtccagctt cagaagcagc agaaaatccc gcaaagcggg taactttatc  84120
tttatttgtt ggcttagctc ttgcgcgata acctttctcg gcaagtttcc tgatgaggga  84180
tgttgcatag gatttaccag cagcgcctgg gtcttgaggg ataaaaatac cagttcgctt  84240
accgtcactt tcagcagtca aattaatttg tgtttcgact ccagagggtc tatctctaaa  84300
tcttactaca tcaatgatat aatagcaacc gtcttttta gatttaccca tcttaacacc  84360
cgctgtccag tctggattag ggttaatctc agatggtaaa gttgctgcta agtcccatgc  84420
tctgacatca aacacatctt ctgggagtga atcaacaatc tcacaccatt gtctttgcca  84480
atagtttgaa ccttctgcac gagccttcca gttaccgaaa cgaagtcttg caacgtttac  84540
aggtgtgttg ttttccaact taccacgata tttaggttct aagaagtcaa gaattgggtt  84600
atcatcaatc gtaccagaga tgaaggtgta tgtctgagga atctcaagag ggaacatttc  84660
aagaatcttg tctctctccc aatcagaaac catcacacca tcattcataa cataccaacg  84720
aatacgaccg cacttctcag ggtctgggta accttcttca tctaagaatg gctctaccca  84780
atcataaatg aagtggtctc tatctgggtt catagaaatc ttcatgtatg aatcaccttc  84840
agcacctgaa cgtagacgag tctgtaggta tgaaatctgt gaagcagaga agtgtgtacc  84900
ttcgtcaaag tagatagctg agtattcaat accctgatga ccttcagcgt gcttttcaag  84960
ttctaggtag gtaaacttga tagttgcccc agaagggaat gtgatagtca ttttctgctc  85020
gtgaggaatc ccaccaaact taccaaatag tttctttgca gcaggccata aaccaccttg  85080
taactgtgtt gtatttcgac ggaaatatac agcattatag ttagggtctt caataaatct  85140
taaagagtcc attaacaatg cagcagtttt accagcacca gcagcaccac catataaaac  85200
caagtcagca ttagtattta aaaacacctc ttgagaaccc ggttgagggg ctacataatt  85260
cttatcagtc atcaatttga agataagtct aacttggtct ggtgtgtatc ttaataaagt  85320
cagaatttga gttggaagga atttagaggg gtctttaccg aatgatttga taatttcttt  85380
tacttcatca gaaagcccca actctccagc taggactttc ctaacgtctt ccactcgctt  85440
ctgcttaaca gcatttaagt ccattaagca cctccgcaaa tagaattatt cagagtctgt  85500
agcagtctct tctttcttaa cttcgaactt tgcatcaaca gcatcaagaa gtgcatccat  85560
agatgcctct ttaatatcaa tacctgttgc tacagataat ctgtctgcaa ttgccatgat  85620
```

-continued

```
agtgttctgc ataaattcca gctttttgtt agcttcataa agttctttat aaacggtctc  85680
actcattatg ttttctccaa ataattaacc atgtttcccc ttaaaaaaga cggtacagag  85740
accgtcaagg agaaaccaca atgtacgtca gagacatact gtataaggct tcttataaag  85800
tataactctg taaaaaagcc ctgtctaaaa atactcttcg gtagcgaaag gaagaatact  85860
tatagcaggg cattattatt attttaattg agagagagag taaaataact tggagaatcc  85920
gaagggactc gaaccccttat aaacctgttt tgcagacagg cacatagcca tttctgtcac  85980
ggattcaaat tggaggaaga taccagactt gaactggtac accgatttct cagctactgg  86040
cagtttagca aactgctccc ttacctttta gggttaatct tccattattt ctgtaatgcg  86100
ctcttcattt ctggtgttgc aatagcatca attacaccag ttttacaggc atcgtcaaac  86160
cagtctggta agatacctgc taagaaccca ttgatattcg ttttaaggta ctctgcaata  86220
agggcagctt cttcttcaat catctgcaca acttcatctg tataagctgt aatctttgag  86280
ataccttcat taatcttact aacagcttgg ttagctaaat cagaaacagt atcaagaccc  86340
ttatcaatag catcttgtaa gtcacttaac acatcgttaa cactatctag tgtactgtta  86400
atcgtgtcaa tagctttttg accatactct gtagcaacac ccataatacc actaaatggt  86460
gtacaaccaa cttgttctcc tgctgcaccc ataacattgg agtatccctt tgctacctgc  86520
atacgtgatg aaaactcatc aatagacttt tgaccgtagt ctgttagggt cttagtagtt  86580
gctgtagtgc ttgtcaggct tgttgtaaag ctgtttagaa ggactgttgt aagtccagca  86640
gcaacaagtt tctccttcat tgtagggtct gttacagaac taatagagct tacaagtgat  86700
gtagaagcag ctacggttcc accgagaact gctgcaccag taataagtgg gttagagaac  86760
cctttaccgg tttttaagag attaaaaatc tccttacctt gttctgtcat ctctttcatt  86820
aagcaccttt gaaattggta gtccagtggg atttgaaccc tcttctcatg tttttcagac  86880
acgcgcttta accatataag ctacttggac tataaattgg ggtgacctac gggatttgaa  86940
cccgtataga ccatgttcac agcatgggtc attaccattt atgataaggc cacatttaag  87000
gactctcgta agaaccctta gaagtggcag cggcataagg atttgaacct taataggaca  87060
gcttcagaga ctgctgcatt gccagttatg ctataccgct aaaattggta ctccatatcg  87120
gattcgaacc gatacataac acagatttta agtctggcct ctctgccaat tggagtaatg  87180
gagcattggc gggggatgtt ggaattgaac caacttcttc gatttcaaag accgaggttt  87240
taaccttgta aactaatccc ctttaaatct ttactttctt agtggatgaa taaagaatgc  87300
caacataact ctttcccttg aaaatgctct ttcttctggg acaacacttt taagtttcca  87360
tccaacataa attctccagt aaaattgttt accaaagatt ttgattgatg gtacaaaagc  87420
gaataacccc caagcattac tgttccacat taggagataa cctgtctgat tatcttcagg  87480
gttagaactt acattgatat tacctttcca cttagtaaca tctttcacat ctcttcctaa  87540
cacatggtaa gagaagttat aagctttgtt tctccagagc catccaactc tctgcatata  87600
gac                                                                87603
```